US009393294B2

(12) United States Patent
Gierahn et al.

(10) Patent No.: US 9,393,294 B2
(45) Date of Patent: *Jul. 19, 2016

(54) **VACCINES AND COMPOSITIONS AGAINST *STREPTOCOCCUS PNEUMONIAE***

(75) Inventors: Todd Gierahn, Brookline, MA (US); Richard Malley, Beverly, MA (US)

(73) Assignees: Genocea Biosciences, Inc., Cambridge, MA (US); Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/355,468

(22) Filed: Jan. 20, 2012

(65) Prior Publication Data

US 2012/0189649 A1     Jul. 26, 2012

Related U.S. Application Data

(60) Provisional application No. 61/434,818, filed on Jan. 20, 2011.

(51) Int. Cl.
*A61K 39/02* (2006.01)
*A61K 38/04* (2006.01)
*C07K 7/00* (2006.01)
*A61K 39/09* (2006.01)

(52) U.S. Cl.
CPC ............... *A61K 39/092* (2013.01); *A61K 38/04* (2013.01); *A61K 39/02* (2013.01)

(58) Field of Classification Search
None
See application file for complete search history.

(56) References Cited

U.S. PATENT DOCUMENTS

| | | | |
|---|---|---|---|
| 5,371,197 A | 12/1994 | Marburg et al. | |
| 5,623,057 A | 4/1997 | Marburg et al. | |
| 5,643,576 A | 7/1997 | Johnston et al. | |
| 5,882,885 A | 3/1999 | Burnham | |
| 5,994,101 A | 11/1999 | Kallender et al. | |
| 6,235,285 B1 | 5/2001 | Burnham | |
| 6,248,558 B1 | 6/2001 | Lin et al. | |
| 6,432,680 B1 | 8/2002 | Lin et al. | |
| 6,573,082 B1 | 6/2003 | Choi et al. | |
| 6,617,156 B1 | 9/2003 | Doucette-Stamm et al. | |
| 6,699,703 B1 | 3/2004 | Doucette-Stamm et al. | |
| 6,783,939 B2 | 8/2004 | Olmsted et al. | |
| 6,887,480 B1 | 5/2005 | Adamou et al. | |
| 6,951,732 B2 | 10/2005 | Clarke et al. | |
| 7,056,510 B1 | 6/2006 | Choi et al. | |
| 7,132,107 B2 | 11/2006 | Adamou et al. | |
| 7,141,418 B2 | 11/2006 | Kunsch et al. | |
| 7,314,974 B2 | 1/2008 | Cao et al. | |
| 7,338,786 B2 | 3/2008 | Doucette-Stamm et al. | |
| 7,378,514 B2 | 5/2008 | Doucette-Stamm et al. | |
| 7,384,775 B2 | 6/2008 | Zagursky et al. | |
| 7,504,110 B2 | 3/2009 | Mizrachi Nebenzahl | |
| 7,635,487 B2 | 12/2009 | Meinke et al. | |
| 2004/0029118 A1 | 2/2004 | Kunsch et al. | |
| 2004/0029129 A1 | 2/2004 | Wang et al. | |
| 2004/0110181 A1 | 6/2004 | Zagursky et al. | |
| 2005/0020813 A1* | 1/2005 | Masignani et al. | ........... 530/350 |
| 2005/0136404 A1 | 6/2005 | Doucette-Stamm et al. | |
| 2005/0196415 A1 | 9/2005 | Mizrachi Nebenzahl | |
| 2006/0210579 A1 | 9/2006 | Telford et al. | |
| 2006/0210580 A1 | 9/2006 | Telford et al. | |
| 2006/0263846 A1 | 11/2006 | Meinke et al. | |
| 2007/0053924 A1 | 3/2007 | Tettelin et al. | |
| 2007/0154986 A1 | 7/2007 | Kunsch et al. | |
| 2007/0184443 A1 | 8/2007 | Covacci | |
| 2008/0175854 A1 | 7/2008 | Doucette-Stamm et al. | |
| 2009/0148470 A1 | 6/2009 | Mizrachi Nebenzahl | |
| 2009/0202528 A1 | 8/2009 | Kofoed et al. | |
| 2009/0215149 A1 | 8/2009 | Doucette-Stamm et al. | |
| 2009/0221499 A1 | 9/2009 | Leng et al. | |
| 2009/0252756 A1 | 10/2009 | Mizrachi-Nebenzahl | |
| 2010/0015168 A1 | 1/2010 | Maione et al. | |
| 2010/0143399 A1 | 6/2010 | Biemans et al. | |
| 2010/0166785 A1 | 7/2010 | Liu et al. | |
| 2010/0221287 A1 | 9/2010 | Kunsch et al. | |
| 2010/0221288 A1 | 9/2010 | Zagursky et al. | |
| 2010/0247547 A1 | 9/2010 | Dong et al. | |
| 2010/0260790 A1 | 10/2010 | Meinke et al. | |
| 2010/0278819 A1 | 11/2010 | Bossuyt et al. | |
| 2010/0303849 A1 | 12/2010 | Chen et al. | |
| 2010/0322953 A1 | 12/2010 | Leng et al. | |
| 2011/0020386 A1* | 1/2011 | Gierahn et al. | ............ 424/190.1 |
| 2011/0135686 A1 | 6/2011 | Pugachev et al. | |
| 2011/0177960 A1 | 7/2011 | Murphy et al. | |
| 2011/0246740 A1 | 10/2011 | Yata et al. | |
| 2011/0283062 A1 | 11/2011 | Kumagai et al. | |
| 2012/0100172 A1 | 4/2012 | Tal et al. | |
| 2012/0128707 A1 | 5/2012 | Masignani et al. | |
| 2012/0189649 A1 | 7/2012 | Gierahn et al. | |

FOREIGN PATENT DOCUMENTS

| | | |
|---|---|---|
| EP | 0942983 A2 | 9/1999 |
| EP | 1328543 A2 | 7/2003 |

(Continued)

OTHER PUBLICATIONS

Klein et al. 1999 (Development and testing of *Streptococcus pneumoniae* conjugate vaccines; Clin. Microbiol. Infect. 5:4S17-4S28).*
Wizemann et al. 2001 (Use of a whole genome approaches to identifying vaccine molecules affording protection against *Streptococcus pneumoniae* infection; Infection and Immunity, 69:1593-1598).*
Allstetter et al. 2004 ("Scientists learn how adjuvants make vaccines effective." Medical News Today. MediLexicon, Intl. Jun. 18, 2004).*
Hogenesch et al. 2011 (Formulation of a killed whole cell pneumococcus vaccine—effect of aluminum adjuvants on the antibody and IL-17 response; Journal of Immune Based Therapies and Vaccines; 9(5):1-10).*

(Continued)

*Primary Examiner* — Gary Nickol
*Assistant Examiner* — Mary Lyons
(74) *Attorney, Agent, or Firm* — Choate, Hall & Stewart LLP

(57) ABSTRACT

*Streptococcus pneumoniae* is a major health concern, especially in very young, elderly, or immunocompromised patients. The present disclosure provides, inter alia, certain highly effective vaccines and pharmaceutical compositions in *Streptococcus pneumoniae*. The antigens may be used therapeutically or prophylactically.

29 Claims, 19 Drawing Sheets

(56) References Cited

FOREIGN PATENT DOCUMENTS

| | | |
|---|---|---|
| EP | 1 572 868 | 9/2005 |
| EP | 1 630 230 A2 | 3/2006 |
| EP | 1 185 297 B1 | 5/2006 |
| EP | 1 855 717 | 11/2007 |
| EP | 2 275 128 A2 | 1/2011 |
| EP | 2 278 008 A2 | 1/2011 |
| EP | 2 311 987 A1 | 4/2011 |
| WO | WO 97/37026 | 10/1997 |
| WO | WO-9737026 A1 | 10/1997 |
| WO | WO 98/18930 | 5/1998 |
| WO | WO 98/18931 | 5/1998 |
| WO | WO 98/50554 | 11/1998 |
| WO | WO 98/59071 | 12/1998 |
| WO | WO 00/06738 | 2/2000 |
| WO | WO-00/39299 A2 | 7/2000 |
| WO | WO 02/077021 A2 | 10/2002 |
| WO | WO 02/083855 A2 | 10/2002 |
| WO | WO 03/082183 A2 | 10/2003 |
| WO | WO 2004/018646 A2 | 3/2004 |
| WO | WO 2004/020609 A2 | 3/2004 |
| WO | WO 2004/092209 A3 | 10/2004 |
| WO | WO 2005/014630 A2 | 2/2005 |
| WO | WO-2006069200 A2 | 6/2006 |
| WO | WO 2006/084467 A1 | 8/2006 |
| WO | WO 2007/106407 A2 | 9/2007 |
| WO | WO 2008/081014 A2 | 7/2008 |
| WO | WO-2008119358 A2 | 10/2008 |
| WO | WO 2008/146164 A2 | 12/2008 |
| WO | WO 2009/011971 A2 | 1/2009 |
| WO | WO-2009/016515 A2 | 2/2009 |
| WO | WO 2009/033742 A2 | 3/2009 |
| WO | WO-2010064243 A1 | 6/2010 |
| WO | WO-2010150242 A2 | 12/2010 |
| WO | WO 2011/008548 A1 | 1/2011 |
| WO | WO 2011/064781 A1 | 6/2011 |
| WO | WO 2011/067758 A2 | 6/2011 |
| WO | WO-2011128892 A2 | 10/2011 |
| WO | WO-2011141968 A1 | 11/2011 |

OTHER PUBLICATIONS

Greenspan et al. 1999 (Defining epitopes: It's not as easy as it seems; Nature Biotechnology, 17:936-937).*

Li, Y. et al., Distinct Effects on Diversifying Selection by Two Mechanisms of Immunity against *Streptococcus pneumoniae*, PLOS Pathogens, 8(11): e1002989 (2012).

Marrack, P., How do white blood cells recognize invaders?, Scientific American, 1-3 (May 18, 1988).

Moffitt, K.L. et al., T17-Based Vaccine Design for Prevention of Colonization, Cell Host & Microbe, 9(2): 158-165 (2011).

Unanue, E. R. et al., Antigen presentation, The FASEB Journal, 3: 2496-2502 (1989).

Database UniParc, F5MIE7, retrieved from internet May 28, 2013 (Jul. 27, 2011).

Database UniParc, F9HBT0, retrieved from internet May 28, 2013 (Oct. 19, 2011).

Database UniParc, F9PYR1, retrieved from internet May 28, 2013 (Oct. 19, 2011).

Database UniParc, G6J1F1, retrieved from internet May 28, 2013 (Jan. 25, 2012).

Database UniParc, G6KAH8, retrieved from internet May 28, 2013 (Jan. 25, 2012).

Database UniParc, G6U2X1, retrieved from internet May 28, 2013 (Jan. 25, 2012).

Database UniParc, G6VVK1, retrieved from internet May 28, 2013 (Jan. 25, 2012).

Database UniprotKB, Lipidation, retrieved from internet May 28, 2013 (Feb. 17, 2011).

Grubaugh et al., Proteins as T Cell Antigens: Methods for High-Throughput Identifications, Vaccine (2013).

International Preliminary Report on Patentability for PCT/US12/22127, issued Jul. 31, 2013, 5 pages.

International Preliminary Report on Patentability for PCT/US12/22128, issued Jul. 31, 2013, 6 pages.

International Search Report for PCT/US12/22127, mailed May 15 2012, 4 pages.

Written Opinion for PCT/US12/22127, mailed May 15 2012, 7 pages.

Written Opinion for PCT/US12/22128, mailed May 21, 2012, 8 pages.

Croucher et al., Role of Conjucative Elements in the Evolution of the Multidrug-Resistant Pandemic Clone *Streptococcus pneumoniae*$^{Spain23F}$ ST81. J Bacteriol.; 191(5): 1480-1489 (2009).

Ding et al., "Genome evolution driven by host adaptations results in a more virulent and antimicrobial-resistant *Streptococcus pneumoniae* serotype 14." BMC Genomics; 13;10: 158 (2009).

Dopazo et al., "Annotated Draft Genomic Sequence from a *Streptococcus pneumoniae* Type 19F Clinical Isolate." Microb. Drug Resist.; 7(2): 99-125 (2001).

Douce et al., "Mutants of *Escherichia coli* heat-labile toxin lacking ADP-ribosyltransferase activity act as nontoxic, mucosal adjuvants." Proc. Nat'l Acad. Sci; 92: 1644-1648 (1995).

Douce et al., "Genetically Detoxified Mutants of Heat-Labile Toxin from *Escherichia coli* Are Able to Act as Oral Adjuvants." Infection and Immunity; 67(9): 4400-6 (1999).

Evans et al., "Enhancement of antigen-specific immunity via the TLR4 ligands MPL™ adjuvant and Ribi.529." Expert Rev. Vaccines; 2(2): 219-229 (2003).

Giefing et al., "Discovery of a novel class of highly conserved vaccine antigens using genomic scale antigenic fingerprinting of pneumococcus with human antibodies." The Journal of Experimental Medicine; 205(1): 117-131 (2008).

Giuliani et al., "Mucosal Adjuvanticity and Immunogenicity of LTR72, a Novel Mutant of *Escherichia coli* Heat-liable Enterotoxin with Partial Knockout of ADP-ribosyltransferase Activity." J. Exp. Med.; 187(7): 1123-32 (1998).

Hoskins et al., "Genome of the Bacertium *Streptococcus pneumoniae* Strain R6." J Bacteriol.; 183(19); 5709-5717 (2001).

Huse et al., "Generation of a Large Combinatorial Library of the Immunoglobulin Repertoire in Phage Lambda." Science; 246: 1275-1281 (1989).

International Search Report for PCT/US12/22128, mailed May 21, 2012.

Ishizaka et al., "E6020: a synthetic Toll-like receptor 4 agonist as a vaccine adjuvant." Expert Review of Vaccines; 6(5):773-84 (2007).

Lanie et al., "Genome Sequence of Avery's Virulent Serotype 2 Strain D39 of *Streptococcus pneumoniae* and Comparison with That of Unencapsulated Laboratory Strain R6." J Bacteriol.; 189(1): 38-51 (2007).

Lu et al., "Interleukin-17A Mediates Acquired Immunity to Pneumococcal Colonization." PLoS Pathogens; 4(9): 1-11 (2008).

Lu et al., "Protection against Pneumococcal Colonization and Fatal Pneumonia by a Trivalent Conjugate of a Fusion Protein with the Cell Wall Polysaccharide." Infection and Immunity; 77(5): 2076-83 (2009).

Singh et al., "Advances in Vaccine Adjuvants for Infectious Diseases." Current HIV Research; 1(3): 309-20 (2003).

Tedder et al., "Isolation and Generation of Human Dendritic Cells." Current Protocols in Immunology Supp.; Supplement 23: 7.32.1-7.32.16 (1997).

Tettelin et al., "Complete Genome Sequence of a Virulent Isolate of *Streptococcus Pneumoniae*." Science; 293(5529): 498-506 (2001).

Williams et al., "Innate Imprinting by the Modified Heat-Labile Toxin of *Escherichia coli* (LTK63) Provides Generic Protection against Lung Infectious Disease." The Journal of Immunology; 173: 7435-7443 (2004).

Wizemann et al., "Use of a Whole Genome Approach to Identify Vaccine Molecules Affording Protection against *Streptococcus Pneumoniae* Infection." Infection and Immunity; 69(3): 1593-1598 (2001).

Wu et al., "Hsp70-Like Protein 1 Fusion Protein Enhances Induction of Carcinoembryonic Antigen-Specific $CD8^+CTL$ Response by Dendritic Cell Vaccine." Cancer Res; 65(11): 4947-4954 (2005).

* cited by examiner

*S. pneumoniae* Aspiration Challenge: Summary of Studies

| | Sepsis 1 | Sepsis 2 | Sepsis 3 | Sepsis 4 | PT1^ | PT2* |
|---|---|---|---|---|---|---|
| alum or NRS | 20% | 10% | 30% | 20% | 0% | 20% |
| 0148 | 44% | 10% | | | 10% | |
| 1912 | | 70% | | 20% | | |
| 2108 | | | | | 30% | |
| PdT | | 50% | | 20% | | |
| PspA | | | | | 10% | 70% |
| 0148 + 1912 | | 40% | 40% | | | |
| 0148 + 2108 | | | | | 20% | |
| 0148 + PdT | 70% | 17% | 25% | | | |
| 0148 + PspA | | | | | 30% | 70% |
| 1912 + PdT | | | | 40% | | |
| 2108 + PspA | | | | | 67% | |
| 0148 + PdT + 0641N | 90% | | | | | |
| 0148 + PdT + 1912 | | 60% | 60% | | | |
| 0148 + 2108 + PspA | | | | | 50% | 70% |
| WCB | 70% | 100% | 100% | 100% | 90% | 90% |

* 10ug protein dose
* PspA - purified IgG
^ PspA - ascites

Figure 19

```
                            SEQUENCE LISTING

<160> NUMBER OF SEQ IDS: 310

<210> SEQ ID NO 1
<211> LENGTH: 165
<212> TYPE: PRT
<213> ORGANISM: Streptococcus pneumoniae

<400> SEQUENCE: 1

Met Ser Tyr Phe Glu Gln Phe Met Gln Ala Asn Gln Ala Tyr Val Ala
1               5                  10                  15

Leu His Gly Gln Leu Asn Leu Pro Leu Lys Pro Lys Thr Arg Val Ala
            20                  25                  30

Ile Val Thr Cys Met Asp Ser Arg Leu His Val Ala Gln Ala Leu Gly
        35                  40                  45
```

```
Leu Ala Leu Gly Asp Ala His Ile Leu Arg Asn Ala Gly Gly Arg Val
 50                  55                  60

Thr Glu Asp Met Ile Arg Ser Leu Val Ile Ser Gln Gln Gln Met Gly
 65                  70                  75                  80

Thr Arg Glu Ile Val Val Leu His His Thr Asp Cys Gly Ala Gln Thr
                     85                  90                  95

Phe Glu Asn Glu Pro Phe Gln Glu Tyr Leu Lys Glu Leu Gly Val
                100                 105                 110

Asp Val Ser Asp Gln Asp Phe Leu Pro Phe Gln Asp Ile Glu Glu Ser
                115                 120                 125

Val Arg Glu Asp Met Gln Leu Leu Ile Glu Ser Pro Leu Ile Pro Asp
130                 135                 140

Asp Val Ile Ile Ser Gly Ala Ile Tyr Asn Val Asp Thr Gly Ser Met
145                 150                 155                 160

Thr Val Val Glu Leu
                165

<210> SEQ ID NO 2
<211> LENGTH: 274
<212> TYPE: PRT
<213> ORGANISM: Streptococcus pneumoniae

<400> SEQUENCE: 2

Met Asn Gln Ser Tyr Phe Tyr Leu Lys Met Lys Glu His Lys Leu Lys
  1               5                  10                  15

Val Pro Tyr Thr Gly Lys Glu Arg Arg Val Arg Ile Leu Leu Pro Lys
                 20                  25                  30

Asp Tyr Glu Lys Asp Thr Asp Arg Ser Tyr Pro Val Val Tyr Phe His
                 35                  40                  45

Asp Gly Gln Asn Val Phe Asn Ser Lys Glu Ser Phe Ile Gly His Ser
             50                  55                  60

Trp Lys Ile Ile Pro Ala Ile Lys Arg Asn Pro Asp Ile Ser Arg Met
 65                  70                  75                  80

Ile Val Val Ala Ile Asp Asn Asp Gly Met Gly Arg Met Asn Glu Tyr
                 85                  90                  95

Ala Ala Trp Lys Phe Gln Glu Ser Pro Ile Pro Gly Gln Gln Phe Gly
                100                 105                 110

Gly Lys Gly Val Glu Tyr Ala Glu Phe Val Met Glu Val Val Lys Pro
                115                 120                 125

Phe Ile Asp Glu Thr Tyr Arg Thr Lys Ala Asp Cys Gln His Thr Ala
130                 135                 140

Met Ile Gly Ser Ser Leu Gly Gly Asn Ile Thr Gln Phe Ile Gly Leu
145                 150                 155                 160

Glu Tyr Gln Asp Gln Ile Gly Cys Leu Gly Val Phe Ser Ser Ala Asn
                165                 170                 175

Trp Leu His Gln Glu Ala Phe Asn Arg Tyr Phe Glu Cys Gln Lys Leu
                180                 185                 190

Ser Pro Asp Gln Arg Ile Phe Ile Tyr Val Gly Thr Glu Glu Ala Asp
                195                 200                 205

Asp Thr Asp Lys Thr Leu Met Asp Gly Asn Ile Lys Gln Ala Tyr Ile
210                 215                 220

Asp Ser Ser Leu Cys Tyr Tyr His Asp Leu Ile Ala Gly Gly Val His
225                 230                 235                 240

Leu Asp Asn Leu Val Leu Lys Val Gln Ser Gly Ala Ile His Ser Glu
                245                 250                 255
```

```
Ile Pro Trp Ser Glu Asn Leu Pro Asp Cys Leu Arg Phe Phe Ala Glu
            260                 265                 270

Lys Trp

<210> SEQ ID NO 3
<211> LENGTH: 130
<212> TYPE: PRT
<213> ORGANISM: Streptococcus pneumoniae

<400> SEQUENCE: 3

Met Asn Gln Ser Tyr Phe Tyr Leu Lys Met Lys Glu His Lys Leu Lys
1               5                   10                  15

Val Pro Tyr Thr Gly Lys Glu Arg Arg Val Arg Ile Leu Leu Pro Lys
            20                  25                  30

Asp Tyr Glu Lys Asp Thr Asp Arg Ser Tyr Pro Val Val Tyr Phe His
        35                  40                  45

Asp Gly Gln Asn Val Phe Asn Ser Lys Glu Ser Phe Ile Gly His Ser
    50                  55                  60

Trp Lys Ile Ile Pro Ala Ile Lys Arg Asn Pro Asp Ile Ser Arg Met
65                  70                  75                  80

Ile Val Val Ala Ile Asp Asn Asp Gly Met Gly Arg Met Asn Glu Tyr
                85                  90                  95

Ala Ala Trp Lys Phe Gln Glu Ser Pro Ile Pro Gly Gln Gln Phe Gly
            100                 105                 110

Gly Lys Gly Val Glu Tyr Ala Glu Phe Val Met Glu Val Val Lys Pro
        115                 120                 125

Phe Ile
    130

<210> SEQ ID NO 4
<211> LENGTH: 299
<212> TYPE: PRT
<213> ORGANISM: Streptococcus pneumoniae

<400> SEQUENCE: 4

Met Ser Ser Lys Phe Met Lys Ser Ala Ala Val Leu Gly Thr Ala Thr
1               5                   10                  15

Leu Ala Ser Leu Leu Leu Val Ala Cys Met Asn Gln Ser Tyr Phe Tyr
            20                  25                  30

Leu Lys Met Lys Glu His Lys Leu Lys Val Pro Tyr Thr Gly Lys Glu
        35                  40                  45

Arg Arg Val Arg Ile Leu Leu Pro Lys Asp Tyr Glu Lys Asp Thr Asp
    50                  55                  60

Arg Ser Tyr Pro Val Val Tyr Phe His Asp Gly Gln Asn Val Phe Asn
65                  70                  75                  80

Ser Lys Glu Ser Phe Ile Gly His Ser Trp Lys Ile Ile Pro Ala Ile
                85                  90                  95

Lys Arg Asn Pro Asp Ile Ser Arg Met Ile Val Val Ala Ile Asp Asn
            100                 105                 110

Asp Gly Met Gly Arg Met Asn Glu Tyr Ala Ala Trp Lys Phe Gln Glu
        115                 120                 125

Ser Pro Ile Pro Gly Gln Gln Phe Gly Gly Lys Gly Val Glu Tyr Ala
    130                 135                 140

Glu Phe Val Met Glu Val Val Lys Pro Phe Ile Asp Glu Thr Tyr Arg
145                 150                 155                 160
```

```
Thr Lys Ala Asp Cys Gln His Thr Ala Met Ile Gly Ser Ser Leu Gly
                165                 170                 175
Gly Asn Ile Thr Gln Phe Ile Gly Leu Glu Tyr Gln Asp Gln Ile Gly
            180                 185                 190
Cys Leu Gly Val Phe Ser Ser Ala Asn Trp Leu His Gln Glu Ala Phe
        195                 200                 205
Asn Arg Tyr Phe Glu Cys Gln Lys Leu Ser Pro Asp Gln Arg Ile Phe
    210                 215                 220
Ile Tyr Val Gly Thr Glu Glu Ala Asp Asp Thr Asp Lys Thr Leu Met
225                 230                 235                 240
Asp Gly Asn Ile Lys Gln Ala Tyr Ile Asp Ser Ser Leu Cys Tyr Tyr
                245                 250                 255
His Asp Leu Ile Ala Gly Gly Val His Leu Asp Asn Leu Val Leu Lys
            260                 265                 270
Val Gln Ser Gly Ala Ile His Ser Glu Ile Pro Trp Ser Glu Asn Leu
        275                 280                 285
Pro Asp Cys Leu Arg Phe Phe Ala Glu Lys Trp
    290                 295
```

<210> SEQ ID NO 5
<211> LENGTH: 155
<212> TYPE: PRT
<213> ORGANISM: Streptococcus pneumoniae

<400> SEQUENCE: 5

```
Met Ser Ser Lys Phe Met Lys Ser Ala Ala Val Leu Gly Thr Ala Thr
1               5                   10                  15
Leu Ala Ser Leu Leu Val Ala Cys Met Asn Gln Ser Tyr Phe Tyr
                20                  25                  30
Leu Lys Met Lys Glu His Lys Leu Lys Val Pro Tyr Thr Gly Lys Glu
            35                  40                  45
Arg Arg Val Arg Ile Leu Leu Pro Lys Asp Tyr Glu Lys Asp Thr Asp
        50                  55                  60
Arg Ser Tyr Pro Val Val Tyr Phe His Asp Gly Gln Asn Val Phe Asn
65                  70                  75                  80
Ser Lys Glu Ser Phe Ile Gly His Ser Trp Lys Ile Ile Pro Ala Ile
                85                  90                  95
Lys Arg Asn Pro Asp Ile Ser Arg Met Ile Val Val Ala Ile Asp Asn
            100                 105                 110
Asp Gly Met Gly Arg Met Asn Glu Tyr Ala Ala Trp Lys Phe Gln Glu
        115                 120                 125
Ser Pro Ile Pro Gly Gln Gln Phe Gly Gly Lys Gly Val Glu Tyr Ala
    130                 135                 140
Glu Phe Val Met Glu Val Val Lys Pro Phe Ile
145                 150                 155
```

<210> SEQ ID NO 6
<211> LENGTH: 254
<212> TYPE: PRT
<213> ORGANISM: Streptococcus pneumoniae

<400> SEQUENCE: 6

```
Met Cys Ser Gly Gly Ala Lys Lys Glu Gly Glu Ala Ala Ser Lys Lys
1               5                   10                  15
Glu Ile Ile Val Ala Thr Asn Gly Ser Pro Lys Pro Phe Ile Tyr Glu
                20                  25                  30
```

```
Glu Asn Gly Glu Leu Thr Gly Tyr Glu Ile Glu Val Arg Ala Ile
             35                  40                  45

Phe Lys Asp Ser Asp Lys Tyr Asp Val Lys Phe Glu Lys Thr Glu Trp
 50                  55                  60

Ser Gly Val Phe Ala Gly Leu Asp Ala Asp Arg Tyr Asn Met Ala Val
 65                  70                  75                  80

Asn Asn Leu Ser Tyr Thr Lys Glu Arg Ala Glu Lys Tyr Leu Tyr Ala
                 85                  90                  95

Ala Pro Ile Ala Gln Asn Pro Asn Val Leu Val Lys Lys Asp Asp
                100                 105                 110

Ser Ser Ile Lys Ser Leu Asp Asp Ile Gly Gly Lys Ser Thr Glu Val
             115                 120                 125

Val Gln Ala Thr Thr Ser Ala Lys Gln Leu Glu Ala Tyr Asn Ala Glu
130                 135                 140

His Thr Asp Asn Pro Thr Ile Leu Asn Tyr Thr Lys Ala Asp Phe Gln
145                 150                 155                 160

Gln Ile Met Val Arg Leu Ser Asp Gly Gln Phe Asp Tyr Lys Ile Phe
                165                 170                 175

Asp Lys Ile Gly Val Glu Thr Val Ile Lys Asn Gln Gly Leu Asp Asn
            180                 185                 190

Leu Lys Val Ile Glu Leu Pro Ser Asp Gln Pro Tyr Val Tyr Pro
            195                 200                 205

Leu Leu Ala Gln Gly Gln Asp Glu Leu Lys Ser Phe Val Asp Lys Arg
210                 215                 220

Ile Lys Glu Leu Tyr Lys Asp Gly Thr Leu Lys Leu Ser Lys Gln
225                 230                 235                 240

Phe Phe Gly Asp Thr Tyr Leu Pro Ala Glu Ala Asp Ile Lys
                245                 250

<210> SEQ ID NO 7
<211> LENGTH: 276
<212> TYPE: PRT
<213> ORGANISM: Streptococcus pneumoniae

<400> SEQUENCE: 7

Met Lys Lys Ile Val Lys Tyr Ser Ser Leu Ala Ala Leu Ala Leu Val
 1               5                  10                  15

Ala Ala Gly Val Leu Ala Ala Cys Ser Gly Gly Ala Lys Lys Glu Gly
                 20                  25                  30

Glu Ala Ala Ser Lys Lys Glu Ile Ile Val Ala Thr Asn Gly Ser Pro
             35                  40                  45

Lys Pro Phe Ile Tyr Glu Glu Asn Gly Glu Leu Thr Gly Tyr Glu Ile
 50                  55                  60

Glu Val Val Arg Ala Ile Phe Lys Asp Ser Lys Tyr Asp Val Lys
 65                  70                  75                  80

Phe Glu Lys Thr Glu Trp Ser Gly Val Phe Ala Gly Leu Asp Ala Asp
                 85                  90                  95

Arg Tyr Asn Met Ala Val Asn Asn Leu Ser Tyr Thr Lys Glu Arg Ala
                100                 105                 110

Glu Lys Tyr Leu Tyr Ala Ala Pro Ile Ala Gln Asn Pro Asn Val Leu
            115                 120                 125

Val Val Lys Lys Asp Asp Ser Ser Ile Lys Ser Leu Asp Asp Ile Gly
130                 135                 140

Gly Lys Ser Thr Glu Val Val Gln Ala Thr Thr Ser Ala Lys Gln Leu
145                 150                 155                 160
```

```
Glu Ala Tyr Asn Ala Glu His Thr Asp Asn Pro Thr Ile Leu Asn Tyr
                165                 170                 175

Thr Lys Ala Asp Phe Gln Gln Ile Met Val Arg Leu Ser Asp Gly Gln
            180                 185                 190

Phe Asp Tyr Lys Ile Phe Asp Lys Ile Gly Val Glu Thr Val Ile Lys
        195                 200                 205

Asn Gln Gly Leu Asp Asn Leu Lys Val Ile Glu Leu Pro Ser Asp Gln
    210                 215                 220

Gln Pro Tyr Val Tyr Pro Leu Leu Ala Gln Gly Gln Asp Glu Leu Lys
225                 230                 235                 240

Ser Phe Val Asp Lys Arg Ile Lys Glu Leu Tyr Lys Asp Gly Thr Leu
                245                 250                 255

Glu Lys Leu Ser Lys Gln Phe Phe Gly Asp Thr Tyr Leu Pro Ala Glu
            260                 265                 270

Ala Asp Ile Lys
        275

<210> SEQ ID NO 8
<211> LENGTH: 586
<212> TYPE: PRT
<213> ORGANISM: Streptococcus pneumoniae

<400> SEQUENCE: 8

Met Val Asp Lys Gln Val Ile Glu Glu Ile Lys Asn Asn Ala Asn Ile
1               5                   10                  15

Val Glu Val Ile Gly Asp Val Ile Ser Leu Gln Lys Ala Gly Arg Asn
            20                  25                  30

Tyr Leu Gly Leu Cys Pro Phe His Gly Glu Lys Thr Pro Ser Phe Asn
        35                  40                  45

Val Val Glu Asp Lys Gln Phe Tyr His Cys Phe Gly Cys Gly Arg Ser
    50                  55                  60

Gly Asp Val Phe Lys Phe Ile Glu Glu Tyr Gln Gly Val Pro Phe Ile
65                  70                  75                  80

Glu Ala Val Gln Ile Leu Gly Gln Arg Val Gly Ile Glu Val Glu Lys
                85                  90                  95

Pro Leu Tyr Ser Glu Gln Lys Ser Ala Ser Pro His Gln Ala Leu Tyr
            100                 105                 110

Asp Met His Glu Asp Ala Ala Lys Phe Tyr His Ala Ile Leu Met Thr
        115                 120                 125

Thr Thr Met Gly Glu Glu Ala Arg Asn Tyr Leu Tyr Gln Arg Gly Leu
    130                 135                 140

Thr Asp Glu Val Leu Lys His Phe Trp Ile Gly Leu Ala Pro Pro Glu
145                 150                 155                 160

Arg Asn Tyr Leu Tyr Gln Arg Leu Ser Asp Gln Tyr Arg Glu Glu Asp
                165                 170                 175

Leu Leu Asp Ser Gly Leu Phe Tyr Leu Ser Asp Ala Asn Gln Phe Val
            180                 185                 190

Asp Thr Phe His Asn Arg Ile Met Phe Pro Leu Thr Asn Asp Gln Gly
        195                 200                 205

Lys Val Ile Ala Phe Ser Gly Arg Ile Trp Gln Lys Thr Asp Ser Gln
    210                 215                 220

Thr Ser Lys Tyr Lys Asn Ser Arg Ser Thr Ala Ile Phe Asn Lys Ser
225                 230                 235                 240

Tyr Glu Leu Tyr His Met Asp Arg Ala Lys Arg Ser Ser Gly Lys Ala
```

```
                245                 250                 255
Ser Glu Ile Tyr Leu Met Glu Gly Phe Met Asp Val Ile Ala Ala Tyr
            260                 265                 270

Arg Ala Gly Ile Glu Asn Ala Val Ala Ser Met Gly Thr Ala Leu Ser
        275                 280                 285

Arg Glu His Val Glu His Leu Lys Arg Leu Thr Lys Lys Leu Val Leu
    290                 295                 300

Val Tyr Asp Gly Asp Lys Ala Gly Gln Ala Ala Thr Leu Lys Ala Leu
305                 310                 315                 320

Asp Glu Ile Gly Asp Met Pro Val Gln Ile Val Ser Met Pro Asp Asn
            325                 330                 335

Leu Asp Pro Asp Glu Tyr Leu Gln Lys Asn Gly Pro Glu Asp Leu Ala
        340                 345                 350

Tyr Leu Leu Thr Lys Thr Arg Ile Ser Pro Ile Glu Phe Tyr Ile His
    355                 360                 365

Gln Tyr Lys Pro Glu Asn Ser Glu Asn Leu Gln Ala Gln Ile Glu Phe
370                 375                 380

Leu Glu Lys Ile Ala Pro Leu Ile Val Gln Glu Lys Ser Ile Ala Ala
385                 390                 395                 400

Gln Asn Ser Tyr Ile His Ile Leu Ala Asp Ser Leu Ala Ser Phe Asp
            405                 410                 415

Tyr Thr Gln Ile Glu Gln Ile Val Asn Glu Ser Arg Gly Val Gln Arg
        420                 425                 430

Gln Asn Arg Met Glu Gly Ile Ser Arg Pro Thr Pro Ile Thr Met Pro
    435                 440                 445

Val Thr Lys Gln Leu Ser Ala Ile Met Arg Ala Glu Ala His Leu Leu
    450                 455                 460

Tyr Arg Met Met Glu Ser Pro Leu Val Leu Asn Asp Tyr Arg Leu Arg
465                 470                 475                 480

Glu Asp Phe Ala Phe Ala Thr Pro Glu Phe Gln Val Leu Tyr Asp Leu
            485                 490                 495

Leu Gly Gln Tyr Gly Asn Leu Pro Pro Glu Val Leu Ala Glu Gln Thr
        500                 505                 510

Glu Glu Val Glu Arg Ala Trp Tyr Gln Val Leu Ala Gln Asp Leu Pro
    515                 520                 525

Ala Glu Ile Ser Pro Gln Glu Leu Ser Glu Val Glu Met Thr Arg Asn
    530                 535                 540

Lys Ala Leu Leu Asn Gln Asp Asn Met Arg Ile Lys Lys Lys Val Gln
545                 550                 555                 560

Glu Ala Ser His Val Gly Asp Thr Asp Thr Ala Leu Glu Glu Leu Glu
            565                 570                 575

Arg Leu Ile Ser Gln Lys Arg Arg Met Glu
        580                 585

<210> SEQ ID NO 9
<211> LENGTH: 423
<212> TYPE: PRT
<213> ORGANISM: Streptococcus pneumoniae

<400> SEQUENCE: 9

Met Ser Ser Lys Phe Met Lys Ser Ala Ala Val Leu Gly Thr Ala Thr
1               5                   10                  15

Leu Ala Ser Leu Leu Leu Val Ala Cys Gly Ser Lys Thr Ala Asp Lys
            20                  25                  30
```

```
Pro Ala Asp Ser Gly Ser Ser Glu Val Lys Glu Leu Thr Val Tyr Val
             35                  40                  45

Asp Glu Gly Tyr Lys Ser Tyr Ile Glu Val Ala Lys Ala Tyr Glu
 50                  55                  60

Lys Glu Ala Gly Val Lys Val Thr Leu Lys Thr Gly Asp Ala Leu Gly
 65                  70                  75                  80

Gly Leu Asp Lys Leu Ser Leu Asp Asn Gln Ser Gly Asn Val Pro Asp
                 85                  90                  95

Val Met Met Ala Pro Tyr Asp Arg Val Gly Ser Leu Gly Ser Asp Gly
                100                 105                 110

Gln Leu Ser Glu Val Lys Leu Ser Asp Gly Ala Lys Thr Asp Asp Thr
                115                 120                 125

Thr Lys Ser Leu Val Thr Ala Ala Asn Gly Lys Val Tyr Gly Ala Pro
        130                 135                 140

Ala Val Ile Glu Ser Leu Val Met Tyr Tyr Asn Lys Asp Leu Val Lys
145                 150                 155                 160

Asp Ala Pro Lys Thr Phe Ala Asp Leu Glu Asn Leu Ala Lys Asp Ser
                165                 170                 175

Lys Tyr Ala Phe Ala Gly Glu Asp Gly Lys Thr Thr Ala Phe Leu Ala
                180                 185                 190

Asp Trp Thr Asn Phe Tyr Tyr Thr Tyr Gly Leu Leu Ala Gly Asn Gly
        195                 200                 205

Ala Tyr Val Phe Gly Gln Asn Gly Lys Asp Ala Lys Asp Ile Gly Leu
        210                 215                 220

Ala Asn Asp Gly Ser Ile Val Gly Ile Asn Tyr Ala Lys Ser Trp Tyr
225                 230                 235                 240

Glu Lys Trp Pro Lys Gly Met Gln Asp Thr Glu Gly Ala Gly Asn Leu
                245                 250                 255

Ile Gln Thr Gln Phe Gln Glu Gly Lys Thr Ala Ala Ile Ile Asp Gly
                260                 265                 270

Pro Trp Lys Ala Gln Ala Phe Lys Asp Ala Lys Val Asn Tyr Gly Val
        275                 280                 285

Ala Thr Ile Pro Thr Leu Pro Asn Gly Lys Glu Tyr Ala Ala Phe Gly
        290                 295                 300

Gly Gly Lys Ala Trp Val Ile Pro Gln Ala Val Lys Asn Leu Glu Ala
305                 310                 315                 320

Ser Gln Lys Phe Val Asp Phe Leu Val Ala Thr Glu Gln Lys Val
                325                 330                 335

Leu Tyr Asp Lys Thr Asn Glu Ile Pro Ala Asn Thr Glu Ala Arg Ser
                340                 345                 350

Tyr Ala Glu Gly Lys Asn Asp Glu Leu Thr Thr Ala Val Ile Lys Gln
        355                 360                 365

Phe Lys Asn Thr Gln Pro Leu Pro Asn Ile Ser Gln Met Ser Ala Val
        370                 375                 380

Trp Asp Pro Ala Lys Asn Met Leu Phe Asp Ala Val Ser Gly Gln Lys
385                 390                 395                 400

Asp Ala Lys Thr Ala Ala Asn Asp Ala Val Thr Leu Ile Lys Glu Thr
                405                 410                 415

Ile Lys Gln Lys Phe Gly Glu
                420
```

<210> SEQ ID NO 10
<211> LENGTH: 400
<212> TYPE: PRT

<213> ORGANISM: Streptococcus pneumoniae

<400> SEQUENCE: 10

```
Met Cys Gly Ser Lys Thr Ala Asp Lys Pro Ala Asp Ser Gly Ser Ser
  1               5                  10                  15
Glu Val Lys Glu Leu Thr Val Tyr Val Asp Glu Gly Tyr Lys Ser Tyr
             20                  25                  30
Ile Glu Glu Val Ala Lys Ala Tyr Gly Lys Glu Ala Gly Val Lys Val
         35                  40                  45
Thr Leu Lys Thr Gly Asp Ala Leu Gly Gly Leu Asp Lys Leu Ser Leu
     50                  55                  60
Asp Asn Gln Ser Gly Asn Val Pro Asp Val Met Met Ala Pro Tyr Asp
 65                  70                  75                  80
Arg Val Gly Ser Leu Gly Ser Asp Gly Gln Leu Ser Glu Val Lys Leu
                 85                  90                  95
Ser Asp Gly Ala Lys Thr Asp Asp Thr Thr Lys Ser Leu Val Thr Ala
            100                 105                 110
Ala Asn Gly Lys Val Tyr Gly Ala Pro Ala Val Ile Glu Ser Leu Val
        115                 120                 125
Met Tyr Tyr Asn Lys Asp Leu Val Lys Asp Ala Pro Lys Thr Phe Ala
130                 135                 140
Asp Leu Glu Asn Leu Ala Lys Asp Ser Lys Tyr Ala Phe Ala Gly Glu
145                 150                 155                 160
Asp Gly Lys Thr Thr Ala Phe Leu Ala Asp Trp Thr Asn Phe Tyr Tyr
                165                 170                 175
Thr Tyr Gly Leu Leu Ala Gly Asn Gly Ala Tyr Val Phe Gly Gln Asn
            180                 185                 190
Gly Lys Asp Ala Lys Asp Ile Gly Leu Ala Asn Asp Gly Ser Ile Val
        195                 200                 205
Gly Ile Asn Tyr Ala Lys Ser Trp Tyr Glu Lys Trp Pro Lys Gly Met
    210                 215                 220
Gln Asp Thr Glu Gly Ala Gly Asn Leu Ile Gln Thr Gln Phe Gln Glu
225                 230                 235                 240
Gly Lys Thr Ala Ala Ile Ile Asp Gly Pro Trp Lys Ala Gln Ala Phe
                245                 250                 255
Lys Asp Ala Lys Val Asn Tyr Gly Val Ala Thr Ile Pro Thr Leu Pro
            260                 265                 270
Asn Gly Lys Glu Tyr Ala Ala Phe Gly Gly Gly Lys Ala Trp Val Ile
        275                 280                 285
Pro Gln Ala Val Lys Asn Leu Glu Ala Ser Gln Lys Phe Val Asp Phe
    290                 295                 300
Leu Val Ala Thr Glu Gln Gln Lys Val Leu Tyr Asp Lys Thr Asn Glu
305                 310                 315                 320
Ile Pro Ala Asn Thr Glu Ala Arg Ser Tyr Ala Glu Gly Lys Asn Asp
                325                 330                 335
Glu Leu Thr Thr Ala Val Ile Lys Gln Phe Lys Asn Thr Gln Pro Leu
            340                 345                 350
Pro Asn Ile Ser Gln Met Ser Ala Val Trp Asp Pro Ala Lys Asn Met
        355                 360                 365
Leu Phe Asp Ala Val Ser Gly Gln Lys Asp Ala Lys Thr Ala Ala Asn
    370                 375                 380
Asp Ala Val Thr Leu Ile Lys Glu Thr Ile Lys Gln Lys Phe Gly Glu
385                 390                 395                 400
```

```
<210> SEQ ID NO 11
<211> LENGTH: 648
<212> TYPE: PRT
<213> ORGANISM: Streptococcus pneumoniae

<400> SEQUENCE: 11

Met Ser Gly Thr Ser Met Ala Thr Pro Ile Val Ala Ser Thr Val
1               5                   10                  15

Leu Ile Arg Pro Lys Leu Lys Glu Met Leu Glu Arg Pro Val Leu Lys
            20                  25                  30

Asn Leu Lys Gly Asp Asp Lys Ile Asp Leu Thr Ser Leu Thr Lys Ile
            35                  40                  45

Ala Leu Gln Asn Thr Ala Arg Pro Met Met Asp Ala Thr Ser Trp Lys
50                  55                  60

Glu Lys Ser Gln Tyr Phe Ala Ser Pro Arg Gln Gln Gly Ala Gly Leu
65                  70                  75                  80

Ile Asn Val Ala Asn Ala Leu Arg Asn Glu Val Val Ala Thr Phe Lys
                85                  90                  95

Asn Thr Asp Ser Lys Gly Leu Val Asn Ser Tyr Gly Ser Ile Ser Leu
            100                 105                 110

Lys Glu Ile Lys Gly Asp Lys Lys Tyr Phe Thr Ile Lys Leu His Asn
            115                 120                 125

Thr Ser Asn Arg Pro Leu Thr Phe Lys Val Ser Ala Ser Ala Ile Thr
130                 135                 140

Thr Asp Ser Leu Thr Asp Arg Leu Lys Leu Asp Glu Thr Tyr Lys Asp
145                 150                 155                 160

Glu Lys Ser Pro Asp Gly Lys Gln Ile Val Pro Glu Ile His Pro Glu
                165                 170                 175

Lys Val Lys Gly Ala Asn Ile Thr Phe Glu His Asp Thr Phe Thr Ile
            180                 185                 190

Gly Ala Asn Ser Ser Phe Asp Leu Asn Ala Val Ile Asn Val Gly Glu
            195                 200                 205

Ala Lys Asn Lys Asn Lys Phe Val Glu Ser Phe Ile His Phe Glu Ser
210                 215                 220

Val Glu Glu Met Glu Ala Leu Asn Ser Asn Gly Lys Lys Ile Asn Phe
225                 230                 235                 240

Gln Pro Ser Leu Ser Met Pro Leu Met Gly Phe Ala Gly Asn Trp Asn
                245                 250                 255

His Glu Pro Ile Leu Asp Lys Trp Ala Trp Glu Glu Gly Ser Arg Ser
            260                 265                 270

Lys Thr Leu Gly Gly Tyr Asp Asp Gly Lys Pro Lys Ile Pro Gly
            275                 280                 285

Thr Leu Asn Lys Gly Ile Gly Gly Glu His Gly Ile Asp Lys Phe Asn
            290                 295                 300

Pro Ala Gly Val Ile Gln Asn Arg Lys Asp Lys Asn Thr Thr Ser Leu
305                 310                 315                 320

Asp Gln Asn Pro Glu Leu Phe Ala Phe Asn Asn Glu Gly Ile Asn Ala
                325                 330                 335

Pro Ser Ser Ser Gly Ser Lys Ile Ala Asn Ile Tyr Pro Leu Asp Ser
            340                 345                 350

Asn Gly Asn Pro Gln Asp Ala Gln Leu Glu Arg Gly Leu Thr Pro Ser
            355                 360                 365

Pro Leu Val Leu Arg Ser Ala Glu Glu Gly Leu Ile Ser Ile Val Asn
370                 375                 380
```

```
Thr Asn Lys Glu Gly Glu Asn Gln Arg Asp Leu Lys Val Ile Ser Arg
385                 390                 395                 400

Glu His Phe Ile Arg Gly Ile Leu Asn Ser Lys Ser Asn Asp Ala Lys
                405                 410                 415

Gly Ile Lys Ser Ser Lys Leu Lys Val Trp Gly Asp Leu Lys Trp Asp
            420                 425                 430

Gly Leu Ile Tyr Asn Pro Arg Gly Arg Glu Glu Asn Ala Pro Glu Ser
            435                 440                 445

Lys Asp Asn Gln Asp Pro Ala Thr Lys Ile Arg Gly Gln Phe Glu Pro
        450                 455                 460

Ile Ala Glu Gly Gln Tyr Phe Tyr Lys Phe Lys Tyr Arg Leu Thr Lys
465                 470                 475                 480

Asp Tyr Pro Trp Gln Val Ser Tyr Ile Pro Val Lys Ile Asp Asn Thr
                485                 490                 495

Ala Pro Lys Ile Val Ser Val Asp Phe Ser Asn Pro Glu Lys Ile Lys
            500                 505                 510

Leu Ile Thr Lys Asp Thr Tyr His Lys Val Lys Asp Gln Tyr Lys Asn
            515                 520                 525

Glu Thr Leu Phe Ala Arg Asp Gln Lys Glu His Pro Gly Lys Phe Asp
530                 535                 540

Glu Ile Ala Asn Glu Val Trp Tyr Ala Gly Ala Leu Val Asn Glu
545                 550                 555                 560

Asp Gly Glu Val Glu Lys Asn Leu Glu Val Thr Tyr Ala Gly Glu Gly
                565                 570                 575

Gln Gly Arg Asn Arg Lys Leu Asp Lys Asp Gly Asn Thr Ile Tyr Glu
                580                 585                 590

Ile Lys Gly Ala Gly Asp Leu Arg Gly Lys Ile Ile Glu Val Ile Ala
            595                 600                 605

Leu Asp Gly Ser Ser Asn Phe Thr Lys Ile His Arg Ile Lys Phe Ala
610                 615                 620

Asn Gln Ala Asp Glu Lys Gly Met Ile Ser Tyr Tyr Leu Val Asp Pro
625                 630                 635                 640

Asp Gln Asp Ser Ser Lys Tyr Gln
                645

<210> SEQ ID NO 12
<211> LENGTH: 2140
<212> TYPE: PRT
<213> ORGANISM: Streptococcus pneumoniae

<400> SEQUENCE: 12

Met Lys Lys Ser Thr Val Leu Ser Leu Thr Thr Ala Ala Val Ile Leu
1               5                   10                  15

Ala Ala Tyr Ala Pro Asn Glu Val Val Leu Ala Asp Thr Ser Ser Ser
                20                  25                  30

Glu Asp Ala Leu Asn Ile Ser Asp Lys Glu Lys Val Ala Glu Asn Lys
            35                  40                  45

Glu Lys His Glu Asn Ile His Ser Ala Met Glu Thr Ser Gln Asp Phe
        50                  55                  60

Lys Glu Lys Lys Thr Ala Val Ile Lys Glu Lys Val Val Ser Lys
65                  70                  75                  80

Asn Pro Val Ile Asp Asn Asn Thr Ser Asn Glu Glu Ala Lys Ile Lys
                85                  90                  95

Glu Glu Asn Ser Asn Lys Ser Gln Gly Asp Tyr Thr Asp Ser Phe Val
```

```
                    100                 105                 110
Asn Lys Asn Thr Glu Asn Pro Lys Lys Glu Asp Lys Val Val Tyr Ile
            115                 120                 125
Ala Glu Phe Lys Asp Lys Ser Gly Glu Lys Ala Ile Lys Glu Leu
            130                 135                 140
Ser Ser Leu Lys Asn Thr Lys Val Leu Tyr Thr Tyr Asp Arg Ile Phe
145                 150                 155                 160
Asn Gly Ser Ala Ile Glu Thr Thr Pro Asp Asn Leu Asp Lys Ile Lys
                165                 170                 175
Gln Ile Glu Gly Ile Ser Ser Val Arg Ala Gln Lys Val Gln Pro
            180                 185                 190
Met Met Asn His Ala Arg Lys Glu Ile Gly Val Glu Glu Ala Ile Asp
            195                 200                 205
Tyr Leu Lys Ser Ile Asn Ala Pro Phe Gly Lys Asn Phe Asp Gly Arg
            210                 215                 220
Gly Met Val Ile Ser Asn Ile Asp Thr Gly Thr Asp Tyr Arg His Lys
225                 230                 235                 240
Ala Met Arg Ile Asp Asp Ala Lys Ala Ser Met Arg Phe Lys Lys
                245                 250                 255
Glu Asp Leu Lys Gly Thr Asp Lys Asn Tyr Trp Leu Ser Asp Lys Ile
            260                 265                 270
Pro His Ala Phe Asn Tyr Tyr Asn Gly Gly Lys Ile Thr Val Glu Lys
            275                 280                 285
Tyr Asp Asp Gly Arg Asp Tyr Phe Asp Pro His Gly Met His Ile Ala
            290                 295                 300
Gly Ile Leu Ala Gly Asn Asp Thr Glu Gln Asp Ile Lys Asn Phe Asn
305                 310                 315                 320
Gly Ile Asp Gly Ile Ala Pro Asn Ala Gln Ile Phe Ser Tyr Lys Met
                325                 330                 335
Tyr Ser Asp Ala Gly Ser Gly Phe Ala Gly Asp Glu Thr Met Phe His
                340                 345                 350
Ala Ile Glu Asp Ser Ile Lys His Asn Val Asp Val Val Ser Val Ser
            355                 360                 365
Ser Gly Phe Thr Gly Thr Gly Leu Val Gly Glu Lys Tyr Trp Gln Ala
            370                 375                 380
Ile Arg Ala Leu Arg Lys Ala Gly Ile Pro Met Val Ala Thr Gly
385                 390                 395                 400
Asn Tyr Ala Thr Ser Ala Ser Ser Ser Trp Asp Leu Val Ala Asn
                405                 410                 415
Asn His Leu Lys Met Thr Asp Thr Gly Asn Val Thr Arg Thr Ala Ala
            420                 425                 430
His Glu Asp Ala Ile Ala Val Ala Ser Ala Lys Asn Gln Thr Val Glu
            435                 440                 445
Phe Asp Lys Val Asn Ile Gly Gly Glu Ser Phe Lys Tyr Arg Asn Ile
            450                 455                 460
Gly Ala Phe Phe Asp Lys Ser Lys Ile Thr Thr Asn Glu Asp Gly Thr
465                 470                 475                 480
Lys Ala Pro Ser Lys Leu Lys Phe Val Tyr Ile Gly Lys Gly Gln Asp
                485                 490                 495
Gln Asp Leu Ile Gly Leu Asp Leu Arg Gly Lys Ile Ala Val Met Asp
            500                 505                 510
Arg Ile Tyr Thr Lys Asp Leu Lys Asn Ala Phe Lys Lys Ala Met Asp
            515                 520                 525
```

```
Lys Gly Ala Arg Ala Ile Met Val Val Asn Thr Val Asn Tyr Tyr Asn
            530                 535                 540

Arg Asp Asn Trp Thr Glu Leu Pro Ala Met Gly Tyr Glu Ala Asp Glu
545                 550                 555                 560

Gly Thr Lys Ser Gln Val Phe Ser Ile Ser Gly Asp Asp Gly Val Lys
                565                 570                 575

Leu Trp Asn Met Ile Asn Pro Asp Lys Lys Thr Glu Val Lys Arg Asn
            580                 585                 590

Asn Lys Glu Asp Phe Lys Asp Lys Leu Glu Gln Tyr Tyr Pro Ile Asp
        595                 600                 605

Met Glu Ser Phe Asn Ser Asn Lys Pro Asn Val Gly Asp Glu Lys Glu
    610                 615                 620

Ile Asp Phe Lys Phe Ala Pro Asp Thr Asp Lys Glu Leu Tyr Lys Glu
625                 630                 635                 640

Asp Ile Ile Val Pro Ala Gly Ser Thr Ser Trp Gly Pro Arg Ile Asp
                645                 650                 655

Leu Leu Leu Lys Pro Asp Val Ser Ala Pro Gly Lys Asn Ile Lys Ser
            660                 665                 670

Thr Leu Asn Val Ile Asn Gly Lys Ser Thr Tyr Gly Tyr Met Ser Gly
        675                 680                 685

Thr Ser Met Ala Thr Pro Ile Val Ala Ala Ser Thr Val Leu Ile Arg
    690                 695                 700

Pro Lys Leu Lys Glu Met Leu Glu Arg Pro Val Leu Lys Asn Leu Lys
705                 710                 715                 720

Gly Asp Asp Lys Ile Asp Leu Thr Ser Leu Thr Lys Ile Ala Leu Gln
                725                 730                 735

Asn Thr Ala Arg Pro Met Met Asp Ala Thr Ser Trp Lys Glu Lys Ser
            740                 745                 750

Gln Tyr Phe Ala Ser Pro Arg Gln Gln Gly Ala Gly Leu Ile Asn Val
        755                 760                 765

Ala Asn Ala Leu Arg Asn Glu Val Val Ala Thr Phe Lys Asn Thr Asp
    770                 775                 780

Ser Lys Gly Leu Val Asn Ser Tyr Gly Ser Ile Ser Leu Lys Glu Ile
785                 790                 795                 800

Lys Gly Asp Lys Lys Tyr Phe Thr Ile Lys Leu His Asn Thr Ser Asn
                805                 810                 815

Arg Pro Leu Thr Phe Lys Val Ser Ala Ser Ala Ile Thr Thr Asp Ser
            820                 825                 830

Leu Thr Asp Arg Leu Lys Leu Asp Glu Thr Tyr Lys Asp Glu Lys Ser
        835                 840                 845

Pro Asp Gly Lys Gln Ile Val Pro Glu Ile His Pro Glu Lys Val Lys
    850                 855                 860

Gly Ala Asn Ile Thr Phe Glu His Asp Thr Phe Thr Ile Gly Ala Asn
865                 870                 875                 880

Ser Ser Phe Asp Leu Asn Ala Val Ile Asn Val Gly Glu Ala Lys Asn
                885                 890                 895

Lys Asn Lys Phe Val Glu Ser Phe Ile His Phe Glu Ser Val Glu Glu
            900                 905                 910

Met Glu Ala Leu Asn Ser Asn Gly Lys Lys Ile Asn Phe Gln Pro Ser
        915                 920                 925

Leu Ser Met Pro Leu Met Gly Phe Ala Gly Asn Trp Asn His Glu Pro
    930                 935                 940
```

```
Ile Leu Asp Lys Trp Ala Trp Glu Glu Gly Ser Arg Ser Lys Thr Leu
945                 950                 955                 960

Gly Gly Tyr Asp Asp Gly Lys Pro Lys Ile Pro Gly Thr Leu Asn
            965                 970                 975

Lys Gly Ile Gly Gly Glu His Gly Ile Asp Lys Phe Asn Pro Ala Gly
        980                 985                 990

Val Ile Gln Asn Arg Lys Asp Lys Asn Thr Thr Ser Leu Asp Gln Asn
        995                 1000                1005

Pro Glu Leu Phe Ala Phe Asn Asn Glu Gly Ile Asn Ala Pro Ser
    1010                1015                1020

Ser Ser Gly Ser Lys Ile Ala Asn Ile Tyr Pro Leu Asp Ser Asn
    1025                1030                1035

Gly Asn Pro Gln Asp Ala Gln Leu Glu Arg Gly Leu Thr Pro Ser
    1040                1045                1050

Pro Leu Val Leu Arg Ser Ala Glu Gly Leu Ile Ser Ile Val
    1055                1060                1065

Asn Thr Asn Lys Glu Gly Glu Asn Gln Arg Asp Leu Lys Val Ile
    1070                1075                1080

Ser Arg Glu His Phe Ile Arg Gly Ile Leu Asn Ser Lys Ser Asn
    1085                1090                1095

Asp Ala Lys Gly Ile Lys Ser Ser Lys Leu Lys Val Trp Gly Asp
    1100                1105                1110

Leu Lys Trp Asp Gly Leu Ile Tyr Asn Pro Arg Gly Arg Glu Glu
    1115                1120                1125

Asn Ala Pro Glu Ser Lys Asp Asn Gln Asp Pro Ala Thr Lys Ile
    1130                1135                1140

Arg Gly Gln Phe Glu Pro Ile Ala Glu Gly Gln Tyr Phe Tyr Lys
    1145                1150                1155

Phe Lys Tyr Arg Leu Thr Lys Asp Tyr Pro Trp Gln Val Ser Tyr
    1160                1165                1170

Ile Pro Val Lys Ile Asp Asn Thr Ala Pro Lys Ile Val Ser Val
    1175                1180                1185

Asp Phe Ser Asn Pro Glu Lys Ile Lys Leu Ile Thr Lys Asp Thr
    1190                1195                1200

Tyr His Lys Val Lys Asp Gln Tyr Lys Asn Glu Thr Leu Phe Ala
    1205                1210                1215

Arg Asp Gln Lys Glu His Pro Glu Lys Phe Asp Glu Ile Ala Asn
    1220                1225                1230

Glu Val Trp Tyr Ala Gly Ala Leu Val Asn Glu Asp Gly Glu
    1235                1240                1245

Val Glu Lys Asn Leu Glu Val Thr Tyr Ala Gly Glu Gly Gln Gly
    1250                1255                1260

Arg Asn Arg Lys Leu Asp Lys Asp Gly Asn Thr Ile Tyr Glu Ile
    1265                1270                1275

Lys Gly Ala Gly Asp Leu Arg Gly Lys Ile Ile Glu Val Ile Ala
    1280                1285                1290

Leu Asp Gly Ser Ser Asn Phe Thr Lys Ile His Arg Ile Lys Phe
    1295                1300                1305

Ala Asn Gln Ala Asp Glu Lys Gly Met Ile Ser Tyr Tyr Leu Val
    1310                1315                1320

Asp Pro Asp Gln Asp Ser Ser Lys Tyr Gln Lys Leu Gly Glu Ile
    1325                1330                1335

Ala Glu Ser Lys Phe Lys Asn Leu Gly Asn Gly Lys Glu Gly Ser
```

-continued

```
              1340                1345                1350
Leu Lys Lys Asp Thr Thr Gly Val Glu His His His Gln Glu Asn
    1355                1360                1365
Glu Glu Ser Ile Lys Glu Lys Ser Ser Phe Thr Ile Asp Arg Asn
    1370                1375                1380
Ile Ser Thr Ile Arg Asp Phe Glu Asn Lys Asp Leu Lys Lys Leu
    1385                1390                1395
Ile Lys Lys Phe Arg Glu Val Asp Asp Phe Thr Ser Glu Thr
    1400                1405                1410
Gly Lys Arg Met Glu Glu Tyr Asp Tyr Lys Tyr Asp Asp Lys Gly
    1415                1420                1425
Asn Ile Ile Ala Tyr Asp Asp Gly Thr Asp Leu Glu Tyr Glu Thr
    1430                1435                1440
Glu Lys Leu Asp Glu Ile Lys Ser Lys Ile Tyr Gly Val Leu Ser
    1445                1450                1455
Pro Ser Lys Asp Gly His Phe Glu Ile Leu Gly Lys Ile Ser Asn
    1460                1465                1470
Val Ser Lys Asn Ala Lys Val Tyr Tyr Gly Asn Asn Tyr Lys Ser
    1475                1480                1485
Ile Glu Ile Lys Ala Thr Lys Tyr Asp Phe His Ser Lys Thr Met
    1490                1495                1500
Thr Phe Asp Leu Tyr Ala Asn Ile Asn Asp Ile Val Asp Gly Leu
    1505                1510                1515
Ala Phe Ala Gly Asp Met Arg Leu Phe Val Lys Asp Asn Asp Gln
    1520                1525                1530
Lys Lys Ala Glu Ile Lys Ile Arg Met Pro Glu Lys Ile Lys Glu
    1535                1540                1545
Thr Lys Ser Glu Tyr Pro Tyr Val Ser Ser Tyr Gly Asn Val Ile
    1550                1555                1560
Glu Leu Gly Glu Gly Asp Leu Ser Lys Asn Lys Pro Asp Asn Leu
    1565                1570                1575
Thr Lys Met Glu Ser Gly Lys Ile Tyr Ser Asp Ser Glu Lys Gln
    1580                1585                1590
Gln Tyr Leu Leu Lys Asp Asn Ile Ile Leu Arg Lys Gly Tyr Ala
    1595                1600                1605
Leu Lys Val Thr Thr Tyr Asn Pro Gly Lys Thr Asp Met Leu Glu
    1610                1615                1620
Gly Asn Gly Val Tyr Ser Lys Glu Asp Ile Ala Lys Ile Gln Lys
    1625                1630                1635
Ala Asn Pro Asn Leu Arg Ala Leu Ser Glu Thr Thr Ile Tyr Ala
    1640                1645                1650
Asp Ser Arg Asn Val Glu Asp Gly Arg Ser Thr Gln Ser Val Leu
    1655                1660                1665
Met Ser Ala Leu Asp Gly Phe Asn Ile Ile Arg Tyr Gln Val Phe
    1670                1675                1680
Thr Phe Lys Met Asn Asp Lys Gly Glu Ala Ile Asp Lys Asp Gly
    1685                1690                1695
Asn Leu Val Thr Asp Ser Ser Lys Leu Val Leu Phe Gly Lys Asp
    1700                1705                1710
Asp Lys Glu Tyr Thr Gly Glu Asp Lys Phe Asn Val Glu Ala Ile
    1715                1720                1725
Lys Glu Asp Gly Ser Met Leu Phe Ile Asp Thr Lys Pro Val Asn
    1730                1735                1740
```

```
Leu Ser Met Asp Lys Asn Tyr Phe Asn Pro Ser Lys Ser Asn Lys
    1745            1750                1755

Ile Tyr Val Arg Asn Pro Glu Phe Tyr Leu Arg Gly Lys Ile Ser
    1760            1765                1770

Asp Lys Gly Gly Phe Asn Trp Glu Leu Arg Val Asn Glu Ser Val
    1775            1780                1785

Val Asp Asn Tyr Leu Ile Tyr Gly Asp Leu His Ile Asp Asn Thr
    1790            1795                1800

Arg Asp Phe Asn Ile Lys Leu Asn Val Lys Asp Gly Asp Ile Met
    1805            1810                1815

Asp Trp Gly Met Lys Asp Tyr Lys Ala Asn Gly Phe Pro Asp Lys
    1820            1825                1830

Val Thr Asp Met Asp Gly Asn Val Tyr Leu Gln Thr Gly Tyr Ser
    1835            1840                1845

Asp Leu Asn Ala Lys Ala Val Gly Val His Tyr Gln Phe Leu Tyr
    1850            1855                1860

Asp Asn Val Lys Pro Glu Val Asn Ile Asp Pro Lys Gly Asn Thr
    1865            1870                1875

Ser Ile Glu Tyr Ala Asp Gly Lys Ser Val Val Phe Asn Ile Asn
    1880            1885                1890

Asp Lys Arg Asn Asn Gly Phe Asp Gly Glu Ile Gln Glu Gln His
    1895            1900                1905

Ile Tyr Ile Asn Gly Lys Glu Tyr Thr Ser Phe Asn Asp Ile Lys
    1910            1915                1920

Gln Ile Ile Asp Lys Thr Leu Asn Ile Lys Ile Val Val Lys Asp
    1925            1930                1935

Phe Ala Arg Asn Thr Thr Val Lys Glu Phe Ile Leu Asn Lys Asp
    1940            1945                1950

Thr Gly Glu Val Ser Glu Leu Lys Pro His Arg Val Thr Val Thr
    1955            1960                1965

Ile Gln Asn Gly Lys Glu Met Ser Ser Thr Ile Val Ser Glu Glu
    1970            1975                1980

Asp Phe Ile Leu Pro Val Tyr Lys Gly Glu Leu Glu Lys Gly Tyr
    1985            1990                1995

Gln Phe Asp Gly Trp Glu Ile Ser Gly Phe Glu Gly Lys Lys Asp
    2000            2005                2010

Ala Gly Tyr Val Ile Asn Leu Ser Lys Asp Thr Phe Ile Lys Pro
    2015            2020                2025

Val Phe Lys Lys Ile Glu Glu Lys Lys Glu Glu Glu Asn Lys Pro
    2030            2035                2040

Thr Phe Asp Val Ser Lys Lys Asp Asn Pro Gln Val Asn His
    2045            2050                2055

Ser Gln Leu Asn Glu Ser His Arg Lys Glu Asp Leu Gln Arg Glu
    2060            2065                2070

Glu His Ser Gln Lys Ser Asp Ser Thr Lys Asp Val Thr Ala Thr
    2075            2080                2085

Val Leu Asp Lys Asn Asn Ile Ser Ser Lys Ser Thr Thr Asn Asn
    2090            2095                2100

Pro Asn Lys Leu Pro Lys Thr Gly Thr Ala Ser Gly Ala Gln Thr
    2105            2110                2115

Leu Leu Ala Ala Gly Ile Met Phe Ile Val Gly Ile Phe Leu Gly
    2120            2125                2130
```

Leu Lys Lys Lys Asn Gln Asp
    2135            2140

<210> SEQ ID NO 13
<211> LENGTH: 662
<212> TYPE: PRT
<213> ORGANISM: Streptococcus pneumoniae

<400> SEQUENCE: 13

Met Val Val Leu Ala Asp Thr Ser Ser Glu Asp Ala Leu Asn Ile
1               5                   10                  15

Ser Asp Lys Glu Lys Val Ala Glu Asn Lys Glu Lys His Glu Asn Ile
                20                  25                  30

His Ser Ala Met Glu Thr Ser Gln Asp Phe Lys Glu Lys Lys Thr Ala
            35                  40                  45

Val Ile Lys Glu Lys Glu Val Val Ser Lys Asn Pro Val Ile Asp Asn
    50                  55                  60

Asn Thr Ser Asn Glu Glu Ala Lys Ile Lys Glu Glu Asn Ser Asn Lys
65                  70                  75                  80

Ser Gln Gly Asp Tyr Thr Asp Ser Phe Val Asn Lys Asn Thr Glu Asn
                85                  90                  95

Pro Lys Lys Glu Asp Lys Val Val Tyr Ile Ala Glu Phe Lys Asp Lys
            100                 105                 110

Glu Ser Gly Glu Lys Ala Ile Lys Glu Leu Ser Ser Leu Lys Asn Thr
        115                 120                 125

Lys Val Leu Tyr Thr Tyr Asp Arg Ile Phe Asn Gly Ser Ala Ile Glu
    130                 135                 140

Thr Thr Pro Asp Asn Leu Asp Lys Ile Lys Gln Ile Glu Gly Ile Ser
145                 150                 155                 160

Ser Val Glu Arg Ala Gln Lys Val Gln Pro Met Met Asn His Ala Arg
                165                 170                 175

Lys Glu Ile Gly Val Glu Glu Ala Ile Asp Tyr Leu Lys Ser Ile Asn
            180                 185                 190

Ala Pro Phe Gly Lys Asn Phe Asp Gly Arg Gly Met Val Ile Ser Asn
        195                 200                 205

Ile Asp Thr Gly Thr Asp Tyr Arg His Lys Ala Met Arg Ile Asp Asp
    210                 215                 220

Asp Ala Lys Ala Ser Met Arg Phe Lys Lys Glu Asp Leu Lys Gly Thr
225                 230                 235                 240

Asp Lys Asn Tyr Trp Leu Ser Asp Lys Ile Pro His Ala Phe Asn Tyr
                245                 250                 255

Tyr Asn Gly Gly Lys Ile Thr Val Glu Lys Tyr Asp Asp Gly Arg Asp
            260                 265                 270

Tyr Phe Asp Pro His Gly Met His Ile Ala Gly Ile Leu Ala Gly Asn
        275                 280                 285

Asp Thr Glu Gln Asp Ile Lys Asn Phe Asn Gly Ile Asp Gly Ile Ala
    290                 295                 300

Pro Asn Ala Gln Ile Phe Ser Tyr Lys Met Tyr Ser Asp Ala Gly Ser
305                 310                 315                 320

Gly Phe Ala Gly Asp Glu Thr Met Phe His Ala Ile Glu Asp Ser Ile
                325                 330                 335

Lys His Asn Val Asp Val Val Ser Val Ser Ser Gly Phe Thr Gly Thr
            340                 345                 350

Gly Leu Val Gly Glu Lys Tyr Trp Gln Ala Ile Arg Ala Leu Arg Lys
        355                 360                 365

```
Ala Gly Ile Pro Met Val Val Ala Thr Gly Asn Tyr Ala Thr Ser Ala
    370                 375                 380

Ser Ser Ser Ser Trp Asp Leu Val Ala Asn Asn His Leu Lys Met Thr
385                 390                 395                 400

Asp Thr Gly Asn Val Thr Arg Thr Ala Ala His Glu Asp Ala Ile Ala
                405                 410                 415

Val Ala Ser Ala Lys Asn Gln Thr Val Glu Phe Asp Lys Val Asn Ile
                420                 425                 430

Gly Gly Glu Ser Phe Lys Tyr Arg Asn Ile Gly Ala Phe Phe Asp Lys
            435                 440                 445

Ser Lys Ile Thr Thr Asn Glu Asp Gly Thr Lys Ala Pro Ser Lys Leu
    450                 455                 460

Lys Phe Val Tyr Ile Gly Lys Gly Gln Asp Gln Asp Leu Ile Gly Leu
465                 470                 475                 480

Asp Leu Arg Gly Lys Ile Ala Val Met Asp Arg Ile Tyr Thr Lys Asp
                485                 490                 495

Leu Lys Asn Ala Phe Lys Lys Ala Met Asp Lys Gly Ala Arg Ala Ile
                500                 505                 510

Met Val Val Asn Thr Val Asn Tyr Tyr Asn Arg Asp Asn Trp Thr Glu
            515                 520                 525

Leu Pro Ala Met Gly Tyr Glu Ala Asp Glu Gly Thr Lys Ser Gln Val
    530                 535                 540

Phe Ser Ile Ser Gly Asp Asp Gly Val Lys Leu Trp Asn Met Ile Asn
545                 550                 555                 560

Pro Asp Lys Lys Thr Glu Val Lys Arg Asn Asn Lys Glu Asp Phe Lys
                565                 570                 575

Asp Lys Leu Glu Gln Tyr Tyr Pro Ile Asp Met Glu Ser Phe Asn Ser
            580                 585                 590

Asn Lys Pro Asn Val Gly Asp Glu Lys Glu Ile Asp Phe Lys Phe Ala
    595                 600                 605

Pro Asp Thr Asp Lys Glu Leu Tyr Lys Glu Asp Ile Ile Val Pro Ala
610                 615                 620

Gly Ser Thr Ser Trp Gly Pro Arg Ile Asp Leu Leu Leu Lys Pro Asp
625                 630                 635                 640

Val Ser Ala Pro Gly Lys Asn Ile Lys Ser Thr Leu Asn Val Ile Asn
                645                 650                 655

Gly Lys Ser Thr Tyr Gly
                660

<210> SEQ ID NO 14
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or Ile
<220> FEATURE:
<221> NAME/KEY: MOD_RES
<222> LOCATION: (55)..(55)
<223> OTHER INFORMATION: Asn or Tyr
<220> FEATURE:
<221> NAME/KEY: MOD_RES
<222> LOCATION: (63)..(63)
<223> OTHER INFORMATION: His or Tyr
<220> FEATURE:
```

-continued

```
<221> NAME/KEY: MOD_RES
<222> LOCATION: (79)..(79)
<223> OTHER INFORMATION: Arg or His
<220> FEATURE:
<221> NAME/KEY: MOD_RES
<222> LOCATION: (97)..(97)
<223> OTHER INFORMATION: Ala or Glu
<220> FEATURE:
<221> NAME/KEY: MOD_RES
<222> LOCATION: (108)..(108)
<223> OTHER INFORMATION: Gly or Glu
<220> FEATURE:
<221> NAME/KEY: MOD_RES
<222> LOCATION: (164)..(164)
<223> OTHER INFORMATION: Asp or Glu
<220> FEATURE:
<221> NAME/KEY: MOD_RES
<222> LOCATION: (165)..(165)
<223> OTHER INFORMATION: Gln or Lys
<220> FEATURE:
<221> NAME/KEY: MOD_RES
<222> LOCATION: (187)..(187)
<223> OTHER INFORMATION: Phe or Ile
<220> FEATURE:
<221> NAME/KEY: MOD_RES
<222> LOCATION: (197)..(197)
<223> OTHER INFORMATION: Arg or His
<220> FEATURE:
<221> NAME/KEY: MOD_RES
<222> LOCATION: (238)..(238)
<223> OTHER INFORMATION: Gly or Arg

<400> SEQUENCE: 14

Xaa Asn Gln Ser Tyr Phe Tyr Leu Lys Met Lys Glu His Lys Leu Lys
1               5                   10                  15

Val Pro Tyr Thr Gly Lys Glu Arg Val Arg Ile Leu Leu Pro Lys
            20                  25                  30

Asp Tyr Glu Lys Asp Thr Asp Arg Ser Tyr Pro Val Val Tyr Phe His
        35                  40                  45

Asp Gly Gln Asn Val Phe Xaa Ser Lys Glu Ser Phe Ile Gly Xaa Ser
50                  55                  60

Trp Lys Ile Ile Pro Ala Ile Lys Arg Asn Pro Asp Ile Ser Xaa Met
65                  70                  75                  80

Ile Val Val Ala Ile Asp Asn Asp Gly Met Gly Arg Met Asn Glu Tyr
                85                  90                  95

Xaa Ala Trp Lys Phe Gln Glu Ser Pro Ile Pro Xaa Gln Gln Phe Gly
            100                 105                 110

Gly Lys Gly Val Glu Tyr Ala Glu Phe Val Met Glu Val Lys Pro
        115                 120                 125

Phe Ile Asp Glu Thr Tyr Arg Thr Lys Ala Asp Cys Gln His Thr Ala
130                 135                 140

Met Ile Gly Ser Ser Leu Gly Gly Asn Ile Thr Gln Phe Ile Gly Leu
145                 150                 155                 160

Glu Tyr Gln Xaa Xaa Ile Gly Cys Leu Gly Val Phe Ser Ser Ala Asn
                165                 170                 175

Trp Leu His Gln Glu Ala Phe Asn Arg Tyr Xaa Glu Cys Gln Lys Leu
            180                 185                 190

Ser Pro Asp Gln Xaa Ile Phe Ile Tyr Val Gly Thr Glu Glu Ala Asp
        195                 200                 205

Asp Thr Asp Lys Thr Leu Met Asp Gly Asn Ile Lys Gln Ala Tyr Ile
        210                 215                 220

Asp Ser Ser Leu Cys Tyr Tyr His Asp Leu Ile Ala Gly Xaa Val His
225                 230                 235                 240
```

```
Leu Asp Asn Leu Val Leu Lys Val Gln Ser Gly Ala Ile His Ser Glu
            245                 250                 255

Ile Pro Trp Ser Glu Asn Leu Pro Asp Cys Leu Arg Phe Phe Ala Glu
        260                 265                 270

Lys Trp

<210> SEQ ID NO 15
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or Ile
<220> FEATURE:
<221> NAME/KEY: MOD_RES
<222> LOCATION: (55)..(55)
<223> OTHER INFORMATION: Asn or Tyr
<220> FEATURE:
<221> NAME/KEY: MOD_RES
<222> LOCATION: (63)..(63)
<223> OTHER INFORMATION: His or Tyr
<220> FEATURE:
<221> NAME/KEY: MOD_RES
<222> LOCATION: (79)..(79)
<223> OTHER INFORMATION: Arg or His
<220> FEATURE:
<221> NAME/KEY: MOD_RES
<222> LOCATION: (97)..(97)
<223> OTHER INFORMATION: Ala or Glu
<220> FEATURE:
<221> NAME/KEY: MOD_RES
<222> LOCATION: (108)..(108)
<223> OTHER INFORMATION: Gly or Glu

<400> SEQUENCE: 15

Xaa Asn Gln Ser Tyr Phe Tyr Leu Lys Met Lys Glu His Lys Leu Lys
1               5                   10                  15

Val Pro Tyr Thr Gly Lys Glu Arg Arg Val Arg Ile Leu Leu Pro Lys
            20                  25                  30

Asp Tyr Glu Lys Asp Thr Asp Arg Ser Tyr Pro Val Val Tyr Phe His
        35                  40                  45

Asp Gly Gln Asn Val Phe Xaa Ser Lys Glu Ser Phe Ile Gly Xaa Ser
    50                  55                  60

Trp Lys Ile Ile Pro Ala Ile Lys Arg Asn Pro Asp Ile Ser Xaa Met
65              70                  75                  80

Ile Val Val Ala Ile Asp Asn Asp Gly Met Gly Arg Met Asn Glu Tyr
                85                  90                  95

Xaa Ala Trp Lys Phe Gln Glu Ser Pro Ile Pro Xaa Gln Gln Phe Gly
            100                 105                 110

Gly Lys Gly Val Glu Tyr Ala Glu Phe Val Met Glu Val Val Lys Pro
        115                 120                 125

Phe Ile
    130

<210> SEQ ID NO 16
<211> LENGTH: 299
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (6)..(6)
<223> OTHER INFORMATION: Met or Thr
<220> FEATURE:
<221> NAME/KEY: MOD_RES
<222> LOCATION: (9)..(9)
<223> OTHER INFORMATION: Ala or Thr
<220> FEATURE:
<221> NAME/KEY: MOD_RES
<222> LOCATION: (15)..(15)
<223> OTHER INFORMATION: Ala or Val
<220> FEATURE:
<221> NAME/KEY: MOD_RES
<222> LOCATION: (26)..(26)
<223> OTHER INFORMATION: Met or Ile
<220> FEATURE:
<221> NAME/KEY: MOD_RES
<222> LOCATION: (80)..(80)
<223> OTHER INFORMATION: Asn or Tyr
<220> FEATURE:
<221> NAME/KEY: MOD_RES
<222> LOCATION: (88)..(88)
<223> OTHER INFORMATION: His or Tyr
<220> FEATURE:
<221> NAME/KEY: MOD_RES
<222> LOCATION: (104)..(104)
<223> OTHER INFORMATION: Arg or His
<220> FEATURE:
<221> NAME/KEY: MOD_RES
<222> LOCATION: (122)..(122)
<223> OTHER INFORMATION: Ala or Glu
<220> FEATURE:
<221> NAME/KEY: MOD_RES
<222> LOCATION: (133)..(133)
<223> OTHER INFORMATION: Gly or Glu
<220> FEATURE:
<221> NAME/KEY: MOD_RES
<222> LOCATION: (189)..(189)
<223> OTHER INFORMATION: Asp or Glu
<220> FEATURE:
<221> NAME/KEY: MOD_RES
<222> LOCATION: (190)..(190)
<223> OTHER INFORMATION: Gln or Lys
<220> FEATURE:
<221> NAME/KEY: MOD_RES
<222> LOCATION: (212)..(212)
<223> OTHER INFORMATION: Phe or Ile
<220> FEATURE:
<221> NAME/KEY: MOD_RES
<222> LOCATION: (222)..(222)
<223> OTHER INFORMATION: Arg or His
<220> FEATURE:
<221> NAME/KEY: MOD_RES
<222> LOCATION: (263)..(263)
<223> OTHER INFORMATION: Arg or His

<400> SEQUENCE: 16

Met Ser Ser Lys Phe Xaa Lys Ser Xaa Ala Val Leu Gly Thr Xaa Thr
1               5                   10                  15

Leu Ala Ser Leu Leu Val Ala Cys Xaa Asn Gln Ser Tyr Phe Tyr
            20                  25                  30

Leu Lys Met Lys Glu His Lys Leu Lys Val Pro Tyr Thr Gly Lys Glu
                35                  40                  45

Arg Arg Val Arg Ile Leu Leu Pro Lys Asp Tyr Glu Lys Asp Thr Asp
    50                  55                  60

Arg Ser Tyr Pro Val Val Tyr Phe His Asp Gly Gln Asn Val Phe Xaa
65                  70                  75                  80

Ser Lys Glu Ser Phe Ile Gly Xaa Ser Trp Lys Ile Ile Pro Ala Ile
                85                  90                  95

Lys Arg Asn Pro Asp Ile Ser Xaa Met Ile Val Val Ala Ile Asp Asn
                100                 105                 110
```

```
Asp Gly Met Gly Arg Met Asn Glu Tyr Xaa Ala Trp Lys Phe Gln Glu
            115                 120                 125

Ser Pro Ile Pro Xaa Gln Gln Phe Gly Gly Lys Gly Val Glu Tyr Ala
        130                 135                 140

Glu Phe Val Met Glu Val Val Lys Pro Phe Ile Asp Glu Thr Tyr Arg
145                 150                 155                 160

Thr Lys Ala Asp Cys Gln His Thr Ala Met Ile Gly Ser Ser Leu Gly
                165                 170                 175

Gly Asn Ile Thr Gln Phe Ile Gly Leu Glu Tyr Gln Xaa Xaa Ile Gly
            180                 185                 190

Cys Leu Gly Val Phe Ser Ser Ala Asn Trp Leu His Gln Glu Ala Phe
        195                 200                 205

Asn Arg Tyr Xaa Glu Cys Gln Lys Leu Ser Pro Asp Gln Xaa Ile Phe
    210                 215                 220

Ile Tyr Val Gly Thr Glu Glu Ala Asp Asp Thr Asp Lys Thr Leu Met
225                 230                 235                 240

Asp Gly Asn Ile Lys Gln Ala Tyr Ile Asp Ser Ser Leu Cys Tyr Tyr
                245                 250                 255

His Asp Leu Ile Ala Gly Xaa Val His Leu Asp Asn Leu Val Leu Lys
            260                 265                 270

Val Gln Ser Gly Ala Ile His Ser Glu Ile Pro Trp Ser Glu Asn Leu
        275                 280                 285

Pro Asp Cys Leu Arg Phe Phe Ala Glu Lys Trp
        290                 295
```

<210> SEQ ID NO 17
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Met or Thr
<220> FEATURE:
<221> NAME/KEY: MOD_RES
<222> LOCATION: (9)..(9)
<223> OTHER INFORMATION: Ala or Thr
<220> FEATURE:
<221> NAME/KEY: MOD_RES
<222> LOCATION: (15)..(15)
<223> OTHER INFORMATION: Ala or Val
<220> FEATURE:
<221> NAME/KEY: MOD_RES
<222> LOCATION: (26)..(26)
<223> OTHER INFORMATION: Met or Ile
<220> FEATURE:
<221> NAME/KEY: MOD_RES
<222> LOCATION: (80)..(80)
<223> OTHER INFORMATION: Asn or Tyr
<220> FEATURE:
<221> NAME/KEY: MOD_RES
<222> LOCATION: (88)..(88)
<223> OTHER INFORMATION: His or Tyr
<220> FEATURE:
<221> NAME/KEY: MOD_RES
<222> LOCATION: (104)..(104)
<223> OTHER INFORMATION: Arg or His
<220> FEATURE:
<221> NAME/KEY: MOD_RES
<222> LOCATION: (122)..(122)
<223> OTHER INFORMATION: Ala or Glu
<220> FEATURE:
<221> NAME/KEY: MOD_RES
<222> LOCATION: (133)..(133)

<223> OTHER INFORMATION: Gly or Glu

<400> SEQUENCE: 17

Met Ser Ser Lys Phe Xaa Lys Ser Xaa Ala Val Leu Gly Thr Xaa Thr
1               5                   10                  15

Leu Ala Ser Leu Leu Val Ala Cys Xaa Asn Gln Ser Tyr Phe Tyr
            20                  25                  30

Leu Lys Met Lys Glu His Lys Leu Lys Val Pro Tyr Thr Gly Lys Glu
        35                  40                  45

Arg Arg Val Arg Ile Leu Leu Pro Lys Asp Tyr Glu Lys Asp Thr Asp
    50                  55                  60

Arg Ser Tyr Pro Val Val Tyr Phe His Asp Gly Gln Asn Val Phe Xaa
65                  70                  75                  80

Ser Lys Glu Ser Phe Ile Gly Xaa Ser Trp Lys Ile Ile Pro Ala Ile
                85                  90                  95

Lys Arg Asn Pro Asp Ile Ser Xaa Met Ile Val Val Ala Ile Asp Asn
                100                 105                 110

Asp Gly Met Gly Arg Met Asn Glu Tyr Xaa Ala Trp Lys Phe Gln Glu
            115                 120                 125

Ser Pro Ile Pro Xaa Gln Gln Phe Gly Gly Lys Gly Val Glu Tyr Ala
        130                 135                 140

Glu Phe Val Met Glu Val Val Lys Pro Phe Ile
145                 150                 155

<210> SEQ ID NO 18
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Gly or Glu
<220> FEATURE:
<221> NAME/KEY: MOD_RES
<222> LOCATION: (24)..(24)
<223> OTHER INFORMATION: Gly or Ser
<220> FEATURE:
<221> NAME/KEY: MOD_RES
<222> LOCATION: (27)..(27)
<223> OTHER INFORMATION: Lys or Arg
<220> FEATURE:
<221> NAME/KEY: MOD_RES
<222> LOCATION: (30)..(30)
<223> OTHER INFORMATION: Ile or Asn
<220> FEATURE:
<221> NAME/KEY: MOD_RES
<222> LOCATION: (56)..(56)
<223> OTHER INFORMATION: Asp or Asn
<220> FEATURE:
<221> NAME/KEY: MOD_RES
<222> LOCATION: (58)..(58)
<223> OTHER INFORMATION: Any amino acid
<220> FEATURE:
<221> NAME/KEY: MOD_RES
<222> LOCATION: (83)..(83)
<223> OTHER INFORMATION: Leu or Ile
<220> FEATURE:
<221> NAME/KEY: MOD_RES
<222> LOCATION: (111)..(111)
<223> OTHER INFORMATION: Asp or Glu
<220> FEATURE:
<221> NAME/KEY: MOD_RES
<222> LOCATION: (159)..(159)
<223> OTHER INFORMATION: Leu or Phe
<220> FEATURE:

```
<221> NAME/KEY: MOD_RES
<222> LOCATION: (192)..(192)
<223> OTHER INFORMATION: Asn or Tyr
<220> FEATURE:
<221> NAME/KEY: MOD_RES
<222> LOCATION: (199)..(199)
<223> OTHER INFORMATION: Pro or Ser

<400> SEQUENCE: 18

Met Cys Ser Gly Gly Ala Lys Lys Glu Gly Xaa Ala Ala Ser Lys Lys
1               5                   10                  15

Glu Ile Ile Val Ala Thr Asn Xaa Ser Pro Xaa Pro Phe Xaa Tyr Glu
            20                  25                  30

Glu Asn Gly Glu Leu Thr Gly Tyr Glu Ile Glu Val Val Arg Ala Ile
            35                  40                  45

Phe Lys Asp Ser Asp Lys Tyr Xaa Val Xaa Phe Glu Lys Thr Glu Trp
50                  55                  60

Ser Gly Val Phe Ala Gly Leu Asp Ala Asp Arg Tyr Asn Met Ala Val
65                  70                  75                  80

Asn Asn Xaa Ser Tyr Thr Lys Glu Arg Ala Glu Lys Tyr Leu Tyr Ala
                85                  90                  95

Ala Pro Ile Ala Gln Asn Pro Asn Val Leu Val Val Lys Lys Xaa Asp
            100                 105                 110

Ser Ser Ile Lys Ser Leu Asp Asp Ile Gly Gly Lys Ser Thr Glu Val
            115                 120                 125

Val Gln Ala Thr Thr Ser Ala Lys Gln Leu Glu Ala Tyr Asn Ala Glu
130                 135                 140

His Thr Asp Asn Pro Thr Ile Leu Asn Tyr Thr Lys Ala Asp Xaa Gln
145                 150                 155                 160

Gln Ile Met Val Arg Leu Ser Asp Gly Gln Phe Asp Tyr Lys Ile Phe
                165                 170                 175

Asp Lys Ile Gly Val Glu Thr Val Ile Lys Asn Gln Gly Leu Asp Xaa
            180                 185                 190

Leu Lys Val Ile Glu Leu Xaa Ser Asp Gln Gln Pro Tyr Val Tyr Pro
            195                 200                 205

Leu Leu Ala Gln Gly Gln Asp Glu Leu Lys Ser Phe Val Asp Lys Arg
            210                 215                 220

Ile Lys Glu Leu Tyr Lys Asp Gly Thr Leu Glu Lys Leu Ser Lys Gln
225                 230                 235                 240

Phe Phe Gly Asp Thr Tyr Leu Pro Ala Glu Ala Asp Ile Lys
                245                 250

<210> SEQ ID NO 19
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Ala or Gly
<220> FEATURE:
<221> NAME/KEY: MOD_RES
<222> LOCATION: (20)..(20)
<223> OTHER INFORMATION: Val or Leu
<220> FEATURE:
<221> NAME/KEY: MOD_RES
<222> LOCATION: (33)..(33)
<223> OTHER INFORMATION: Glu or Gln
<220> FEATURE:
```

<221> NAME/KEY: MOD_RES
<222> LOCATION: (46)..(46)
<223> OTHER INFORMATION: Gly or Ser
<220> FEATURE:
<221> NAME/KEY: MOD_RES
<222> LOCATION: (49)..(49)
<223> OTHER INFORMATION: Lys or Arg
<220> FEATURE:
<221> NAME/KEY: MOD_RES
<222> LOCATION: (52)..(52)
<223> OTHER INFORMATION: Ile or Asn
<220> FEATURE:
<221> NAME/KEY: MOD_RES
<222> LOCATION: (78)..(78)
<223> OTHER INFORMATION: Asp or Asn
<220> FEATURE:
<221> NAME/KEY: MOD_RES
<222> LOCATION: (80)..(80)
<223> OTHER INFORMATION: Any amino acid
<220> FEATURE:
<221> NAME/KEY: MOD_RES
<222> LOCATION: (105)..(105)
<223> OTHER INFORMATION: Leu or Ile
<220> FEATURE:
<221> NAME/KEY: MOD_RES
<222> LOCATION: (133)..(133)
<223> OTHER INFORMATION: Asp or Glu
<220> FEATURE:
<221> NAME/KEY: MOD_RES
<222> LOCATION: (181)..(181)
<223> OTHER INFORMATION: Asp or Glu
<220> FEATURE:
<221> NAME/KEY: MOD_RES
<222> LOCATION: (214)..(214)
<223> OTHER INFORMATION: Asn or Tyr
<220> FEATURE:
<221> NAME/KEY: MOD_RES
<222> LOCATION: (221)..(221)
<223> OTHER INFORMATION: Pro or Ser

<400> SEQUENCE: 19

Met Lys Lys Ile Val Lys Tyr Ser Ser Leu Ala Ala Leu Xaa Leu Val
1               5                   10                  15

Ala Ala Gly Xaa Leu Ala Ala Cys Ser Gly Gly Ala Lys Lys Glu Gly
            20                  25                  30

Xaa Ala Ala Ser Lys Lys Glu Ile Ile Val Ala Thr Asn Xaa Ser Pro
        35                  40                  45

Xaa Pro Phe Xaa Tyr Glu Glu Asn Gly Glu Leu Thr Gly Tyr Glu Ile
    50                  55                  60

Glu Val Val Arg Ala Ile Phe Lys Asp Ser Asp Lys Tyr Xaa Val Xaa
65                  70                  75                  80

Phe Glu Lys Thr Glu Trp Ser Gly Val Phe Ala Gly Leu Asp Ala Asp
                85                  90                  95

Arg Tyr Asn Met Ala Val Asn Asn Xaa Ser Tyr Thr Lys Glu Arg Ala
            100                 105                 110

Glu Lys Tyr Leu Tyr Ala Ala Pro Ile Ala Gln Asn Pro Asn Val Leu
        115                 120                 125

Val Val Lys Lys Xaa Asp Ser Ser Ile Lys Ser Leu Asp Asp Ile Gly
    130                 135                 140

Gly Lys Ser Thr Glu Val Val Gln Ala Thr Thr Ser Ala Lys Gln Leu
145                 150                 155                 160

Glu Ala Tyr Asn Ala Glu His Thr Asp Asn Pro Thr Ile Leu Asn Tyr
                165                 170                 175

Thr Lys Ala Asp Xaa Gln Gln Ile Met Val Arg Leu Ser Asp Gly Gln
            180                 185                 190

Phe Asp Tyr Lys Ile Phe Asp Lys Ile Gly Val Glu Thr Val Ile Lys

```
            195                 200                 205
Asn Gln Gly Leu Asp Xaa Leu Lys Val Ile Glu Leu Xaa Ser Asp Gln
    210                 215                 220

Gln Pro Tyr Val Tyr Pro Leu Leu Ala Gln Gly Gln Asp Glu Leu Lys
225                 230                 235                 240

Ser Phe Val Asp Lys Arg Ile Lys Glu Leu Tyr Lys Asp Gly Thr Leu
                245                 250                 255

Glu Lys Leu Ser Lys Gln Phe Phe Gly Asp Thr Tyr Leu Pro Ala Glu
            260                 265                 270

Ala Asp Ile Lys
        275

<210> SEQ ID NO 20
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: Val or Ala
<220> FEATURE:
<221> NAME/KEY: MOD_RES
<222> LOCATION: (48)..(48)
<223> OTHER INFORMATION: Val or Ile
<220> FEATURE:
<221> NAME/KEY: MOD_RES
<222> LOCATION: (74)..(74)
<223> OTHER INFORMATION: Val or Ile
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (100)..(100)
<223> OTHER INFORMATION: Ala or Thr
<220> FEATURE:
<221> NAME/KEY: MOD_RES
<222> LOCATION: (177)..(177)
<223> OTHER INFORMATION: Thr or Ala
<220> FEATURE:
<221> NAME/KEY: MOD_RES
<222> LOCATION: (186)..(186)
<223> OTHER INFORMATION: Ala or Gly
<220> FEATURE:
<221> NAME/KEY: MOD_RES
<222> LOCATION: (196)..(196)
<223> OTHER INFORMATION: Ala or Pro
<220> FEATURE:
<221> NAME/KEY: MOD_RES
<222> LOCATION: (208)..(208)
<223> OTHER INFORMATION: Val or Ala
<220> FEATURE:
<221> NAME/KEY: MOD_RES
<222> LOCATION: (214)..(214)
<223> OTHER INFORMATION: Any amino acid
<220> FEATURE:
<221> NAME/KEY: MOD_RES
<222> LOCATION: (237)..(237)
<223> OTHER INFORMATION: Gln or His
<220> FEATURE:
<221> NAME/KEY: MOD_RES
<222> LOCATION: (298)..(298)
<223> OTHER INFORMATION: Ser or Ala
<220> FEATURE:
<221> NAME/KEY: MOD_RES
<222> LOCATION: (307)..(307)
<223> OTHER INFORMATION: Ala or Ser
<220> FEATURE:
<221> NAME/KEY: MOD_RES
```

```
<222> LOCATION: (313)..(313)
<223> OTHER INFORMATION: Val or Ala
<220> FEATURE:
<221> NAME/KEY: MOD_RES
<222> LOCATION: (348)..(348)
<223> OTHER INFORMATION: Asn or Ser

<400> SEQUENCE: 20

Met Cys Gly Ser Lys Thr Ala Asp Lys Pro Ala Asp Ser Gly Ser Ser
1               5                   10                  15

Glu Xaa Lys Glu Leu Thr Val Tyr Val Asp Gly Tyr Lys Ser Tyr
            20                  25                  30

Ile Glu Glu Val Ala Lys Ala Tyr Glu Lys Ala Gly Val Lys Xaa
        35                  40                  45

Thr Leu Lys Thr Gly Asp Ala Leu Gly Gly Leu Asp Lys Leu Ser Leu
    50                  55                  60

Asp Asn Gln Ser Gly Asn Val Pro Asp Xaa Met Met Ala Pro Tyr Asp
65                  70                  75                  80

Arg Val Xaa Ser Leu Gly Ser Asp Gly Gln Leu Ser Glu Val Lys Leu
                85                  90                  95

Ser Asp Gly Xaa Lys Thr Asp Asp Thr Thr Lys Ser Leu Val Thr Ala
            100                 105                 110

Ala Asn Gly Lys Val Tyr Gly Ala Pro Ala Val Ile Glu Ser Leu Val
        115                 120                 125

Met Tyr Tyr Asn Lys Asp Leu Val Lys Asp Ala Pro Lys Thr Phe Ala
130                 135                 140

Asp Leu Glu Asn Leu Ala Lys Asp Ser Lys Tyr Ala Phe Ala Gly Glu
145                 150                 155                 160

Asp Gly Lys Thr Thr Ala Phe Leu Ala Asp Trp Thr Asn Phe Tyr Tyr
                165                 170                 175

Xaa Tyr Gly Leu Leu Ala Gly Asn Gly Xaa Tyr Val Phe Gly Gln Asn
            180                 185                 190

Gly Lys Asp Xaa Lys Asp Ile Gly Leu Ala Asn Asp Gly Ser Ile Xaa
        195                 200                 205

Gly Ile Asn Tyr Ala Xaa Ser Trp Tyr Glu Lys Trp Pro Lys Gly Met
210                 215                 220

Gln Asp Thr Glu Gly Ala Gly Asn Leu Ile Gln Thr Xaa Phe Gln Glu
225                 230                 235                 240

Gly Lys Thr Ala Ala Ile Ile Asp Gly Pro Trp Lys Ala Gln Ala Phe
                245                 250                 255

Lys Asp Ala Lys Val Asn Tyr Gly Val Ala Thr Ile Pro Thr Leu Pro
            260                 265                 270

Asn Gly Lys Glu Tyr Ala Ala Phe Gly Gly Gly Lys Ala Trp Val Ile
        275                 280                 285

Pro Gln Ala Val Lys Asn Leu Glu Ala Xaa Gln Lys Phe Val Asp Phe
290                 295                 300

Leu Val Xaa Thr Glu Gln Gln Lys Xaa Leu Tyr Asp Lys Thr Asn Glu
305                 310                 315                 320

Ile Pro Ala Asn Thr Glu Ala Arg Ser Tyr Ala Glu Gly Lys Asn Asp
                325                 330                 335

Glu Leu Thr Thr Ala Val Ile Lys Gln Phe Lys Xaa Thr Gln Pro Leu
            340                 345                 350

Pro Asn Ile Ser Gln Met Ser Ala Val Trp Asp Pro Ala Lys Asn Met
        355                 360                 365

Leu Phe Asp Ala Val Ser Gly Gln Lys Asp Ala Lys Thr Ala Ala Asn
```

```
            370                 375                 380
Asp Ala Val Thr Leu Ile Lys Glu Thr Ile Lys Gln Lys Phe Gly Glu
385                 390                 395                 400
```

<210> SEQ ID NO 21
<211> LENGTH: 423
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Met or Thr
<220> FEATURE:
<221> NAME/KEY: MOD_RES
<222> LOCATION: (9)..(9)
<223> OTHER INFORMATION: Ala or Thr
<220> FEATURE:
<221> NAME/KEY: MOD_RES
<222> LOCATION: (15)..(15)
<223> OTHER INFORMATION: Ala or Val
<220> FEATURE:
<221> NAME/KEY: MOD_RES
<222> LOCATION: (41)..(41)
<223> OTHER INFORMATION: Val or Ala
<220> FEATURE:
<221> NAME/KEY: MOD_RES
<222> LOCATION: (71)..(71)
<223> OTHER INFORMATION: Val or Ile
<220> FEATURE:
<221> NAME/KEY: MOD_RES
<222> LOCATION: (97)..(97)
<223> OTHER INFORMATION: Val or Ile
<220> FEATURE:
<221> NAME/KEY: MOD_RES
<222> LOCATION: (106)..(106)
<223> OTHER INFORMATION: Any amino acid
<220> FEATURE:
<221> NAME/KEY: MOD_RES
<222> LOCATION: (123)..(123)
<223> OTHER INFORMATION: Ala or Thr
<220> FEATURE:
<221> NAME/KEY: MOD_RES
<222> LOCATION: (200)..(200)
<223> OTHER INFORMATION: Thr or Ala
<220> FEATURE:
<221> NAME/KEY: MOD_RES
<222> LOCATION: (209)..(209)
<223> OTHER INFORMATION: Ala or Gly
<220> FEATURE:
<221> NAME/KEY: MOD_RES
<222> LOCATION: (219)..(219)
<223> OTHER INFORMATION: Ala or Pro
<220> FEATURE:
<221> NAME/KEY: MOD_RES
<222> LOCATION: (231)..(231)
<223> OTHER INFORMATION: Val or Ala
<220> FEATURE:
<221> NAME/KEY: MOD_RES
<222> LOCATION: (237)..(237)
<223> OTHER INFORMATION: Any amino acid
<220> FEATURE:
<221> NAME/KEY: MOD_RES
<222> LOCATION: (260)..(260)
<223> OTHER INFORMATION: Gln or His
<220> FEATURE:
<221> NAME/KEY: MOD_RES
<222> LOCATION: (321)..(321)
<223> OTHER INFORMATION: Ser or Ala
<220> FEATURE:
<221> NAME/KEY: MOD_RES
<222> LOCATION: (330)..(330)
<223> OTHER INFORMATION: Ala or Ser
<220> FEATURE:
<221> NAME/KEY: MOD_RES
<222> LOCATION: (336)..(336)
<223> OTHER INFORMATION: Val or Ala
<220> FEATURE:
<221> NAME/KEY: MOD_RES
<222> LOCATION: (371)..(371)
<223> OTHER INFORMATION: Asn or Ser

<400> SEQUENCE: 21

Met Ser Ser Lys Phe Xaa Lys Ser Xaa Ala Val Leu Gly Thr Xaa Thr
1               5                   10                  15

Leu Ala Ser Leu Leu Val Ala Cys Gly Ser Lys Thr Ala Asp Lys
            20                  25                  30

Pro Ala Asp Ser Gly Ser Ser Glu Xaa Lys Glu Leu Thr Val Tyr Val
        35                  40                  45

Asp Glu Gly Tyr Lys Ser Tyr Ile Glu Val Ala Lys Ala Tyr Glu
50                  55                  60

Lys Glu Ala Gly Val Lys Xaa Thr Leu Lys Thr Gly Asp Ala Leu Gly
65                  70                  75                  80

Gly Leu Asp Lys Leu Ser Leu Asp Asn Gln Ser Gly Asn Val Pro Asp
                85                  90                  95

Xaa Met Met Ala Pro Tyr Asp Arg Val Xaa Ser Leu Gly Ser Asp Gly
            100                 105                 110

Gln Leu Ser Glu Val Lys Leu Ser Asp Gly Xaa Lys Thr Asp Asp Thr
        115                 120                 125

Thr Lys Ser Leu Val Thr Ala Ala Asn Gly Lys Val Tyr Gly Ala Pro
130                 135                 140

Ala Val Ile Glu Ser Leu Val Met Tyr Tyr Asn Lys Asp Leu Val Lys
145                 150                 155                 160

Asp Ala Pro Lys Thr Phe Ala Asp Leu Glu Asn Leu Ala Lys Asp Ser
                165                 170                 175

Lys Tyr Ala Phe Ala Gly Glu Asp Gly Lys Thr Thr Ala Phe Leu Ala
            180                 185                 190

Asp Trp Thr Asn Phe Tyr Tyr Xaa Tyr Gly Leu Leu Ala Gly Asn Gly
        195                 200                 205

Xaa Tyr Val Phe Gly Gln Asn Gly Lys Asp Xaa Lys Asp Ile Gly Leu
210                 215                 220

Ala Asn Asp Gly Ser Ile Xaa Gly Ile Asn Tyr Ala Xaa Ser Trp Tyr
225                 230                 235                 240

Glu Lys Trp Pro Lys Gly Met Gln Asp Thr Glu Gly Ala Gly Asn Leu
                245                 250                 255

Ile Gln Thr Xaa Phe Gln Glu Gly Lys Thr Ala Ile Ile Asp Gly
            260                 265                 270

Pro Trp Lys Ala Gln Ala Phe Lys Asp Ala Lys Val Asn Tyr Gly Val
        275                 280                 285

Ala Thr Ile Pro Thr Leu Pro Asn Gly Lys Glu Tyr Ala Ala Phe Gly
290                 295                 300

Gly Gly Lys Ala Trp Val Ile Pro Gln Ala Val Lys Asn Leu Glu Ala
305                 310                 315                 320

Xaa Gln Lys Phe Val Asp Phe Leu Val Xaa Thr Glu Gln Gln Lys Xaa
                325                 330                 335

Leu Tyr Asp Lys Thr Asn Glu Ile Pro Ala Asn Thr Glu Ala Arg Ser
            340                 345                 350

Tyr Ala Glu Gly Lys Asn Asp Glu Leu Thr Thr Ala Val Ile Lys Gln
        355                 360                 365

Phe Lys Xaa Thr Gln Pro Leu Pro Asn Ile Ser Gln Met Ser Ala Val

```
                370                 375                 380
Trp Asp Pro Ala Lys Asn Met Leu Phe Asp Ala Val Ser Gly Gln Lys
385                 390                 395                 400

Asp Ala Lys Thr Ala Ala Asn Asp Ala Val Thr Leu Ile Lys Glu Thr
                405                 410                 415

Ile Lys Gln Lys Phe Gly Glu
            420

<210> SEQ ID NO 22
<211> LENGTH: 357
<212> TYPE: PRT
<213> ORGANISM: Streptococcus pneumoniae

<400> SEQUENCE: 22

Met Ala Asn Ile Phe Asp Tyr Leu Lys Asp Val Ala Tyr Asp Ser Tyr
1               5                   10                  15

Tyr Asp Leu Pro Leu Asn Glu Leu Asp Ile Leu Thr Leu Ile Glu Ile
                20                  25                  30

Thr Tyr Leu Ser Phe Asp Asn Leu Val Ser Thr Leu Pro Gln Arg Leu
            35                  40                  45

Leu Asp Leu Ala Pro Gln Val Pro Arg Asp Pro Thr Met Leu Thr Ser
50                  55                  60

Lys Asn Arg Leu Gln Leu Leu Asp Glu Leu Ala Gln His Lys Arg Phe
65                  70                  75                  80

Lys Asn Cys Lys Leu Ser His Phe Ile Asn Asp Ile Asp Pro Glu Leu
                85                  90                  95

Gln Lys Gln Phe Ala Ala Met Thr Tyr Arg Val Ser Leu Asp Thr Tyr
            100                 105                 110

Leu Ile Val Phe Arg Gly Thr Asp Asp Ser Ile Ile Gly Trp Lys Glu
        115                 120                 125

Asp Phe His Leu Thr Tyr Met Lys Glu Ile Pro Ala Gln Lys His Ala
130                 135                 140

Leu Arg Tyr Leu Lys Asn Phe Phe Ala His His Pro Lys Gln Lys Val
145                 150                 155                 160

Ile Leu Ala Gly His Ser Lys Gly Gly Asn Leu Ala Ile Tyr Ala Ala
                165                 170                 175

Ser Gln Ile Glu Gln Ser Leu Gln Asn Gln Ile Thr Ala Val Tyr Thr
            180                 185                 190

Phe Asp Ala Pro Gly Leu His Gln Glu Leu Thr Gln Thr Ala Gly Tyr
        195                 200                 205

Gln Arg Ile Met Asp Arg Ser Lys Ile Phe Ile Pro Gln Gly Ser Ile
210                 215                 220

Ile Gly Met Met Leu Glu Ile Pro Ala His Gln Ile Val Gln Ser
225                 230                 235                 240

Thr Ala Leu Gly Gly Ile Ala Gln His Asp Thr Phe Ser Trp Gln Ile
                245                 250                 255

Glu Asp Lys His Phe Val Gln Leu Asp Lys Thr Asn Ser Asp Ser Gln
            260                 265                 270

Gln Val Asp Thr Thr Phe Lys Glu Trp Val Ala Thr Val Pro Asp Glu
        275                 280                 285

Glu Leu Gln Leu Tyr Phe Asp Leu Phe Phe Gly Thr Ile Leu Asp Ala
290                 295                 300

Gly Ile Ser Ser Ile Asn Asp Leu Ala Ser Leu Lys Ala Leu Glu Tyr
305                 310                 315                 320
```

```
Ile His His Leu Phe Val Gln Ala Gln Ser Leu Thr Pro Glu Glu Arg
                325                 330                 335

Glu Thr Leu Gly Arg Leu Thr Gln Leu Leu Ile Asp Thr Arg Tyr Gln
            340                 345                 350

Ala Trp Lys Asn Arg
        355

<210> SEQ ID NO 23
<211> LENGTH: 1066
<212> TYPE: PRT
<213> ORGANISM: Streptococcus pneumoniae

<400> SEQUENCE: 23

Met Gln Thr Lys Thr Lys Lys Leu Ile Val Ser Leu Ser Ser Leu Val
1               5                   10                  15

Leu Ser Gly Phe Leu Leu Asn His Tyr Met Thr Ile Gly Ala Glu Glu
            20                  25                  30

Thr Thr Thr Asn Thr Ile Gln Gln Ser Gln Lys Glu Val Gln Tyr Gln
        35                  40                  45

Gln Arg Asp Thr Lys Asn Leu Val Glu Asn Gly Asp Phe Gly Gln Thr
    50                  55                  60

Glu Asp Gly Ser Ser Pro Trp Thr Gly Ser Lys Ala Gln Gly Trp Ser
65                  70                  75                  80

Ala Trp Val Asp Gln Lys Asn Ser Ala Asp Ala Ser Thr Arg Val Ile
                85                  90                  95

Glu Ala Lys Asp Gly Ala Ile Thr Ile Ser Ser His Glu Lys Leu Arg
            100                 105                 110

Ala Ala Leu His Arg Met Val Pro Ile Glu Ala Lys Lys Lys Tyr Lys
        115                 120                 125

Leu Arg Phe Lys Ile Lys Thr Asp Asn Lys Ile Gly Ile Ala Lys Val
    130                 135                 140

Arg Ile Ile Glu Glu Ser Gly Lys Asp Lys Arg Leu Trp Asn Ser Ala
145                 150                 155                 160

Thr Thr Ser Gly Thr Lys Asp Trp Gln Thr Ile Glu Ala Asp Tyr Ser
                165                 170                 175

Pro Thr Leu Asp Val Asp Lys Ile Lys Leu Glu Leu Phe Tyr Glu Thr
            180                 185                 190

Gly Thr Gly Thr Val Ser Phe Lys Asp Ile Glu Leu Val Glu Val Ala
        195                 200                 205

Asp Gln Leu Ser Glu Asp Ser Gln Thr Asp Lys Gln Leu Glu Glu Lys
    210                 215                 220

Ile Asp Leu Pro Ile Gly Lys Lys His Val Phe Ser Leu Ala Asp Tyr
225                 230                 235                 240

Thr Tyr Lys Val Glu Asn Pro Asp Val Ala Ser Val Lys Asn Gly Ile
                245                 250                 255

Leu Glu Pro Leu Lys Glu Gly Thr Thr Asn Val Ile Val Ser Lys Asp
            260                 265                 270

Gly Lys Glu Val Lys Lys Ile Pro Leu Lys Ile Leu Ala Ser Val Lys
        275                 280                 285

Asp Ala Tyr Thr Asp Arg Leu Asp Asp Trp Asn Gly Ile Ile Ala Gly
    290                 295                 300

Asn Gln Tyr Tyr Asp Ser Lys Asn Glu Gln Met Ala Lys Leu Asn Gln
305                 310                 315                 320

Glu Leu Glu Gly Lys Val Ala Asp Ser Leu Ser Ser Ile Ser Ser Gln
                325                 330                 335
```

```
Ala Asp Arg Thr Tyr Leu Trp Glu Lys Phe Ser Asn Tyr Lys Thr Ser
            340                 345                 350

Ala Asn Leu Thr Ala Thr Tyr Arg Lys Leu Glu Met Ala Lys Gln
            355                 360                 365

Val Thr Asn Pro Ser Ser Arg Tyr Tyr Gln Asp Glu Thr Val Val Arg
    370                 375                 380

Thr Val Arg Asp Ser Met Glu Trp Met His Lys His Val Tyr Asn Ser
385                 390                 395                 400

Glu Lys Ser Ile Val Gly Asn Trp Trp Asp Tyr Glu Ile Gly Thr Pro
                405                 410                 415

Arg Ala Ile Asn Asn Thr Leu Ser Leu Met Lys Glu Tyr Phe Ser Asp
            420                 425                 430

Glu Glu Ile Lys Lys Tyr Thr Asp Val Ile Glu Lys Phe Val Pro Asp
            435                 440                 445

Pro Glu His Phe Arg Lys Thr Thr Asp Asn Pro Phe Lys Ala Leu Gly
    450                 455                 460

Gly Asn Leu Val Asp Met Gly Arg Val Lys Val Ile Ala Gly Leu Leu
465                 470                 475                 480

Arg Lys Asp Asp Gln Glu Ile Ser Ser Thr Ile Arg Ser Ile Glu Gln
                485                 490                 495

Val Phe Lys Leu Val Asp Gln Gly Gly Phe Tyr Gln Asp Gly Ser
            500                 505                 510

Tyr Ile Asp His Thr Asn Val Ala Tyr Thr Gly Ala Tyr Gly Asn Val
            515                 520                 525

Leu Ile Asp Gly Leu Ser Gln Leu Leu Pro Val Ile Gln Lys Thr Lys
            530                 535                 540

Asn Pro Ile Asp Lys Asp Lys Met Gln Thr Met Tyr His Trp Ile Asp
545                 550                 555                 560

Lys Ser Phe Ala Pro Leu Leu Val Asn Gly Glu Leu Met Asp Met Ser
                565                 570                 575

Arg Gly Arg Ser Ile Ser Arg Ala Asn Ser Glu Gly His Val Ala Ala
            580                 585                 590

Val Glu Val Leu Arg Gly Ile His Arg Ile Ala Asp Met Ser Glu Gly
            595                 600                 605

Glu Thr Lys Gln Cys Leu Gln Ser Leu Val Lys Thr Ile Val Gln Ser
            610                 615                 620

Asp Ser Tyr Tyr Asp Val Phe Lys Asn Leu Lys Thr Tyr Lys Asp Ile
625                 630                 635                 640

Ser Leu Met Gln Ser Leu Leu Ser Asp Ala Gly Val Ala Ser Val Pro
                645                 650                 655

Arg Pro Ser Tyr Leu Ser Ala Phe Asn Lys Met Asp Lys Thr Ala Met
            660                 665                 670

Tyr Asn Ala Glu Lys Gly Phe Gly Phe Gly Leu Ser Leu Phe Ser Ser
            675                 680                 685

Arg Thr Leu Asn Tyr Glu His Met Asn Lys Glu Asn Lys Arg Gly Trp
            690                 695                 700

Tyr Thr Ser Asp Gly Met Phe Tyr Leu Tyr Asn Gly Asp Leu Ser His
705                 710                 715                 720

Tyr Ser Asp Gly Tyr Trp Pro Thr Val Asn Pro Tyr Lys Met Pro Gly
                725                 730                 735

Thr Thr Glu Thr Asp Ala Lys Arg Ala Asp Ser Asp Thr Gly Lys Val
            740                 745                 750
```

| | | | | | | | | | | | | |
|---|---|---|---|---|---|---|---|---|---|---|---|---|
|Leu|Pro|Ser|Ala|Phe|Val|Gly|Thr|Ser|Lys|Leu|Asp|Ala|Asn|Ala|
| | |755| | | |760| | | |765| | | | |

Leu Pro Ser Ala Phe Val Gly Thr Ser Lys Leu Asp Ala Asn Ala
            755            760            765

Thr Ala Thr Met Asp Phe Thr Asn Trp Asn Gln Thr Leu Thr Ala His
    770            775            780

Lys Ser Trp Phe Met Leu Lys Asp Lys Ile Ala Phe Leu Gly Ser Asn
785            790            795            800

Ile Gln Asn Thr Ser Thr Asp Thr Ala Ala Thr Thr Ile Asp Gln Arg
            805            810            815

Lys Leu Glu Ser Gly Asn Pro Tyr Lys Val Tyr Val Asn Asp Lys Glu
        820            825            830

Ala Ser Leu Thr Glu Gln Glu Lys Asp Tyr Pro Glu Thr Gln Ser Val
    835            840            845

Phe Leu Glu Ser Phe Asp Ser Lys Lys Asn Ile Gly Tyr Phe Phe Phe
850            855            860

Lys Lys Ser Ser Ile Ser Met Ser Lys Ala Leu Gln Lys Gly Ala Trp
865            870            875            880

Lys Asp Ile Asn Glu Gly Gln Ser Asp Lys Glu Val Glu Asn Glu Phe
        885            890            895

Leu Thr Ile Ser Gln Ala His Lys Gln Asn Arg Asp Ser Tyr Gly Tyr
    900            905            910

Met Leu Ile Pro Asn Val Asp Arg Ala Thr Phe Asn Gln Met Ile Lys
        915            920            925

Glu Leu Glu Ser Ser Leu Ile Glu Asn Asn Glu Thr Leu Gln Ser Val
    930            935            940

Tyr Asp Ala Lys Gln Gly Val Trp Gly Ile Val Lys Tyr Asp Asp Ser
945            950            955            960

Val Ser Thr Ile Ser Asn Gln Phe Gln Val Leu Lys Arg Gly Val Tyr
        965            970            975

Thr Ile Arg Lys Glu Gly Asp Glu Tyr Lys Ile Ala Tyr Tyr Asn Pro
    980            985            990

Glu Thr Gln Glu Ser Ala Pro Asp Gln Glu Val Phe Lys Lys Leu Glu
        995            1000          1005

Gln Ala Ala Gln Pro Gln Val Gln Asn Ser Lys Glu Lys Glu Lys
    1010            1015          1020

Ser Glu Glu Glu Lys Asn His Ser Asp Gln Lys Asn Leu Pro Gln
    1025            1030          1035

Thr Gly Glu Gly Gln Ser Ile Leu Ala Ser Leu Gly Phe Leu Leu
    1040            1045          1050

Leu Gly Ala Phe Tyr Leu Phe Arg Arg Gly Lys Asn Asn
    1055            1060          1065

<210> SEQ ID NO 24
<211> LENGTH: 390
<212> TYPE: DNA
<213> ORGANISM: Streptococcus pneumoniae

<400> SEQUENCE: 24

```
atgaatcaat cctactttta tctaaaaatg aaagaacaca aactcaaggt tccttataca    60
ggtaaggagc gccgtgtacg tattcttctt cctaaagatt atgagaaaga tacagaccgt   120
tcctatcctg ttgtatactt tcatgacggg caaaatgttt taatagcaa  agagtctttc   180 attggacatt catggaagat tatcccagct atcaaacgaa atccggatat cagtcgcatg   240
attgtcgttg ctattgacaa tgatggtatg ggcggatga atgagtatgc ggcttggaag   300
ttccaagaat ctcctatccc agggcagcag tttggtggta agggtgtgga gtatgctgag   360
```

```
tttgtcatgg aggtggtcaa gccttttatc                                      390

<210> SEQ ID NO 25
<211> LENGTH: 900
<212> TYPE: DNA
<213> ORGANISM: Streptococcus pneumoniae

<400> SEQUENCE: 25
atgtcatcta aatttatgaa gagcgctgcg gtgcttggaa ctgctacact tgctagcttg     60
cttttggtag cttgcatgaa tcaatcctac ttttatctaa aaatgaaaga acacaaactc    120
aaggttcctt atacaggtaa ggagcgccgt gtacgtattc ttcttcctaa agattatgag    180
aaagatacag accgttccta tcctgttgta tactttcatg acgggcaaaa tgtttttaat    240
agcaaagagt ctttcattgg acattcatgg aagattatcc cagctatcaa acgaaatccg    300
gatatcagtc gcatgattgt cgttgctatt gacaatgatg gtatggggcg gatgaatgag    360
tatgcggctt ggaagttcca agaatctcct atcccagggc agcagtttgg tggtaagggt    420
gtggagtatg ctgagtttgt catggaggtg gtcaagcctt ttatcgatga gacctatcgt    480
acaaaagcag actgccagca tacggctatg attggttcct cactaggagg caatattacc    540
cagtttatcg gtttggaata ccaagaccaa attggttgct gggcgttttt ttcatctgca    600
aactggctcc accaagaagc ctttaaccgc tatttcgagt gccagaaact atcgcctgac    660
cagcgcatct tcatctatgt aggaacagaa gaagcagatg atacagacaa gaccttgatg    720
gatggcaata tcaaacaagc ctatatcgac tcgtcgcttt gctattacca tgatttgata    780 gcaggggag tacatctgga taatcttgtg ctaaaagttc agtctggtgc catccatagt    840
gaaatccctt ggtcagaaaa tctaccagat tgtctgagat tttttgcaga aaaatggtaa    900

<210> SEQ ID NO 26
<211> LENGTH: 465
<212> TYPE: DNA
<213> ORGANISM: Streptococcus pneumoniae

<400> SEQUENCE: 26
atgtcatcta aatttatgaa gagcgctgcg gtgcttggaa ctgctacact tgctagcttg     60
cttttggtag cttgcatgaa tcaatcctac ttttatctaa aaatgaaaga acacaaactc    120
aaggttcctt atacaggtaa ggagcgccgt gtacgtattc ttcttcctaa agattatgag    180
aaagatacag accgttccta tcctgttgta tactttcatg acgggcaaaa tgtttttaat    240
agcaaagagt ctttcattgg acattcatgg aagattatcc cagctatcaa acgaaatccg    300
gatatcagtc gcatgattgt cgttgctatt gacaatgatg gtatggggcg gatgaatgag    360
tatgcggctt ggaagttcca agaatctcct atcccagggc agcagtttgg tggtaagggt    420
gtggagtatg ctgagtttgt catggaggtg gtcaagcctt ttatc                    465

<210> SEQ ID NO 27
<211> LENGTH: 765
<212> TYPE: DNA
<213> ORGANISM: Streptococcus pneumoniae

<400> SEQUENCE: 27
atgtgctcag ggggtgctaa gaaagaagga gaagcagcta gcaagaaaga aatcatcgtt     60
gcaaccaatg gatcaccaaa gccatttatc tatgaagaaa atggcgaatt gactggttac    120
gagattgaag tcgttcgcgc tatctttaaa gattctgaca aatatgatgt caagtttgaa    180
```

| aagacagaat ggtcaggtgt cttttgctggt cttgacgctg atcgttacaa tatggctgtc | 240 |
| aacaatctta gctacactaa agaacgtgcg gagaaatacc tctatgccgc accaattgcc | 300 |
| caaaatccta atgtccttgt cgtgaagaaa gatgactcta gtatcaagtc tctcgatgat | 360 |
| atcggtggaa aatcgacgga agtcgttcaa gccactacat cagctaagca gttagaagca | 420 |
| tacaatgctg aacacacgga caacccaact atccttaact atactaaggc agacttccaa | 480 |
| caaatcatgg tacgtttgag cgatggacaa tttgactata agattttga taaaatcggt | 540 |
| gttgaaacag tgatcaagaa ccaaggtttg gacaacttga agttatcga acttccaagc | 600 |
| gaccaacaac cgtacgttta cccacttctt gctcagggtc aagatgagtt gaaatcgttt | 660 |
| gtagacaaac gcatcaaaga actttataaa gatggaactc ttgaaaaatt gtctaaacaa | 720 |
| ttcttcggag acacttatct accggcagaa gctgatatta aataa | 765 |

<210> SEQ ID NO 28
<211> LENGTH: 831
<212> TYPE: DNA
<213> ORGANISM: Streptococcus pneumoniae

<400> SEQUENCE: 28

| atgaaaaaaa tcgttaaata ctcatctctt gcagcccttg ctcttgttgc tgcaggtgtg | 60 |
| cttgcggctt gctcaggggg tgctaagaaa gaaggagaag cagctagcaa gaaagaaatc | 120 |
| atcgttgcaa ccaatggatc accaaagcca tttatctatg aagaaaatgg cgaattgact | 180 |
| ggttacgaga ttgaagtcgt tcgcgctatc tttaaagatt ctgacaaata tgatgtcaag | 240 |
| tttgaaaaga cagaatggtc aggtgtcttt gctggtcttg acgctgatcg ttacaatatg | 300 |
| gctgtcaaca atcttagcta cactaaagaa cgtgcggaga atacctcta tgccgcacca | 360 |
| attgcccaaa atcctaatgt ccttgtcgtg aagaaagatg actctagtat caagtctctc | 420 |
| gatgatatcg gtggaaaatc gacggaagtc gttcaagcca ctacatcagc taagcagtta | 480 |
| gaagcataca atgctgaaca cacggacaac ccaactatcc ttaactatac taaggcagac | 540 |
| ttccaacaaa tcatggtacg tttgagcgat ggacaatttg actataagat ttttgataaa | 600 |
| atcggtgttg aaacagtgat caagaaccaa ggtttggaca acttgaaagt tatcgaactt | 660 |
| ccaagcgacc aacaaccgta cgtttaccca cttcttgctc agggtcaaga tgagttgaaa | 720 |
| tcgtttgtag acaaacgcat caaagaactt tataaagatg gaactcttga aaaattgtct | 780 |
| aaacaattct tcggagacac ttatctaccg gcagaagctg atattaaata a | 831 |

<210> SEQ ID NO 29
<211> LENGTH: 1203
<212> TYPE: DNA
<213> ORGANISM: Streptococcus pneumoniae

<400> SEQUENCE: 29

| atgtgcggaa gcaaaactgc tgataagcct gctgattctg gttcatctga agtcaaagaa | 60 |
| ctcactgtat atgtagacga gggatataag agctatattg aagaggttgc taagcttat | 120 |
| gaaaaagaag ctggagtaaa agtcactctt aaaactggtg atgctctagg aggtcttgat | 180 |
| aaactttctc ttgacaacca atctggtaat gtccctgatg ttatgatggc tccatacgac | 240 |
| cgtgtaggta gccttggttc tgacggacaa cttcagaag tgaaattgag cgatggtgct | 300 |
| aaaacagacg acacaactaa atctcttgta acagctgcta atggtaaagt ttacggtgct | 360 |
| cctgccgtta tcgagtcact tgttatgtac tacaacaaag acttggtgaa agatgctcca | 420 |
| aaaacatttg ctgacttgga aaaccttgct aaagatagca aatacgcatt cgctggtgaa | 480 |

```
gatggtaaaa ctactgcctt cctagctgac tggacaaact tctactatac atatggactt      540
cttgccggta acggtgctta cgtctttggc caaaacggta agacgctaa  agacatcggt      600 cttgcaaacg acggttctat cgtaggtatc aactacgcta atcttggta  cgaaaaatgg     660 cctaaaggta tgcaagatac agaaggtgct ggaaacttaa tccaaactca attccaagaa     720
ggtaaaacag ctgctatcat cgacggacct tggaaagctc aagcctttaa agatgctaaa     780
gtaaactacg gagttgcaac tatcccaact cttccaaatg gaaagaata  tgctgcattc    840 ggtggtggta aagcttgggt cattcctcaa gccgttaaga accttgaagc ttctcaaaaa     900
tttgtagact tccttgttgc aactgaacaa caaaaagtat tatatgataa gactaacgaa     960
atcccagcta atactgaggc tcgttcatac gctgaaggta aaaacgatga gttgacaaca    1020
gctgttatca acagttcaa  gaacactcaa ccactgccaa acatctctca aatgtctgca    1080
gtttgggatc cagcgaaaaa tatgctcttt gatgctgtaa gtggtcaaaa agatgctaaa    1140
acagctgcta acgatgctgt aacattgatc aaagaaacaa tcaaacaaaa atttggtgaa    1200
taa                                                                   1203

<210> SEQ ID NO 30
<211> LENGTH: 1944
<212> TYPE: DNA
<213> ORGANISM: Streptococcus pneumoniae

<400> SEQUENCE: 30
atgtcaggaa ctagtatggc gactccaatc gtggcagctt ctactgtttt gattagaccg      60
aaattaaagg aaatgcttga agacctgta  ttgaaaaatc ttaagggaga tgacaaaata     120
gatcttacaa gtcttacaaa aattgcccta caaaatactg cgcgacctat gatggatgca     180
acttcttgga agaaaaaag  tcaatacttt gcatcaccta gacaacaggg agcaggccta     240
attaatgtgg ccaatgcttt gagaaatgaa gttgtagcaa cttttcaaaaa cactgattct     300 aaaggttttgg taaactcata tggttccatt tctcttaaag aaataaaagg tgataaaaaa    360
tactttacaa tcaagcttca caatacatca aacagacctt tgacttttaa agtttcagca     420
tcagcgataa ctacagattc tctaactgac agattaaaac ttgatgaaac atataaagat     480
gaaaaatctc cagatggtaa gcaaattgtt ccagaaattc acccagaaaa agtcaaagga     540
gcaaatatca catttgagca tgatactttc actataggcg caaattctag ctttgatttg     600
aatgcggtta taaatgttgg agaggccaaa aacaaaaata aatttgtaga atcatttatt     660
cattttgagt cagtggaaga atggaagct  ctaaactcca acgggaagaa aataaacttc     720
caaccttctt tgtcgatgcc tctaatggga tttgctggga attggaacca cgaaccaatc     780
cttgataaat gggcttggga agaagggtca agatcaaaaa cactgggagg ttatgatgat     840
gatggtaaac cgaaaattcc aggaaccta  aataagggaa ttggtggaga acatggtata     900
gataaattta atccagcagg agttataca  aatagaaaag ataaaaatac aacatccctg     960
gatcaaaatc cagaattatt tgctttcaat aacgaaggga tcaacgctcc atcatcaagt    1020
ggttctaaga ttgctaacat ttatccttta gattcaaatg gaaatcctca agatgctcaa    1080
cttgaaagag gattaacacc ttctccactt gtattaagaa gtgcagaaga aggattgatt    1140
tcaatagtaa atacaaataa agagggagaa atcaaagag  acttaaaagt catttcgaga    1200 gaacactta  ttagaggaat tttaaattct aaaagcaatg atgcaagggg aatcaaatca    1260
tctaaactaa aagtttgggg tgacttgaag tgggatggac tcatctataa tcctagaggt    1320
```

-continued

| | |
|---|---|
| agagaagaaa atgcaccaga aagtaaggat aatcaagatc ctgctactaa gataagaggt | 1380 |
| caatttgaac cgattgcgga aggtcaatat ttctataaat ttaaatatag attaactaaa | 1440 |
| gattacccat ggcaggtttc ctatattcct gtaaaaattg ataacaccgc ccctaagatt | 1500 |
| gtttcggttg attttccaaa tcctgaaaaa attaagttga ttacaaagga tacttatcat | 1560 |
| aaggtaaaag atcagtataa gaatgaaacg ctatttgcga gagatcaaaa agaacatcct | 1620 |
| gaaaaatttg acgagattgc gaacgaagtt tggtatgctg cgccgctct tgttaatgaa | 1680 |
| gatggagagg ttgaaaaaaa tcttgaagta acttacgcag gtgagggtca aggaagaaat | 1740 |
| agaaaacttg ataagacgg aaataccatt tatgaaatta aggtgcggg agatttaagg | 1800 |
| ggaaaaatca ttgaagtcat tgcattagat ggttctagca atttcacaaa gattcataga | 1860 |
| attaaatttg ctaatcaggc tgatgaaaag gggatgattt cctattatct agtagatcct | 1920 |
| gatcaagatt catctaaata tcaa | 1944 |

<210> SEQ ID NO 31
<211> LENGTH: 1986
<212> TYPE: DNA
<213> ORGANISM: Streptococcus pneumoniae

<400> SEQUENCE: 31

| | |
|---|---|
| atggtagtct tagcagacac atctagctct gaagatgctt taaacatctc tgataaagaa | 60 |
| aaagtagcag aaaataaaga gaaacatgaa aatatcccata gtgctatgga aacttcacag | 120 |
| gattttaaag agaagaaaac agcagtcatt aaggaaaaag aagttgttag taaaaatcct | 180 |
| gtgatagaca ataacactag caatgaagaa gcaaaaatca agaagaaaa ttccaataaa | 240 |
| tcccaaggag attatacgga ctcatttgtg aataaaaaca cagaaaatcc caaaaaagaa | 300 |
| gataaagttg tctatattgc tgaatttaaa gataaagaat ctggagaaaa agcaatcaag | 360 |
| gaactatcca gtcttaagaa tacaaaagtt ttatatactt atgatagaat ttttaacggt | 420 |
| agtgccatag aaacaactcc agataacttg gacaaaatta acaaataga aggtatttca | 480 |
| tcggttgaaa gggcacaaaa agtccaaccc atgatgaatc atgccagaaa ggaaattgga | 540 |
| gttgaggaag ctattgatta cctaaagtct atcaatgctc cgtttgggaa aaattttgat | 600 |
| ggtagaggta tggtcatttc aaatatcgat actggaacag attatagaca taaggctatg | 660 |
| agaatcgatg atgatgccaa agcctcaatg agatttaaaa aagaagactt aaaaggcact | 720 |
| gataaaaatt attggttgag tgataaaatc cctcatgcgt tcaattatta taatggtggc | 780 |
| aaaatcactg tagaaaaata tgatgatgga agggattatt ttgacccaca tgggatgcat | 840 |
| attgcaggga ttcttgctgg aaatgatact gaacaagaca tcaaaaactt aacggcata | 900 |
| gatggaattg cacctaatgc acaaattttc tcttacaaaa tgtattctga cgcaggatct | 960 |
| gggtttgcgg gtgatgaaac aatgtttcat gctattgaag attctatcaa acacaacgtt | 1020 |
| gatgttgttt cggtatcatc tggttttaca ggaacaggtc ttgtaggtga aaatattgg | 1080 |
| caagctattc gggcattaag aaaagcaggc attccaatgg ttgtcgctac gggtaactat | 1140 |
| gcgacttctg cttcaagttc ttcatgggat ttagtagcaa ataatcatct gaaaatgacc | 1200 |
| gacactggaa atgtaacacg aactgcagca catgaagatg cgatagcggt cgcttctgct | 1260 |
| aaaaatcaaa cagttgagtt tgataaagtt aacataggtg gagaaagttt taaatacaga | 1320 |
| aatataggg cctttttcga taagagtaaa atcacaacaa atgaagatgg aacaaaagct | 1380 |
| cctagtaaat taaatttgt atatataggc aaggggcaag accaagattt gataggtttg | 1440 |
| gatcttaggg gcaaaattgc agtaatggat agaatttata caaggatttt aaaaaatgct | 1500 |

```
tttaaaaaag ctatggataa gggtgcacgc gccattatgg ttgtaaatac tgtaaattac    1560
tacaatagag ataattggac agagcttcca gctatgggat atgaagcgga tgaaggtact    1620
aaaagtcaag tgttttcaat ttcaggagat gatggtgtaa agctatggaa catgattaat    1680
cctgataaaa aaactgaagt caaaagaaat aataaagaag attttaaaga taaattggag    1740
caatactatc caattgatat ggaaagtttt aattccaaca aaccgaatgt aggtgacgaa    1800
aaagagattg actttaagtt tgcacctgac acagacaaag aactctataa agaagatatc    1860
atcgttccag caggatctac atcttggggg ccaagaatag atttactttt aaaacccgat    1920
gtttcagcac ctggtaaaaa tattaaatcc acgcttaatg ttattaatgg caaatcaact    1980
tatggc                                                              1986
```

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 32

His His His His His His
1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Ser Tyr Tyr His His His His His His
1               5                   10

<210> SEQ ID NO 34
<211> LENGTH: 9
<212> TYPE: PRT
<213> ORGANISM: Streptococcus pneumoniae

<400> SEQUENCE: 34

Ala Ile Ile Asp Gly Pro Trp Lys Ala
1               5

<210> SEQ ID NO 35
<211> LENGTH: 9
<212> TYPE: PRT
<213> ORGANISM: Streptococcus pneumoniae

<400> SEQUENCE: 35

Val Met Met Ala Pro Tyr Asp Arg Val
1               5

<210> SEQ ID NO 36
<211> LENGTH: 9
<212> TYPE: PRT
<213> ORGANISM: Streptococcus pneumoniae

<400> SEQUENCE: 36

Ser Ile Ala Gly Ile Asn Tyr Ala Lys
1               5

<210> SEQ ID NO 37
<211> LENGTH: 9
<212> TYPE: PRT
<213> ORGANISM: Streptococcus pneumoniae

<400> SEQUENCE: 37

Val Trp Asp Pro Ala Lys Asn Met Leu
1               5

<210> SEQ ID NO 38
<211> LENGTH: 9
<212> TYPE: PRT
<213> ORGANISM: Streptococcus pneumoniae

<400> SEQUENCE: 38

Gln Pro Leu Pro Asn Ile Ser Gln Met
1               5

<210> SEQ ID NO 39
<211> LENGTH: 9
<212> TYPE: PRT
<213> ORGANISM: Streptococcus pneumoniae

<400> SEQUENCE: 39

Ala Pro Tyr Asp Arg Val Gly Ser Leu
1               5

<210> SEQ ID NO 40
<211> LENGTH: 9
<212> TYPE: PRT
<213> ORGANISM: Streptococcus pneumoniae

<400> SEQUENCE: 40

Ala Pro Ala Val Ile Glu Ser Leu Val
1               5

<210> SEQ ID NO 41
<211> LENGTH: 9
<212> TYPE: PRT
<213> ORGANISM: Streptococcus pneumoniae

<400> SEQUENCE: 41

Phe Tyr Tyr Thr Tyr Gly Leu Leu Ala
1               5

<210> SEQ ID NO 42
<211> LENGTH: 8
<212> TYPE: PRT
<213> ORGANISM: Streptococcus pneumoniae

<400> SEQUENCE: 42

Ser Lys Tyr Ala Phe Ala Gly Glu
1               5

<210> SEQ ID NO 43
<211> LENGTH: 8
<212> TYPE: PRT
<213> ORGANISM: Streptococcus pneumoniae

<400> SEQUENCE: 43

Thr Glu Gly Ala Gly Asn Leu Ile
1               5

-continued

```
<210> SEQ ID NO 44
<211> LENGTH: 9
<212> TYPE: PRT
<213> ORGANISM: Streptococcus pneumoniae

<400> SEQUENCE: 44

Leu Ala Asp Trp Thr Asn Phe Tyr Tyr
1               5

<210> SEQ ID NO 45
<211> LENGTH: 9
<212> TYPE: PRT
<213> ORGANISM: Streptococcus pneumoniae

<400> SEQUENCE: 45

Ser Leu Val Met Tyr Tyr Asn Lys Asp
1               5

<210> SEQ ID NO 46
<211> LENGTH: 9
<212> TYPE: PRT
<213> ORGANISM: Streptococcus pneumoniae

<400> SEQUENCE: 46

Lys Glu Ala Gly Val Lys Val Thr Leu
1               5

<210> SEQ ID NO 47
<211> LENGTH: 9
<212> TYPE: PRT
<213> ORGANISM: Streptococcus pneumoniae

<400> SEQUENCE: 47

Lys Ser Thr Ala Val Leu Gly Thr Val
1               5

<210> SEQ ID NO 48
<211> LENGTH: 9
<212> TYPE: PRT
<213> ORGANISM: Streptococcus pneumoniae

<400> SEQUENCE: 48

Gly Ala Lys Thr Asp Asp Thr Thr Lys
1               5

<210> SEQ ID NO 49
<211> LENGTH: 9
<212> TYPE: PRT
<213> ORGANISM: Streptococcus pneumoniae

<400> SEQUENCE: 49

Ser Gln Lys Phe Val Asp Phe Leu Val
1               5

<210> SEQ ID NO 50
<211> LENGTH: 9
<212> TYPE: PRT
<213> ORGANISM: Streptococcus pneumoniae

<400> SEQUENCE: 50

Gln Ala Phe Lys Asp Ala Lys Val Asn
1               5

<210> SEQ ID NO 51
<211> LENGTH: 9
```

```
<212> TYPE: PRT
<213> ORGANISM: Streptococcus pneumoniae

<400> SEQUENCE: 51

Ala Val Ile Glu Ser Leu Val Met Tyr
1               5

<210> SEQ ID NO 52
<211> LENGTH: 9
<212> TYPE: PRT
<213> ORGANISM: Streptococcus pneumoniae

<400> SEQUENCE: 52

Asp Ala Lys Thr Ala Ala Asn Asp Ala
1               5

<210> SEQ ID NO 53
<211> LENGTH: 9
<212> TYPE: PRT
<213> ORGANISM: Streptococcus pneumoniae

<400> SEQUENCE: 53

Tyr Gly Val Ala Thr Ile Pro Thr Leu
1               5

<210> SEQ ID NO 54
<211> LENGTH: 9
<212> TYPE: PRT
<213> ORGANISM: Streptococcus pneumoniae

<400> SEQUENCE: 54

Lys Thr Ala Ala Ile Ile Asp Gly Pro
1               5

<210> SEQ ID NO 55
<211> LENGTH: 9
<212> TYPE: PRT
<213> ORGANISM: Streptococcus pneumoniae

<400> SEQUENCE: 55

Lys Ala Tyr Glu Lys Glu Ala Gly Val
1               5

<210> SEQ ID NO 56
<211> LENGTH: 9
<212> TYPE: PRT
<213> ORGANISM: Streptococcus pneumoniae

<400> SEQUENCE: 56

Ala Gly Asn Gly Ala Tyr Val Phe Gly
1               5

<210> SEQ ID NO 57
<211> LENGTH: 9
<212> TYPE: PRT
<213> ORGANISM: Streptococcus pneumoniae

<400> SEQUENCE: 57

Ala Trp Val Ile Pro Gln Ala Val Lys
1               5

<210> SEQ ID NO 58
<211> LENGTH: 9
<212> TYPE: PRT
<213> ORGANISM: Streptococcus pneumoniae
```

```
<400> SEQUENCE: 58

Ala Leu Gly Leu Val Ala Ala Gly Val
1               5

<210> SEQ ID NO 59
<211> LENGTH: 9
<212> TYPE: PRT
<213> ORGANISM: Streptococcus pneumoniae

<400> SEQUENCE: 59

Glu Leu Thr Gly Tyr Glu Ile Glu Val
1               5

<210> SEQ ID NO 60
<211> LENGTH: 9
<212> TYPE: PRT
<213> ORGANISM: Streptococcus pneumoniae

<400> SEQUENCE: 60

Ala Val Asn Asn Leu Ser Tyr Thr Lys
1               5

<210> SEQ ID NO 61
<211> LENGTH: 9
<212> TYPE: PRT
<213> ORGANISM: Streptococcus pneumoniae

<400> SEQUENCE: 61

Thr Tyr Leu Pro Ala Glu Ala Asp Ile
1               5

<210> SEQ ID NO 62
<211> LENGTH: 9
<212> TYPE: PRT
<213> ORGANISM: Streptococcus pneumoniae

<400> SEQUENCE: 62

Arg Tyr Asn Met Ala Val Asn Asn Leu
1               5

<210> SEQ ID NO 63
<211> LENGTH: 9
<212> TYPE: PRT
<213> ORGANISM: Streptococcus pneumoniae

<400> SEQUENCE: 63

Asp Phe Gln Gln Ile Met Val Arg Leu
1               5

<210> SEQ ID NO 64
<211> LENGTH: 9
<212> TYPE: PRT
<213> ORGANISM: Streptococcus pneumoniae

<400> SEQUENCE: 64

Glu His Thr Asp Asn Pro Thr Ile Leu
1               5

<210> SEQ ID NO 65
<211> LENGTH: 9
<212> TYPE: PRT
<213> ORGANISM: Streptococcus pneumoniae

<400> SEQUENCE: 65
```

```
Ala Pro Ile Ala Gln Asn Pro Asn Val
1               5

<210> SEQ ID NO 66
<211> LENGTH: 9
<212> TYPE: PRT
<213> ORGANISM: Streptococcus pneumoniae

<400> SEQUENCE: 66

Leu Pro Ser Asp Gln Gln Pro Tyr Val
1               5

<210> SEQ ID NO 67
<211> LENGTH: 9
<212> TYPE: PRT
<213> ORGANISM: Streptococcus pneumoniae

<400> SEQUENCE: 67

Tyr Val Tyr Pro Leu Leu Ala Gln Gly
1               5

<210> SEQ ID NO 68
<211> LENGTH: 9
<212> TYPE: PRT
<213> ORGANISM: Streptococcus pneumoniae

<400> SEQUENCE: 68

Gln Gly Leu Asp Asn Leu Lys Val Ile
1               5

<210> SEQ ID NO 69
<211> LENGTH: 8
<212> TYPE: PRT
<213> ORGANISM: Streptococcus pneumoniae

<400> SEQUENCE: 69

Lys Tyr Leu Tyr Ala Ala Pro Ile
1               5

<210> SEQ ID NO 70
<211> LENGTH: 8
<212> TYPE: PRT
<213> ORGANISM: Streptococcus pneumoniae

<400> SEQUENCE: 70

Gly Glu Leu Thr Gly Tyr Glu Ile
1               5

<210> SEQ ID NO 71
<211> LENGTH: 9
<212> TYPE: PRT
<213> ORGANISM: Streptococcus pneumoniae

<400> SEQUENCE: 71

Asn Pro Asn Val Leu Val Val Lys Lys
1               5

<210> SEQ ID NO 72
<211> LENGTH: 9
<212> TYPE: PRT
<213> ORGANISM: Streptococcus pneumoniae

<400> SEQUENCE: 72

Lys Leu Ser Lys Gln Phe Phe Gly Asp
```

```
1               5

<210> SEQ ID NO 73
<211> LENGTH: 9
<212> TYPE: PRT
<213> ORGANISM: Streptococcus pneumoniae

<400> SEQUENCE: 73

Gly Ser Pro Arg Pro Phe Ile Tyr Glu
1               5

<210> SEQ ID NO 74
<211> LENGTH: 9
<212> TYPE: PRT
<213> ORGANISM: Streptococcus pneumoniae

<400> SEQUENCE: 74

Ala Val Asn Asn Leu Ser Tyr Thr Lys
1               5

<210> SEQ ID NO 75
<211> LENGTH: 9
<212> TYPE: PRT
<213> ORGANISM: Streptococcus pneumoniae

<400> SEQUENCE: 75

Lys Ile Phe Asp Lys Ile Gly Val Glu
1               5

<210> SEQ ID NO 76
<211> LENGTH: 9
<212> TYPE: PRT
<213> ORGANISM: Streptococcus pneumoniae

<400> SEQUENCE: 76

Met Val Arg Leu Ser Asp Gly Gln Phe
1               5

<210> SEQ ID NO 77
<211> LENGTH: 9
<212> TYPE: PRT
<213> ORGANISM: Streptococcus pneumoniae

<400> SEQUENCE: 77

Tyr Val Tyr Pro Leu Leu Ala Gln Gly
1               5

<210> SEQ ID NO 78
<211> LENGTH: 9
<212> TYPE: PRT
<213> ORGANISM: Streptococcus pneumoniae

<400> SEQUENCE: 78

Val Val Gln Ala Thr Thr Ser Ala Lys
1               5

<210> SEQ ID NO 79
<211> LENGTH: 9
<212> TYPE: PRT
<213> ORGANISM: Streptococcus pneumoniae

<400> SEQUENCE: 79

Thr Leu Glu Lys Leu Ser Lys Gln Phe
1               5
```

<210> SEQ ID NO 80
<211> LENGTH: 9
<212> TYPE: PRT
<213> ORGANISM: Streptococcus pneumoniae

<400> SEQUENCE: 80

Val Ala Ala Gly Val Leu Ala Ala Cys
1               5

<210> SEQ ID NO 81
<211> LENGTH: 9
<212> TYPE: PRT
<213> ORGANISM: Streptococcus pneumoniae

<400> SEQUENCE: 81

Leu Asp Asn Leu Lys Val Ile Glu Leu
1               5

<210> SEQ ID NO 82
<211> LENGTH: 9
<212> TYPE: PRT
<213> ORGANISM: Streptococcus pneumoniae

<400> SEQUENCE: 82

Asn Met Ala Val Asn Asn Leu Ser Tyr
1               5

<210> SEQ ID NO 83
<211> LENGTH: 9
<212> TYPE: PRT
<213> ORGANISM: Streptococcus pneumoniae

<400> SEQUENCE: 83

Arg Leu Leu Asp Leu Ala Pro Gln Val
1               5

<210> SEQ ID NO 84
<211> LENGTH: 9
<212> TYPE: PRT
<213> ORGANISM: Streptococcus pneumoniae

<400> SEQUENCE: 84

Met Leu Glu Ile Pro Ala His Gln Ile
1               5

<210> SEQ ID NO 85
<211> LENGTH: 9
<212> TYPE: PRT
<213> ORGANISM: Streptococcus pneumoniae

<400> SEQUENCE: 85

Lys Asn Phe Phe Ala His His Pro Lys
1               5

<210> SEQ ID NO 86
<211> LENGTH: 9
<212> TYPE: PRT
<213> ORGANISM: Streptococcus pneumoniae

<400> SEQUENCE: 86

Lys Val Ile Leu Ala Gly His Ser Lys
1               5

<210> SEQ ID NO 87

```
<211> LENGTH: 9
<212> TYPE: PRT
<213> ORGANISM: Streptococcus pneumoniae

<400> SEQUENCE: 87

Ser Phe Asp Asn Leu Val Ser Thr Leu
1               5

<210> SEQ ID NO 88
<211> LENGTH: 9
<212> TYPE: PRT
<213> ORGANISM: Streptococcus pneumoniae

<400> SEQUENCE: 88

Tyr Tyr Asp Leu Pro Leu Asn Glu Leu
1               5

<210> SEQ ID NO 89
<211> LENGTH: 9
<212> TYPE: PRT
<213> ORGANISM: Streptococcus pneumoniae

<400> SEQUENCE: 89

Tyr Phe Asp Leu Phe Phe Gly Thr Ile
1               5

<210> SEQ ID NO 90
<211> LENGTH: 9
<212> TYPE: PRT
<213> ORGANISM: Streptococcus pneumoniae

<400> SEQUENCE: 90

Ala Leu Glu Tyr Ile His His Leu Phe
1               5

<210> SEQ ID NO 91
<211> LENGTH: 9
<212> TYPE: PRT
<213> ORGANISM: Streptococcus pneumoniae

<400> SEQUENCE: 91

Leu Pro Leu Asn Glu Leu Asp Ile Leu
1               5

<210> SEQ ID NO 92
<211> LENGTH: 9
<212> TYPE: PRT
<213> ORGANISM: Streptococcus pneumoniae

<400> SEQUENCE: 92

Ile Pro Gln Gly Ser Ile Ile Gly Met
1               5

<210> SEQ ID NO 93
<211> LENGTH: 9
<212> TYPE: PRT
<213> ORGANISM: Streptococcus pneumoniae

<400> SEQUENCE: 93

Asp Pro Glu Leu Gln Lys Gln Phe Ala
1               5

<210> SEQ ID NO 94
<211> LENGTH: 9
<212> TYPE: PRT
```

```
<213> ORGANISM: Streptococcus pneumoniae

<400> SEQUENCE: 94

Ala Val Tyr Thr Phe Asp Ala Pro Gly
1               5

<210> SEQ ID NO 95
<211> LENGTH: 9
<212> TYPE: PRT
<213> ORGANISM: Streptococcus pneumoniae

<400> SEQUENCE: 95

Gln Ser Leu Thr Pro Glu Glu Arg Glu
1               5

<210> SEQ ID NO 96
<211> LENGTH: 8
<212> TYPE: PRT
<213> ORGANISM: Streptococcus pneumoniae

<400> SEQUENCE: 96

Ala Ile Tyr Ala Ala Ser Gln Ile
1               5

<210> SEQ ID NO 97
<211> LENGTH: 8
<212> TYPE: PRT
<213> ORGANISM: Streptococcus pneumoniae

<400> SEQUENCE: 97

Leu Glu Ile Pro Ala His Gln Ile
1               5

<210> SEQ ID NO 98
<211> LENGTH: 9
<212> TYPE: PRT
<213> ORGANISM: Streptococcus pneumoniae

<400> SEQUENCE: 98

Leu Leu Asp Leu Ala Pro Gln Val Pro
1               5

<210> SEQ ID NO 99
<211> LENGTH: 9
<212> TYPE: PRT
<213> ORGANISM: Streptococcus pneumoniae

<400> SEQUENCE: 99

Trp Gln Ile Glu Asp Lys His Phe Val
1               5

<210> SEQ ID NO 100
<211> LENGTH: 9
<212> TYPE: PRT
<213> ORGANISM: Streptococcus pneumoniae

<400> SEQUENCE: 100

Thr Leu Gly Arg Leu Thr Gln Leu Leu
1               5

<210> SEQ ID NO 101
<211> LENGTH: 9
<212> TYPE: PRT
<213> ORGANISM: Streptococcus pneumoniae
```

```
<400> SEQUENCE: 101

Leu Tyr Phe Asp Leu Phe Phe Gly Thr
1               5

<210> SEQ ID NO 102
<211> LENGTH: 9
<212> TYPE: PRT
<213> ORGANISM: Streptococcus pneumoniae

<400> SEQUENCE: 102

Ser Ile Asn Asp Leu Ala Ser Leu Lys
1               5

<210> SEQ ID NO 103
<211> LENGTH: 9
<212> TYPE: PRT
<213> ORGANISM: Streptococcus pneumoniae

<400> SEQUENCE: 103

Ser Ile Asn Asp Leu Ala Ser Leu Lys
1               5

<210> SEQ ID NO 104
<211> LENGTH: 9
<212> TYPE: PRT
<213> ORGANISM: Streptococcus pneumoniae

<400> SEQUENCE: 104

Tyr Tyr Asp Leu Pro Leu Asn Glu Leu
1               5

<210> SEQ ID NO 105
<211> LENGTH: 9
<212> TYPE: PRT
<213> ORGANISM: Streptococcus pneumoniae

<400> SEQUENCE: 105

Gln Lys Val Ile Leu Ala Gly His Ser
1               5

<210> SEQ ID NO 106
<211> LENGTH: 9
<212> TYPE: PRT
<213> ORGANISM: Streptococcus pneumoniae

<400> SEQUENCE: 106

Gly Thr Asp Asp Ser Ile Ile Gly Trp
1               5

<210> SEQ ID NO 107
<211> LENGTH: 9
<212> TYPE: PRT
<213> ORGANISM: Streptococcus pneumoniae

<400> SEQUENCE: 107

Thr Tyr Leu Ser Phe Asp Asn Leu Val
1               5

<210> SEQ ID NO 108
<211> LENGTH: 9
<212> TYPE: PRT
<213> ORGANISM: Streptococcus pneumoniae

<400> SEQUENCE: 108
```

```
Phe Gly Thr Ile Leu Asp Ala Gly Ile
1               5

<210> SEQ ID NO 109
<211> LENGTH: 9
<212> TYPE: PRT
<213> ORGANISM: Streptococcus pneumoniae

<400> SEQUENCE: 109

Asn Gln Ile Thr Ala Val Tyr Thr Phe
1               5

<210> SEQ ID NO 110
<211> LENGTH: 9
<212> TYPE: PRT
<213> ORGANISM: Streptococcus pneumoniae

<400> SEQUENCE: 110

His Leu Asp Asn Leu Val Leu Lys Val
1               5

<210> SEQ ID NO 111
<211> LENGTH: 9
<212> TYPE: PRT
<213> ORGANISM: Streptococcus pneumoniae

<400> SEQUENCE: 111

Asp Leu Ile Ala Gly Arg Val His Leu
1               5

<210> SEQ ID NO 112
<211> LENGTH: 9
<212> TYPE: PRT
<213> ORGANISM: Streptococcus pneumoniae

<400> SEQUENCE: 112

Ile Leu Leu Pro Lys Asp Tyr Glu Lys
1               5

<210> SEQ ID NO 113
<211> LENGTH: 9
<212> TYPE: PRT
<213> ORGANISM: Streptococcus pneumoniae

<400> SEQUENCE: 113

Glu Tyr Gln Asp Gln Ile Gly Cys Leu
1               5

<210> SEQ ID NO 114
<211> LENGTH: 9
<212> TYPE: PRT
<213> ORGANISM: Streptococcus pneumoniae

<400> SEQUENCE: 114

Tyr Phe His Asp Gly Gln Asn Val Phe
1               5

<210> SEQ ID NO 115
<211> LENGTH: 9
<212> TYPE: PRT
<213> ORGANISM: Streptococcus pneumoniae

<400> SEQUENCE: 115

Asn Pro Asp Ile Ser Arg Met Ile Val
1               5
```

```
<210> SEQ ID NO 116
<211> LENGTH: 9
<212> TYPE: PRT
<213> ORGANISM: Streptococcus pneumoniae

<400> SEQUENCE: 116

Ile Pro Trp Ser Glu Asn Leu Pro Asp
1               5

<210> SEQ ID NO 117
<211> LENGTH: 9
<212> TYPE: PRT
<213> ORGANISM: Streptococcus pneumoniae

<400> SEQUENCE: 117

Gln Phe Gly Gly Lys Gly Val Glu Tyr
1               5

<210> SEQ ID NO 118
<211> LENGTH: 9
<212> TYPE: PRT
<213> ORGANISM: Streptococcus pneumoniae

<400> SEQUENCE: 118

Ile Gly Leu Glu Tyr Gln Asp Gln Ile
1               5

<210> SEQ ID NO 119
<211> LENGTH: 8
<212> TYPE: PRT
<213> ORGANISM: Streptococcus pneumoniae

<400> SEQUENCE: 119

Val Tyr Phe His Asp Gly Gln Asn
1               5

<210> SEQ ID NO 120
<211> LENGTH: 8
<212> TYPE: PRT
<213> ORGANISM: Streptococcus pneumoniae

<400> SEQUENCE: 120

Met Glu Val Val Lys Pro Phe Ile
1               5

<210> SEQ ID NO 121
<211> LENGTH: 9
<212> TYPE: PRT
<213> ORGANISM: Streptococcus pneumoniae

<400> SEQUENCE: 121

Tyr Leu Lys Met Lys Glu His Lys Leu
1               5

<210> SEQ ID NO 122
<211> LENGTH: 9
<212> TYPE: PRT
<213> ORGANISM: Streptococcus pneumoniae

<400> SEQUENCE: 122

Lys Leu Ser Pro Asp Gln Arg Ile Phe
1               5
```

-continued

<210> SEQ ID NO 123
<211> LENGTH: 9
<212> TYPE: PRT
<213> ORGANISM: Streptococcus pneumoniae

<400> SEQUENCE: 123

Arg Ile Phe Ile Tyr Val Gly Thr Glu
1               5

<210> SEQ ID NO 124
<211> LENGTH: 9
<212> TYPE: PRT
<213> ORGANISM: Streptococcus pneumoniae

<400> SEQUENCE: 124

Phe Ile Asp Glu Thr Tyr Arg Thr Lys
1               5

<210> SEQ ID NO 125
<211> LENGTH: 9
<212> TYPE: PRT
<213> ORGANISM: Streptococcus pneumoniae

<400> SEQUENCE: 125

Asp Thr Asp Arg Ser Tyr Pro Val Val
1               5

<210> SEQ ID NO 126
<211> LENGTH: 9
<212> TYPE: PRT
<213> ORGANISM: Streptococcus pneumoniae

<400> SEQUENCE: 126

Tyr Ile Asp Ser Ser Leu Cys Tyr Tyr
1               5

<210> SEQ ID NO 127
<211> LENGTH: 9
<212> TYPE: PRT
<213> ORGANISM: Streptococcus pneumoniae

<400> SEQUENCE: 127

Thr Gln Phe Ile Gly Leu Glu Tyr Gln
1               5

<210> SEQ ID NO 128
<211> LENGTH: 9
<212> TYPE: PRT
<213> ORGANISM: Streptococcus pneumoniae

<400> SEQUENCE: 128

Lys Asp Thr Asp Arg Ser Tyr Pro Val
1               5

<210> SEQ ID NO 129
<211> LENGTH: 9
<212> TYPE: PRT
<213> ORGANISM: Streptococcus pneumoniae

<400> SEQUENCE: 129

Leu Cys Tyr Tyr His Asp Leu Ile Ala
1               5

<210> SEQ ID NO 130
<211> LENGTH: 9

```
<212> TYPE: PRT
<213> ORGANISM: Streptococcus pneumoniae

<400> SEQUENCE: 130

Asn Val Phe Asn Ser Lys Glu Ser Phe
1               5

<210> SEQ ID NO 131
<211> LENGTH: 9
<212> TYPE: PRT
<213> ORGANISM: Streptococcus pneumoniae

<400> SEQUENCE: 131

Met Leu Lys Asp Lys Ile Ala Phe Leu
1               5

<210> SEQ ID NO 132
<211> LENGTH: 9
<212> TYPE: PRT
<213> ORGANISM: Streptococcus pneumoniae

<400> SEQUENCE: 132

Ser Leu Ala Asp Tyr Thr Tyr Lys Val
1               5

<210> SEQ ID NO 133
<211> LENGTH: 9
<212> TYPE: PRT
<213> ORGANISM: Streptococcus pneumoniae

<400> SEQUENCE: 133

Phe Leu Leu Leu Gly Ala Phe Tyr Leu
1               5

<210> SEQ ID NO 134
<211> LENGTH: 9
<212> TYPE: PRT
<213> ORGANISM: Streptococcus pneumoniae

<400> SEQUENCE: 134

Val Leu Ile Asp Gly Leu Ser Gln Leu
1               5

<210> SEQ ID NO 135
<211> LENGTH: 9
<212> TYPE: PRT
<213> ORGANISM: Streptococcus pneumoniae

<400> SEQUENCE: 135

Ile Leu Ala Ser Leu Gly Phe Leu Leu
1               5

<210> SEQ ID NO 136
<211> LENGTH: 9
<212> TYPE: PRT
<213> ORGANISM: Streptococcus pneumoniae

<400> SEQUENCE: 136

Gly Leu Ser Gln Leu Leu Pro Val Ile
1               5

<210> SEQ ID NO 137
<211> LENGTH: 9
<212> TYPE: PRT
<213> ORGANISM: Streptococcus pneumoniae
```

<400> SEQUENCE: 137

Phe Leu Leu Asn His Tyr Met Thr Val
1               5

<210> SEQ ID NO 138
<211> LENGTH: 9
<212> TYPE: PRT
<213> ORGANISM: Streptococcus pneumoniae

<400> SEQUENCE: 138

Met Leu Ile Pro Asn Val Asp Arg Ala
1               5

<210> SEQ ID NO 139
<211> LENGTH: 9
<212> TYPE: PRT
<213> ORGANISM: Streptococcus pneumoniae

<400> SEQUENCE: 139

Lys Leu Glu Glu Met Ala Lys Gln Val
1               5

<210> SEQ ID NO 140
<211> LENGTH: 9
<212> TYPE: PRT
<213> ORGANISM: Streptococcus pneumoniae

<400> SEQUENCE: 140

Val Leu Lys Arg Gly Val Tyr Thr Ile
1               5

<210> SEQ ID NO 141
<211> LENGTH: 9
<212> TYPE: PRT
<213> ORGANISM: Streptococcus pneumoniae

<400> SEQUENCE: 141

Lys Val Ile Ala Gly Leu Leu Arg Lys
1               5

<210> SEQ ID NO 142
<211> LENGTH: 9
<212> TYPE: PRT
<213> ORGANISM: Streptococcus pneumoniae

<400> SEQUENCE: 142

Thr Leu Asn Tyr Glu His Met Asn Lys
1               5

<210> SEQ ID NO 143
<211> LENGTH: 9
<212> TYPE: PRT
<213> ORGANISM: Streptococcus pneumoniae

<400> SEQUENCE: 143

Asn Ile Gly Tyr Phe Phe Phe Lys Lys
1               5

<210> SEQ ID NO 144
<211> LENGTH: 9
<212> TYPE: PRT
<213> ORGANISM: Streptococcus pneumoniae

<400> SEQUENCE: 144

Lys Tyr Thr Asp Val Ile Glu Lys Phe
1               5

<210> SEQ ID NO 145
<211> LENGTH: 9
<212> TYPE: PRT
<213> ORGANISM: Streptococcus pneumoniae

<400> SEQUENCE: 145

Lys Tyr Asp Asp Ser Val Ser Thr Ile
1               5

<210> SEQ ID NO 146
<211> LENGTH: 9
<212> TYPE: PRT
<213> ORGANISM: Streptococcus pneumoniae

<400> SEQUENCE: 146

Thr Phe Asn Gln Met Ile Lys Glu Leu
1               5

<210> SEQ ID NO 147
<211> LENGTH: 9
<212> TYPE: PRT
<213> ORGANISM: Streptococcus pneumoniae

<400> SEQUENCE: 147

Asp Tyr Pro Glu Thr Gln Ser Val Phe
1               5

<210> SEQ ID NO 148
<211> LENGTH: 9
<212> TYPE: PRT
<213> ORGANISM: Streptococcus pneumoniae

<400> SEQUENCE: 148

Thr Pro Arg Ala Ile Asn Asn Thr Leu
1               5

<210> SEQ ID NO 149
<211> LENGTH: 9
<212> TYPE: PRT
<213> ORGANISM: Streptococcus pneumoniae

<400> SEQUENCE: 149

Ala Pro Leu Leu Val Asn Gly Glu Leu
1               5

<210> SEQ ID NO 150
<211> LENGTH: 9
<212> TYPE: PRT
<213> ORGANISM: Streptococcus pneumoniae

<400> SEQUENCE: 150

Tyr Ile Asp His Thr Asn Val Ala Tyr
1               5

<210> SEQ ID NO 151
<211> LENGTH: 9
<212> TYPE: PRT
<213> ORGANISM: Streptococcus pneumoniae

<400> SEQUENCE: 151

Lys Gln Asn Gly Asp Ser Tyr Gly Tyr

```
1               5
```

<210> SEQ ID NO 152
<211> LENGTH: 9
<212> TYPE: PRT
<213> ORGANISM: Streptococcus pneumoniae

<400> SEQUENCE: 152

```
Phe Leu Leu Asn His Tyr Met Thr Val
1               5
```

<210> SEQ ID NO 153
<211> LENGTH: 9
<212> TYPE: PRT
<213> ORGANISM: Streptococcus pneumoniae

<400> SEQUENCE: 153

```
Phe Tyr Leu Tyr Asn Gly Asp Leu Ser
1               5
```

<210> SEQ ID NO 154
<211> LENGTH: 8
<212> TYPE: PRT
<213> ORGANISM: Streptococcus pneumoniae

<400> SEQUENCE: 154

```
Lys Ser Phe Ala Pro Leu Leu Val
1               5
```

<210> SEQ ID NO 155
<211> LENGTH: 8
<212> TYPE: PRT
<213> ORGANISM: Streptococcus pneumoniae

<400> SEQUENCE: 155

```
Asp Glu Thr Val Val Arg Thr Val
1               5
```

<210> SEQ ID NO 156
<211> LENGTH: 9
<212> TYPE: PRT
<213> ORGANISM: Streptococcus pneumoniae

<400> SEQUENCE: 156

```
Tyr Ile Asp His Thr Asn Val Ala Tyr
1               5
```

<210> SEQ ID NO 157
<211> LENGTH: 9
<212> TYPE: PRT
<213> ORGANISM: Streptococcus pneumoniae

<400> SEQUENCE: 157

```
Met Leu Lys Asp Lys Ile Ala Phe Leu
1               5
```

<210> SEQ ID NO 158
<211> LENGTH: 9
<212> TYPE: PRT
<213> ORGANISM: Streptococcus pneumoniae

<400> SEQUENCE: 158

```
Lys Leu Arg Phe Lys Ile Lys Thr Asp
1               5
```

```
<210> SEQ ID NO 159
<211> LENGTH: 9
<212> TYPE: PRT
<213> ORGANISM: Streptococcus pneumoniae

<400> SEQUENCE: 159

Lys Leu Glu Leu Phe Tyr Glu Thr Gly
1               5

<210> SEQ ID NO 160
<211> LENGTH: 9
<212> TYPE: PRT
<213> ORGANISM: Streptococcus pneumoniae

<400> SEQUENCE: 160

Lys Ile Ala Phe Leu Gly Ser Asn Ile
1               5

<210> SEQ ID NO 161
<211> LENGTH: 9
<212> TYPE: PRT
<213> ORGANISM: Streptococcus pneumoniae

<400> SEQUENCE: 161

Ser Val Pro Arg Thr Ser Tyr Leu Ser
1               5

<210> SEQ ID NO 162
<211> LENGTH: 9
<212> TYPE: PRT
<213> ORGANISM: Streptococcus pneumoniae

<400> SEQUENCE: 162

Phe Gly Phe Gly Leu Ser Leu Phe Ser
1               5

<210> SEQ ID NO 163
<211> LENGTH: 9
<212> TYPE: PRT
<213> ORGANISM: Streptococcus pneumoniae

<400> SEQUENCE: 163

Ser Thr Ile Arg Ser Ile Glu Gln Val
1               5

<210> SEQ ID NO 164
<211> LENGTH: 9
<212> TYPE: PRT
<213> ORGANISM: Streptococcus pneumoniae

<400> SEQUENCE: 164

Phe Arg Lys Thr Thr Asp Asn Pro Phe
1               5

<210> SEQ ID NO 165
<211> LENGTH: 9
<212> TYPE: PRT
<213> ORGANISM: Streptococcus pneumoniae

<400> SEQUENCE: 165

Thr Val Val Arg Thr Val Arg Asp Ser
1               5

<210> SEQ ID NO 166
```

```
<211> LENGTH: 9
<212> TYPE: PRT
<213> ORGANISM: Streptococcus pneumoniae

<400> SEQUENCE: 166

Ser Thr Ile Arg Ser Ile Glu Gln Val
1               5

<210> SEQ ID NO 167
<211> LENGTH: 9
<212> TYPE: PRT
<213> ORGANISM: Streptococcus pneumoniae

<400> SEQUENCE: 167

Asp Gly Leu Ser Gln Leu Leu Pro Val
1               5

<210> SEQ ID NO 168
<211> LENGTH: 9
<212> TYPE: PRT
<213> ORGANISM: Streptococcus pneumoniae

<400> SEQUENCE: 168

Phe Gly Phe Gly Leu Ser Leu Phe Ser
1               5

<210> SEQ ID NO 169
<211> LENGTH: 9
<212> TYPE: PRT
<213> ORGANISM: Streptococcus pneumoniae

<400> SEQUENCE: 169

Lys Leu Val Asp Gln Gly Glu Gly Phe
1               5

<210> SEQ ID NO 170
<211> LENGTH: 9
<212> TYPE: PRT
<213> ORGANISM: Streptococcus pneumoniae

<400> SEQUENCE: 170

Ala Ile Val Thr Cys Met Asp Ser Arg
1               5

<210> SEQ ID NO 171
<211> LENGTH: 9
<212> TYPE: PRT
<213> ORGANISM: Streptococcus pneumoniae

<400> SEQUENCE: 171

Ala Gln Thr Phe Glu Asn Glu Pro Phe
1               5

<210> SEQ ID NO 172
<211> LENGTH: 9
<212> TYPE: PRT
<213> ORGANISM: Streptococcus pneumoniae

<400> SEQUENCE: 172

Ala Tyr Val Ala Leu His Gly Gln Leu
1               5

<210> SEQ ID NO 173
<211> LENGTH: 9
<212> TYPE: PRT
```

```
<213> ORGANISM: Streptococcus pneumoniae

<400> SEQUENCE: 173

Asp Asp Val Ile Ile Ser Gly Ala Ile
1               5

<210> SEQ ID NO 174
<211> LENGTH: 9
<212> TYPE: PRT
<213> ORGANISM: Streptococcus pneumoniae

<400> SEQUENCE: 174

Phe Glu Asn Glu Pro Phe Gln Glu Tyr
1               5

<210> SEQ ID NO 175
<211> LENGTH: 9
<212> TYPE: PRT
<213> ORGANISM: Streptococcus pneumoniae

<400> SEQUENCE: 175

Phe Met Gln Ala Asn Gln Ala Tyr Val
1               5

<210> SEQ ID NO 176
<211> LENGTH: 9
<212> TYPE: PRT
<213> ORGANISM: Streptococcus pneumoniae

<400> SEQUENCE: 176

Ile Ser Gln Gln Gln Met Gly Thr Arg
1               5

<210> SEQ ID NO 177
<211> LENGTH: 9
<212> TYPE: PRT
<213> ORGANISM: Streptococcus pneumoniae

<400> SEQUENCE: 177

Lys Pro Lys Thr Arg Val Ala Ile Val
1               5

<210> SEQ ID NO 178
<211> LENGTH: 9
<212> TYPE: PRT
<213> ORGANISM: Streptococcus pneumoniae

<400> SEQUENCE: 178

Leu His Gly Gln Leu Asn Leu Pro Leu
1               5

<210> SEQ ID NO 179
<211> LENGTH: 9
<212> TYPE: PRT
<213> ORGANISM: Streptococcus pneumoniae

<400> SEQUENCE: 179

Leu His Val Ala Gln Ala Leu Gly Leu
1               5

<210> SEQ ID NO 180
<211> LENGTH: 9
<212> TYPE: PRT
<213> ORGANISM: Streptococcus pneumoniae
```

```
<400> SEQUENCE: 180

Leu Pro Leu Lys Pro Lys Thr Arg Val
1               5

<210> SEQ ID NO 181
<211> LENGTH: 9
<212> TYPE: PRT
<213> ORGANISM: Streptococcus pneumoniae

<400> SEQUENCE: 181

Met Gly Thr Arg Glu Ile Val Val Leu
1               5

<210> SEQ ID NO 182
<211> LENGTH: 9
<212> TYPE: PRT
<213> ORGANISM: Streptococcus pneumoniae

<400> SEQUENCE: 182

Met Gln Leu Leu Ile Glu Ser Pro Leu
1               5

<210> SEQ ID NO 183
<211> LENGTH: 9
<212> TYPE: PRT
<213> ORGANISM: Streptococcus pneumoniae

<400> SEQUENCE: 183

Gln Ala Asn Gln Ala Tyr Val Ala Leu
1               5

<210> SEQ ID NO 184
<211> LENGTH: 9
<212> TYPE: PRT
<213> ORGANISM: Streptococcus pneumoniae

<400> SEQUENCE: 184

Gln Phe Met Gln Ala Asn Gln Ala Tyr
1               5

<210> SEQ ID NO 185
<211> LENGTH: 9
<212> TYPE: PRT
<213> ORGANISM: Streptococcus pneumoniae

<400> SEQUENCE: 185

Gln Leu Asn Leu Pro Leu Lys Pro Lys
1               5

<210> SEQ ID NO 186
<211> LENGTH: 9
<212> TYPE: PRT
<213> ORGANISM: Streptococcus pneumoniae

<400> SEQUENCE: 186

Gln Gln Met Gly Thr Arg Glu Ile Val
1               5

<210> SEQ ID NO 187
<211> LENGTH: 9
<212> TYPE: PRT
<213> ORGANISM: Streptococcus pneumoniae

<400> SEQUENCE: 187
```

Arg Glu Ile Val Val Leu His His Thr
1               5

<210> SEQ ID NO 188
<211> LENGTH: 9
<212> TYPE: PRT
<213> ORGANISM: Streptococcus pneumoniae

<400> SEQUENCE: 188

Ser Pro Leu Ile Pro Asp Asp Val Ile
1               5

<210> SEQ ID NO 189
<211> LENGTH: 9
<212> TYPE: PRT
<213> ORGANISM: Streptococcus pneumoniae

<400> SEQUENCE: 189

Ser Arg Leu His Val Ala Gln Ala Leu
1               5

<210> SEQ ID NO 190
<211> LENGTH: 9
<212> TYPE: PRT
<213> ORGANISM: Streptococcus pneumoniae

<400> SEQUENCE: 190

Thr Glu Asp Met Ile Arg Ser Leu Val
1               5

<210> SEQ ID NO 191
<211> LENGTH: 9
<212> TYPE: PRT
<213> ORGANISM: Streptococcus pneumoniae

<400> SEQUENCE: 191

Val Asp Val Ser Asp Gln Asp Phe Leu
1               5

<210> SEQ ID NO 192
<211> LENGTH: 9
<212> TYPE: PRT
<213> ORGANISM: Streptococcus pneumoniae

<400> SEQUENCE: 192

Val Ser Asp Gln Asp Phe Leu Pro Phe
1               5

<210> SEQ ID NO 193
<211> LENGTH: 9
<212> TYPE: PRT
<213> ORGANISM: Streptococcus pneumoniae

<400> SEQUENCE: 193

Val Thr Glu Asp Met Ile Arg Ser Leu
1               5

<210> SEQ ID NO 194
<211> LENGTH: 9
<212> TYPE: PRT
<213> ORGANISM: Streptococcus pneumoniae

<400> SEQUENCE: 194

Gly Ile Glu Val Glu Lys Pro Leu Tyr
1               5

```
<210> SEQ ID NO 195
<211> LENGTH: 9
<212> TYPE: PRT
<213> ORGANISM: Streptococcus pneumoniae

<400> SEQUENCE: 195

Ala Glu Ala His Leu Leu Tyr Arg Met
1               5

<210> SEQ ID NO 196
<211> LENGTH: 9
<212> TYPE: PRT
<213> ORGANISM: Streptococcus pneumoniae

<400> SEQUENCE: 196

Ala Leu Leu Asn Gln Asp Asn Met Arg
1               5

<210> SEQ ID NO 197
<211> LENGTH: 9
<212> TYPE: PRT
<213> ORGANISM: Streptococcus pneumoniae

<400> SEQUENCE: 197

Ala Pro Pro Glu Arg Asn Tyr Leu Tyr
1               5

<210> SEQ ID NO 198
<211> LENGTH: 9
<212> TYPE: PRT
<213> ORGANISM: Streptococcus pneumoniae

<400> SEQUENCE: 198

Ala Gln Asn Ser Tyr Ile His Ile Leu
1               5

<210> SEQ ID NO 199
<211> LENGTH: 9
<212> TYPE: PRT
<213> ORGANISM: Streptococcus pneumoniae

<400> SEQUENCE: 199

Ala Val Ala Ser Met Gly Thr Ala Leu
1               5

<210> SEQ ID NO 200
<211> LENGTH: 9
<212> TYPE: PRT
<213> ORGANISM: Streptococcus pneumoniae

<400> SEQUENCE: 200

Ala Tyr Leu Leu Thr Lys Thr Arg Ile
1               5

<210> SEQ ID NO 201
<211> LENGTH: 9
<212> TYPE: PRT
<213> ORGANISM: Streptococcus pneumoniae

<400> SEQUENCE: 201

Asp Ala Ala Lys Phe Tyr His Ala Ile
1               5
```

<210> SEQ ID NO 202
<211> LENGTH: 9
<212> TYPE: PRT
<213> ORGANISM: Streptococcus pneumoniae

<400> SEQUENCE: 202

Asp Thr Ala Leu Glu Glu Leu Glu Arg
1               5

<210> SEQ ID NO 203
<211> LENGTH: 9
<212> TYPE: PRT
<213> ORGANISM: Streptococcus pneumoniae

<400> SEQUENCE: 203

Glu Glu Tyr Gln Gly Val Pro Phe Ile
1               5

<210> SEQ ID NO 204
<211> LENGTH: 9
<212> TYPE: PRT
<213> ORGANISM: Streptococcus pneumoniae

<400> SEQUENCE: 204

Glu Phe Leu Glu Lys Ile Ala Pro Leu
1               5

<210> SEQ ID NO 205
<211> LENGTH: 9
<212> TYPE: PRT
<213> ORGANISM: Streptococcus pneumoniae

<400> SEQUENCE: 205

Glu Phe Gln Val Leu Tyr Asp Leu Leu
1               5

<210> SEQ ID NO 206
<211> LENGTH: 9
<212> TYPE: PRT
<213> ORGANISM: Streptococcus pneumoniae

<400> SEQUENCE: 206

Glu His Val Glu His Leu Lys Arg Leu
1               5

<210> SEQ ID NO 207
<211> LENGTH: 9
<212> TYPE: PRT
<213> ORGANISM: Streptococcus pneumoniae

<400> SEQUENCE: 207

Glu Leu Ser Glu Val Glu Met Thr Arg
1               5

<210> SEQ ID NO 208
<211> LENGTH: 9
<212> TYPE: PRT
<213> ORGANISM: Streptococcus pneumoniae

<400> SEQUENCE: 208

Glu Ser Pro Leu Val Leu Asn Asp Tyr
1               5

<210> SEQ ID NO 209
<211> LENGTH: 9

```
<212> TYPE: PRT
<213> ORGANISM: Streptococcus pneumoniae

<400> SEQUENCE: 209

Gly Glu Lys Thr Pro Ser Phe Asn Val
1               5

<210> SEQ ID NO 210
<211> LENGTH: 9
<212> TYPE: PRT
<213> ORGANISM: Streptococcus pneumoniae

<400> SEQUENCE: 210

Gly Leu Cys Pro Phe His Gly Glu Lys
1               5

<210> SEQ ID NO 211
<211> LENGTH: 9
<212> TYPE: PRT
<213> ORGANISM: Streptococcus pneumoniae

<400> SEQUENCE: 211

Ile Gly Asp Met Pro Val Gln Ile Val
1               5

<210> SEQ ID NO 212
<211> LENGTH: 9
<212> TYPE: PRT
<213> ORGANISM: Streptococcus pneumoniae

<400> SEQUENCE: 212

Ile Thr Met Pro Val Thr Lys Gln Leu
1               5

<210> SEQ ID NO 213
<211> LENGTH: 9
<212> TYPE: PRT
<213> ORGANISM: Streptococcus pneumoniae

<400> SEQUENCE: 213

Lys Ala Leu Leu Asn Gln Asp Asn Met
1               5

<210> SEQ ID NO 214
<211> LENGTH: 9
<212> TYPE: PRT
<213> ORGANISM: Streptococcus pneumoniae

<400> SEQUENCE: 214

Lys Arg Leu Thr Lys Lys Leu Val Leu
1               5

<210> SEQ ID NO 215
<211> LENGTH: 9
<212> TYPE: PRT
<213> ORGANISM: Streptococcus pneumoniae

<400> SEQUENCE: 215

Leu Thr Lys Thr Arg Ile Ser Pro Ile
1               5

<210> SEQ ID NO 216
<211> LENGTH: 9
<212> TYPE: PRT
<213> ORGANISM: Streptococcus pneumoniae
```

<400> SEQUENCE: 216

Leu Val Leu Val Tyr Asp Gly Asp Lys
1               5

<210> SEQ ID NO 217
<211> LENGTH: 9
<212> TYPE: PRT
<213> ORGANISM: Streptococcus pneumoniae

<400> SEQUENCE: 217

Met Arg Ala Glu Ala His Leu Leu Tyr
1               5

<210> SEQ ID NO 218
<211> LENGTH: 9
<212> TYPE: PRT
<213> ORGANISM: Streptococcus pneumoniae

<400> SEQUENCE: 218

Asn Gly Pro Glu Asp Leu Ala Tyr Leu
1               5

<210> SEQ ID NO 219
<211> LENGTH: 9
<212> TYPE: PRT
<213> ORGANISM: Streptococcus pneumoniae

<400> SEQUENCE: 219

Gln Thr Glu Glu Val Glu Arg Ala Trp
1               5

<210> SEQ ID NO 220
<211> LENGTH: 9
<212> TYPE: PRT
<213> ORGANISM: Streptococcus pneumoniae

<400> SEQUENCE: 220

Ser Glu Ile Tyr Leu Met Glu Gly Phe
1               5

<210> SEQ ID NO 221
<211> LENGTH: 9
<212> TYPE: PRT
<213> ORGANISM: Streptococcus pneumoniae

<400> SEQUENCE: 221

Ser Pro His Gln Ala Leu Tyr Asp Met
1               5

<210> SEQ ID NO 222
<211> LENGTH: 9
<212> TYPE: PRT
<213> ORGANISM: Streptococcus pneumoniae

<400> SEQUENCE: 222

Val Asp Lys Gln Val Ile Glu Glu Ile
1               5

<210> SEQ ID NO 223
<211> LENGTH: 9
<212> TYPE: PRT
<213> ORGANISM: Streptococcus pneumoniae

<400> SEQUENCE: 223

Val Glu Met Thr Arg Asn Lys Ala Leu
1               5

<210> SEQ ID NO 224
<211> LENGTH: 9
<212> TYPE: PRT
<213> ORGANISM: Streptococcus pneumoniae

<400> SEQUENCE: 224

Val Leu Tyr Asp Leu Leu Gly Gln Tyr
1               5

<210> SEQ ID NO 225
<211> LENGTH: 9
<212> TYPE: PRT
<213> ORGANISM: Streptococcus pneumoniae

<400> SEQUENCE: 225

Val Pro Phe Ile Glu Ala Val Gln Ile
1               5

<210> SEQ ID NO 226
<211> LENGTH: 9
<212> TYPE: PRT
<213> ORGANISM: Streptococcus pneumoniae

<400> SEQUENCE: 226

Trp Tyr Gln Val Leu Ala Gln Asp Leu
1               5

<210> SEQ ID NO 227
<211> LENGTH: 9
<212> TYPE: PRT
<213> ORGANISM: Streptococcus pneumoniae

<400> SEQUENCE: 227

Tyr Leu Met Glu Gly Phe Met Asp Val
1               5

<210> SEQ ID NO 228
<211> LENGTH: 9
<212> TYPE: PRT
<213> ORGANISM: Streptococcus pneumoniae

<400> SEQUENCE: 228

Ala Ala Tyr Ala Pro Asn Glu Val Val
1               5

<210> SEQ ID NO 229
<211> LENGTH: 9
<212> TYPE: PRT
<213> ORGANISM: Streptococcus pneumoniae

<400> SEQUENCE: 229

Ala Gly Asp Leu Arg Gly Lys Ile Ile
1               5

<210> SEQ ID NO 230
<211> LENGTH: 9
<212> TYPE: PRT
<213> ORGANISM: Streptococcus pneumoniae

<400> SEQUENCE: 230

Asp Glu Ile Ala Asn Glu Val Trp Tyr

```
1               5

<210> SEQ ID NO 231
<211> LENGTH: 9
<212> TYPE: PRT
<213> ORGANISM: Streptococcus pneumoniae

<400> SEQUENCE: 231

Asp Asn Tyr Leu Ile Tyr Gly Asp Leu
1               5

<210> SEQ ID NO 232
<211> LENGTH: 9
<212> TYPE: PRT
<213> ORGANISM: Streptococcus pneumoniae

<400> SEQUENCE: 232

Asp Gln Lys Glu His Pro Glu Lys Phe
1               5

<210> SEQ ID NO 233
<211> LENGTH: 9
<212> TYPE: PRT
<213> ORGANISM: Streptococcus pneumoniae

<400> SEQUENCE: 233

Asp Ser Leu Thr Asp Arg Leu Lys Leu
1               5

<210> SEQ ID NO 234
<211> LENGTH: 9
<212> TYPE: PRT
<213> ORGANISM: Streptococcus pneumoniae

<400> SEQUENCE: 234

Glu Ala Lys Asn Lys Asn Lys Phe Val
1               5

<210> SEQ ID NO 235
<211> LENGTH: 9
<212> TYPE: PRT
<213> ORGANISM: Streptococcus pneumoniae

<400> SEQUENCE: 235

Glu Gly Gln Gly Arg Asn Arg Lys Leu
1               5

<210> SEQ ID NO 236
<211> LENGTH: 9
<212> TYPE: PRT
<213> ORGANISM: Streptococcus pneumoniae

<400> SEQUENCE: 236

Glu Ile Lys Gly Ala Gly Asp Leu Arg
1               5

<210> SEQ ID NO 237
<211> LENGTH: 9
<212> TYPE: PRT
<213> ORGANISM: Streptococcus pneumoniae

<400> SEQUENCE: 237

Glu Pro Ile Ala Glu Gly Gln Tyr Phe
1               5
```

```
<210> SEQ ID NO 238
<211> LENGTH: 9
<212> TYPE: PRT
<213> ORGANISM: Streptococcus pneumoniae

<400> SEQUENCE: 238

Glu Val Ser Glu Leu Lys Pro His Arg
1               5

<210> SEQ ID NO 239
<211> LENGTH: 9
<212> TYPE: PRT
<213> ORGANISM: Streptococcus pneumoniae

<400> SEQUENCE: 239

Gly Ala Phe Phe Asp Lys Ser Lys Ile
1               5

<210> SEQ ID NO 240
<211> LENGTH: 9
<212> TYPE: PRT
<213> ORGANISM: Streptococcus pneumoniae

<400> SEQUENCE: 240

Gly Asp Leu Lys Trp Asp Gly Leu Ile
1               5

<210> SEQ ID NO 241
<211> LENGTH: 9
<212> TYPE: PRT
<213> ORGANISM: Streptococcus pneumoniae

<400> SEQUENCE: 241

Gly Glu Val Glu Lys Asn Leu Glu Val
1               5

<210> SEQ ID NO 242
<211> LENGTH: 9
<212> TYPE: PRT
<213> ORGANISM: Streptococcus pneumoniae

<400> SEQUENCE: 242

Ile His Phe Glu Ser Val Glu Glu Met
1               5

<210> SEQ ID NO 243
<211> LENGTH: 9
<212> TYPE: PRT
<213> ORGANISM: Streptococcus pneumoniae

<400> SEQUENCE: 243

Ile Met Phe Ile Val Gly Ile Phe Leu
1               5

<210> SEQ ID NO 244
<211> LENGTH: 9
<212> TYPE: PRT
<213> ORGANISM: Streptococcus pneumoniae

<400> SEQUENCE: 244

Ile Pro Gly Thr Leu Asn Lys Gly Ile
1               5

<210> SEQ ID NO 245
```

```
<211> LENGTH: 9
<212> TYPE: PRT
<213> ORGANISM: Streptococcus pneumoniae

<400> SEQUENCE: 245

Ile Arg Tyr Gln Val Phe Thr Phe Lys
1               5

<210> SEQ ID NO 246
<211> LENGTH: 9
<212> TYPE: PRT
<213> ORGANISM: Streptococcus pneumoniae

<400> SEQUENCE: 246

Ile Ser Asp Lys Gly Gly Phe Asn Trp
1               5

<210> SEQ ID NO 247
<211> LENGTH: 9
<212> TYPE: PRT
<213> ORGANISM: Streptococcus pneumoniae

<400> SEQUENCE: 247

Ile Val Ser Glu Glu Asp Phe Ile Leu
1               5

<210> SEQ ID NO 248
<211> LENGTH: 9
<212> TYPE: PRT
<213> ORGANISM: Streptococcus pneumoniae

<400> SEQUENCE: 248

Lys Glu Ile Gly Val Glu Glu Ala Ile
1               5

<210> SEQ ID NO 249
<211> LENGTH: 9
<212> TYPE: PRT
<213> ORGANISM: Streptococcus pneumoniae

<400> SEQUENCE: 249

Lys Ile Val Val Lys Asp Phe Ala Arg
1               5

<210> SEQ ID NO 250
<211> LENGTH: 9
<212> TYPE: PRT
<213> ORGANISM: Streptococcus pneumoniae

<400> SEQUENCE: 250

Lys Lys Ile Asn Phe Gln Pro Ser Leu
1               5

<210> SEQ ID NO 251
<211> LENGTH: 9
<212> TYPE: PRT
<213> ORGANISM: Streptococcus pneumoniae

<400> SEQUENCE: 251

Lys Leu Lys Phe Val Tyr Ile Gly Lys
1               5

<210> SEQ ID NO 252
<211> LENGTH: 9
<212> TYPE: PRT
```

-continued

<213> ORGANISM: Streptococcus pneumoniae

<400> SEQUENCE: 252

Lys Val Tyr Tyr Gly Asn Asn Tyr Lys
1               5

<210> SEQ ID NO 253
<211> LENGTH: 9
<212> TYPE: PRT
<213> ORGANISM: Streptococcus pneumoniae

<400> SEQUENCE: 253

Lys Tyr Trp Gln Ala Ile Arg Ala Leu
1               5

<210> SEQ ID NO 254
<211> LENGTH: 9
<212> TYPE: PRT
<213> ORGANISM: Streptococcus pneumoniae

<400> SEQUENCE: 254

Leu His Ile Asp Asn Thr Arg Asp Phe
1               5

<210> SEQ ID NO 255
<211> LENGTH: 9
<212> TYPE: PRT
<213> ORGANISM: Streptococcus pneumoniae

<400> SEQUENCE: 255

Met Arg Phe Lys Lys Glu Asp Leu Lys
1               5

<210> SEQ ID NO 256
<211> LENGTH: 9
<212> TYPE: PRT
<213> ORGANISM: Streptococcus pneumoniae

<400> SEQUENCE: 256

Asn Glu Ser Val Val Asp Asn Tyr Leu
1               5

<210> SEQ ID NO 257
<211> LENGTH: 9
<212> TYPE: PRT
<213> ORGANISM: Streptococcus pneumoniae

<400> SEQUENCE: 257

Asn Glu Val Trp Tyr Ala Gly Ala Ala
1               5

<210> SEQ ID NO 258
<211> LENGTH: 9
<212> TYPE: PRT
<213> ORGANISM: Streptococcus pneumoniae

<400> SEQUENCE: 258

Asn Ile Asn Asp Ile Val Asp Gly Leu
1               5

<210> SEQ ID NO 259
<211> LENGTH: 9
<212> TYPE: PRT
<213> ORGANISM: Streptococcus pneumoniae

```
<400> SEQUENCE: 259

Gln Tyr Leu Leu Lys Asp Asn Ile Ile
1               5

<210> SEQ ID NO 260
<211> LENGTH: 9
<212> TYPE: PRT
<213> ORGANISM: Streptococcus pneumoniae

<400> SEQUENCE: 260

Ser Pro Arg Gln Gln Gly Ala Gly Leu
1               5

<210> SEQ ID NO 261
<211> LENGTH: 9
<212> TYPE: PRT
<213> ORGANISM: Streptococcus pneumoniae

<400> SEQUENCE: 261

Ser Arg Ser Lys Thr Leu Gly Gly Tyr
1               5

<210> SEQ ID NO 262
<211> LENGTH: 9
<212> TYPE: PRT
<213> ORGANISM: Streptococcus pneumoniae

<400> SEQUENCE: 262

Ser Ser Leu Lys Asn Thr Lys Val Leu
1               5

<210> SEQ ID NO 263
<211> LENGTH: 9
<212> TYPE: PRT
<213> ORGANISM: Streptococcus pneumoniae

<400> SEQUENCE: 263

Thr Ala Ala Val Ile Leu Ala Ala Tyr
1               5

<210> SEQ ID NO 264
<211> LENGTH: 9
<212> TYPE: PRT
<213> ORGANISM: Streptococcus pneumoniae

<400> SEQUENCE: 264

Trp Thr Glu Leu Pro Ala Met Gly Tyr
1               5

<210> SEQ ID NO 265
<211> LENGTH: 99
<212> TYPE: PRT
<213> ORGANISM: Streptococcus pneumoniae

<400> SEQUENCE: 265

Met Asn Gly Met Lys Ala Lys Lys Met Trp Met Ala Gly Leu Ala Leu
1               5                   10                  15

Leu Gly Ile Gly Ser Leu Ala Leu Ala Thr Lys Lys Val Ala Asp Asp
                20                  25                  30

Arg Lys Leu Met Lys Thr Gln Glu Glu Leu Thr Glu Ile Val Arg Asp
            35                  40                  45

His Phe Ser Asp Met Gly Glu Ile Ala Thr Leu Tyr Val Gln Val Tyr
        50                  55                  60
```

Glu Ser Ser Leu Glu Ser Leu Val Gly Gly Val Ile Phe Glu Asp Gly
65                  70                  75                  80

Arg His Tyr Thr Phe Val Tyr Glu Asn Glu Asp Leu Val Tyr Glu Glu
                85                  90                  95

Glu Val Leu

<210> SEQ ID NO 266
<211> LENGTH: 92
<212> TYPE: PRT
<213> ORGANISM: Streptococcus pneumoniae

<400> SEQUENCE: 266

Met Arg Tyr Leu Ala Thr Leu Leu Ser Leu Ala Val Leu Ile Thr
1               5                   10                  15

Ala Gly Cys Lys Lys Val Ala Asp Asp Arg Lys Leu Met Lys Thr Gln
                20                  25                  30

Glu Glu Leu Thr Glu Ile Val Arg Asp His Phe Ser Asp Met Gly Glu
                35                  40                  45

Ile Ala Thr Leu Tyr Val Gln Val Tyr Glu Ser Ser Leu Glu Ser Leu
50                  55                  60

Val Gly Gly Val Ile Phe Glu Asp Gly Arg His Tyr Thr Phe Val Tyr
65                  70                  75                  80

Glu Asn Glu Asp Leu Val Tyr Glu Glu Val Leu
                85                  90

<210> SEQ ID NO 267
<211> LENGTH: 978
<212> TYPE: PRT
<213> ORGANISM: Streptococcus pneumoniae

<400> SEQUENCE: 267

Asp Thr Ser Ser Glu Asp Ala Leu Asn Ile Ser Asp Lys Glu Lys
1               5                   10                  15

Val Ala Glu Asn Lys Glu Lys His Glu Asn Ile His Ser Ala Met Glu
                20                  25                  30

Thr Ser Gln Asp Phe Lys Glu Lys Lys Thr Ala Val Ile Lys Glu Lys
                35                  40                  45

Glu Val Val Ser Lys Asn Pro Val Ile Asp Asn Asn Thr Ser Asn Glu
50                  55                  60

Glu Ala Lys Ile Lys Glu Glu Asn Ser Asn Lys Ser Gln Gly Asp Tyr
65                  70                  75                  80

Thr Asp Ser Phe Val Asn Lys Asn Thr Glu Asn Pro Lys Lys Glu Asp
                85                  90                  95

Lys Val Val Tyr Ile Ala Glu Phe Lys Asp Lys Glu Ser Gly Glu Lys
                100                 105                 110

Ala Ile Lys Glu Leu Ser Ser Leu Lys Asn Thr Lys Val Leu Tyr Thr
                115                 120                 125

Tyr Asp Arg Ile Phe Asn Gly Ser Ala Ile Glu Thr Thr Pro Asp Asn
                130                 135                 140

Leu Asp Lys Ile Lys Gln Ile Glu Gly Ile Ser Ser Val Glu Arg Ala
145                 150                 155                 160

Gln Lys Val Gln Pro Met Met Asn His Ala Arg Lys Glu Ile Gly Val
                165                 170                 175

Glu Glu Ala Ile Asp Tyr Leu Ser Ile Asn Ala Pro Phe Gly Lys
                180                 185                 190

-continued

```
Asn Phe Asp Gly Arg Gly Met Val Ile Ser Asn Ile Asp Thr Gly Thr
            195                 200                 205

Asp Tyr Arg His Lys Ala Met Arg Ile Asp Asp Ala Lys Ala Ser
    210                 215                 220

Met Arg Phe Lys Lys Glu Asp Leu Lys Gly Thr Asp Lys Asn Tyr Trp
225                 230                 235                 240

Leu Ser Asp Lys Ile Pro His Ala Phe Asn Tyr Tyr Asn Gly Gly Lys
                245                 250                 255

Ile Thr Val Glu Lys Tyr Asp Asp Gly Arg Asp Tyr Phe Asp Pro His
            260                 265                 270

Gly Met His Ile Ala Gly Ile Leu Ala Gly Asn Asp Thr Glu Gln Asp
    275                 280                 285

Ile Lys Asn Phe Asn Gly Ile Asp Gly Ile Ala Pro Asn Ala Gln Ile
    290                 295                 300

Phe Ser Tyr Lys Met Tyr Ser Asp Ala Gly Ser Gly Phe Ala Gly Asp
305                 310                 315                 320

Glu Thr Met Phe His Ala Ile Glu Asp Ser Ile Lys His Asn Val Asp
                325                 330                 335

Val Val Ser Val Ser Ser Gly Phe Thr Gly Thr Gly Leu Val Gly Glu
            340                 345                 350

Lys Tyr Trp Gln Ala Ile Arg Ala Leu Arg Lys Ala Gly Ile Pro Met
    355                 360                 365

Val Val Ala Thr Gly Asn Tyr Ala Thr Ser Ala Ser Ser Ser Ser Trp
    370                 375                 380

Asp Leu Val Ala Asn His Leu Lys Met Thr Asp Thr Gly Asn Val
385                 390                 395                 400

Thr Arg Thr Ala Ala His Glu Asp Ala Ile Ala Val Ala Ser Ala Lys
                405                 410                 415

Asn Gln Thr Val Glu Phe Asp Lys Val Asn Ile Gly Gly Glu Ser Phe
            420                 425                 430

Lys Tyr Arg Asn Ile Gly Ala Phe Phe Asp Lys Ser Lys Ile Thr Thr
    435                 440                 445

Asn Glu Asp Gly Thr Lys Ala Pro Ser Lys Leu Lys Phe Val Tyr Ile
450                 455                 460

Gly Lys Gly Gln Asp Gln Asp Leu Ile Gly Leu Asp Leu Arg Gly Lys
465                 470                 475                 480

Ile Ala Val Met Asp Arg Ile Tyr Thr Lys Asp Leu Lys Asn Ala Phe
                485                 490                 495

Lys Lys Ala Met Asp Lys Gly Ala Arg Ala Ile Met Val Val Asn Thr
            500                 505                 510

Val Asn Tyr Tyr Asn Arg Asp Asn Trp Thr Glu Leu Pro Ala Met Gly
    515                 520                 525

Tyr Glu Ala Asp Glu Gly Thr Lys Ser Gln Val Phe Ser Ile Ser Gly
    530                 535                 540

Asp Asp Gly Val Lys Leu Trp Asn Met Ile Asn Pro Asp Lys Lys Thr
545                 550                 555                 560

Glu Val Lys Arg Asn Asn Lys Glu Asp Phe Lys Asp Lys Leu Glu Gln
                565                 570                 575

Tyr Tyr Pro Ile Asp Met Glu Ser Phe Asn Ser Asn Lys Pro Asn Val
            580                 585                 590

Gly Asp Glu Lys Glu Ile Asp Phe Lys Phe Ala Pro Asp Thr Asp Lys
    595                 600                 605

Glu Leu Tyr Lys Glu Asp Ile Ile Val Pro Ala Gly Ser Thr Ser Trp
```

```
                610             615                 620
Gly Pro Arg Ile Asp Leu Leu Lys Pro Asp Val Ser Ala Pro Gly
625                 630                 635                 640

Lys Asn Ile Lys Ser Thr Leu Asn Val Ile Asn Gly Lys Ser Thr Tyr
                645                 650                 655

Gly Tyr Met Ser Gly Thr Ser Met Ala Thr Pro Ile Val Ala Ala Ser
                660                 665                 670

Thr Val Leu Ile Arg Pro Lys Leu Lys Glu Met Leu Glu Arg Pro Val
                675                 680                 685

Leu Lys Asn Leu Lys Gly Asp Asp Lys Ile Asp Leu Thr Ser Leu Thr
                690                 695                 700

Lys Ile Ala Leu Gln Asn Thr Ala Arg Pro Met Met Asp Ala Thr Ser
705                 710                 715                 720

Trp Lys Glu Lys Ser Gln Tyr Phe Ala Ser Pro Arg Gln Gln Gly Ala
                725                 730                 735

Gly Leu Ile Asn Val Ala Asn Ala Leu Arg Asn Glu Val Val Ala Thr
                740                 745                 750

Phe Lys Asn Thr Asp Ser Lys Gly Leu Val Asn Ser Tyr Gly Ser Ile
                755                 760                 765

Ser Leu Lys Glu Ile Lys Gly Asp Lys Lys Tyr Phe Thr Ile Lys Leu
770                 775                 780

His Asn Thr Ser Asn Arg Pro Leu Thr Phe Lys Val Ser Ala Ser Ala
785                 790                 795                 800

Ile Thr Thr Asp Ser Leu Thr Asp Arg Leu Lys Leu Asp Glu Thr Tyr
                805                 810                 815

Lys Asp Glu Lys Ser Pro Asp Gly Lys Gln Ile Val Pro Glu Ile His
                820                 825                 830

Pro Glu Lys Val Lys Gly Ala Asn Ile Thr Phe Glu His Asp Thr Phe
                835                 840                 845

Thr Ile Gly Ala Asn Ser Ser Phe Asp Leu Asn Ala Val Ile Asn Val
                850                 855                 860

Gly Glu Ala Lys Asn Lys Asn Lys Phe Val Glu Ser Phe Ile His Phe
865                 870                 875                 880

Glu Ser Val Glu Glu Met Glu Ala Leu Asn Ser Asn Gly Lys Lys Ile
                885                 890                 895

Asn Phe Gln Pro Ser Leu Ser Met Pro Leu Met Gly Phe Ala Gly Asn
                900                 905                 910

Trp Asn His Glu Pro Ile Leu Asp Lys Trp Ala Trp Glu Gly Ser
                915                 920                 925

Arg Ser Lys Thr Leu Gly Gly Tyr Asp Asp Gly Lys Pro Lys Ile
930                 935                 940

Pro Gly Thr Leu Asn Lys Gly Ile Gly Gly Glu His Gly Ile Asp Lys
945                 950                 955                 960

Phe Asn Pro Ala Gly Val Ile Gln Asn Arg Lys Asp Lys Asn Thr Thr
                965                 970                 975

Ser Leu

<210> SEQ ID NO 268
<211> LENGTH: 99
<212> TYPE: PRT
<213> ORGANISM: Streptococcus pneumoniae
<220> FEATURE:
<221> NAME/KEY: MISC_FEATURE
<222> LOCATION: (33)..(33)
<223> OTHER INFORMATION: Arg or His
```

```
<220> FEATURE:
<221> NAME/KEY: MISC_FEATURE
<222> LOCATION: (44)..(44)
<223> OTHER INFORMATION: Glu or Ala
<220> FEATURE:
<221> NAME/KEY: MISC_FEATURE
<222> LOCATION: (49)..(49)
<223> OTHER INFORMATION: His or Leu
<220> FEATURE:
<221> NAME/KEY: MISC_FEATURE
<222> LOCATION: (61)..(61)
<223> OTHER INFORMATION: Val or Ile
<220> FEATURE:
<221> NAME/KEY: MISC_FEATURE
<222> LOCATION: (72)..(72)
<223> OTHER INFORMATION: Val or Leu
<220> FEATURE:
<221> NAME/KEY: MISC_FEATURE
<222> LOCATION: (74)..(74)
<223> OTHER INFORMATION: Gly or Ser
<220> FEATURE:
<221> NAME/KEY: MISC_FEATURE
<222> LOCATION: (86)..(86)
<223> OTHER INFORMATION: Val or Ile

<400> SEQUENCE: 268

Met Asn Gly Met Lys Ala Lys Lys Met Trp Met Ala Gly Leu Ala Leu
1               5                   10                  15

Leu Gly Ile Gly Ser Leu Ala Leu Ala Thr Lys Lys Val Ala Asp Asp
            20                  25                  30

Xaa Lys Leu Met Lys Thr Gln Glu Glu Leu Thr Xaa Ile Val Arg Asp
        35                  40                  45

Xaa Phe Ser Asp Met Gly Glu Ile Ala Thr Leu Tyr Xaa Gln Val Tyr
50                  55                  60

Glu Ser Ser Leu Glu Ser Leu Xaa Gly Xaa Val Ile Phe Glu Asp Gly
65                  70                  75                  80

Arg His Tyr Thr Phe Xaa Tyr Glu Asn Glu Asp Leu Val Tyr Glu Glu
                85                  90                  95

Glu Val Leu

<210> SEQ ID NO 269
<211> LENGTH: 667
<212> TYPE: PRT
<213> ORGANISM: Streptococcus pneumoniae
<220> FEATURE:
<221> NAME/KEY: MISC_FEATURE
<222> LOCATION: (1)..(1)
<223> OTHER INFORMATION: Met or absent
<220> FEATURE:
<221> NAME/KEY: MISC_FEATURE
<222> LOCATION: (9)..(9)
<223> OTHER INFORMATION: Ser or Asn
<220> FEATURE:
<221> NAME/KEY: MISC_FEATURE
<222> LOCATION: (15)..(15)
<223> OTHER INFORMATION: Asn or Ser
<220> FEATURE:
<221> NAME/KEY: MISC_FEATURE
<222> LOCATION: (23)..(23)
<223> OTHER INFORMATION: Ala or Val
<220> FEATURE:
<221> NAME/KEY: MISC_FEATURE
<222> LOCATION: (24)..(24)
<223> OTHER INFORMATION: absent or Val or Leu
<220> FEATURE:
<221> NAME/KEY: MISC_FEATURE
<222> LOCATION: (25)..(25)
<223> OTHER INFORMATION: absent or Asp
<220> FEATURE:
<221> NAME/KEY: MISC_FEATURE
<222> LOCATION: (26)..(26)
```

```
<223> OTHER INFORMATION: absent or Lys
<220> FEATURE:
<221> NAME/KEY: MISC_FEATURE
<222> LOCATION: (27)..(27)
<223> OTHER INFORMATION: absent or Glu
<220> FEATURE:
<221> NAME/KEY: MISC_FEATURE
<222> LOCATION: (28)..(28)
<223> OTHER INFORMATION: absent or Thr
<220> FEATURE:
<221> NAME/KEY: MISC_FEATURE
<222> LOCATION: (35)..(35)
<223> OTHER INFORMATION: Glu or Lys
<220> FEATURE:
<221> NAME/KEY: MISC_FEATURE
<222> LOCATION: (36)..(36)
<223> OTHER INFORMATION: Asn or Asp
<220> FEATURE:
<221> NAME/KEY: MISC_FEATURE
<222> LOCATION: (39)..(39)
<223> OTHER INFORMATION: Ser or Asn
<220> FEATURE:
<221> NAME/KEY: MISC_FEATURE
<222> LOCATION: (41)..(41)
<223> OTHER INFORMATION: Met or Ile
<220> FEATURE:
<221> NAME/KEY: MISC_FEATURE
<222> LOCATION: (45)..(45)
<223> OTHER INFORMATION: Gln or Lys
<220> FEATURE:
<221> NAME/KEY: MISC_FEATURE
<222> LOCATION: (47)..(47)
<223> OTHER INFORMATION: Phe or Thr
<220> FEATURE:
<221> NAME/KEY: MISC_FEATURE
<222> LOCATION: (48)..(48)
<223> OTHER INFORMATION: Lys or Glu
<220> FEATURE:
<221> NAME/KEY: MISC_FEATURE
<222> LOCATION: (53)..(53)
<223> OTHER INFORMATION: Ala or Thr
<220> FEATURE:
<221> NAME/KEY: MISC_FEATURE
<222> LOCATION: (54)..(54)
<223> OTHER INFORMATION: Val or Ile
<220> FEATURE:
<221> NAME/KEY: MISC_FEATURE
<222> LOCATION: (56)..(56)
<223> OTHER INFORMATION: Lys or Glu
<220> FEATURE:
<221> NAME/KEY: MISC_FEATURE
<222> LOCATION: (57)..(57)
<223> OTHER INFORMATION: Glu or Gly
<220> FEATURE:
<221> NAME/KEY: MISC_FEATURE
<222> LOCATION: (59)..(59)
<223> OTHER INFORMATION: Glu or Ala
<220> FEATURE:
<221> NAME/KEY: MISC_FEATURE
<222> LOCATION: (67)..(67)
<223> OTHER INFORMATION: Ile or Thr
<220> FEATURE:
<221> NAME/KEY: MISC_FEATURE
<222> LOCATION: (69)..(69)
<223> OTHER INFORMATION: Asn or Thr
<220> FEATURE:
<221> NAME/KEY: MISC_FEATURE
<222> LOCATION: (70)..(70)
<223> OTHER INFORMATION: Asn or Lys
<220> FEATURE:
<221> NAME/KEY: MISC_FEATURE
<222> LOCATION: (77)..(77)
<223> OTHER INFORMATION: Lys or Arg
<220> FEATURE:
<221> NAME/KEY: MISC_FEATURE
<222> LOCATION: (81)..(81)
<223> OTHER INFORMATION: Glu or Asp
<220> FEATURE:
<221> NAME/KEY: MISC_FEATURE
```

```
<222> LOCATION: (82)..(82)
<223> OTHER INFORMATION: Asn or absent
<220> FEATURE:
<221> NAME/KEY: MISC_FEATURE
<222> LOCATION: (85)..(85)
<223> OTHER INFORMATION: Lys or Gln
<220> FEATURE:
<221> NAME/KEY: MISC_FEATURE
<222> LOCATION: (90)..(90)
<223> OTHER INFORMATION: Tyr or His or Asn
<220> FEATURE:
<221> NAME/KEY: MISC_FEATURE
<222> LOCATION: (91)..(91)
<223> OTHER INFORMATION: Thr or Ala
<220> FEATURE:
<221> NAME/KEY: MISC_FEATURE
<222> LOCATION: (92)..(92)
<223> OTHER INFORMATION: Asp or His
<220> FEATURE:
<221> NAME/KEY: MISC_FEATURE
<222> LOCATION: (94)..(94)
<223> OTHER INFORMATION: Phe or Ser
<220> FEATURE:
<221> NAME/KEY: MISC_FEATURE
<222> LOCATION: (95)..(95)
<223> OTHER INFORMATION: Val or Ala
<220> FEATURE:
<221> NAME/KEY: MISC_FEATURE
<222> LOCATION: (98)..(98)
<223> OTHER INFORMATION: Asn or Gly
<220> FEATURE:
<221> NAME/KEY: MISC_FEATURE
<222> LOCATION: (105)..(105)
<223> OTHER INFORMATION: Glu or Gln
<220> FEATURE:
<221> NAME/KEY: MISC_FEATURE
<222> LOCATION: (107)..(107)
<223> OTHER INFORMATION: Lys or Arg
<220> FEATURE:
<221> NAME/KEY: MISC_FEATURE
<222> LOCATION: (108)..(108)
<223> OTHER INFORMATION: Val or Leu
<220> FEATURE:
<221> NAME/KEY: MISC_FEATURE
<222> LOCATION: (121)..(121)
<223> OTHER INFORMATION: Glu or Ser
<220> FEATURE:
<221> NAME/KEY: MISC_FEATURE
<222> LOCATION: (126)..(126)
<223> OTHER INFORMATION: Glu or Gln or Gly
<220> FEATURE:
<221> NAME/KEY: MISC_FEATURE
<222> LOCATION: (129)..(129)
<223> OTHER INFORMATION: Ser or Asn
<220> FEATURE:
<221> NAME/KEY: MISC_FEATURE
<222> LOCATION: (146)..(146)
<223> OTHER INFORMATION: Ser or Gly
<220> FEATURE:
<221> NAME/KEY: MISC_FEATURE
<222> LOCATION: (152)..(152)
<223> OTHER INFORMATION: Pro or Gln
<220> FEATURE:
<221> NAME/KEY: MISC_FEATURE
<222> LOCATION: (165)..(165)
<223> OTHER INFORMATION: Ser or Thr
<220> FEATURE:
<221> NAME/KEY: MISC_FEATURE
<222> LOCATION: (167)..(167)
<223> OTHER INFORMATION: Val or Ile
<220> FEATURE:
<221> NAME/KEY: MISC_FEATURE
<222> LOCATION: (440)..(440)
<223> OTHER INFORMATION: Glu or Gln
<220> FEATURE:
<221> NAME/KEY: MISC_FEATURE
<222> LOCATION: (454)..(454)
<223> OTHER INFORMATION: Ser or Asn
<220> FEATURE:
```

```
<221> NAME/KEY: MISC_FEATURE
<222> LOCATION: (567)..(567)
<223> OTHER INFORMATION: Asp or Asn

<400> SEQUENCE: 269

Xaa Val Val Leu Ala Asp Thr Ser Xaa Ser Glu Asp Ala Leu Xaa Ile
1               5                   10                  15

Ser Asp Lys Glu Lys Val Xaa Xaa Xaa Xaa Xaa Xaa Glu Asn Lys Glu
            20                  25                  30

Lys His Xaa Xaa Ile His Xaa Ala Xaa Glu Thr Ser Xaa Asp Xaa Xaa
        35                  40                  45

Glu Lys Lys Thr Xaa Xaa Ile Xaa Xaa Lys Xaa Val Val Ser Lys Asn
    50                  55                  60

Pro Val Xaa Asp Xaa Xaa Thr Ser Asn Glu Glu Ala Xaa Ile Lys Glu
65                  70                  75                  80

Xaa Xaa Ser Asn Xaa Ser Gln Gly Asp Xaa Xaa Xaa Ser Xaa Xaa Asn
                85                  90                  95

Lys Xaa Thr Glu Asn Pro Lys Lys Xaa Asp Xaa Xaa Val Tyr Ile Ala
            100                 105                 110

Glu Phe Lys Asp Lys Glu Ser Gly Xaa Lys Ala Ile Lys Xaa Leu Ser
        115                 120                 125

Xaa Leu Lys Asn Thr Lys Val Leu Tyr Thr Tyr Asp Arg Ile Phe Asn
    130                 135                 140

Gly Xaa Ala Ile Glu Thr Thr Xaa Asp Asn Leu Asp Lys Ile Lys Gln
145                 150                 155                 160

Ile Glu Gly Ile Xaa Ser Xaa Glu Arg Ala Gln Lys Val Gln Pro Met
                165                 170                 175

Met Asn His Ala Arg Lys Glu Ile Gly Val Glu Glu Ala Ile Asp Tyr
            180                 185                 190

Leu Lys Ser Ile Asn Ala Pro Phe Gly Lys Asn Phe Asp Gly Arg Gly
        195                 200                 205

Met Val Ile Ser Asn Ile Asp Thr Gly Thr Asp Tyr Arg His Lys Ala
    210                 215                 220

Met Arg Ile Asp Asp Asp Ala Lys Ala Ser Met Arg Phe Lys Lys Glu
225                 230                 235                 240

Asp Leu Lys Gly Thr Asp Lys Asn Tyr Trp Leu Ser Asp Lys Ile Pro
                245                 250                 255

His Ala Phe Asn Tyr Tyr Asn Gly Gly Lys Ile Thr Val Glu Lys Tyr
            260                 265                 270

Asp Asp Gly Arg Asp Tyr Phe Asp Pro His Gly Met His Ile Ala Gly
        275                 280                 285

Ile Leu Ala Gly Asn Asp Thr Glu Gln Asp Ile Lys Asn Phe Asn Gly
    290                 295                 300

Ile Asp Gly Ile Ala Pro Asn Ala Gln Ile Phe Ser Tyr Lys Met Tyr
305                 310                 315                 320

Ser Asp Ala Gly Ser Gly Phe Ala Gly Asp Glu Thr Met Phe His Ala
                325                 330                 335

Ile Glu Asp Ser Ile Lys His Asn Val Asp Val Val Ser Val Ser Ser
            340                 345                 350

Gly Phe Thr Gly Thr Gly Leu Val Gly Glu Lys Tyr Trp Gln Ala Ile
        355                 360                 365

Arg Ala Leu Arg Lys Ala Gly Ile Pro Met Val Val Ala Thr Gly Asn
    370                 375                 380

Tyr Ala Thr Ser Ala Ser Ser Ser Ser Trp Asp Leu Val Ala Asn Asn
```

```
                385                 390                 395                 400
        His Leu Lys Met Thr Asp Thr Gly Asn Val Thr Arg Thr Ala Ala His
                        405                 410                 415

Glu Asp Ala Ile Ala Val Ala Ser Ala Lys Asn Gln Thr Val Glu Phe
                        420                 425                 430

Asp Lys Val Asn Ile Gly Gly Xaa Ser Phe Lys Tyr Arg Asn Ile Gly
                        435                 440                 445

Ala Phe Phe Asp Lys Xaa Lys Ile Thr Thr Asn Glu Asp Gly Thr Lys
                    450                 455                 460

Ala Pro Ser Lys Leu Lys Phe Val Tyr Ile Gly Lys Gly Gln Asp Gln
        465                 470                 475                 480

Asp Leu Ile Gly Leu Asp Leu Arg Gly Lys Ile Ala Val Met Asp Arg
                        485                 490                 495

Ile Tyr Thr Lys Asp Leu Lys Asn Ala Phe Lys Ala Met Asp Lys
                        500                 505                 510

Gly Ala Arg Ala Ile Met Val Val Asn Thr Val Asn Tyr Tyr Asn Arg
                        515                 520                 525

Asp Asn Trp Thr Glu Leu Pro Ala Met Gly Tyr Glu Ala Asp Glu Gly
                    530                 535                 540

Thr Lys Ser Gln Val Phe Ser Ile Ser Gly Asp Asp Gly Val Lys Leu
        545                 550                 555                 560

Trp Asn Met Ile Asn Pro Xaa Lys Lys Thr Glu Val Lys Arg Asn Asn
                        565                 570                 575

Lys Glu Asp Phe Lys Asp Lys Leu Glu Gln Tyr Tyr Pro Ile Asp Met
                        580                 585                 590

Glu Ser Phe Asn Ser Asn Lys Pro Asn Val Gly Asp Glu Lys Glu Ile
                    595                 600                 605

Asp Phe Lys Phe Ala Pro Asp Thr Asp Lys Glu Leu Tyr Lys Glu Asp
                        610                 615                 620

Ile Ile Val Pro Ala Gly Ser Thr Ser Trp Gly Pro Arg Ile Asp Leu
        625                 630                 635                 640

Leu Leu Lys Pro Asp Val Ser Ala Pro Gly Lys Asn Ile Lys Ser Thr
                        645                 650                 655

Leu Asn Val Ile Asn Gly Lys Ser Thr Tyr Gly
                        660                 665

<210> SEQ ID NO 270
<211> LENGTH: 621
<212> TYPE: PRT
<213> ORGANISM: Streptococcus pneumoniae
<220> FEATURE:
<221> NAME/KEY: MISC_FEATURE
<222> LOCATION: (28)..(28)
<223> OTHER INFORMATION: Arg or Lys
<220> FEATURE:
<221> NAME/KEY: MISC_FEATURE
<222> LOCATION: (35)..(35)
<223> OTHER INFORMATION: Lys or Thr
<220> FEATURE:
<221> NAME/KEY: MISC_FEATURE
<222> LOCATION: (143)..(143)
<223> OTHER INFORMATION: Ile or Val
<220> FEATURE:
<221> NAME/KEY: MISC_FEATURE
<222> LOCATION: (165)..(165)
<223> OTHER INFORMATION: Asp or Tyr
<220> FEATURE:
<221> NAME/KEY: MISC_FEATURE
<222> LOCATION: (210)..(210)
<223> OTHER INFORMATION: Lys or Arg
<220> FEATURE:
```

```
<221> NAME/KEY: MISC_FEATURE
<222> LOCATION: (227)..(227)
<223> OTHER INFORMATION: Glu or Ala
<220> FEATURE:
<221> NAME/KEY: MISC_FEATURE
<222> LOCATION: (232)..(232)
<223> OTHER INFORMATION: Asn or Ser
<220> FEATURE:
<221> NAME/KEY: MISC_FEATURE
<222> LOCATION: (238)..(238)
<223> OTHER INFORMATION: Ile or Thr
<220> FEATURE:
<221> NAME/KEY: MISC_FEATURE
<222> LOCATION: (239)..(239)
<223> OTHER INFORMATION: Asn or Asp
<220> FEATURE:
<221> NAME/KEY: MISC_FEATURE
<222> LOCATION: (271)..(271)
<223> OTHER INFORMATION: Arg or Lys
<220> FEATURE:
<221> NAME/KEY: MISC_FEATURE
<222> LOCATION: (275)..(275)
<223> OTHER INFORMATION: Leu or Met
<220> FEATURE:
<221> NAME/KEY: MISC_FEATURE
<222> LOCATION: (276)..(276)
<223> OTHER INFORMATION: Gly or Glu
<220> FEATURE:
<221> NAME/KEY: MISC_FEATURE
<222> LOCATION: (317)..(317)
<223> OTHER INFORMATION: Thr or Arg
<220> FEATURE:
<221> NAME/KEY: MISC_FEATURE
<222> LOCATION: (323)..(323)
<223> OTHER INFORMATION: Asn or Asp
<220> FEATURE:
<221> NAME/KEY: MISC_FEATURE
<222> LOCATION: (325)..(325)
<223> OTHER INFORMATION: Glu or Asp
<220> FEATURE:
<221> NAME/KEY: MISC_FEATURE
<222> LOCATION: (332)..(332)
<223> OTHER INFORMATION: Glu or Gln
<220> FEATURE:
<221> NAME/KEY: MISC_FEATURE
<222> LOCATION: (334)..(334)
<223> OTHER INFORMATION: Ile or Val
<220> FEATURE:
<221> NAME/KEY: MISC_FEATURE
<222> LOCATION: (335)..(335)
<223> OTHER INFORMATION: Asn or His
<220> FEATURE:
<221> NAME/KEY: MISC_FEATURE
<222> LOCATION: (337)..(337)
<223> OTHER INFORMATION: Pro or Glu
<220> FEATURE:
<221> NAME/KEY: MISC_FEATURE
<222> LOCATION: (339)..(339)
<223> OTHER INFORMATION: Ser or Thr
<220> FEATURE:
<221> NAME/KEY: MISC_FEATURE
<222> LOCATION: (393)..(393)
<223> OTHER INFORMATION: Arg or Lys
<220> FEATURE:
<221> NAME/KEY: MISC_FEATURE
<222> LOCATION: (398)..(398)
<223> OTHER INFORMATION: Ile or Val
<220> FEATURE:
<221> NAME/KEY: MISC_FEATURE
<222> LOCATION: (412)..(412)
<223> OTHER INFORMATION: Ser or Gly
<220> FEATURE:
<221> NAME/KEY: MISC_FEATURE
<222> LOCATION: (594)..(594)
<223> OTHER INFORMATION: Lys or Ser
<220> FEATURE:
<221> NAME/KEY: MISC_FEATURE
<222> LOCATION: (612)..(612)
<223> OTHER INFORMATION: Ser or Ala
```

<400> SEQUENCE: 270

Met Ser Gly Thr Ser Met Ala Thr Pro Ile Val Ala Ala Ser Thr Val
1               5                   10                  15

Leu Ile Arg Pro Lys Leu Lys Glu Met Leu Glu Xaa Pro Val Leu Lys
            20                  25                  30

Asn Leu Xaa Gly Asp Asp Lys Ile Asp Leu Thr Ser Leu Thr Lys Ile
        35                  40                  45

Ala Leu Gln Asn Thr Ala Arg Pro Met Met Asp Ala Thr Ser Trp Lys
    50                  55                  60

Glu Lys Ser Gln Tyr Phe Ala Ser Pro Arg Gln Gln Gly Ala Gly Leu
65                  70                  75                  80

Ile Asn Val Ala Asn Ala Leu Arg Asn Glu Val Val Ala Thr Phe Lys
                85                  90                  95

Asn Thr Asp Ser Lys Gly Leu Val Asn Ser Tyr Gly Ser Ile Ser Leu
            100                 105                 110

Lys Glu Ile Lys Gly Asp Lys Lys Tyr Phe Thr Ile Lys Leu His Asn
        115                 120                 125

Thr Ser Asn Arg Pro Leu Thr Phe Lys Val Ser Ala Ser Ala Xaa Thr
    130                 135                 140

Thr Asp Ser Leu Thr Asp Arg Leu Lys Leu Asp Glu Thr Tyr Lys Asp
145                 150                 155                 160

Glu Lys Ser Pro Xaa Gly Lys Gln Ile Val Pro Glu Ile His Pro Glu
                165                 170                 175

Lys Val Lys Gly Ala Asn Ile Thr Phe Glu His Asp Thr Phe Thr Ile
            180                 185                 190

Gly Ala Asn Ser Ser Phe Asp Leu Asn Ala Val Ile Asn Val Gly Glu
        195                 200                 205

Ala Xaa Asn Lys Asn Lys Phe Val Glu Ser Phe Ile His Phe Glu Ser
    210                 215                 220

Val Glu Xaa Met Glu Ala Leu Xaa Ser Asn Gly Lys Lys Xaa Xaa Phe
225                 230                 235                 240

Gln Pro Ser Leu Ser Met Pro Leu Met Gly Phe Ala Gly Asn Trp Asn
                245                 250                 255

His Glu Pro Ile Leu Asp Lys Trp Ala Trp Glu Glu Gly Ser Xaa Ser
            260                 265                 270

Lys Thr Xaa Xaa Gly Tyr Asp Asp Asp Gly Lys Pro Lys Ile Pro Gly
        275                 280                 285

Thr Leu Asn Lys Gly Ile Gly Gly Glu His Gly Ile Asp Lys Phe Asn
    290                 295                 300

Pro Ala Gly Val Ile Gln Asn Arg Lys Asp Lys Asn Xaa Thr Ser Leu
305                 310                 315                 320

Asp Gln Xaa Pro Xaa Leu Phe Ala Phe Asn Asn Xaa Gly Xaa Xaa Ala
                325                 330                 335

Xaa Ser Xaa Ser Gly Ser Lys Ile Ala Asn Ile Tyr Pro Leu Asp Ser
            340                 345                 350

Asn Gly Asn Pro Gln Asp Ala Gln Leu Glu Arg Gly Leu Thr Pro Ser
        355                 360                 365

Pro Leu Val Leu Arg Ser Ala Glu Glu Gly Leu Ile Ser Ile Val Asn
    370                 375                 380

Thr Asn Lys Glu Gly Glu Asn Gln Xaa Asp Leu Lys Val Xaa Ser Arg
385                 390                 395                 400

Glu His Phe Ile Arg Gly Ile Leu Asn Ser Lys Xaa Asn Asp Ala Lys

```
                       405                 410                 415
Gly Ile Lys Ser Ser Lys Leu Lys Val Trp Gly Asp Leu Lys Trp Asp
            420                 425                 430

Gly Leu Ile Tyr Asn Pro Arg Gly Glu Glu Asn Ala Pro Glu Ser
        435                 440                 445

Lys Asp Asn Gln Asp Pro Ala Thr Lys Ile Arg Gly Gln Phe Glu Pro
    450                 455                 460

Ile Ala Glu Gly Gln Tyr Phe Tyr Lys Phe Lys Tyr Arg Leu Thr Lys
465                 470                 475                 480

Asp Tyr Pro Trp Gln Val Ser Tyr Ile Pro Val Lys Ile Asp Asn Thr
                485                 490                 495

Ala Pro Lys Ile Val Ser Val Asp Phe Ser Asn Pro Glu Lys Ile Lys
            500                 505                 510

Leu Ile Thr Lys Asp Thr Tyr His Lys Val Lys Asp Gln Tyr Lys Asn
        515                 520                 525

Glu Thr Leu Phe Ala Arg Asp Gln Lys Glu His Pro Glu Lys Phe Asp
    530                 535                 540

Glu Ile Ala Asn Glu Val Trp Tyr Ala Gly Ala Leu Val Asn Glu
545                 550                 555                 560

Asp Gly Glu Val Glu Lys Asn Leu Glu Val Thr Tyr Ala Gly Glu Gly
                565                 570                 575

Gln Gly Arg Asn Arg Lys Leu Lys Asp Gly Asn Thr Ile Tyr Glu
            580                 585                 590

Ile Xaa Gly Ala Gly Asp Leu Arg Gly Lys Ile Ile Glu Val Ile Ala
        595                 600                 605

Leu Asp Gly Xaa Ser Asn Phe Thr Asp His Lys Ala Glu
    610                 615                 620

<210> SEQ ID NO 271
<211> LENGTH: 300
<212> TYPE: DNA
<213> ORGANISM: Streptococcus pneumoniae

<400> SEQUENCE: 271
atgaatggta tgaaagctaa aaaaatgtgg atggcaggct tggctctgct aggtatcgga      60
agccttgctc ttgctacgaa aaaagttgca gatgaccgta agctcatgaa gactcaggaa     120
gagttgacag agattgtgcg agaccatttt tccgacatgg ggaaattgc gacccttat     180 gttcaagttt acgaaagcag tctggagagc ttggttggtg cgtcattttt gaggatggc     240 cgtcattata cctttgtcta tgaaaatgaa gacctagtct atgaggagga agtcttatga    300

<210> SEQ ID NO 272
<211> LENGTH: 279
<212> TYPE: DNA
<213> ORGANISM: Streptococcus pneumoniae

<400> SEQUENCE: 272
atgagatacc tggcaacatt gttgttatct ctggcggtgt taatcaccgc cgggtgcaaa      60
aaagttgcag atgaccgtaa gctcatgaag actcaggaag agttgacaga gattgtgcga    120
gaccattttt ccgacatggg ggaaattgcg acccttatg ttcaagttta cgaaagcagt    180
ctggagagct tggttggtgg cgtcattttt gaggatggcc gtcattatac ctttgtctat    240
gaaaatgaag acctagtcta tgaggaggaa gtcttatga                             279

<210> SEQ ID NO 273
```

<211> LENGTH: 2934
<212> TYPE: DNA
<213> ORGANISM: Streptococcus pneumoniae

<400> SEQUENCE: 273

```
gacacatcta gctctgaaga tgctttaaac atctctgata aagaaaaagt agcagaaaat      60
aaagagaaac atgaaaatat ccatagtgct atggaaactt cacaggattt taaagagaag     120
aaaacagcag tcattaagga aaaagaagtt gttagtaaaa atcctgtgat agacaataac     180
actagcaatg aagaagcaaa aatcaaagaa gaaaattcca ataaatccca aggagattat     240
acggactcat ttgtgaataa aaacacagaa aatcccaaaa aagaagataa agttgtctat     300
attgctgaat ttaaagataa agaatctgga gaaaaagcaa tcaaggaact atccagtctt     360
aagaatacaa agttttata tacttatgat agaatttta acggtagtgc catagaaaca       420
actccagata acttggacaa aattaaacaa ataagaggta tttcatcggt tgaaagggca     480
caaaaagtcc aacccatgat gaatcatgcc agaaaggaaa ttggagttga ggaagctatt     540
gattacctaa agtctatcaa tgctccgttt gggaaaaatt ttgatggtag aggtatggtc     600
atttcaaata tcgatactgg aacagattat agacataagg ctatgagaat cgatgatgat     660
gccaaagcct caatgagatt taaaaaagaa gacttaaaag gcactgataa aaattattgg     720
ttgagtgata aaatccctca tgcgttcaat tattataatg gtggcaaaat cactgtagaa     780
aaatatgatg atggaaggga ttattttgac ccacatggga tgcatattgc agggattctt     840
gctggaaatg atactgaaca agacatcaaa aactttaacg gcatagatgg aattgcacct     900
aatgcacaaa ttttctctta caaaatgtat tctgacgcag atctgggtt tgcgggtgat      960
gaaacaatgt tcatgctat tgaagattct atcaaacaca acgttgatgt tgtttcggta     1020
tcatctggtt ttacaggaac aggtcttgta ggtgagaaat attggcaagc tattcgggca    1080
ttaagaaaag caggcattcc aatggttgtc gctacgggta actatgcgac ttctgcttca    1140
agttcttcat gggatttagt agcaaataat catctgaaaa tgaccgacac tggaaatgta    1200
acacgaactg cagcacatga agatgcgata gcggtcgctt ctgctaaaaa tcaaacagtt    1260
gagtttgata agttaacat aggtggagaa agttttaaat acagaaatat aggggccttt     1320
ttcgataaga gtaaaatcac aacaaatgaa gatggaacaa aagctcctag taaattaaaa    1380
tttgtatata taggcaaggg gcaagaccaa gatttgatag gtttggatct taggggcaaa    1440
attgcagtaa tggatagaat ttatacaaag gatttaaaaa atgcttttaa aaaagctatg    1500
gataagggtg cacgcgccat tatggttgta aatactgtaa attactacaa tagagataat    1560
tggacagagc ttccagctat gggatatgaa gcggatgaag gtactaaaag tcaagtgttt    1620
tcaatttcag gagatgatgg tgtaaagcta tggaacatga ttaatcctga taaaaaaact    1680
gaagtcaaaa gaaataataa agaagatttt aaagataaat tggagcaata ctatccaatt    1740
gatatggaaa gttttaattc caacaaaccg aatgtaggtg acgaaaaaga gattgacttt    1800
aagtttgcac ctgacacaga caagaactc tataaagaag atatcatcgt tccagcagga    1860
tctacatctt gggggccaag aatagattta cttttaaaac ccgatgtttc agcacctggt    1920
aaaaatatta atccacgct taatgttatt aatggcaaat caacttatgg ctatatgtca    1980
ggaactagta tggcgactcc aatcgtggca gcttctactg ttttgattag accgaaatta    2040
aaggaaatgc ttgaaagacc tgtattgaaa atcttaaggg agatgacaa aatagatctt    2100
acaagtctta caaaaattgc cctacaaaat actgcgcgac ctatgatgga tgcaacttct    2160
tggaaagaaa aaagtcaata ctttgcatca cctagacaac agggagcagg cctaattaat    2220
```

```
gtggccaatg ctttgagaaa tgaagttgta gcaactttca aaaacactga ttctaaaggt    2280
ttggtaaact catatggttc catttctctt aagaaataa aaggtgataa aaaatacttt     2340
acaatcaagc ttcacaatac atcaaacaga cctttgactt ttaaagtttc agcatcagcg    2400
ataactacag attctctaac tgacagatta aaacttgatg aaacatataa agatgaaaaa    2460
tctccagatg gtaagcaaat tgttccagaa attcacccag aaaaagtcaa aggagcaaat    2520
atcacatttg agcatgatac tttcactata ggcgcaaatt ctagctttga tttgaatgcg    2580
gttataaatg ttggagaggc caaaaacaaa aataaatttg tagaatcatt tattcatttt    2640
gagtcagtgg aagaaatgga agctctaaac tccaacggga agaaaataaa cttccaacct    2700
tctttgtcga tgcctctaat gggatttgct gggaattgga accacgaacc aatccttgat    2760
aaatgggctt gggaagaagg gtcaagatca aaaacactgg gaggttatga tgatgatggt    2820
aaaccgaaaa ttccaggaac cttaaataag ggaattggtg gagaacatgg tatagataaa    2880
tttaatccag caggagttat acaaaataga aagataaaa atacaacatc cctg           2934
```

<210> SEQ ID NO 274
<211> LENGTH: 5
<212> TYPE: PRT
<213> ORGANISM: Streptococcus pneumoniae
<220> FEATURE:
<221> NAME/KEY: MISC_FEATURE
<222> LOCATION: (1)..(1)
<223> OTHER INFORMATION: Leu or Ile or Val or Met or Phe or Glu or Ser
       or Thr or Ala or Gly or Pro or Cys
<220> FEATURE:
<221> NAME/KEY: MISC_FEATURE
<222> LOCATION: (2)..(2)
<223> OTHER INFORMATION: Leu or Val or Ile or Ala or Met or Phe or Thr
       or Gly
<220> FEATURE:
<221> NAME/KEY: MISC_FEATURE
<222> LOCATION: (3)..(3)
<223> OTHER INFORMATION: Ile or Val or Met or Ser or Thr or Ala or Gly
       or Cys or Pro
<220> FEATURE:
<221> NAME/KEY: MISC_FEATURE
<222> LOCATION: (4)..(4)
<223> OTHER INFORMATION: Ala or Gly or Ser

<400> SEQUENCE: 274

Xaa Xaa Xaa Xaa Cys
1               5

<210> SEQ ID NO 275
<211> LENGTH: 25
<212> TYPE: PRT
<213> ORGANISM: Streptococcus pneumoniae

<400> SEQUENCE: 275

Met Ser Ser Lys Phe Met Lys Ser Ala Ala Val Leu Gly Thr Ala Thr
1               5                   10                  15

Leu Ala Ser Leu Leu Leu Val Ala Cys
            20                  25

<210> SEQ ID NO 276
<211> LENGTH: 19
<212> TYPE: PRT
<213> ORGANISM: Escherichia coli

<400> SEQUENCE: 276

Met Arg Tyr Leu Ala Thr Leu Leu Leu Ser Leu Ala Val Leu Ile Thr
1               5                   10                  15

Ala Gly Cys

<210> SEQ ID NO 277
<211> LENGTH: 15
<212> TYPE: PRT
<213> ORGANISM: Streptococcus pneumoniae

<400> SEQUENCE: 277

Lys Met Trp Met Ala Gly Leu Ala Leu Leu Gly Ile Gly Ser Leu
1               5                   10                  15

<210> SEQ ID NO 278
<211> LENGTH: 15
<212> TYPE: PRT
<213> ORGANISM: Streptococcus pneumoniae

<400> SEQUENCE: 278

Leu Leu Gly Ile Gly Ser Leu Ala Leu Ala Thr Lys Lys Val Ala
1               5                   10                  15

<210> SEQ ID NO 279
<211> LENGTH: 15
<212> TYPE: PRT
<213> ORGANISM: Streptococcus pneumoniae

<400> SEQUENCE: 279

Met Ala Gly Leu Ala Leu Leu Gly Ile Gly Ser Leu Ala Leu Ala
1               5                   10                  15

<210> SEQ ID NO 280
<211> LENGTH: 15
<212> TYPE: PRT
<213> ORGANISM: Streptococcus pneumoniae

<400> SEQUENCE: 280

Trp Met Ala Gly Leu Ala Leu Leu Gly Ile Gly Ser Leu Ala Leu
1               5                   10                  15

<210> SEQ ID NO 281
<211> LENGTH: 15
<212> TYPE: PRT
<213> ORGANISM: Streptococcus pneumoniae

<400> SEQUENCE: 281

Gly Leu Ala Leu Leu Gly Ile Gly Ser Leu Ala Leu Ala Thr Lys
1               5                   10                  15

<210> SEQ ID NO 282
<211> LENGTH: 15
<212> TYPE: PRT
<213> ORGANISM: Streptococcus pneumoniae

<400> SEQUENCE: 282

Leu Ala Leu Leu Gly Ile Gly Ser Leu Ala Leu Ala Thr Lys Lys
1               5                   10                  15

<210> SEQ ID NO 283
<211> LENGTH: 15
<212> TYPE: PRT
<213> ORGANISM: Streptococcus pneumoniae

<400> SEQUENCE: 283

Phe Ser Asp Met Gly Glu Ile Ala Thr Leu Tyr Val Gln Val Tyr
1               5                   10                  15

```
<210> SEQ ID NO 284
<211> LENGTH: 15
<212> TYPE: PRT
<213> ORGANISM: Streptococcus pneumoniae

<400> SEQUENCE: 284

Lys Ala Lys Lys Met Trp Met Ala Gly Leu Ala Leu Leu Gly Ile
1               5                   10                  15

<210> SEQ ID NO 285
<211> LENGTH: 17
<212> TYPE: PRT
<213> ORGANISM: Streptococcus pneumoniae

<400> SEQUENCE: 285

Ala Leu Leu Gly Ile Gly Ser Leu Ala Leu Ala Thr Lys Lys Val Ala
1               5                   10                  15

Lys

<210> SEQ ID NO 286
<211> LENGTH: 13
<212> TYPE: PRT
<213> ORGANISM: Streptococcus pneumoniae

<400> SEQUENCE: 286

Lys Met Trp Met Ala Gly Leu Ala Leu Leu Gly Ile Gly
1               5                   10

<210> SEQ ID NO 287
<211> LENGTH: 15
<212> TYPE: PRT
<213> ORGANISM: Streptococcus pneumoniae

<400> SEQUENCE: 287

Ser Asp Met Gly Glu Ile Ala Thr Leu Tyr Val Gln Val Tyr Glu
1               5                   10                  15

<210> SEQ ID NO 288
<211> LENGTH: 15
<212> TYPE: PRT
<213> ORGANISM: Streptococcus pneumoniae

<400> SEQUENCE: 288

Asp Met Gly Glu Ile Ala Thr Leu Tyr Val Gln Val Tyr Glu Ser
1               5                   10                  15

<210> SEQ ID NO 289
<211> LENGTH: 15
<212> TYPE: PRT
<213> ORGANISM: Streptococcus pneumoniae

<400> SEQUENCE: 289

Ala Gly Leu Ala Leu Leu Gly Ile Gly Ser Leu Ala Leu Ala Thr
1               5                   10                  15

<210> SEQ ID NO 290
<211> LENGTH: 15
<212> TYPE: PRT
<213> ORGANISM: Streptococcus pneumoniae

<400> SEQUENCE: 290

Met Gly Glu Ile Ala Thr Leu Tyr Val Gln Val Tyr Glu Ser Ser
1               5                   10                  15
```

<210> SEQ ID NO 291
<211> LENGTH: 15
<212> TYPE: PRT
<213> ORGANISM: Streptococcus pneumoniae

<400> SEQUENCE: 291

Lys Lys Met Trp Met Ala Gly Leu Ala Leu Leu Gly Ile Gly Ser
1               5                   10                  15

<210> SEQ ID NO 292
<211> LENGTH: 15
<212> TYPE: PRT
<213> ORGANISM: Streptococcus pneumoniae

<400> SEQUENCE: 292

Gly Met Lys Ala Lys Lys Met Trp Met Ala Gly Leu Ala Leu Leu
1               5                   10                  15

<210> SEQ ID NO 293
<211> LENGTH: 15
<212> TYPE: PRT
<213> ORGANISM: Streptococcus pneumoniae

<400> SEQUENCE: 293

Met Lys Ala Lys Lys Met Trp Met Ala Gly Leu Ala Leu Leu Gly
1               5                   10                  15

<210> SEQ ID NO 294
<211> LENGTH: 15
<212> TYPE: PRT
<213> ORGANISM: Streptococcus pneumoniae

<400> SEQUENCE: 294

His Phe Ser Asp Met Gly Glu Ile Ala Thr Leu Tyr Val Gln Val
1               5                   10                  15

<210> SEQ ID NO 295
<211> LENGTH: 15
<212> TYPE: PRT
<213> ORGANISM: Streptococcus pneumoniae

<400> SEQUENCE: 295

Met Asn Gly Met Lys Ala Lys Lys Met Trp Met Ala Gly Leu Ala
1               5                   10                  15

<210> SEQ ID NO 296
<211> LENGTH: 15
<212> TYPE: PRT
<213> ORGANISM: Streptococcus pneumoniae

<400> SEQUENCE: 296

Met Trp Met Ala Gly Leu Ala Leu Leu Gly Ile Gly Ser Leu Ala
1               5                   10                  15

<210> SEQ ID NO 297
<211> LENGTH: 15
<212> TYPE: PRT
<213> ORGANISM: Streptococcus pneumoniae

<400> SEQUENCE: 297

Asp His Phe Ser Asp Met Gly Glu Ile Ala Thr Leu Tyr Val Gln
1               5                   10                  15

<210> SEQ ID NO 298
<211> LENGTH: 15
<212> TYPE: PRT
<213> ORGANISM: Streptococcus pneumoniae

<400> SEQUENCE: 298

Arg Asp His Phe Ser Asp Met Gly Glu Ile Ala Thr Leu Tyr Val
1               5                   10                  15

<210> SEQ ID NO 299
<211> LENGTH: 15
<212> TYPE: PRT
<213> ORGANISM: Streptococcus pneumoniae

<400> SEQUENCE: 299

Asn Gly Met Lys Ala Lys Lys Met Trp Met Ala Gly Leu Ala Leu
1               5                   10                  15

<210> SEQ ID NO 300

<400> SEQUENCE: 300

000

<210> SEQ ID NO 301
<211> LENGTH: 283
<212> TYPE: PRT
<213> ORGANISM: Streptococcus pneumoniae

<400> SEQUENCE: 301

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Lys Ala Met
145                 150                 155                 160

Ala Asp Leu Lys Lys Ala Val Asn Glu Pro Glu Lys Pro Ala Glu Glu
                165                 170                 175

Pro Glu Asn Pro Ala Pro Ala Pro Lys Pro Ala Pro Ala Pro Gln Pro
            180                 185                 190

Glu Lys Pro Ala Pro Ala Pro Lys Pro Glu Lys Ser Ala Asp
        195                 200                 205

Gln Gln Ala Glu Glu Asp Tyr Ala Arg Arg Ser Glu Glu Tyr Asn
    210                 215                 220

Arg Leu Thr Gln Gln Gln Pro Pro Lys Ala Glu Lys Pro Ala Pro Ala

```
                225                 230                 235                 240
Pro Val Lys Pro Glu Gln Pro Ala Pro Ala Pro Lys Thr Gly Trp
                245                 250                 255

Gly Gln Glu Asn Gly Met Trp Cys Arg Gln Ala Cys Gly Arg Thr Arg
                260                 265                 270

Ala Pro Pro Pro Pro Leu Arg Ser Gly Cys
                275                 280

<210> SEQ ID NO 302
<211> LENGTH: 286
<212> TYPE: PRT
<213> ORGANISM: Streptococcus pneumoniae

<400> SEQUENCE: 302

Met Ser Asp Lys Ile Ile His Leu Thr Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
                35                  40                  45

Glu Tyr Gln Gly Lys Leu Thr Val Ala Lys Leu Asn Ile Asp Gln Asn
            50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
                100                 105                 110

Ser Gly His Met His His His His His His Ser Ser Gly Leu Val Pro
            115                 120                 125

Arg Gly Ser Gly Met Lys Glu Thr Ala Ala Ala Lys Phe Glu Arg Gln
            130                 135                 140

His Met Asp Ser Pro Asp Leu Gly Thr Asp Asp Asp Asp Lys Ala Met
145                 150                 155                 160

Ala Asp Leu Lys Lys Ala Val Asn Glu Pro Glu Thr Pro Ala Pro Ala
                165                 170                 175

Pro Ala Pro Ala Pro Ala Pro Thr Pro Glu Ala Pro Ala Pro
                180                 185                 190

Ala Pro Ala Pro Ala Pro Lys Pro Ala Pro Ala Pro Lys Pro Ala Pro
                195                 200                 205

Ala Pro Lys Pro Ala Pro Ala Pro Lys Pro Ala Pro Ala Pro Lys Pro
                210                 215                 220

Ala Pro Ala Pro Lys Pro Ala Pro Ala Pro Ala Pro Ala Pro Lys Pro
225                 230                 235                 240

Glu Lys Pro Ala Glu Lys Pro Ala Pro Lys Pro Glu Thr Pro
                245                 250                 255

Lys Thr Gly Trp Lys Gln Glu Asn Gly Met Trp Cys Arg Gln Ala Cys
                260                 265                 270

Gly Arg Thr Arg Ala Pro Pro Pro Pro Leu Arg Ser Gly
            275                 280                 285

<210> SEQ ID NO 303
<211> LENGTH: 102
<212> TYPE: PRT
<213> ORGANISM: Streptococcus pneumoniae
```

```
<400> SEQUENCE: 303

Asp Leu Lys Lys Ala Val Asn Glu Pro Glu Lys Pro Ala Glu Pro
1               5                   10                  15

Glu Asn Pro Ala Pro Ala Pro Lys Pro Ala Pro Ala Pro Gln Pro Glu
                20                  25                  30

Lys Pro Ala Pro Ala Pro Ala Pro Lys Pro Glu Lys Ser Ala Asp Gln
            35                  40                  45

Gln Ala Glu Glu Asp Tyr Ala Arg Arg Ser Glu Glu Tyr Asn Arg
    50                  55                  60

Leu Thr Gln Gln Gln Pro Pro Lys Ala Glu Lys Pro Ala Pro Ala Pro
65                  70                  75                  80

Val Pro Lys Pro Glu Gln Pro Ala Pro Ala Pro Lys Thr Gly Trp Gly
                85                  90                  95

Gln Glu Asn Gly Met Trp
            100

<210> SEQ ID NO 304
<211> LENGTH: 106
<212> TYPE: PRT
<213> ORGANISM: Streptococcus pneumoniae

<400> SEQUENCE: 304

Asp Leu Lys Lys Ala Val Asn Glu Pro Thr Pro Ala Pro Ala Pro
1               5                   10                  15

Ala Pro Ala Pro Ala Pro Thr Pro Glu Ala Pro Ala Pro Ala
                20                  25                  30

Pro Ala Pro Ala Pro Lys Pro Ala Pro Ala Pro Lys Pro Ala Pro Ala
            35                  40                  45

Pro Lys Pro Ala Pro Ala Pro Lys Pro Ala Pro Ala Pro Lys Pro Ala
    50                  55                  60

Pro Ala Pro Lys Pro Ala Pro Ala Pro Ala Pro Lys Pro Glu
65                  70                  75                  80

Lys Pro Ala Glu Lys Pro Ala Pro Ala Pro Lys Pro Glu Thr Pro Lys
                85                  90                  95

Thr Gly Trp Lys Gln Glu Asn Gly Met Trp
            100                 105

<210> SEQ ID NO 305
<211> LENGTH: 58
<212> TYPE: PRT
<213> ORGANISM: Streptococcus pneumoniae

<400> SEQUENCE: 305

Met Ala Lys Lys Ala Glu Leu Glu Lys Thr Pro Glu Lys Pro Ala Glu
1               5                   10                  15

Glu Pro Glu Asn Pro Ala Pro Ala Pro Gln Pro Glu Lys Ser Ala Asp
                20                  25                  30

Gln Gln Ala Glu Glu Asp Tyr Ala Arg Arg Ser Glu Glu Glu Tyr Asn
            35                  40                  45

Arg Leu Thr Gln Gln Gln Pro Pro Lys Ala
    50                  55

<210> SEQ ID NO 306
<211> LENGTH: 27
<212> TYPE: PRT
<213> ORGANISM: Streptococcus pneumoniae

<400> SEQUENCE: 306
```

```
Glu Lys Ser Ala Asp Gln Gln Ala Glu Glu Asp Tyr Ala Arg Arg Ser
1               5                   10                  15

Glu Glu Glu Tyr Asn Arg Leu Thr Gln Gln Gln
                20                  25

<210> SEQ ID NO 307
<211> LENGTH: 23
<212> TYPE: PRT
<213> ORGANISM: Streptococcus pneumoniae

<400> SEQUENCE: 307

Asp Gln Gln Ala Glu Glu Asp Tyr Ala Arg Arg Ser Glu Glu Glu Tyr
1               5                   10                  15

Asn Arg Leu Thr Gln Gln Gln
                20

<210> SEQ ID NO 308
<211> LENGTH: 28
<212> TYPE: PRT
<213> ORGANISM: Streptococcus pneumoniae

<400> SEQUENCE: 308

Met Glu Lys Ser Ala Asp Gln Gln Ala Glu Glu Asp Tyr Ala Arg Arg
1               5                   10                  15

Ser Glu Glu Glu Tyr Asn Arg Leu Thr Gln Gln Gln
                20                  25

<210> SEQ ID NO 309
<211> LENGTH: 8
<212> TYPE: PRT
<213> ORGANISM: Streptococcus pneumoniae

<400> SEQUENCE: 309

Asp Leu Lys Lys Ala Val Asn Glu
1               5

<210> SEQ ID NO 310
<211> LENGTH: 11
<212> TYPE: PRT
<213> ORGANISM: Streptococcus pneumoniae
<220> FEATURE:
<221> NAME/KEY: MISC_FEATURE
<222> LOCATION: (1)..(1)
<223> OTHER INFORMATION: Lys or Gly
<220> FEATURE:
<221> NAME/KEY: MISC_FEATURE
<222> LOCATION: (5)..(5)
<223> OTHER INFORMATION: Lys or Gly

<400> SEQUENCE: 310

Xaa Thr Gly Trp Xaa Gln Glu Asn Gly Met Trp
1               5                   10
```

VACCINES AND COMPOSITIONS AGAINST *STREPTOCOCCUS PNEUMONIAE*

RELATED APPLICATION

This application claims the benefit of the filing date of U.S. Provisional Application No. 61/434,818, filed Jan. 20, 2011. The entire teachings of the referenced application are expressly incorporated herein by reference.

GOVERNMENT SUPPORT

This work was made with Government support under Grant AI066013 awarded by the National Institutes of Health. Therefore, the U.S. Government has certain rights in this invention.

I. BACKGROUND

Pneumococcal disease continues to be a leading cause of sickness and death in the United States and throughout the world. Each year, millions of cases of pneumonia, meningitis, bacteremia, and otitis media are attributed to infection with the pathogen *Streptococcus pneumoniae*. *S. pneumoniae* is a Gram-positive encapsulated coccus that colonizes the nasopharynx in about 5-10% of healthy adults and 20-40% of healthy children. Normal colonization becomes infectious when *S. pneumoniae* is carried into the Eustachian tubes, nasal sinuses, lungs, bloodstream, meninges, joint spaces, bones and peritoneal cavity. *S. pneumoniae* has several virulence factors that enable the organism to evade the immune system. Examples include a polysaccharide capsule that prevents phagocytosis by host immune cells, proteases that inhibit complement-mediated opsonization, and proteins that cause lysis of host cells. In the polysaccharide capsule, the presence of complex polysaccharides forms the basis for dividing pneumococci into different serotypes. To date, 93 serotypes of *S. pneumoniae* have been identified.

Various pharmaceutical compositions have been used to harness an immune response against infection by *S. pneumoniae*. A polyvalent pneumococcal vaccine, PPV-23, was developed for preventing pneumonia and other invasive diseases due to *S. pneumoniae* in the adult and aging populations. The vaccine contains capsular polysaccharides (CPs) from 23 serotypes of *S. pneumoniae*. As T cell-independent antigens, these CPs induce only short-lived antibody responses, necessitating repeated doses, which increases the risk of immunological tolerance. The antibodies raised against *S. pneumoniae*, termed anticapsular antibodies, are recognized as protective in adult and immunocompetent individuals. However, children under 2 years of age and immunocompromised individuals, including the elderly, do not respond well to T cell-independent antigens and, therefore, are not afforded optimal protection by PPV-23. Another *S. pneumoniae* vaccine, Prevnar, includes bacterial polysaccharides from 7 *S. pneumoniae* strains conjugated to the diphtheria toxoid protein. This vaccine induces both B and T cell responses. However, because it only protects against 7 pneumococcal serotypes, serotype replacement can render Prevnar ineffective. Serotype replacement has already been demonstrated in several clinical trials and epidemiologic studies, necessitating development of different formulations of these vaccines. An example is the recently introduced Prevnar 13, directed to 13 pneumococcal serotypes. Furthermore, the two Prevnar formulations are expensive to manufacture, greatly limiting their availability in the developing world. PPV-23, which consists of 23 purified but unconjugated polysaccharides, has broader coverage, but does not provide protection to children under the age of 2 years, a population which is at the highest risk for pneumococcal disease.

Thus, there remains a need to design more effective pharmaceutical compositions than the current strategies offer. In particular, such compositions need to incorporate novel or specific antigens that elicit an immune response against *S. pneumoniae*.

II. SUMMARY

*Streptococcus pneumoniae* is a major health concern, especially in very young, elderly, or immunocompromised patients. While DNA and protein sequence information for *S. pneumoniae* has been known for some time, and researchers have long attempted to produce vaccines against *S. pneumoniae*, a major problem was how to identify protective polypeptides from among the approximately 2100 genes in the *S. pneumoniae* genome. The instant application presents the results of whole-genome screens designed to identify the most immunogenic proteins in the *S. pneumoniae* genome. Several of the hits from the screen have been shown to protect against *S. pneumoniae* colonization in a mouse model, and in some instances against both colonization and *S. pneumoniae*-induced sepsis. Accordingly, the present disclosure provides, inter alia, certain highly effective vaccines against *Streptococcus pneumoniae*. The vaccines may be used therapeutically or prophylactically. The present disclosure also provides specific antigens and methods for using the antigens to elicit an immune response against *S. pneumoniae*.

In certain aspects, the present disclosure provides a vaccine formulation comprising a pharmaceutically acceptable carrier and a polypeptide having an amino acid sequence comprising (or consisting of) SEQ ID NO: 265 or 268 or an immunogenic fragment thereof. In some embodiments, the polypeptide comprises an exogenous signal sequence. For instance, the polypeptide may have an amino acid sequence comprising SEQ ID NO: 266 or an immunogenic fragment thereof. The polypeptide may have an amino acid sequence consisting of SEQ ID NO: 265, 266, or 268.

In some embodiments, the vaccine formulation further comprises a first polypeptide having an amino acid sequence comprising (or consisting of) one of SEQ ID NOS: 1-23, 267, and 269-270 or an immunogenic fragment thereof. In certain embodiments, the vaccine formulation further comprises a second polypeptide having an amino acid sequence comprising any of SEQ ID NOS: 1-23, 267, and 269-270 or an immunogenic fragment thereof.

In certain embodiments, the first and the second polypeptides belong to a different group of (i)-(vi): (i) SEQ ID NO: 1 or an immunogenic fragment thereof, (ii) one of SEQ ID NOS: 2-5 and 14-17 or an immunogenic fragment thereof, (iii) one of SEQ ID NOS: 6-7 and 18-19 or an immunogenic fragment thereof, (iv) SEQ ID NO: 8 or an immunogenic fragment thereof, (v) one of SEQ ID NOS: 9-10 and 20-21 or an immunogenic fragment thereof, and (vi) one of SEQ ID NO: 11-13, 267, and 269-270 or an immunogenic fragment thereof.

In some such embodiments, the vaccine formulation comprises a polypeptide having an amino acid sequence comprising SEQ ID NO: 6, SEQ ID NO: 7, SEQ ID NO: 9, or SEQ ID NO: 10. In some embodiments, the vaccine formulation comprises a polypeptide consisting of SEQ ID NO: 6 or 7 and a polypeptide consisting of SEQ ID NO: 9 or 10.

In any of the aspects or embodiments herein, the vaccine formulation may comprise a polypeptide of SEQ ID NO: 265, 266, or 268 which is a truncated fragment having from 1-20 amino acid residues removed from the N-terminus, C-terminus, or both. In some embodiments, the vaccine formulation contains substantially no other *S. pneumoniae* polypeptides other than polypeptides having an amino acid sequence comprising any of SEQ ID NOS: 1-21 and 265-270.

In certain embodiments, the vaccine formulation comprises one or more polypeptides having an amino acid sequence comprising SEQ ID NOS: 22 or 23 or an immunogenic fragment thereof.

In another aspect, the invention provides vaccine formulations comprising a known *S. pneumoniae* antigen, such as a pneumolysoid, Choline-binding protein A (CbpA), or Pneumococcal surface protein A (PspA), or derivatives thereof, and one, two, or three polypeptides from Table 1 or Table 2. An exemplary vaccine formulation comprises: (i) a polypeptide having an amino acid sequence comprising (or consisting of) one or more of SEQ ID NOS: 1-23 and 265-270 or an immunogenic fragment thereof, (ii) a pneumolysoid, and (iii) a pharmaceutically acceptable carrier. A further exemplary vaccine formulation comprises: (i) a polypeptide having an amino acid sequence comprising (or consisting of) one or more of SEQ ID NOS: 1-23 and 265-270 or an immunogenic fragment thereof, (ii) CbpA or a derivative thereof, and (iii) a pharmaceutically acceptable carrier. A further exemplary vaccine formulation comprises: (i) a polypeptide having an amino acid sequence comprising (or consisting of) one or more of SEQ ID NOS: 1-23 and 265-270 or an immunogenic fragment thereof, (ii) PspA or a derivative thereof, and (iii) a pharmaceutically acceptable carrier. In some such embodiments, the polypeptide of (i) comprises any one of SEQ ID NO: 2-5, 6, 7, 9-13, and 265-267. In some embodiments, the vaccine formulation further comprises a second polypeptide having an amino acid sequence comprising one of SEQ ID NO: 1-23 and 265-270. In some embodiments, the pneumolysoid is PdT, Pd-A, Pd-B, rPd2, rPd3, Ply8, Δ6PLY, L460D (see, e.g., US 2009/0285846 and L. Mitchell, Protective Immune Responses to *Streptococcus pneumoniae* Pneumolysoids, ASM2011 conference abstract, 2011), or a variant thereof. In some embodiments, the derivative of PspA comprises all or a fragment of the proline-rich region of PspA.

In certain embodiments, the polypeptide is conjugated to an immunogenic carrier. In some embodiments, the vaccine formulation comprises at least one lipidated polypeptide.

In some embodiments, the vaccine formulation further comprises conjugated *S. pneumoniae* polysaccharides. The conjugated polysaccharides may be, for example, as described in U.S. Pat. No. 5,623,057, U.S. Pat. No. 5,371,197, or PCT/US2011/023526.

In some embodiments, the vaccine formulation further comprises an adjuvant. The adjuvant may be, for example, an agonist of toll-like receptors (TLRs). The adjuvant may be, for example, alum. In some embodiments, the vaccine formulation comprises 1-1000 μg of each polypeptide and 1-250 μg of the adjuvant.

In certain embodiments, the vaccine formulation induces a $T_H17$ cell response at least 1.5-fold greater than that induced by a control unrelated antigen after contacting $T_H17$ cells. In some embodiments, the vaccine formulation inhibits infection by *S. pneumoniae* in an uninfected subject. In certain embodiments, the vaccine formulation inhibits *S. pneumoniae* colonization in an individual. In some embodiments, the vaccine formulation inhibits *S. pneumoniae* symptoms or sequelae. For instance, the vaccine formulation inhibits *S. pneumoniae*-induced sepsis.

In certain aspects, the present disclosure provides a method for treating a subject suffering from or susceptible to *S. pneumoniae* infection, comprising administering an effective amount of any of the vaccine formulations described herein. In some embodiments, the method inhibits infection by *S. pneumoniae* in an uninfected subject. In some embodiments, the method inhibits *S. pneumoniae* colonization in a subject. In some embodiments, the method inhibits *S. pneumoniae* symptoms or sequelae. An exemplary sequela is sepsis.

In certain embodiments, the method treats a subject with one dose. In other embodiments, the method treats a subject with two or three doses. In some embodiments, the method treats a subject within three doses.

In certain embodiments, the subject is a human.

The present disclosure provides, for example, a vaccine formulation comprising a pharmaceutically acceptable carrier and one or more polypeptides having an amino acid sequence comprising any of SEQ ID NOS: 1-13, 265, 266 and 267, or an immunogenic fragment thereof.

The present disclosure also provides a vaccine formulation comprising a pharmaceutically acceptable carrier and at least one polypeptide having an amino acid sequence comprising SEQ ID NO: 6, SEQ ID NO:10 or SEQ ID NO: 265, or an immunogenic fragment thereof. The present disclosure further provides a vaccine formulation comprising a pharmaceutically acceptable carrier and at least one polypeptide having an amino acid sequence consisting of SEQ ID NO: 7, SEQ ID NO: 9 or SEQ ID NO: 265, or an immunogenic fragment thereof.

Furthermore, the instant application provides a vaccine formulation comprising a pharmaceutically acceptable carrier and one or more polypeptides having an amino acid sequence comprising any of SEQ ID NOS: 14-23, 268, 269 and 270, or an immunogenic fragment thereof.

The present disclosure further provides an immunogenic composition comprising a pharmaceutically acceptable carrier and two or more polypeptides having amino acid sequences comprising any of SEQ ID NOS: 1-13, 265, 266 and 267, or an immunogenic fragment thereof.

The present disclosure also provides a vaccine formulation comprising a pharmaceutically acceptable carrier and two or more polypeptides having amino acid sequences comprising SEQ ID NO: 6, SEQ ID NO:10 or SEQ ID NO: 265, or an immunogenic fragment thereof. The present disclosure further provides a vaccine formulation comprising a pharmaceutically acceptable carrier and two or more polypeptides having amino acid sequences consisting of SEQ ID NO: 7, SEQ ID NO: 9 or SEQ ID NO: 265, or an immunogenic fragment thereof. This disclosure also provides a vaccine formulation comprising a pharmaceutically acceptable carrier and two or more polypeptides having amino acid sequences comprising SEQ ID NO: 6, SEQ ID NO: 9, and SEQ ID NO: 265, or an immunogenic fragment thereof. In addition, this disclosure provides a vaccine formulation comprising a pharmaceutically acceptable carrier and two or more polypeptides having amino acid sequences comprising SEQ ID NO: 7, SEQ ID NO: 10, and SEQ ID NO: 265, or an immunogenic fragment thereof. In some embodiments, the amino acid sequence comprising SEQ ID NO: 265 comprises an exogenous signal sequence.

The present disclosure also provides a vaccine formulation comprising a pharmaceutically acceptable carrier and three or more polypeptides having amino acid sequences comprising SEQ ID NO: 6, SEQ ID NO:10 and SEQ ID NO: 265, respectively, or an immunogenic fragment thereof. The present disclosure further provides a vaccine formulation comprising a pharmaceutically acceptable carrier and three or more polypeptides having amino acid sequences consisting of SEQ ID NO: 7, SEQ ID NO: 9 and SEQ ID NO: 265, respectively, or an immunogenic fragment thereof.

III. BRIEF DESCRIPTION OF THE DRAWINGS

FIG. 1 shows the concentration of IL-17 generated by blood samples from mice that were immunized with the indicated protein(s) and cholera toxin adjuvant, then stimulated with killed, unencapsulated whole cell *S. pneumoniae*, as described in Example 5. The left panel shows the data in scatter format, and the right panel shows the average and standard deviation for each sample. Immunization group "All 3" represents animals immunized with a combination of SP2108, SP0148, and SP1634.

Figure 6:
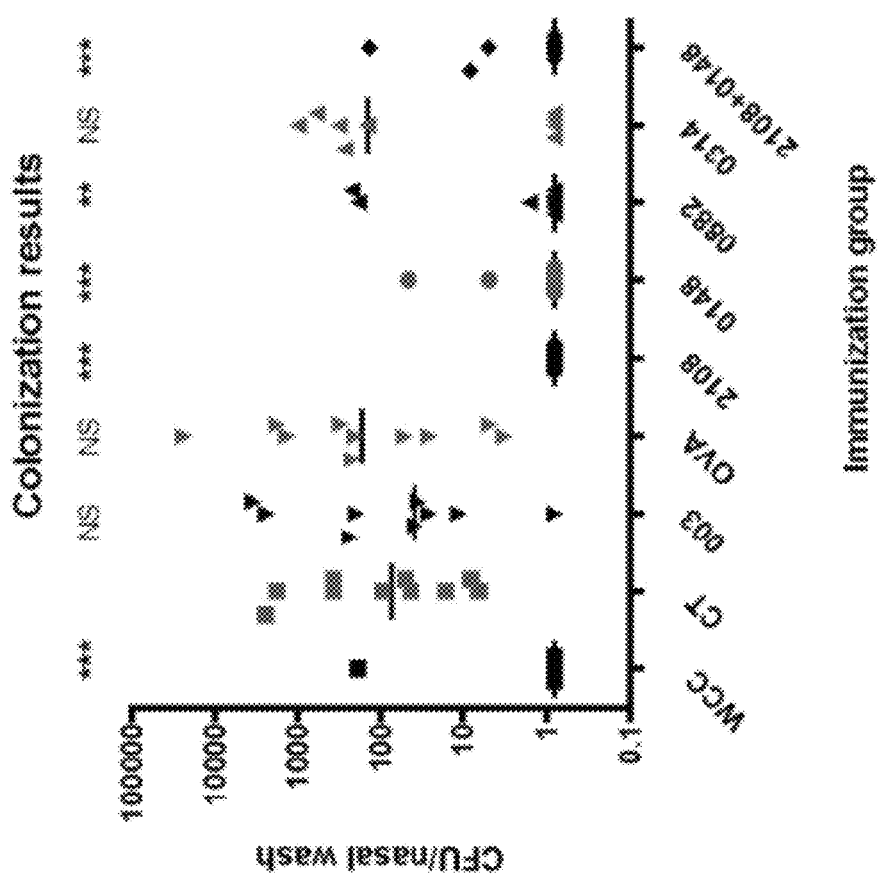

FIG. 6 shows the number of *S. pneumoniae* colonies obtained from a nasal wash in mice that were immunized with the indicated protein(s) and cholera toxin adjuvant, then challenged with intranasal administration of *S. pneumoniae*, as described in Example 6. The HSV-2 protein ICP47 with the gene name US12 (NP_044543.1, NC_001798.1; shown in the figure as 003) and ovalbumin (OVA) represent control antigens.

Figure 7:
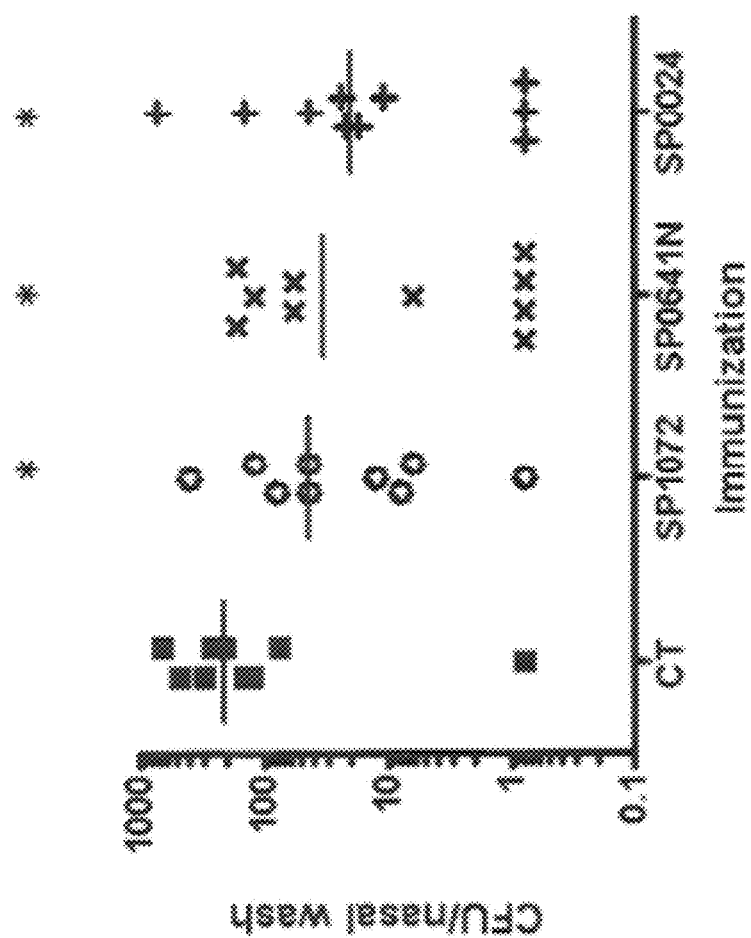

FIG. 7 shows the number of *S. pneumoniae* colonies obtained from a nasal wash in mice that were immunized with the indicated protein(s) and cholera toxin adjuvant, then challenged with intranasal administration of *S. pneumoniae*, as described in Example 7.

Figure 8:
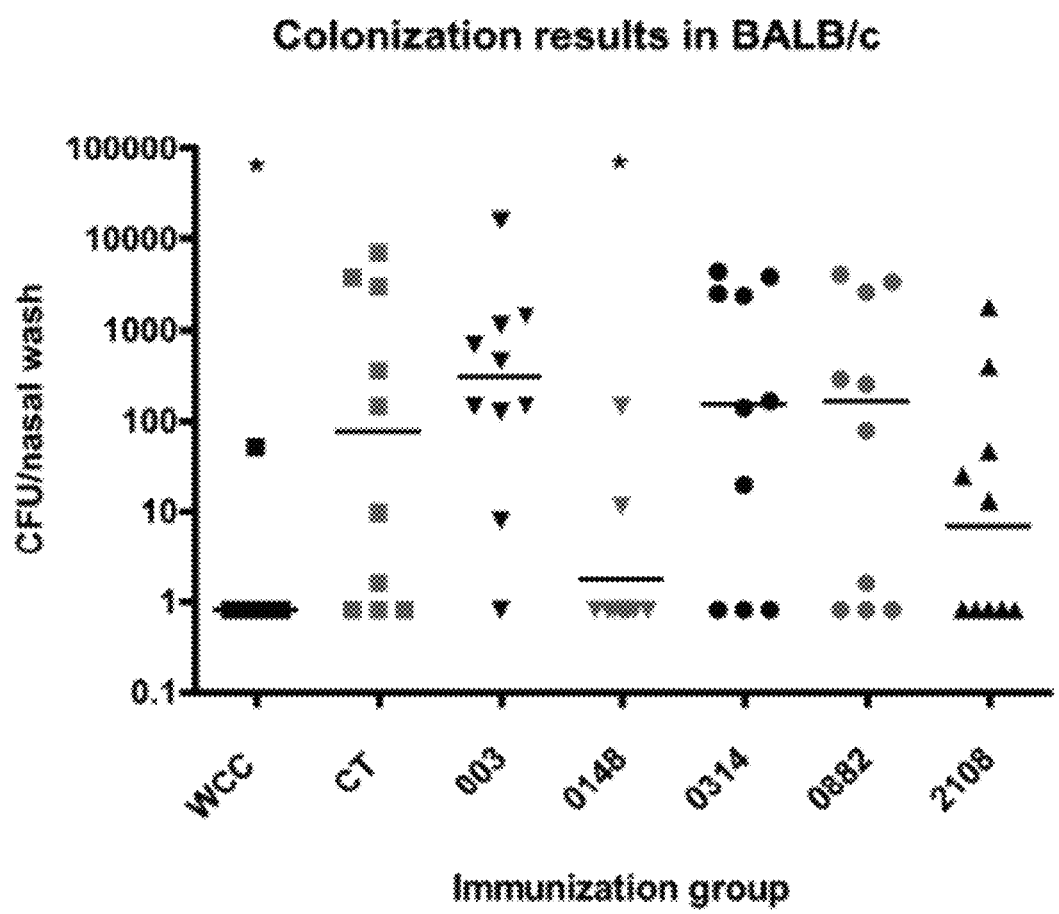

FIG. 8 shows the number of *S. pneumoniae* colonies obtained from a nasal wash in BALB/c mice that were immunized with the indicated protein(s) and cholera toxin adjuvant, then challenged with intranasal administration of *S. pneumoniae*, as described in Example 8.

Figure 9:
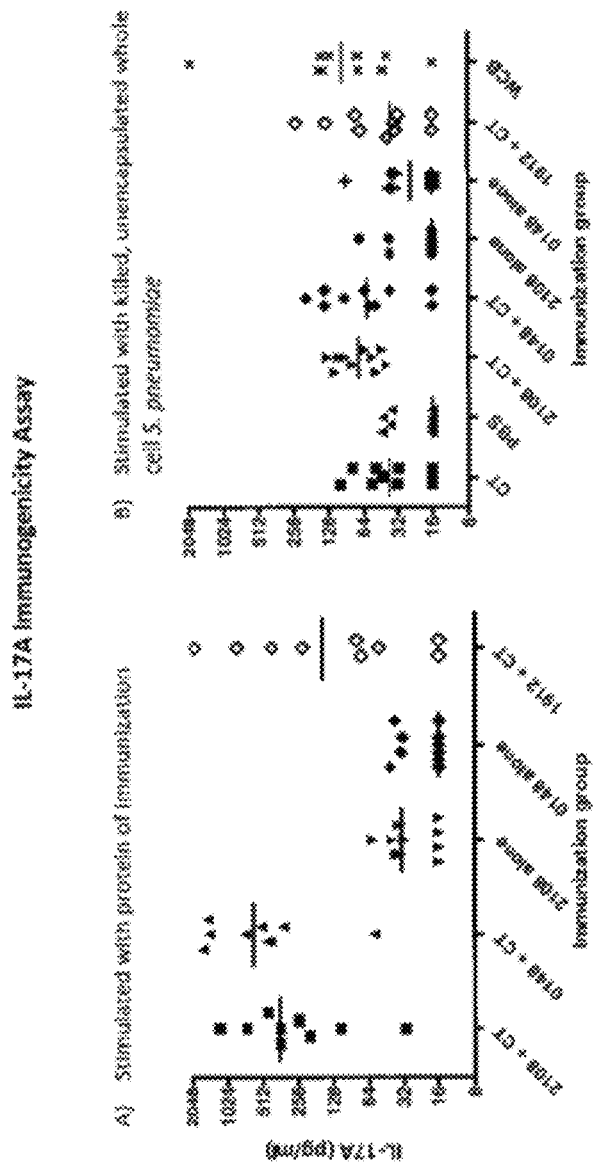

FIG. 9 shows the concentration of IL-17A generated by blood samples from mice that were immunized with the indicated proteins and cholera toxin adjuvant, then stimulated with the protein of immunization (left panel) or killed, unencapsulated whole cell *S. pneumoniae* (right panel), as described in Example 9.

Figure 10:
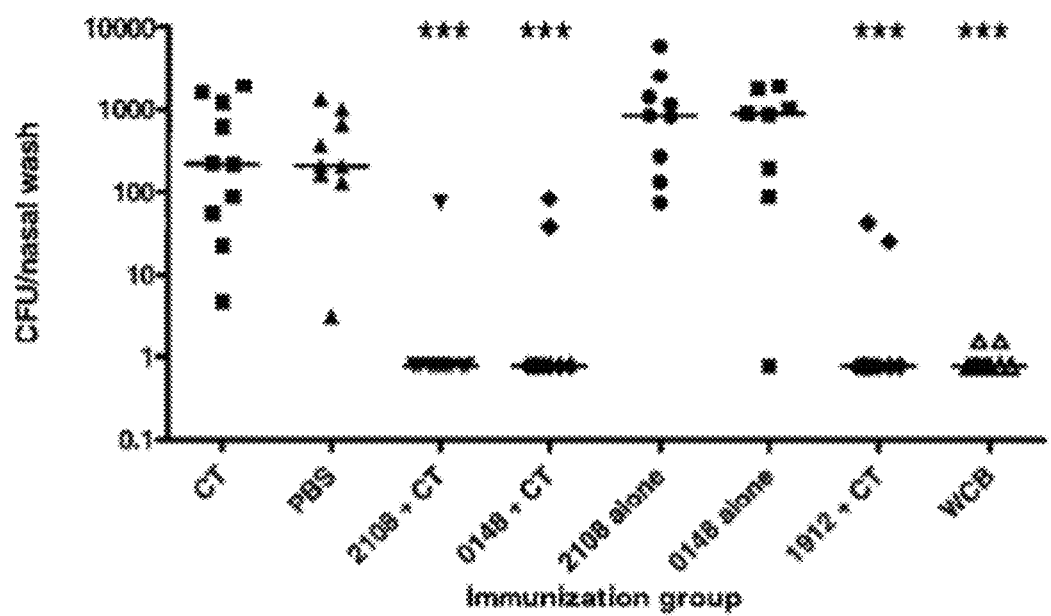

FIG. 10 shows the number of *S. pneumoniae* colonies obtained from a nasal wash in mice that were immunized with the indicated proteins and cholera toxin adjuvant, then challenged with intranasal administration of *S. pneumoniae*, as described in Example 10.

Figure 11:
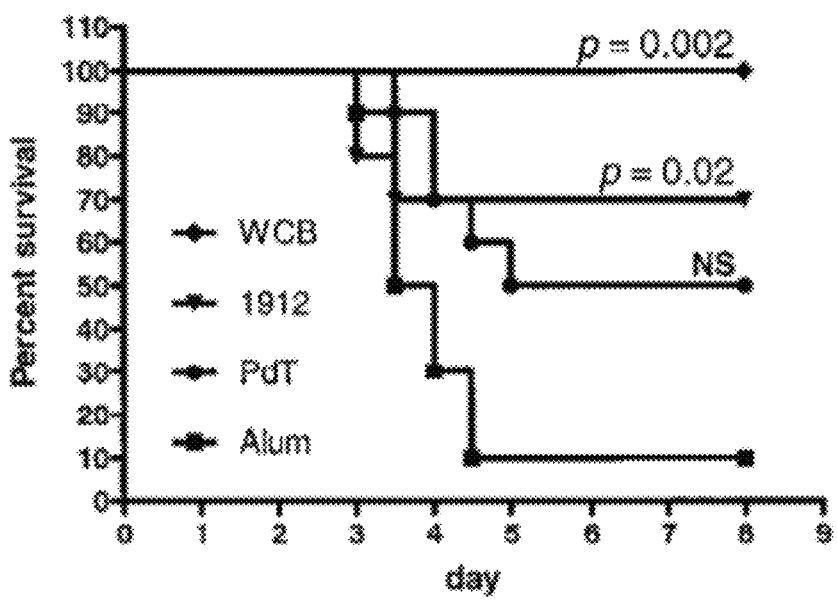

FIG. 11 shows survival of mice that were immunized with the indicated proteins and the adjuvant alum, then underwent aspiration challenge with *S. pneumoniae* as described in Example 11.

Figure 12:
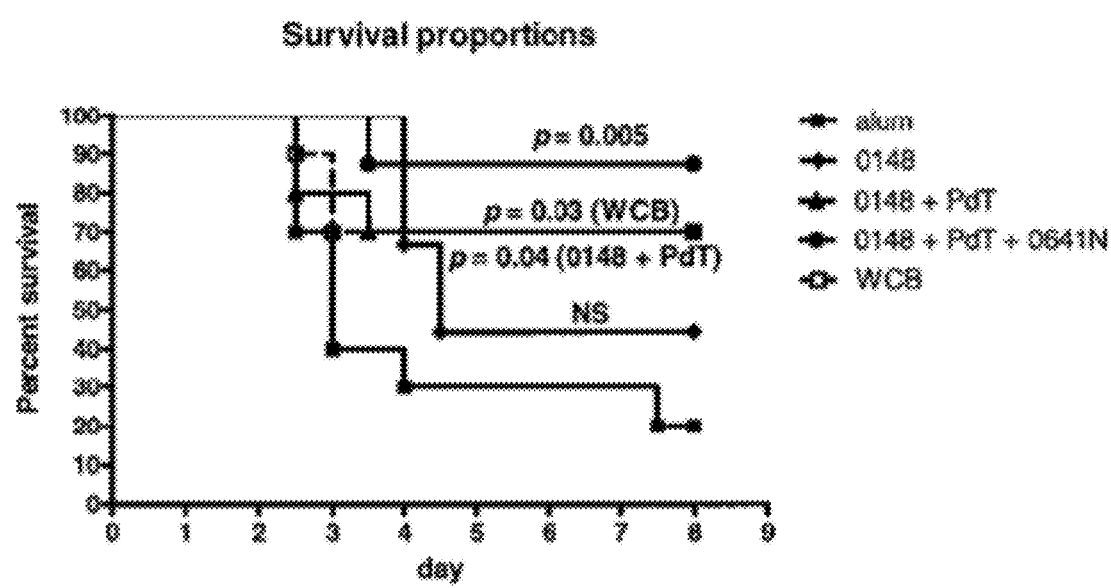

FIG. 12 shows survival of mice that were immunized with the indicated proteins and the adjuvant alum, then underwent aspiration challenge with *S. pneumoniae* as described in Example 12.

Figure 13:
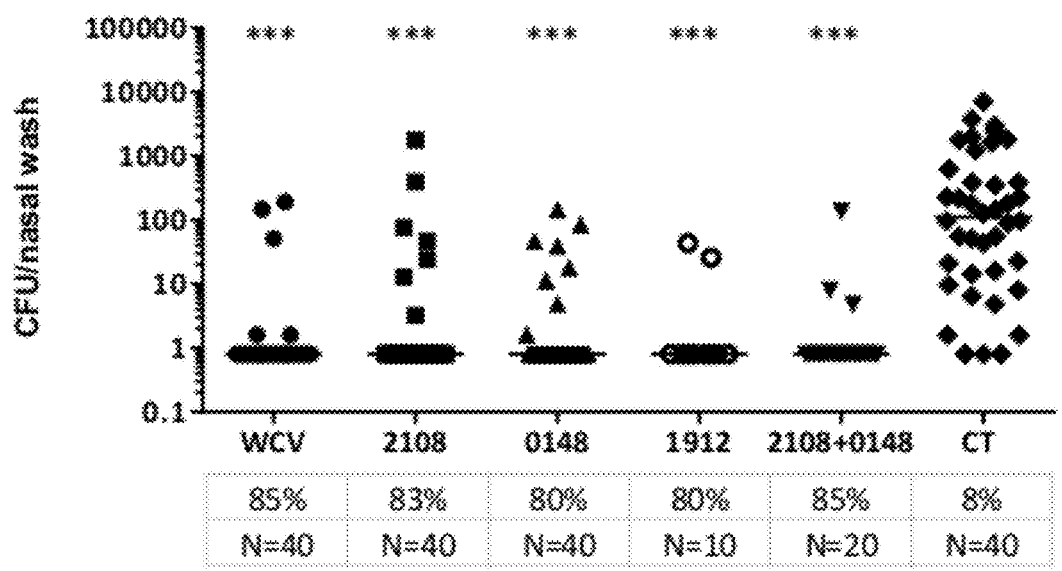

FIG. 13 shows the number of *S. pneumoniae* colonies obtained from a nasal wash in mice that were immunized with the indicated proteins and cholera toxin adjuvant, then challenged with intranasal administration of *S. pneumoniae*, as described in Example 13.

Figure 14:
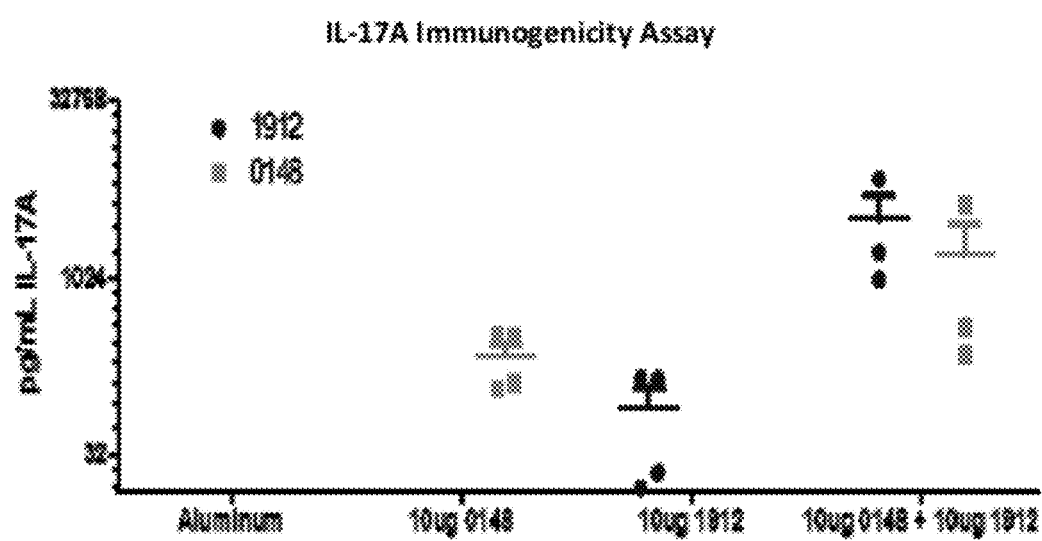

FIG. 14 shows the concentration of IL-17A generated by blood samples form mice that were immunized with the indicated proteins and alum, then stimulated with the proteins indicated at upper left, as described in Example 14.

Figure 15:
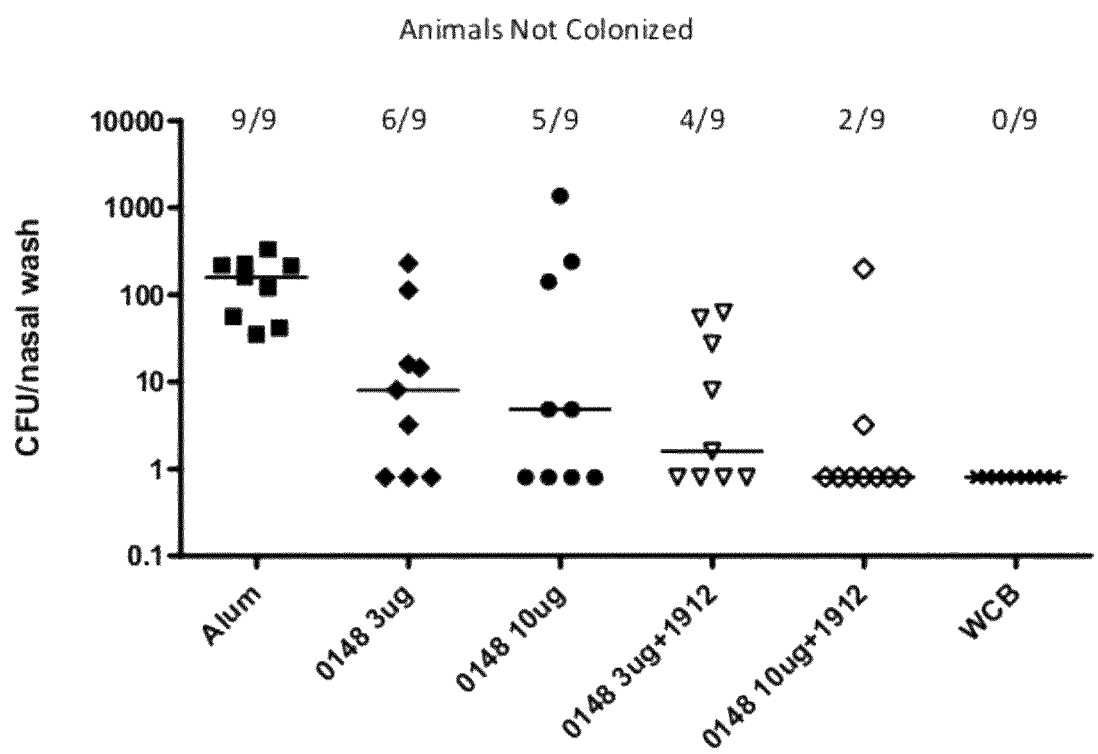

FIG. 15 shows the number of *S. pneumoniae* colonies obtained from a nasal wash in mice that were immunized with the indicated proteins and alum or with killed, unencapsulated whole cell *S. pneumoniae* plus alum (WCV), then challenged with intranasal administration of *S. pneumoniae*, as described in Example 15.

Figure 16:
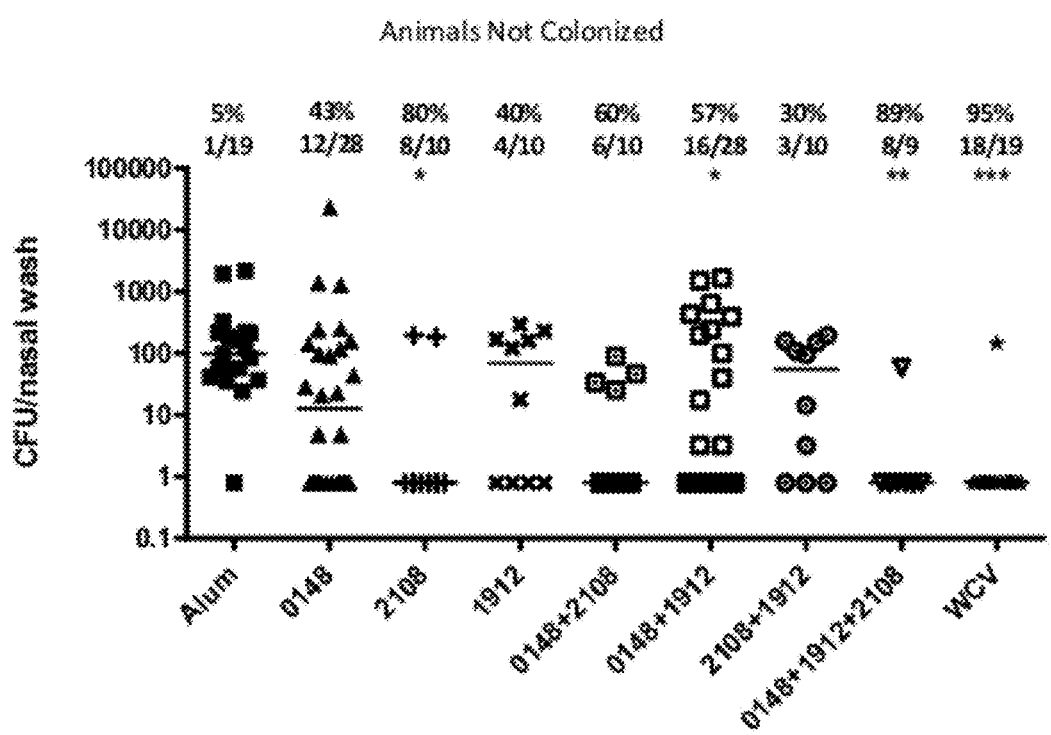

FIG. 16 shows the number of *S. pneumoniae* colonies obtained from a nasal wash in mice that were immunized with the indicated proteins and alum or with killed, unencapsulated whole cell *S. pneumoniae* plus alum (WCV), then challenged with intranasal administration of *S. pneumoniae*, in two pooled studies as described in Example 16.

Figure 17:
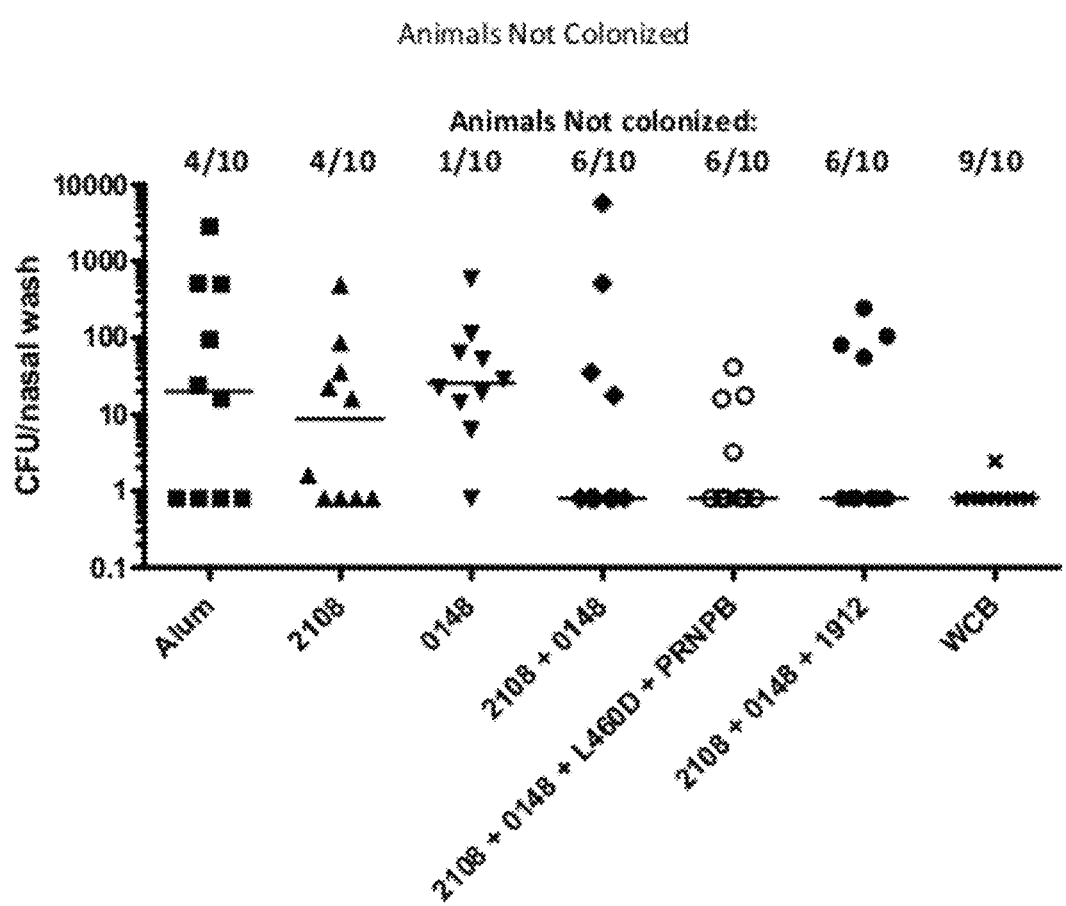

FIG. 17 shows the number of *S. pneumoniae* colonies obtained from a nasal wash in mice that were immunized with the indicated proteins and alum or with killed, unencapsulated whole cell *S. pneumoniae* plus alum (WCB), then challenged with intranasal administration of *S. pneumoniae*, as described in Example 17.

Figure 18:
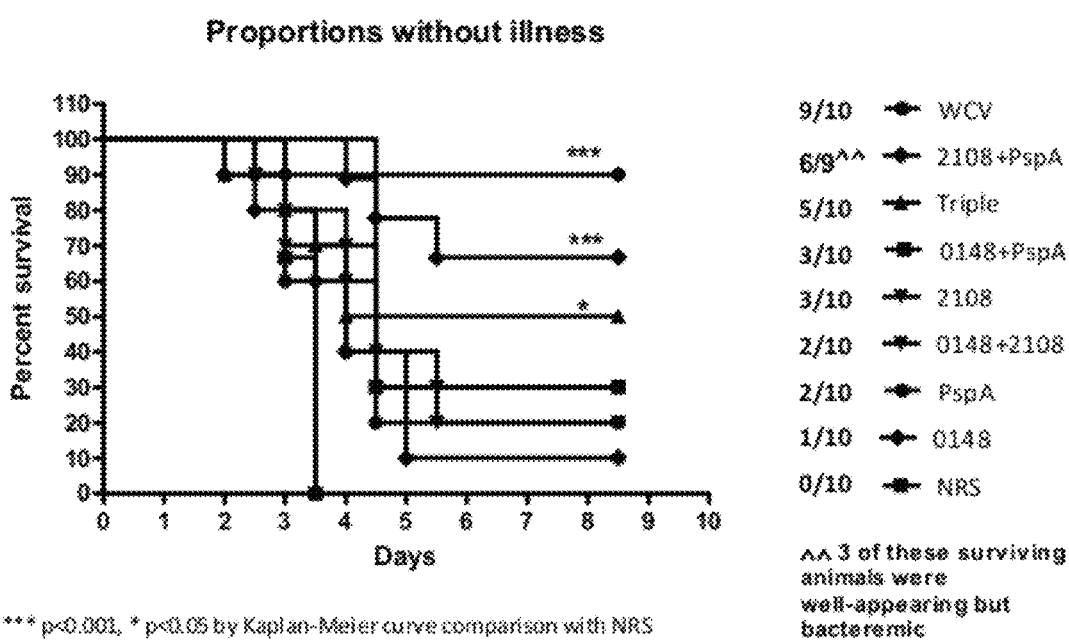

FIG. 18 shows survival of mice that were injected with antibodies or sera specific to the indicated proteins, then underwent aspiration challenge with *S. pneumoniae*, as described in Example 18.

FIG. 19 shows the percent of animals protected from sepsis in six separate aspiration challenge studies, two of which are described in more detail in Examples 12 and 18.

IV. DETAILED DESCRIPTION

A. Specific Polypeptides and Nucleic Acids for Use in *S. pneumoniae* Vaccines and Immunogenic Compositions This application describes *S. pneumoniae* vaccines that include one or more of the polypeptides or genes listed in Table 1, or variants or fragments thereof as described below. The vaccine may include a polypeptide that comprises a sequence of Table 1 or a variant or immunogenic fragment thereof or a polypeptide that consists of a sequence of Table 1 or a variant or immunogenic fragment thereof. The DNA and protein sequence of each gene and polypeptide may be found by searching for the Locus Tag in the publicly available database, Entrez Gene (on the NCBI NIH web site on the World Wide Web, at www.ncbi.nlm.nih.gov/sites/entrez?db=gene), in the *Streptococcus pneumoniae* TIGR4 genome, and the indicated sequences are also included in this application.

TABLE 1

Immunogenic polypeptides for vaccine formulations

| Locus tag name and description | Protein SEQ ID No. | DNA SEQ ID No. | DNA GenBank Accession No. (from Mar. 30, 2010) |
|---|---|---|---|
| SP0024 | 1 | — | NC_003028.3\|: 27381-27878 |
| SP0882 | 2 | — | NC_003028.3\|: 831804-832628 |
| SP0882N | 3 | 24 | — |
| SP0882 with exogenous signal sequence | 4 | 25 | — |
| SP0882N with exogenous signal sequence | 5 | 26 | — |
| SP0148 lacking signal sequence | 6 | 27 | — |
| SP0148 including signal sequence | 7 | 28 | NC_003028.3\|: 145,513-146,343* |
| SP1072 | 8 | — | NC_003028.3\|: 1008420-1010180 |
| SP2108 including signal sequence | 9 | — | NC_003028.3\|: 2020750-2022021 |
| SP2108 lacking signal sequence | 10 | 29 | — |
| SP0641M | 11 | 30 | — |
| SP0641 | 12 | — | NC_003028.3\|: 2020750-2022021 |
| SP0641N | 13 | 31 | — |
| SP0882 consensus | 14 | — | — |
| SP0882N consensus | 15 | — | — |
| SP0882 consensus with exogenous leader | 16 | — | — |
| SP0882N consensus with exogenous leader | 17 | — | — |
| SP0148 consensus lacking signal sequence | 18 | — | — |
| SP0148 consensus including signal sequence | 19 | — | — |
| SP2108 consensus lacking signal sequence | 20 | — | — |
| SP2108 consensus including signal sequence | 21 | — | — |
| SP1634 | 22 | — | NC_003028.3\|: 1534348-1535421 |
| SP0314 | 23 | — | NC_003028.3\|: 287483-290683 |
| SP1912 | 265 | 271 | NC_003028.3\|: 1824672-1824971 |
| SP1912L | 266 | 272 | — |
| SP0641.1 | 267 | 273 | — |
| SP1912 consensus | 268 | — | — |
| SP0641N consensus | 269 | — | — |
| SP0641M consensus | 270 | — | — |

*NB: The database sequence incorrectly lists TTG (encoding Leu) at nucleotide positions 541-543. The correct sequence, as shown in SEQ ID NO: 28, has TTC at that codon and encodes Phe. The database sequence further does not include a C-terminal Glu found in certain isolates.

Certain polypeptides of Table 1, and variants thereof, are described in greater detail below.

1. SP1912 (SEQ ID NO: 265) and Variants Thereof

SP1912 is a hypothetical protein of 99 amino acids. While the protein function is not definitively known, sequence analysis suggests it is a putative thioredoxin.

In some embodiments, vaccines or pharmaceutical compositions comprising an S. pneumoniae polypeptide include a polypeptide containing at least 20 consecutive amino acid residues selected from SP1912. The polypeptide may also be a variant of the at least 20 residue fragment. In certain embodiments, the polypeptide includes no more than 90, 75, 60, 45 or 30 consecutive amino acids from SP1912.

In some embodiments, the compositions and methods herein call for the use of an SP1912 variant that comprises an exogenous lipidation sequence. In some embodiments, a signal sequence directs lipidation. Thus, the lipidation signal may be, e.g., the signal sequence of SP2108 (SEQ ID NO: 275) or SP0148, or an E. coli signal sequence. The exemplary variant SP1912L, comprising the signal sequence of the E. coli gene RlpB (SEQ ID NO: 276) is represented by polypeptide sequence SEQ ID NO: 266. SP1912 (SEQ ID NO: 265) and SP1912L (SEQ ID NO: 266) may be encoded, respectively, by nucleic acids according to SEQ ID NO: 271 and 272, although due to degeneracy in the genetic code, other DNA sequences (including codon-optimized sequences) may be used.

Consensus sequences illustrating combinations of SP1912 sequences from different serotypes are provided as SEQ ID NO: 268. Thus, in certain embodiments, the vaccine formulation comprises a polypeptide having an amino acid sequence comprising, or consisting of, SEQ ID NO: 268, or an immunogenic fragment thereof (e.g., in place of a polypeptide having an amino acid sequence comprising SEQ ID NO: 265).

2. SP0024 (SEQ ID NO: 1) and Variants Thereof

SP0024 represents a hypothetical protein of 165 amino acids, containing a conserved carbonic anhydrase domain that extends from amino acid 27 to amino acid 163. Based on this consensus motif, SP0024 may be a zinc-binding protein.

In some embodiments, vaccines or pharmaceutical compositions comprising an S. pneumoniae polypeptide include a polypeptide containing at least 20 consecutive amino acid residues selected from SP0024. The polypeptide may also be a variant of the at least 20 residue fragment. In certain embodiments, the polypeptide includes no more than 150, 125, or 100 consecutive amino acids from SP0024.

3. SP0882 (SEQ ID NO: 2) and Variants Thereof

SP0882 is a conserved hypothetical protein of 274 amino acids. Much of the protein (amino acids 2-270) forms an esterase or lipase-like region.

In some embodiments, vaccines or pharmaceutical compositions comprising an S. pneumoniae polypeptide include a polypeptide containing at least 20 consecutive amino acid residues selected from SP0882. The polypeptide may also be a variant of the at least 20 residue fragment. In certain embodiments, the polypeptide includes no more than 250, 275, 200, 175, 150, 125, or 100 consecutive amino acids from SP0882.

One particular truncation variant named SP0882N consists of the N-terminal 130 amino acids of SP0882, and is shown as SEQ ID NO: 3. SP0882N includes a region that is particularly well conserved among different serotypes. In certain embodiments, a polypeptide comprising SP0882 or SP0882N, or an immunogenic fragment of either, also comprises an exogenous signal sequence. In some embodiments, the signal sequence is an *E. coli* or *S. pneumoniae* signal sequence. The signal sequence may be, for example, the signal sequence of SP2108. Two exemplary such polypeptides are SEQ ID NOS: 4 and 5.

Variants of DNA and protein sequences of SP0882 are described, inter alia, in US Patent Application Publication No. 2009/0215149 and International Applications WO2002/077021, WO98/18931, and WO2007/106407. A variant of SP0882N is disclosed in International Application WO2008/146164.

Sequence variation occurs at the protein level between different *S. pneumoniae* serotypes, and consensus sequences illustrating combinations of SP0882 sequences from different *S. pneumoniae* serotypes are provided as SEQ ID NOS: 14-17. Accordingly, in certain embodiments, the vaccine formulation comprises a polypeptide having an amino acid sequence comprising, or consisting of, any of SEQ ID NOS: 14-17, or an immunogenic fragment thereof (e.g., in place of a polypeptide having an amino acid sequence comprising one of SEQ ID NOS: 2-5).

Nucleic acid sequences encoding different variants of SP0882 (SEQ ID NOS: 2-5) are provided as SEQ ID NOS: 24-26, although due to degeneracy in the genetic code, other DNA sequences (including codon-optimized sequences) could encode these polypeptides.

4. SP0148 (SEQ ID NO: 7) and Variants Thereof.

The protein SP0148 is named "ABC transporter, substrate-binding protein". Proteins of this class are typically extracellular proteins that interact transiently with a transmembrane protein complex. Such complexes use energy generated by ATP hydrolysis to translocate specific substrates across a cell membrane. SP0148 is a 276 or 277 (depending on the isolate) amino acid protein that contains a conserved PBPb (periplasmic binding protein) domain, spanning amino acids 40-246, which is typical of membrane-bound transport complexes. In addition, SP0148 has a bacterial extracellular solute-binding proteins family 3 domain which is largely co-extensive with the PBPb domain and extends from amino acid 40 to 244. In some embodiments, a vaccine or other composition comprises a truncation mutant of SP0148 comprising or lacking one or more of said domains and motifs.

In some embodiments, vaccines or pharmaceutical compositions comprising an *S. pneumoniae* polypeptide include a polypeptide containing at least 20 consecutive amino acid residues selected from SP0148. The polypeptide may also be a variant of the at least 20 residue fragment. In certain embodiments, the polypeptide includes no more than 250, 275, 200, 175, 150, 125, or 100 consecutive amino acids from SP0148.

Endogenous SP0148 comprises a signal sequence that directs its secretion and potential lipidation. In some embodiments, the signal sequence of the polypeptide of SEQ ID NO: 7 is partially or fully processed by an expression host, e.g. *E. coli*. In some embodiments, a variant of SP0148 that lacks the signal sequence (SEQ ID NO: 6) is used. The polypeptide of SEQ ID NO: 6 is encoded by the nucleic acid of SEQ ID NO: 27, although other nucleic acid sequences (including codon-optimized sequences) may be used. SEQ ID NO: 28 encodes the full length sequence of SP0148 used in the screens herein.

Variants of the amino acid sequence and nucleotide sequence of SP0148 may be found in U.S. Patent Application Publication No. 2005/0020813, U.S. Pat. Nos. 7,378,514 and 7,504,110, and European Patent Application No. EP1572868 and EP1855717.

Consensus sequences illustrating combinations of SP0148 sequences from different *S. pneumoniae* serotypes are provided as SEQ ID NOS: 18 and 19. Accordingly, in certain embodiments, the vaccine formulation comprises a polypeptide having an amino acid sequence comprising, or consisting of, either of SEQ ID NOS: 18-19, or an immunogenic fragment thereof (e.g., in place of a polypeptide having an amino acid sequence comprising one of SEQ ID NOS: 6 or 7).

5. SP1072 (SEQ ID NO: 8) and Variants Thereof

SP1072, also known as dnaG, is a DNA primase enzyme that catalyzes formation of an RNA primer which allows DNA polymerase to initiate DNA replication. A protein of 586 amino acids, SP1072 contains several conserved motifs. Beginning at the N-terminus, amino acids 2-96 form a zinc finger domain, the DNA primase catalytic core spans amino acids 122-250, and a highly conserved topoisomerase-primase (TORPIM) nucleotidyl transferase/hydrolase domain region extends from amino acid 258 to 330. In some embodiments, a vaccine or other composition comprises a truncation mutant of SP1072 comprising or lacking one or more of said domains and motifs.

In some embodiments, vaccines or pharmaceutical compositions comprising an *S. pneumoniae* polypeptide include a polypeptide containing at least 20 consecutive amino acid residues selected form SP1072. The polypeptide may also be a variant of the at least 20 residue fragment. In certain embodiments, the polypeptide includes no more than 550, 500, 450, 400, 350, 300, 250, 200, 150, or 100 consecutive amino acids from SP1072.

6. SP2108 (SEQ ID NO: 9) and Variants Thereof.

The polypeptide SP2108 is 423 amino acids in length and is alternatively known as MalX, maltose/maltodextrin ABC transporter, or maltose/maltodextrin-binding protein. Much of the protein (amino acids 3-423) is classified as a MalE (Maltose-binding periplasmic) domain. In addition, SP2108 contains a signal sequence that directs its secretion and potential lipidation. In some embodiments, the signal sequence of the polypeptide of SEQ ID NO: 9 is partially or fully processed by an expression host, e.g. *E. coli*. In some embodiments, a vaccine or other composition comprises a truncation mutant of SP2108 comprising one or more of said domains and motifs.

In some embodiments, the compositions and methods herein call for the use of an SP2108 variant that lacks the signal sequence. This variant is represented by polypeptide sequence SEQ ID NO: 10 and may be encoded by, for example, a nucleic acid according to SEQ ID NO: 29, although due to degeneracy in the genetic code, other DNA sequences (including codon-optimized sequences) may be used.

In some embodiments, vaccines or pharmaceutical compositions comprising an *S. pneumoniae* polypeptide include a polypeptide containing at least 20 consecutive amino acid residues selected from SP2108. The polypeptide may also be a variant of the at least 20 residue fragment. In certain embodiments, the polypeptide includes no more than 400, 350, 300, 250, 200, 150, or 100 consecutive amino acids from SP2108.

Consensus sequences illustrating combinations of SP2108 sequences from different serotypes are provided as SEQ ID NOS: 20 and 21. Thus, in certain embodiments, the vaccine formulation comprises a polypeptide having an amino acid sequence comprising, or consisting of, either of SEQ ID NOS: 20-21, or an immunogenic fragment thereof (e.g., in place of a polypeptide having an amino acid sequence comprising one of SEQ ID NOS: 9 or 10).

7. SP0641 (SEQ ID NO: 12) and Variants Thereof.

At 2144 amino acids in length, SP0641 is also known as PrtA, a cell wall-associated serine protease. Full-length SP0641 contains a number of conserved motifs: the PA_2 motif, extending between amino acids 485 and 597, which may form a protein binding surface; the Fn3-like domain (amino acids 800-939); and two predicted catalytic domains of the S8 C5a type located at amino acids 226-449 and 639-777. In some embodiments, a vaccine or other composition comprises a truncation mutant of SP0641 comprising or lacking one or more of said domains and motifs.

In some embodiments, vaccines or pharmaceutical compositions comprising an S. pneumoniae polypeptide include a polypeptide containing at least 20 consecutive amino acid residues selected from SP0641. The polypeptide may also be a variant of the at least 20 residue fragment. In certain embodiments, the polypeptide includes no more than 1000, 900, 800, 700, 600, 500, 400, 300, 200, or 100 consecutive amino acids from SP0641.

Certain other truncation mutants of SP0641 may also be used. For instance, the polypeptide designated SP0641N (SEQ ID NO: 13) consists of 661 amino acids corresponding to amino acids 24-684 near the N-terminus of SP0641. Roughly adjacent to SP0641N (and corresponding to amino acids 686-1333 of SP0641) lies the 648 residue region captured by the truncation variant SP0641M (SEQ ID NO: 11). The polypeptide designated SP0641.1 (SEQ ID NO: 267) consists of 978 amino acids corresponding to amino acids 28-1006 of SP0641.

Variants of SP0641 are disclosed in, for example, U.S. Pat. Nos. 7,338,786, 6,573,082, and 7,132,107, as well as International Application WO00/06738.

SEQ ID NOS: 30, 31 and 273 display the DNA sequences of SP0641M (SEQ ID NO: 11), SP0641N (SEQ ID NO: 13) and SP641.1 (SEQ ID NO: 267), respectively, although due to degeneracy in the genetic code, other DNA sequences (including codon-optimized sequences) could encode these SP0641 variants.

Consensus sequences illustrating combinations of SP0641N and SP0641M sequences from different S. pneumoniae serotypes are provided as SEQ ID NOS: 269 and 270. Accordingly, in certain embodiments, the vaccine formulation comprises a polypeptide having an amino acid sequence comprising, or consisting of, either of SEQ ID NOS: 269 or 270, or an immunogenic fragment thereof (e.g., in place of a polypeptide having an amino acid sequence comprising one of SEQ ID NOS: 11 or 13).

Polypeptides homologous to the polypeptides of Tables 1 and 2 (for example, SP1912, SP1912L, SP0024, SP0882, SP0882N, SP0148 with or without a signal sequence, SP1072, SP2108 with or without a signal sequence, SP0641, SP0641M, SP0641N, or SP0641.1) may also be used in the compositions and methods disclosed herein. Individual strains of S. pneumoniae contain numerous mutations relative to each other, and some of these result in different protein sequences between the different strains. One of skill in the art may readily substitute an amino acid sequence, or a portion thereof, with the homologous amino acid sequence from a different S. pneumoniae strain. In certain aspects, this application provides immunogenic polypeptides with at least 90%, 95%, 97%, 98%, 99%, or 99.5% identity to the polypeptides of Tables 1 and 2 or an immunogenic fragment thereof. Serotypic variation may be used to design such variants of the polypeptides of Tables 1 and 2.

In some embodiments, the vaccine compositions herein comprise a fragment of a protein of Table 1 or 2 (for example, fragments of SP1912, SP1912L, SP0024, SP0882, SP0882N, 0SP148 with or without a signal sequence, SP1072, SP2108 with or without a signal sequence, SP0641, SP0641M, SP0641N, or SP0641.1). In some embodiments, this application provides truncation mutants that are close in size to the polypeptide of Table 1 or 2 (for example, one of SEQ ID NOS: 1-13, 265, 266 or 267). For example, they may lack at most one, two three, four, five, ten, or twenty amino acids from one or both termini. Internal deletions, e.g., of 1-10, 11-20, 21-30, or 31-40 amino acids, are also contemplated.

In certain embodiments the vaccine formulation comprises one or more polypeptides having an amino acid sequence comprising, or consisting of, any of SEQ ID NOS: 14-21, 268, 269 and 270. In certain embodiments, the fragment is a truncated fragment of any of SEQ ID NOS: 14-21, 268, 269 and 270, wherein from 1-5, 1-10, or 1-20 amino acid residues are removed from the N-terminus, C-terminus, or both. In certain embodiments, the fragment is a truncated fragment of any of SEQ ID NOS: 14-21, 268, 269 and 270, wherein from 1-10 amino acid residues are removed from the N-terminus, C-terminus, or both. For instance, 10 amino acid residues may be removed from each of the N-terminus and C-terminus resulting in a protein with 20 amino acid residues removed.

In certain embodiments, the vaccine formulations provided herein comprise or further comprise one or more, or two or more, known S. pneumoniae antigens. In some instances, the known S. pneumoniae antigens are predominantly antibody targets. In some instances, the known S. pneumoniae antigens protect from S. pneumoniae colonization, or from S. pneumoniae-induced sepsis. One appropriate art-recognized class of S. pneumoniae antigen is the pneumolysoids. Pneumolysoids have homology to the S. pneumoniae protein pneumolysin (PLY), but have reduced toxicity compared to pneumolysin. Pneumolysoids can be naturally occurring or engineered derivatives of pneumolysin. In some embodiments, a pneumolysoid has at least 70%, 80%, 85%, 90%, 95%, 97%, 98%, or 99% identity to pneumolysin. In some embodiments, the pneumolysoid demonstrates less than 1/2, 1/5, 1/10, 1/20, 1/50, 1/100, 1/200, 1/500, or 1/1000 the toxicity of pneumolysin in an assay for one or both of hemolytic activity towards erythrocytes and inhibition of polymorphonuclear leukocytes. Both assays are described in Saunders F. K. et al. ("Pneumolysin, the thiol-activated toxin of Streptococcus pneumoniae, does not require a thiol group for in vitro activity" Infect Immun. 1989 August; 57 (8):2547-52).

Exemplary pneumolysoids include PdT (a triple mutant further described in Berry, A. M. et al. (1995) Infection and Immunity 63:1969-74); Pd-A and Pd-B (Paton J. C. et al. "Purification and immunogenicity of genetically obtained pneumolysin toxoids and their conjugation to Streptococcus pneumoniae type 19F polysaccharide" Infect Immun. 1991 July; 59 (7):2297-304); rPd2 and rPd3 (Ferreira et al. "DNA vaccines based on genetically detoxified derivatives of pneumolysin fail to protect mice against challenge with Streptococcus pneumoniae" FEMS Immunol Med Microbiol (2006) 46: 291-297); Ply8, Δ6PLY, L460D, or a variant thereof. In some embodiments, the pneumolysin has a mutation in the catalytic center, such as at amino acid 428 or 433 or the vicinity.

Other appropriate S. pneumoniae antigens for combination vaccines include Pneumococcal surface protein A (PspA); derivatives of PspA, Choline-binding protein A (CbpA) and derivatives thereof (AD Ogunniyi et al., "Protection against Streptococcus pneumoniae elicited by immunization with pneumolysin and CbpA," Infect Immun. 2001 October; 69 (10):5997-6003); Pneumococcal surface adhesin A (PsaA); caseinolytic protease; sortase A (SrtA); pilus 1 RrgA adhesin; PpmA; PrtA; PavA; LytA; Stk-PR; PcsB; RrgB and derivatives thereof.

Derivatives of PspA include proline-rich segments with the non-proline block (PR+NPB, further described below as well as in Daniels, C. C. et al. (2010) Infection and Immunity 78:2163-72) and related constructs comprising all or a fragment of the proline-rich region of PspA (e.g., regions containing one or more of the sequences PAPAP, PKP, PKEPEQ and PEKP and optionally including a non-proline block). An example of the non-proline-block has the exemplary sequence EKSADQQAEEDYARRSEEEYNRLTQQQ (SEQ ID NO: 306), which generally has no proline residues in an otherwise proline-rich area of the non-coiled region of PspA. Other embodiments of non-proline block (NPB) sequences include SEQ ID NOs: 307 and 308. PspA and its derivatives can include genes expressing similar proline-rich structures (i.e. PKP, PKEPEQ and PEKP), with or without the NPB. The amino acids at either end of the NPB mark the boundaries of the proline-rich region. In one example, the amino-terminal boundary to the PR-region is DLKKAVNE (SEQ ID NO: 309), and the carboxy-terminal boundary is (K/G)TGW(K/G)QENGMW (SEQ ID NO: 310). Peptides containing the NPB are particularly immunogenic, suggesting that the NPB may be an important epitope. Exemplary immunogenic PspA polypeptide derivatives containing the coiled-coil structure include SEQ ID NOs: 301 and 302. Particular embodiments of the immunogenic PspA polypeptide derivatives lacking the coiled-coil structure have the amino acid sequences shown as SEQ ID NOS: 303-305. Immunogenic PspA polypeptides SEQ ID NO: 301, 303 and 305 include both PR and NPB sequences (PR+NPB). Immunogenic PspA polypeptides of SEQ ID NOS: 302 and 304 include only a PR sequence (PR only) and lack the NPB.

In some cases, the other appropriate *S. pneumoniae* antigen is at least at least 70%, 80%, 85%, 90%, 95%, 97%, 98%, or 99% identity to the corresponding wild-type *S. pneumoniae* protein. Sequences of the above-mentioned polypeptides, and nucleic acids that encode them, are known; see, for example, the *S. pneumoniae* ATCC 700669 complete genome sequence under GenBank accession number FM211187.1 and linked polypeptide sequences therein.

Further *S. pneumoniae* antigens for combination vaccines include conjugated *S. pneumoniae* polysaccharides. The conjugated polysaccharides may be, for example, as described in U.S. Pat. No. 5,623,057, U.S. Pat. No. 5,371,197, or PCT/US2011/023526.

In addition to those nucleic acids and polypeptides described in Table 1 above, this application also provides immunogenic compositions that include one or more of the polypeptides or genes listed in Table 2, or variants or fragments thereof as described herein. The DNA and protein sequence of each gene and protein may be found by searching for the Locus Tag in the publicly available database, Entrez Gene, as described above.

TABLE 2

Immunogenic proteins identified in human and mouse screens

| Locus tag name | Protein accession number | DNA accession number (from Mar. 30, 2010) |
|---|---|---|
| SP1574 | AAK75660.1 | NC_003028.3\|: c1481367-1480609 |
| SP1655 | AAK75734.1 | NC_003028.3\|: c1557922-1557230 |
| SP2106 | AAK76165.1 | NC_003028.3\|: c2018657-2016399 |
| SP1473 | AAK75567.1 | NC_003028.3\|: c1386534-1386277 |
| SP0605 | AAK74757.1 | NC_003028.3\|: 571604-572485 |
| SP1177 | AAK75286.1 | NC_003028.3\|: c1115580-1115317 |
| SP0335 | AAK74510.1 | NC_003028.3\|: 306559-306876 |
| SP0906 | AAK75031.1 | NC_003028.3\|: c859160-859029 |
| SP1828 | AAK75901.1 | NC_003028.3\|: c1740010-1739000 |
| SP2157 | AAK76211.1 | NC_003028.3\|: c2072146-2070995 |
| SP1229 | AAK75335.1 | NC_003028.3\|: c1163388-1161718 |

TABLE 2-continued

Immunogenic proteins identified in human and mouse screens

| Locus tag name | Protein accession number | DNA accession number (from Mar. 30, 2010) |
|---|---|---|
| SP1128 | AAK75238.1 | NC_003028.3\|: 1061773-1063077 |
| SP1836 | AAK75909.1 | NC_003028.3\|: 1746104-1746280 |
| SP1865 | AAK75937.1 | NC_003028.3\|: c1772987-1771923 |
| SP0904 | AAK75029.1 | NC_003028.3\|: c858126-857311 |
| SP0765 | AAK74903.1 | NC_003028.3\|: 724170-725207 |
| SP1634 | AAK75714.1 | NC_003028.3\|: 1534348-1535421 |
| SP0418 | AAK74581.1 | NC_003028.3\|: 396692-396916 |
| SP1923 | AAK75991.1 | NC_003028.3\|: c1833311-1831896 |
| SP1313 | AAK75991.1 | NC_003028.3\|: c1833311-1831896 |
| SP0775 | AAK74913.1 | NC_003028.3\|: 731798-732070 |
| SP0314 | AAK74491.1 | NC_003028.3\|: 287483-290683 |
| SP0912 | AAK75037.1 | NC_003028.3\|: 864707-865465 |
| SP0159 | AAK74341.1 | NC_003028.3\|: c157554-156292 |
| SP0910 | AAK75035.1 | NC_003028.3\|: 863462-863734 |
| SP2148 | AAK76205.1 | NC_003028.3\|: 2062144-2063373 |
| SP1412 | AAK75510.1 | NC_003028.3\|: c1332393-1331605 |
| SP0372 | AAK74539.1 | NC_003028.3\|: 350268-350597 |
| SP1304 | AAK75407.1 | NC_003028.3\|: c1232491-1232390 |
| SP2002 | AAK76069.1 | NC_003028.3\|: c1906183-1905446 |
| SP0612 | AAK74764.1 | NC_003028.3\|: 579708-579806 |
| SP1988 | AAK76055.1 | NC_003028.3\|: c1892598-1890565 |
| SP0484 | AAK74643.1 | NC_003028.3\|: 465572-466402 |
| SP0847 | AAK74978.1 | NC_003028.3\|: 794144-795202 |
| SP1527 | AAK75616.1 | NC_003028.3\|: c1439494-1437536 |
| SP0542 | AAK74699.1 | NC_003028.3\|: 515940-516059 |
| SP0441 | AAK74602.1 | NC_003028.3\|: 414869-415057 |
| SP0350 | AAK74523.1 | NC_003028.3\|: 323990-324625 |
| SP0014 | AAK74207.1 | NC_003028.3\|: 14450-14929 |
| SP1965 | AAK76032.1 | NC_003028.3\|: c1873279-1873073 |
| SP0117 | AAK74303.1 | NC_003028.3\|: 118423-120657 |
| SP0981 | AAK75102.1 | NC_003028.3\|: 927115-928056 |
| SP2229 | AAK76277.1 | NC_003028.3\|: c2148627-2147602 |
| SP2136 | AAK76194.1 | NC_003028.3\|: c2048521-2046656 |
| SP1179 | AAK75288.1 | NC_003028.3\|: 1116230-1118389 |
| SP1174 | AAK75283.1 | NC_003028.3\|: c1110717-1108258 |
| SP2216 | AAK76264.1 | NC_003028.3\|: c2136445-2135267 |
| SP1393 | AAK75491.1 | NC_003028.3\|: 1316756-1318027 |
| SP1384 | AAK75482.1 | NC_003028.3\|: c1309464-1308967 |
| SP2032 | AAK76097.1 | NC_003028.3\|: c1939994-1938321 |

Typically, the polypeptides present in compounds of the invention are immunogenic, either alone or as a variant, which includes polypeptides fused to another polypeptide or mixed with or complexed to an adjuvant. Variants also include sequences with less than 100% sequence identity, as described herein. In certain embodiments, an antigen of Table 1 or 2 is provided as a full length polypeptide. In addition, one may use fragments, precursors and analogs that have an appropriate immunogenicity.

These polypeptides may be immunogenic in mammals, for example mice, guinea pigs, or humans. An immunogenic polypeptide is typically one capable of raising a significant immune response in an assay or in a subject. The immune response may be innate, humoral, cell-mediated, or mucosal (combining elements of innate, humoral and cell-mediated immunity). For instance, an immunogenic polypeptide may increase the amount of IL-17 produced by T cells. The IL-17 assay described in Examples 1-4 is an example of an assay that may be used to identify an immunogenic polypeptide. Alternatively or additionally, an immunogenic polypeptide may (i) induce production of antibodies, e.g., neutralizing antibodies, that bind to the polypeptide and/or the whole bacteria, (ii) induce $T_H17$ immunity, (iii) activate the CD4$^+$ T cell response, for example by increasing CD4$^+$ T cells and/or increasing localization of CD4$^+$ T cells to the site of infection or reinfection, (iv) activate the CD8$^+$ CTL response, for example by increasing CD8$^+$ T cells and/or increasing localization of CD8$^+$ T cells to the site of infection or reinfection, (v) induce T$_H$1 immunity, and/or (vi) activate innate immunity. In some embodiments, an immunogenic polypeptide causes the production of a detectable amount of antibody specific to that antigen.

In certain embodiments, polypeptides have less than 20%, 30%, 40%, 50%, 60% or 70% identity to human autoantigens and/or gut commensal bacteria (e.g., certain *Bacteroides, Clostridium, Fusobacterium, Eubacterium, Ruminococcus, Peptococcus, Peptostreptococcus, Bifidobacterium, Escherichia* and *Lactobacillus* species). Examples of human autoantigens include insulin, proliferating cell nuclear antigen, cytochrome P450, and myelin basic protein.

The present invention also provides an immunogenic composition comprising a pharmaceutically acceptable carrier, a polypeptide having an amino acid sequence comprising SEQ ID NO: 265, 266, or 268 or an immunogenic fragment thereof, and one or more polypeptides having amino acid sequences comprising any of SEQ ID NOS: 1-23 and SP1574, SP1655, SP2106, SP1473, SP0605, SP1177, SP0335, SP0906, SP1828, SP2157, SP1229, SP1128, SP1836, SP1865, SP0904, SP0765, SP1634, SP0418, SP1923, SP1313, SP0775, SP0314, SP0912, SP0159, SP0910, SP2148, SP1412, SP0372, SP1304, SP2002, SP0612, SP1988, SP0484, SP0847, SP1527, SP0542, SP0441, SP0350, SP0014, SP1965, SP0117, SP0981, SP2229, SP2136, SP1179, SP1174, SP2216, SP1393, SP0641.1, SP1384, and SP2032, or an immunogenic fragment thereof.

In some embodiments, the vaccine formulation comprises at least two polypeptides, each polypeptide belonging to a different group of (i)-(vii): (i) SEQ ID NO: 1 or an immunogenic fragment thereof, (ii) one of SEQ ID NOS: 2-5 and 14-17 or an immunogenic fragment thereof, (iii) one of SEQ ID NOS: 6-7 and 18-19 or an immunogenic fragment thereof, (iv) SEQ ID NO: 8 or an immunogenic fragment thereof, (v) one of SEQ ID NOS: 9-10 and 20-21 or an immunogenic fragment thereof, (vi) one of SEQ ID NOS: 11-13, 267, and 269-270 or an immunogenic fragment thereof, and (vii) one of SEQ ID NOS: 265-266 and 268 or an immunogenic fragment thereof. Examples of such combinations are listed below. Additional combinations may be made by replacing one of the sequences below with the corresponding consensus sequence, e.g., one of SEQ ID NOS: 14-21 or 268-270. In some embodiments, one of the polypeptides is one of SEQ ID NOS: 265-266 and 268 or an immunogenic fragment thereof. In some embodiments, the vaccine formulation further comprises a pneumolysoid. In some embodiments, the vaccine formulation further comprises CbpA or a derivative thereof. In some embodiments, the vaccine formulation further comprises PspA or a derivative thereof comprising all or a fragment of the proline-rich region of PspA.

SEQ ID NO: 1 and SEQ ID NO: 2
SEQ ID NO: 1 and SEQ ID NO: 3
SEQ ID NO: 1 and SEQ ID NO: 4
SEQ ID NO: 1 and SEQ ID NO: 5
SEQ ID NO: 1 and SEQ ID NO: 6
SEQ ID NO: 1 and SEQ ID NO: 7
SEQ ID NO: 1 and SEQ ID NO: 8
SEQ ID NO: 1 and SEQ ID NO: 9
SEQ ID NO: 1 and SEQ ID NO: 10
SEQ ID NO: 1 and SEQ ID NO: 11
SEQ ID NO: 1 and SEQ ID NO: 12
SEQ ID NO: 1 and SEQ ID NO: 13
SEQ ID NO: 1 and SEQ ID NO: 265
SEQ ID NO: 1 and SEQ ID NO: 266
SEQ ID NO: 1 and SEQ ID NO: 267
SEQ ID NO: 2 and SEQ ID NO: 6
SEQ ID NO: 2 and SEQ ID NO: 7
SEQ ID NO: 2 and SEQ ID NO: 8
SEQ ID NO: 2 and SEQ ID NO: 9
SEQ ID NO: 2 and SEQ ID NO: 10
SEQ ID NO: 2 and SEQ ID NO: 11
SEQ ID NO: 2 and SEQ ID NO: 12
SEQ ID NO: 2 and SEQ ID NO: 13
SEQ ID NO: 2 and SEQ ID NO: 265
SEQ ID NO: 2 and SEQ ID NO: 266
SEQ ID NO: 2 and SEQ ID NO: 267
SEQ ID NO: 3 and SEQ ID NO: 6
SEQ ID NO: 3 and SEQ ID NO: 7
SEQ ID NO: 3 and SEQ ID NO: 8
SEQ ID NO: 3 and SEQ ID NO: 9
SEQ ID NO: 3 and SEQ ID NO: 10
SEQ ID NO: 3 and SEQ ID NO: 11
SEQ ID NO: 3 and SEQ ID NO: 12
SEQ ID NO: 3 and SEQ ID NO: 13
SEQ ID NO: 3 and SEQ ID NO: 265
SEQ ID NO: 3 and SEQ ID NO: 266
SEQ ID NO: 3 and SEQ ID NO: 267
SEQ ID NO: 4 and SEQ ID NO: 6
SEQ ID NO: 4 and SEQ ID NO: 7
SEQ ID NO: 4 and SEQ ID NO: 8
SEQ ID NO: 4 and SEQ ID NO: 9
SEQ ID NO: 4 and SEQ ID NO: 10
SEQ ID NO: 4 and SEQ ID NO: 11
SEQ ID NO: 4 and SEQ ID NO: 12
SEQ ID NO: 4 and SEQ ID NO: 13
SEQ ID NO: 4 and SEQ ID NO: 265
SEQ ID NO: 4 and SEQ ID NO: 266
SEQ ID NO: 4 and SEQ ID NO: 267
SEQ ID NO: 5 and SEQ ID NO: 6
SEQ ID NO: 5 and SEQ ID NO: 7
SEQ ID NO: 5 and SEQ ID NO: 8
SEQ ID NO: 5 and SEQ ID NO: 9
SEQ ID NO: 5 and SEQ ID NO: 10
SEQ ID NO: 5 and SEQ ID NO: 11
SEQ ID NO: 5 and SEQ ID NO: 12
SEQ ID NO: 5 and SEQ ID NO: 13
SEQ ID NO: 5 and SEQ ID NO: 265
SEQ ID NO: 5 and SEQ ID NO: 266
SEQ ID NO: 5 and SEQ ID NO: 267
SEQ ID NO: 6 and SEQ ID NO: 8
SEQ ID NO: 6 and SEQ ID NO: 9
SEQ ID NO: 6 and SEQ ID NO: 10
SEQ ID NO: 6 and SEQ ID NO: 11
SEQ ID NO: 6 and SEQ ID NO: 12
SEQ ID NO: 6 and SEQ ID NO: 13
SEQ ID NO: 6 and SEQ ID NO: 265
SEQ ID NO: 6 and SEQ ID NO: 266
SEQ ID NO: 6 and SEQ ID NO: 267
SEQ ID NO: 7 and SEQ ID NO: 8
SEQ ID NO: 7 and SEQ ID NO: 9
SEQ ID NO: 7 and SEQ ID NO: 10
SEQ ID NO: 7 and SEQ ID NO: 11
SEQ ID NO: 7 and SEQ ID NO: 12
SEQ ID NO: 7 and SEQ ID NO: 13
SEQ ID NO: 7 and SEQ ID NO: 265
SEQ ID NO: 7 and SEQ ID NO: 266
SEQ ID NO: 7 and SEQ ID NO: 267
SEQ ID NO: 8 and SEQ ID NO: 9
SEQ ID NO: 8 and SEQ ID NO: 10
SEQ ID NO: 8 and SEQ ID NO: 11
SEQ ID NO: 8 and SEQ ID NO: 12
SEQ ID NO: 8 and SEQ ID NO: 13
SEQ ID NO: 8 and SEQ ID NO: 265

SEQ ID NO: 8 and SEQ ID NO: 266
SEQ ID NO: 8 and SEQ ID NO: 267
SEQ ID NO: 9 and SEQ ID NO: 11
SEQ ID NO: 9 and SEQ ID NO: 12
SEQ ID NO: 9 and SEQ ID NO: 13
SEQ ID NO: 9 and SEQ ID NO: 265
SEQ ID NO: 9 and SEQ ID NO: 266
SEQ ID NO: 9 and SEQ ID NO: 267
SEQ ID NO: 10 and SEQ ID NO: 11
SEQ ID NO: 10 and SEQ ID NO: 12
SEQ ID NO: 10 and SEQ ID NO: 13
SEQ ID NO: 10 and SEQ ID NO: 265
SEQ ID NO: 10 and SEQ ID NO: 266
SEQ ID NO: 10 and SEQ ID NO: 267
SEQ ID NO: 11 and SEQ ID NO: 265
SEQ ID NO: 11 and SEQ ID NO: 266
SEQ ID NO: 12 and SEQ ID NO: 265
SEQ ID NO: 12 and SEQ ID NO: 266
SEQ ID NO: 13 and SEQ ID NO: 265
SEQ ID NO: 13 and SEQ ID NO: 266

In certain embodiments, the vaccine formulation comprises at least three different polypeptides having an amino acid sequence comprising any of SEQ ID NOS: 1-13, 265, 266, and 267, or an immunogenic fragment thereof, each polypeptide belonging to a different group of (i)-(vii): (i) SEQ ID NO: 1 or an immunogenic fragment thereof, (ii) one of SEQ ID NOS: 2-5 or an immunogenic fragment thereof, (iii) one of SEQ ID NOS: 6-7 or an immunogenic fragment thereof, (iv) SEQ ID NO: 8 or an immunogenic fragment thereof, (v) one of SEQ ID NOS: 9-10 or an immunogenic fragment thereof, (vi) one of SEQ ID NO: 11-13 and 267, or an immunogenic fragment thereof, and (vii) one of SEQ ID NOS: 265-266 or an immunogenic fragment thereof. Examples of such combinations are listed below. Additional combinations may be made by replacing one of the sequences below with the corresponding consensus sequence, e.g., one of SEQ ID NOS: 14-21 or 268-270. In some embodiments, one of the polypeptides is one of SEQ ID NOS: 265-266 and 268 or an immunogenic fragment thereof. In some embodiments, the vaccine formulation further comprises a pneumolysoid. In some embodiments, the vaccine formulation further comprises CbpA or a derivative thereof. In some embodiments, the vaccine formulation further comprises PspA or a derivative thereof comprising all or a fragment of the proline-rich region of PspA.

SEQ ID NO: 1, SEQ ID NO: 2, and SEQ ID NO: 6
SEQ ID NO: 1, SEQ ID NO: 2, and SEQ ID NO: 7
SEQ ID NO: 1, SEQ ID NO: 2, and SEQ ID NO: 8
SEQ ID NO: 1, SEQ ID NO: 2, and SEQ ID NO: 9
SEQ ID NO: 1, SEQ ID NO: 2, and SEQ ID NO: 10
SEQ ID NO: 1, SEQ ID NO: 2, and SEQ ID NO: 11
SEQ ID NO: 1, SEQ ID NO: 2, and SEQ ID NO: 12
SEQ ID NO: 1, SEQ ID NO: 2, and SEQ ID NO: 13
SEQ ID NO: 1, SEQ ID NO: 2, and SEQ ID NO: 265
SEQ ID NO: 1, SEQ ID NO: 2, and SEQ ID NO: 266
SEQ ID NO: 1, SEQ ID NO: 2, and SEQ ID NO: 267
SEQ ID NO: 1, SEQ ID NO: 3, and SEQ ID NO: 6
SEQ ID NO: 1, SEQ ID NO: 3, and SEQ ID NO: 7
SEQ ID NO: 1, SEQ ID NO: 3, and SEQ ID NO: 8
SEQ ID NO: 1, SEQ ID NO: 3, and SEQ ID NO: 9
SEQ ID NO: 1, SEQ ID NO: 3, and SEQ ID NO: 10
SEQ ID NO: 1, SEQ ID NO: 3, and SEQ ID NO: 11
SEQ ID NO: 1, SEQ ID NO: 3, and SEQ ID NO: 12
SEQ ID NO: 1, SEQ ID NO: 3, and SEQ ID NO: 13
SEQ ID NO: 1, SEQ ID NO: 3, and SEQ ID NO: 265
SEQ ID NO: 1, SEQ ID NO: 3, and SEQ ID NO: 266
SEQ ID NO: 1, SEQ ID NO: 3, and SEQ ID NO: 267
SEQ ID NO: 1, SEQ ID NO: 4; and SEQ ID NO: 6
SEQ ID NO: 1, SEQ ID NO: 4; and SEQ ID NO: 7
SEQ ID NO: 1, SEQ ID NO: 4; and SEQ ID NO: 8
SEQ ID NO: 1, SEQ ID NO: 4; and SEQ ID NO: 9
SEQ ID NO: 1, SEQ ID NO: 4; and SEQ ID NO: 10
SEQ ID NO: 1, SEQ ID NO: 4; and SEQ ID NO: 11
SEQ ID NO: 1, SEQ ID NO: 4; and SEQ ID NO: 12
SEQ ID NO: 1, SEQ ID NO: 4; and SEQ ID NO: 13
SEQ ID NO: 1, SEQ ID NO: 4, and SEQ ID NO: 265
SEQ ID NO: 1, SEQ ID NO: 4, and SEQ ID NO: 266
SEQ ID NO: 1, SEQ ID NO: 4, and SEQ ID NO: 267
SEQ ID NO: 1, SEQ ID NO: 5; and SEQ ID NO: 6
SEQ ID NO: 1, SEQ ID NO: 5; and SEQ ID NO: 7
SEQ ID NO: 1, SEQ ID NO: 5; and SEQ ID NO: 8
SEQ ID NO: 1, SEQ ID NO: 5; and SEQ ID NO: 9
SEQ ID NO: 1, SEQ ID NO: 5; and SEQ ID NO: 10
SEQ ID NO: 1, SEQ ID NO: 5; and SEQ ID NO: 11
SEQ ID NO: 1, SEQ ID NO: 5; and SEQ ID NO: 12
SEQ ID NO: 1, SEQ ID NO: 5; and SEQ ID NO: 13
SEQ ID NO: 1, SEQ ID NO: 5, and SEQ ID NO: 265
SEQ ID NO: 1, SEQ ID NO: 5, and SEQ ID NO: 266
SEQ ID NO: 1, SEQ ID NO: 5, and SEQ ID NO: 267
SEQ ID NO: 1, SEQ ID NO: 6; and SEQ ID NO: 8
SEQ ID NO: 1, SEQ ID NO: 6; and SEQ ID NO: 9
SEQ ID NO: 1, SEQ ID NO: 6; and SEQ ID NO: 10
SEQ ID NO: 1, SEQ ID NO: 6; and SEQ ID NO: 11
SEQ ID NO: 1, SEQ ID NO: 6; and SEQ ID NO: 12
SEQ ID NO: 1, SEQ ID NO: 6; and SEQ ID NO: 13
SEQ ID NO: 1, SEQ ID NO: 6, and SEQ ID NO: 265
SEQ ID NO: 1, SEQ ID NO: 6, and SEQ ID NO: 266
SEQ ID NO: 1, SEQ ID NO: 6, and SEQ ID NO: 267
SEQ ID NO: 1, SEQ ID NO: 7; and SEQ ID NO: 8
SEQ ID NO: 1, SEQ ID NO: 7; and SEQ ID NO: 9
SEQ ID NO: 1, SEQ ID NO: 7; and SEQ ID NO: 10
SEQ ID NO: 1, SEQ ID NO: 7; and SEQ ID NO: 11
SEQ ID NO: 1, SEQ ID NO: 7; and SEQ ID NO: 12
SEQ ID NO: 1, SEQ ID NO: 7; and SEQ ID NO: 13
SEQ ID NO: 1, SEQ ID NO: 7, and SEQ ID NO: 265
SEQ ID NO: 1, SEQ ID NO: 7, and SEQ ID NO: 266
SEQ ID NO: 1, SEQ ID NO: 7, and SEQ ID NO: 267
SEQ ID NO: 1, SEQ ID NO: 8; and SEQ ID NO: 9
SEQ ID NO: 1, SEQ ID NO: 8; and SEQ ID NO: 10
SEQ ID NO: 1, SEQ ID NO: 8; and SEQ ID NO: 11
SEQ ID NO: 1, SEQ ID NO: 8; and SEQ ID NO: 12
SEQ ID NO: 1, SEQ ID NO: 8; and SEQ ID NO: 13
SEQ ID NO: 1, SEQ ID NO: 8, and SEQ ID NO: 265
SEQ ID NO: 1, SEQ ID NO: 8, and SEQ ID NO: 266
SEQ ID NO: 1, SEQ ID NO: 8, and SEQ ID NO: 267
SEQ ID NO: 1, SEQ ID NO: 9; and SEQ ID NO: 11
SEQ ID NO: 1, SEQ ID NO: 9; and SEQ ID NO: 12
SEQ ID NO: 1, SEQ ID NO: 9; and SEQ ID NO: 13
SEQ ID NO: 1, SEQ ID NO: 9, and SEQ ID NO: 265
SEQ ID NO: 1, SEQ ID NO: 9, and SEQ ID NO: 266
SEQ ID NO: 1, SEQ ID NO: 9, and SEQ ID NO: 267
SEQ ID NO: 1, SEQ ID NO: 10; and SEQ ID NO: 11
SEQ ID NO: 1, SEQ ID NO: 10; and SEQ ID NO: 12
SEQ ID NO: 1, SEQ ID NO: 10; and SEQ ID NO: 13
SEQ ID NO: 1, SEQ ID NO: 10, and SEQ ID NO: 265
SEQ ID NO: 1, SEQ ID NO: 10, and SEQ ID NO: 266
SEQ ID NO: 1, SEQ ID NO: 10, and SEQ ID NO: 267
SEQ ID NO: 1, SEQ ID NO: 11, and SEQ ID NO: 265
SEQ ID NO: 1, SEQ ID NO: 11, and SEQ ID NO: 266
SEQ ID NO: 1, SEQ ID NO: 12, and SEQ ID NO: 265
SEQ ID NO: 1, SEQ ID NO: 12, and SEQ ID NO: 266
SEQ ID NO: 1, SEQ ID NO: 13, and SEQ ID NO: 265
SEQ ID NO: 1, SEQ ID NO: 13, and SEQ ID NO: 266
SEQ ID NO: 1, SEQ ID NO: 267, and SEQ ID NO: 265

SEQ ID NO: 1, SEQ ID NO: 267, and SEQ ID NO: 266
SEQ ID NO: 2, SEQ ID NO: 6; and SEQ ID NO: 8
SEQ ID NO: 2, SEQ ID NO: 6; and SEQ ID NO: 9
SEQ ID NO: 2, SEQ ID NO: 6; and SEQ ID NO: 10
SEQ ID NO: 2, SEQ ID NO: 6; and SEQ ID NO: 11
SEQ ID NO: 2, SEQ ID NO: 6; and SEQ ID NO: 12
SEQ ID NO: 2, SEQ ID NO: 6; and SEQ ID NO: 13
SEQ ID NO: 2, SEQ ID NO: 6, and SEQ ID NO: 265
SEQ ID NO: 2, SEQ ID NO: 6, and SEQ ID NO: 266
SEQ ID NO: 2, SEQ ID NO: 6, and SEQ ID NO: 267
SEQ ID NO: 2, SEQ ID NO: 7; and SEQ ID NO: 8
SEQ ID NO: 2, SEQ ID NO: 7; and SEQ ID NO: 9
SEQ ID NO: 2, SEQ ID NO: 7; and SEQ ID NO: 10
SEQ ID NO: 2, SEQ ID NO: 7; and SEQ ID NO: 11
SEQ ID NO: 2, SEQ ID NO: 7; and SEQ ID NO: 12
SEQ ID NO: 2, SEQ ID NO: 7; and SEQ ID NO: 13
SEQ ID NO: 2, SEQ ID NO: 7, and SEQ ID NO: 265
SEQ ID NO: 2, SEQ ID NO: 7, and SEQ ID NO: 266
SEQ ID NO: 2, SEQ ID NO: 7, and SEQ ID NO: 267
SEQ ID NO: 2, SEQ ID NO: 8; and SEQ ID NO: 9
SEQ ID NO: 2, SEQ ID NO: 8; and SEQ ID NO: 10
SEQ ID NO: 2, SEQ ID NO: 8; and SEQ ID NO: 11
SEQ ID NO: 2, SEQ ID NO: 8; and SEQ ID NO: 12
SEQ ID NO: 2, SEQ ID NO: 8; and SEQ ID NO: 13
SEQ ID NO: 2, SEQ ID NO: 8, and SEQ ID NO: 265
SEQ ID NO: 2, SEQ ID NO: 8, and SEQ ID NO: 266
SEQ ID NO: 2, SEQ ID NO: 8, and SEQ ID NO: 267
SEQ ID NO: 2, SEQ ID NO: 9; and SEQ ID NO: 11
SEQ ID NO: 2, SEQ ID NO: 9; and SEQ ID NO: 12
SEQ ID NO: 2, SEQ ID NO: 9; and SEQ ID NO: 13
SEQ ID NO: 2, SEQ ID NO: 9, and SEQ ID NO: 265
SEQ ID NO: 2, SEQ ID NO: 9, and SEQ ID NO: 266
SEQ ID NO: 2, SEQ ID NO: 9, and SEQ ID NO: 267
SEQ ID NO: 2, SEQ ID NO: 10; and SEQ ID NO: 11
SEQ ID NO: 2, SEQ ID NO: 10; and SEQ ID NO: 12
SEQ ID NO: 2, SEQ ID NO: 10; and SEQ ID NO: 13
SEQ ID NO: 2, SEQ ID NO: 10, and SEQ ID NO: 265
SEQ ID NO: 2, SEQ ID NO: 10, and SEQ ID NO: 266
SEQ ID NO: 2, SEQ ID NO: 10, and SEQ ID NO: 267
SEQ ID NO: 2, SEQ ID NO: 11, and SEQ ID NO: 265
SEQ ID NO: 2, SEQ ID NO: 11, and SEQ ID NO: 266
SEQ ID NO: 2, SEQ ID NO: 12, and SEQ ID NO: 265
SEQ ID NO: 2, SEQ ID NO: 12, and SEQ ID NO: 266
SEQ ID NO: 2, SEQ ID NO: 13, and SEQ ID NO: 265
SEQ ID NO: 2, SEQ ID NO: 13, and SEQ ID NO: 266
SEQ ID NO: 2, SEQ ID NO: 267, and SEQ ID NO: 265
SEQ ID NO: 2, SEQ ID NO: 267, and SEQ ID NO: 266
SEQ ID NO: 3, SEQ ID NO: 6; and SEQ ID NO: 8
SEQ ID NO: 3, SEQ ID NO: 6; and SEQ ID NO: 9
SEQ ID NO: 3, SEQ ID NO: 6; and SEQ ID NO: 10
SEQ ID NO: 3, SEQ ID NO: 6; and SEQ ID NO: 11
SEQ ID NO: 3, SEQ ID NO: 6; and SEQ ID NO: 12
SEQ ID NO: 3, SEQ ID NO: 6; and SEQ ID NO: 13
SEQ ID NO: 3, SEQ ID NO: 6, and SEQ ID NO: 265
SEQ ID NO: 3, SEQ ID NO: 6, and SEQ ID NO: 266
SEQ ID NO: 3, SEQ ID NO: 6, and SEQ ID NO: 267
SEQ ID NO: 3, SEQ ID NO: 7; and SEQ ID NO: 8
SEQ ID NO: 3, SEQ ID NO: 7; and SEQ ID NO: 9
SEQ ID NO: 3, SEQ ID NO: 7; and SEQ ID NO: 10
SEQ ID NO: 3, SEQ ID NO: 7; and SEQ ID NO: 11
SEQ ID NO: 3, SEQ ID NO: 7; and SEQ ID NO: 12
SEQ ID NO: 3, SEQ ID NO: 7; and SEQ ID NO: 13
SEQ ID NO: 3, SEQ ID NO: 7, and SEQ ID NO: 265
SEQ ID NO: 3, SEQ ID NO: 7, and SEQ ID NO: 266
SEQ ID NO: 3, SEQ ID NO: 7, and SEQ ID NO: 267
SEQ ID NO: 3, SEQ ID NO: 8; and SEQ ID NO: 9
SEQ ID NO: 3, SEQ ID NO: 8; and SEQ ID NO: 10
SEQ ID NO: 3, SEQ ID NO: 8; and SEQ ID NO: 11
SEQ ID NO: 3, SEQ ID NO: 8; and SEQ ID NO: 12
SEQ ID NO: 3, SEQ ID NO: 8; and SEQ ID NO: 13
SEQ ID NO: 3, SEQ ID NO: 8, and SEQ ID NO: 265
SEQ ID NO: 3, SEQ ID NO: 8, and SEQ ID NO: 266
SEQ ID NO: 3, SEQ ID NO: 8, and SEQ ID NO: 267
SEQ ID NO: 3, SEQ ID NO: 9; and SEQ ID NO: 11
SEQ ID NO: 3, SEQ ID NO: 9; and SEQ ID NO: 12
SEQ ID NO: 3, SEQ ID NO: 9; and SEQ ID NO: 13
SEQ ID NO: 3, SEQ ID NO: 9, and SEQ ID NO: 265
SEQ ID NO: 3, SEQ ID NO: 9, and SEQ ID NO: 266
SEQ ID NO: 3, SEQ ID NO: 9, and SEQ ID NO: 267
SEQ ID NO: 3, SEQ ID NO: 10; and SEQ ID NO: 11
SEQ ID NO: 3, SEQ ID NO: 10; and SEQ ID NO: 12
SEQ ID NO: 3, SEQ ID NO: 10; and SEQ ID NO: 13
SEQ ID NO: 3, SEQ ID NO: 10, and SEQ ID NO: 265
SEQ ID NO: 3, SEQ ID NO: 10, and SEQ ID NO: 266
SEQ ID NO: 3, SEQ ID NO: 10, and SEQ ID NO: 267
SEQ ID NO: 3, SEQ ID NO: 11, and SEQ ID NO: 265
SEQ ID NO: 3, SEQ ID NO: 11, and SEQ ID NO: 266
SEQ ID NO: 3, SEQ ID NO: 12, and SEQ ID NO: 265
SEQ ID NO: 3, SEQ ID NO: 12, and SEQ ID NO: 266
SEQ ID NO: 3, SEQ ID NO: 13, and SEQ ID NO: 265
SEQ ID NO: 3, SEQ ID NO: 13, and SEQ ID NO: 266
SEQ ID NO: 3, SEQ ID NO: 267, and SEQ ID NO: 265
SEQ ID NO: 3, SEQ ID NO: 267, and SEQ ID NO: 266
SEQ ID NO: 4, SEQ ID NO: 6; and SEQ ID NO: 8
SEQ ID NO: 4, SEQ ID NO: 6; and SEQ ID NO: 9
SEQ ID NO: 4, SEQ ID NO: 6; and SEQ ID NO: 10
SEQ ID NO: 4, SEQ ID NO: 6; and SEQ ID NO: 11
SEQ ID NO: 4, SEQ ID NO: 6; and SEQ ID NO: 12
SEQ ID NO: 4, SEQ ID NO: 6; and SEQ ID NO: 13
SEQ ID NO: 4, SEQ ID NO: 6, and SEQ ID NO: 265
SEQ ID NO: 4, SEQ ID NO: 6, and SEQ ID NO: 266
SEQ ID NO: 4, SEQ ID NO: 6, and SEQ ID NO: 267
SEQ ID NO: 4, SEQ ID NO: 7; and SEQ ID NO: 8
SEQ ID NO: 4, SEQ ID NO: 7; and SEQ ID NO: 9
SEQ ID NO: 4, SEQ ID NO: 7; and SEQ ID NO: 10
SEQ ID NO: 4, SEQ ID NO: 7; and SEQ ID NO: 11
SEQ ID NO: 4, SEQ ID NO: 7; and SEQ ID NO: 12
SEQ ID NO: 4, SEQ ID NO: 7; and SEQ ID NO: 13
SEQ ID NO: 4, SEQ ID NO: 7, and SEQ ID NO: 265
SEQ ID NO: 4, SEQ ID NO: 7, and SEQ ID NO: 266
SEQ ID NO: 4, SEQ ID NO: 7, and SEQ ID NO: 267
SEQ ID NO: 4, SEQ ID NO: 8; and SEQ ID NO: 9
SEQ ID NO: 4, SEQ ID NO: 8; and SEQ ID NO: 10
SEQ ID NO: 4, SEQ ID NO: 8; and SEQ ID NO: 11
SEQ ID NO: 4, SEQ ID NO: 8; and SEQ ID NO: 12
SEQ ID NO: 4, SEQ ID NO: 8; and SEQ ID NO: 13
SEQ ID NO: 4, SEQ ID NO: 8, and SEQ ID NO: 265
SEQ ID NO: 4, SEQ ID NO: 8, and SEQ ID NO: 266
SEQ ID NO: 4, SEQ ID NO: 8, and SEQ ID NO: 267
SEQ ID NO: 4, SEQ ID NO: 9; and SEQ ID NO: 11
SEQ ID NO: 4, SEQ ID NO: 9; and SEQ ID NO: 12
SEQ ID NO: 4, SEQ ID NO: 9; and SEQ ID NO: 13
SEQ ID NO: 4, SEQ ID NO: 9, and SEQ ID NO: 265
SEQ ID NO: 4, SEQ ID NO: 9, and SEQ ID NO: 266
SEQ ID NO: 4, SEQ ID NO: 9, and SEQ ID NO: 267
SEQ ID NO: 4, SEQ ID NO: 10; and SEQ ID NO: 11
SEQ ID NO: 4, SEQ ID NO: 10; and SEQ ID NO: 12
SEQ ID NO: 4, SEQ ID NO: 10; and SEQ ID NO: 13
SEQ ID NO: 4, SEQ ID NO: 10, and SEQ ID NO: 265
SEQ ID NO: 4, SEQ ID NO: 10, and SEQ ID NO: 266
SEQ ID NO: 4, SEQ ID NO: 10, and SEQ ID NO: 267
SEQ ID NO: 4, SEQ ID NO: 11, and SEQ ID NO: 265
SEQ ID NO: 4, SEQ ID NO: 11, and SEQ ID NO: 266
SEQ ID NO: 4, SEQ ID NO: 12, and SEQ ID NO: 265

SEQ ID NO: 4, SEQ ID NO: 12, and SEQ ID NO: 266
SEQ ID NO: 4, SEQ ID NO: 13, and SEQ ID NO: 265
SEQ ID NO: 4, SEQ ID NO: 13, and SEQ ID NO: 266
SEQ ID NO: 4, SEQ ID NO: 267, and SEQ ID NO: 265
SEQ ID NO: 4, SEQ ID NO: 267, and SEQ ID NO: 266
SEQ ID NO: 5, SEQ ID NO: 6; and SEQ ID NO: 8
SEQ ID NO: 5, SEQ ID NO: 6; and SEQ ID NO: 9
SEQ ID NO: 5, SEQ ID NO: 6; and SEQ ID NO: 10
SEQ ID NO: 5, SEQ ID NO: 6; and SEQ ID NO: 11
SEQ ID NO: 5, SEQ ID NO: 6; and SEQ ID NO: 12
SEQ ID NO: 5, SEQ ID NO: 6; and SEQ ID NO: 13
SEQ ID NO: 5, SEQ ID NO: 6, and SEQ ID NO: 265
SEQ ID NO: 5, SEQ ID NO: 6, and SEQ ID NO: 266
SEQ ID NO: 5, SEQ ID NO: 6, and SEQ ID NO: 267
SEQ ID NO: 5, SEQ ID NO: 7; and SEQ ID NO: 8
SEQ ID NO: 5, SEQ ID NO: 7; and SEQ ID NO: 9
SEQ ID NO: 5, SEQ ID NO: 7; and SEQ ID NO: 10
SEQ ID NO: 5, SEQ ID NO: 7; and SEQ ID NO: 11
SEQ ID NO: 5, SEQ ID NO: 7; and SEQ ID NO: 12
SEQ ID NO: 5, SEQ ID NO: 7; and SEQ ID NO: 13
SEQ ID NO: 5, SEQ ID NO: 7, and SEQ ID NO: 265
SEQ ID NO: 5, SEQ ID NO: 7, and SEQ ID NO: 266
SEQ ID NO: 5, SEQ ID NO: 7, and SEQ ID NO: 267
SEQ ID NO: 5, SEQ ID NO: 8; and SEQ ID NO: 9
SEQ ID NO: 5, SEQ ID NO: 8; and SEQ ID NO: 10
SEQ ID NO: 5, SEQ ID NO: 8; and SEQ ID NO: 11
SEQ ID NO: 5, SEQ ID NO: 8; and SEQ ID NO: 12
SEQ ID NO: 5, SEQ ID NO: 8; and SEQ ID NO: 13
SEQ ID NO: 5, SEQ ID NO: 8, and SEQ ID NO: 265
SEQ ID NO: 5, SEQ ID NO: 8, and SEQ ID NO: 266
SEQ ID NO: 5, SEQ ID NO: 8, and SEQ ID NO: 267
SEQ ID NO: 5, SEQ ID NO: 9; and SEQ ID NO: 11
SEQ ID NO: 5, SEQ ID NO: 9; and SEQ ID NO: 12
SEQ ID NO: 5, SEQ ID NO: 9; and SEQ ID NO: 13
SEQ ID NO: 5, SEQ ID NO: 9, and SEQ ID NO: 265
SEQ ID NO: 5, SEQ ID NO: 9, and SEQ ID NO: 266
SEQ ID NO: 5, SEQ ID NO: 9, and SEQ ID NO: 267
SEQ ID NO: 5, SEQ ID NO: 10; and SEQ ID NO: 11
SEQ ID NO: 5, SEQ ID NO: 10; and SEQ ID NO: 12
SEQ ID NO: 5, SEQ ID NO: 10; and SEQ ID NO: 13
SEQ ID NO: 5, SEQ ID NO: 10, and SEQ ID NO: 265
SEQ ID NO: 5, SEQ ID NO: 10, and SEQ ID NO: 266
SEQ ID NO: 5, SEQ ID NO: 10, and SEQ ID NO: 267
SEQ ID NO: 5, SEQ ID NO: 11, and SEQ ID NO: 265
SEQ ID NO: 5, SEQ ID NO: 11, and SEQ ID NO: 266
SEQ ID NO: 5, SEQ ID NO: 12, and SEQ ID NO: 265
SEQ ID NO: 5, SEQ ID NO: 12, and SEQ ID NO: 266
SEQ ID NO: 5, SEQ ID NO: 13, and SEQ ID NO: 265
SEQ ID NO: 5, SEQ ID NO: 13, and SEQ ID NO: 266
SEQ ID NO: 5, SEQ ID NO: 267, and SEQ ID NO: 265
SEQ ID NO: 5, SEQ ID NO: 267, and SEQ ID NO: 266
SEQ ID NO: 6, SEQ ID NO: 8; and SEQ ID NO: 9
SEQ ID NO: 6, SEQ ID NO: 8; and SEQ ID NO: 10
SEQ ID NO: 6, SEQ ID NO: 8; and SEQ ID NO: 11
SEQ ID NO: 6, SEQ ID NO: 8; and SEQ ID NO: 12
SEQ ID NO: 6, SEQ ID NO: 8; and SEQ ID NO: 13
SEQ ID NO: 6, SEQ ID NO: 8, and SEQ ID NO: 265
SEQ ID NO: 6, SEQ ID NO: 8, and SEQ ID NO: 266
SEQ ID NO: 6, SEQ ID NO: 8, and SEQ ID NO: 267
SEQ ID NO: 6, SEQ ID NO: 9; and SEQ ID NO: 11
SEQ ID NO: 6, SEQ ID NO: 9; and SEQ ID NO: 12
SEQ ID NO: 6, SEQ ID NO: 9; and SEQ ID NO: 13
SEQ ID NO: 6, SEQ ID NO: 9, and SEQ ID NO: 265
SEQ ID NO: 6, SEQ ID NO: 9, and SEQ ID NO: 266
SEQ ID NO: 6, SEQ ID NO: 9, and SEQ ID NO: 267
SEQ ID NO: 6, SEQ ID NO: 10; and SEQ ID NO: 11
SEQ ID NO: 6, SEQ ID NO: 10; and SEQ ID NO: 12
SEQ ID NO: 6, SEQ ID NO: 10; and SEQ ID NO: 13
SEQ ID NO: 6, SEQ ID NO: 10, and SEQ ID NO: 265
SEQ ID NO: 6, SEQ ID NO: 10, and SEQ ID NO: 266
SEQ ID NO: 6, SEQ ID NO: 10, and SEQ ID NO: 267
SEQ ID NO: 6, SEQ ID NO: 11, and SEQ ID NO: 265
SEQ ID NO: 6, SEQ ID NO: 11, and SEQ ID NO: 266
SEQ ID NO: 6, SEQ ID NO: 12, and SEQ ID NO: 265
SEQ ID NO: 6, SEQ ID NO: 12, and SEQ ID NO: 266
SEQ ID NO: 6, SEQ ID NO: 13, and SEQ ID NO: 265
SEQ ID NO: 6, SEQ ID NO: 13, and SEQ ID NO: 266
SEQ ID NO: 6, SEQ ID NO: 267, and SEQ ID NO: 265
SEQ ID NO: 6, SEQ ID NO: 267, and SEQ ID NO: 266
SEQ ID NO: 7, SEQ ID NO: 8; and SEQ ID NO: 9
SEQ ID NO: 7, SEQ ID NO: 8; and SEQ ID NO: 10
SEQ ID NO: 7, SEQ ID NO: 8; and SEQ ID NO: 11
SEQ ID NO: 7, SEQ ID NO: 8; and SEQ ID NO: 12
SEQ ID NO: 7, SEQ ID NO: 8; and SEQ ID NO: 13
SEQ ID NO: 7, SEQ ID NO: 8, and SEQ ID NO: 265
SEQ ID NO: 7, SEQ ID NO: 8, and SEQ ID NO: 266
SEQ ID NO: 7, SEQ ID NO: 8, and SEQ ID NO: 267
SEQ ID NO: 7, SEQ ID NO: 9; and SEQ ID NO: 11
SEQ ID NO: 7, SEQ ID NO: 9; and SEQ ID NO: 12
SEQ ID NO: 7, SEQ ID NO: 9; and SEQ ID NO: 13
SEQ ID NO: 7, SEQ ID NO: 9, and SEQ ID NO: 265
SEQ ID NO: 7, SEQ ID NO: 9, and SEQ ID NO: 266
SEQ ID NO: 7, SEQ ID NO: 9, and SEQ ID NO: 267
SEQ ID NO: 7, SEQ ID NO: 10; and SEQ ID NO: 11
SEQ ID NO: 7, SEQ ID NO: 10; and SEQ ID NO: 12
SEQ ID NO: 7, SEQ ID NO: 10; and SEQ ID NO: 13
SEQ ID NO: 7, SEQ ID NO: 10, and SEQ ID NO: 265
SEQ ID NO: 7, SEQ ID NO: 10, and SEQ ID NO: 266
SEQ ID NO: 7, SEQ ID NO: 10, and SEQ ID NO: 267
SEQ ID NO: 7, SEQ ID NO: 11, and SEQ ID NO: 265
SEQ ID NO: 7, SEQ ID NO: 11, and SEQ ID NO: 266
SEQ ID NO: 7, SEQ ID NO: 12, and SEQ ID NO: 265
SEQ ID NO: 7, SEQ ID NO: 12, and SEQ ID NO: 266
SEQ ID NO: 7, SEQ ID NO: 13, and SEQ ID NO: 265
SEQ ID NO: 7, SEQ ID NO: 13, and SEQ ID NO: 266
SEQ ID NO: 7, SEQ ID NO: 267, and SEQ ID NO: 265
SEQ ID NO: 7, SEQ ID NO: 267, and SEQ ID NO: 266
SEQ ID NO: 8, SEQ ID NO: 9; and SEQ ID NO: 11
SEQ ID NO: 8, SEQ ID NO: 9; and SEQ ID NO: 12
SEQ ID NO: 8, SEQ ID NO: 9; and SEQ ID NO: 13
SEQ ID NO: 8, SEQ ID NO: 9, and SEQ ID NO: 265
SEQ ID NO: 8, SEQ ID NO: 9, and SEQ ID NO: 266
SEQ ID NO: 8, SEQ ID NO: 9, and SEQ ID NO: 267
SEQ ID NO: 8, SEQ ID NO: 10; and SEQ ID NO: 11
SEQ ID NO: 8, SEQ ID NO: 10; and SEQ ID NO: 12
SEQ ID NO: 8, SEQ ID NO: 10; and SEQ ID NO: 13
SEQ ID NO: 8, SEQ ID NO: 10, and SEQ ID NO: 265
SEQ ID NO: 8, SEQ ID NO: 10, and SEQ ID NO: 266
SEQ ID NO: 8, SEQ ID NO: 10, and SEQ ID NO: 267
SEQ ID NO: 8, SEQ ID NO: 11, and SEQ ID NO: 265
SEQ ID NO: 8, SEQ ID NO: 11, and SEQ ID NO: 266
SEQ ID NO: 8, SEQ ID NO: 12, and SEQ ID NO: 265
SEQ ID NO: 8, SEQ ID NO: 12, and SEQ ID NO: 266
SEQ ID NO: 8, SEQ ID NO: 13, and SEQ ID NO: 265
SEQ ID NO: 8, SEQ ID NO: 13, and SEQ ID NO: 266
SEQ ID NO: 8, SEQ ID NO: 267, and SEQ ID NO: 265
SEQ ID NO: 8, SEQ ID NO: 267, and SEQ ID NO: 266
SEQ ID NO: 9, SEQ ID NO: 10, and SEQ ID NO: 265
SEQ ID NO: 9, SEQ ID NO: 10, and SEQ ID NO: 266
SEQ ID NO: 9, SEQ ID NO: 10, and SEQ ID NO: 267
SEQ ID NO: 9, SEQ ID NO: 11, and SEQ ID NO: 265
SEQ ID NO: 9, SEQ ID NO: 11, and SEQ ID NO: 266
SEQ ID NO: 9, SEQ ID NO: 12, and SEQ ID NO: 265
SEQ ID NO: 8, SEQ ID NO: 12, and SEQ ID NO: 266

SEQ ID NO: 9, SEQ ID NO: 13, and SEQ ID NO: 265
SEQ ID NO: 9, SEQ ID NO: 13, and SEQ ID NO: 266
SEQ ID NO: 9, SEQ ID NO: 267, and SEQ ID NO: 265
SEQ ID NO: 9, SEQ ID NO: 267, and SEQ ID NO: 266
SEQ ID NO: 10, SEQ ID NO: 11, and SEQ ID NO: 265
SEQ ID NO: 10, SEQ ID NO: 11, and SEQ ID NO: 266
SEQ ID NO: 10, SEQ ID NO: 12, and SEQ ID NO: 265
SEQ ID NO: 10, SEQ ID NO: 12, and SEQ ID NO: 266
SEQ ID NO: 10, SEQ ID NO: 13, and SEQ ID NO: 265
SEQ ID NO: 10, SEQ ID NO: 13, and SEQ ID NO: 266
SEQ ID NO: 10, SEQ ID NO: 267, and SEQ ID NO: 265
SEQ ID NO: 10, SEQ ID NO: 267, and SEQ ID NO: 266

In some embodiments, the vaccine formulation comprises at least two different polypeptides having an amino acid sequence comprising any of SEQ ID NOS: 14-21, 268, 269 and 270, or an immunogenic fragment thereof. In certain such embodiments, the vaccine formulation comprises at least two polypeptides, each polypeptide belonging to a different group of (i)-(v): (i) one of SEQ ID NOS: 14-17 or an immunogenic fragment thereof, (ii) one of SEQ ID NOS: 18-19 or an immunogenic fragment thereof; (iii) one of SEQ ID NOS: 20-21 or an immunogenic fragment thereof, (iv) one of SEQ ID NO: 268 or an immunogenic fragment thereof, and (v) one of SEQ ID NOS: 269-279 or an immunogenic fragment thereof. Examples of such combinations are listed below. The combinations below specify consensus sequences. However, additional combinations may be made by replacing one of the consensus sequences with the corresponding non-consensus sequence, e.g., one of SEQ ID NOS: 1-13 or 266-267. In some embodiments, one of the polypeptides is SEQ ID NO: 268 or an immunogenic fragment thereof. In some embodiments, the vaccine formulation further comprises a pneumolysoid. In some embodiments, the vaccine formulation further comprises CbpA or a derivative thereof. In some embodiments, the vaccine formulation further comprises PspA or a derivative thereof comprising all or a fragment of the proline-rich region of PspA.

SEQ ID NO: 14 and SEQ ID NO: 18
SEQ ID NO: 14 and SEQ ID NO: 19
SEQ ID NO: 14 and SEQ ID NO: 20
SEQ ID NO: 14 and SEQ ID NO: 21
SEQ ID NO: 14 and SEQ ID NO: 268
SEQ ID NO: 14 and SEQ ID NO: 269
SEQ ID NO: 14 and SEQ ID NO: 270
SEQ ID NO: 15 and SEQ ID NO: 18
SEQ ID NO: 15 and SEQ ID NO: 19
SEQ ID NO: 15 and SEQ ID NO: 20
SEQ ID NO: 15 and SEQ ID NO: 21
SEQ ID NO: 15 and SEQ ID NO: 268
SEQ ID NO: 15 and SEQ ID NO: 269
SEQ ID NO: 15 and SEQ ID NO: 270
SEQ ID NO: 16 and SEQ ID NO: 18
SEQ ID NO: 16 and SEQ ID NO: 19
SEQ ID NO: 16 and SEQ ID NO: 20
SEQ ID NO: 16 and SEQ ID NO: 21
SEQ ID NO: 16 and SEQ ID NO: 268
SEQ ID NO: 16 and SEQ ID NO: 269
SEQ ID NO: 16 and SEQ ID NO: 270
SEQ ID NO: 17 and SEQ ID NO: 18
SEQ ID NO: 17 and SEQ ID NO: 19
SEQ ID NO: 17 and SEQ ID NO: 20
SEQ ID NO: 17 and SEQ ID NO: 21
SEQ ID NO: 17 and SEQ ID NO: 268
SEQ ID NO: 17 and SEQ ID NO: 269
SEQ ID NO: 17 and SEQ ID NO: 270
SEQ ID NO: 18 and SEQ ID NO: 20
SEQ ID NO: 18 and SEQ ID NO: 21
SEQ ID NO: 18 and SEQ ID NO: 268
SEQ ID NO: 18 and SEQ ID NO: 269
SEQ ID NO: 18 and SEQ ID NO: 270
SEQ ID NO: 19 and SEQ ID NO: 20
SEQ ID NO: 19 and SEQ ID NO: 21
SEQ ID NO: 19 and SEQ ID NO: 268
SEQ ID NO: 19 and SEQ ID NO: 269
SEQ ID NO: 19 and SEQ ID NO: 270
SEQ ID NO: 20 and SEQ ID NO: 268
SEQ ID NO: 20 and SEQ ID NO: 269
SEQ ID NO: 20 and SEQ ID NO: 270
SEQ ID NO: 21 and SEQ ID NO: 268
SEQ ID NO: 21 and SEQ ID NO: 269
SEQ ID NO: 21 and SEQ ID NO: 270
SEQ ID NO: 268 and SEQ ID NO: 269
SEQ ID NO: 268 and SEQ ID NO: 270

In some embodiments, the fragment is a truncated fragment of any of SEQ ID NOS: 14-21 and 268-270 wherein from 1-20 amino acid residues are removed from the N-terminus, C-terminus, or both.

In some embodiments, the vaccine formulation comprises a polypeptide having an amino acid sequence comprising any of SEQ ID NOS: 14-17. In some embodiments, the vaccine formulation comprises a polypeptide having an amino acid sequence comprising either of SEQ ID NOS: 18-19. In some embodiments, the vaccine formulation comprises a polypeptide having an amino acid sequence comprising either of SEQ ID NOS: 20-21. In some embodiments, the vaccine formulation comprises a polypeptide having an amino acid sequence comprising any of SEQ ID NOS: 268-270.

In some aspects, a vaccine formulation comprising one or more of SEQ ID NOS: 14-21, 268, 269 and 270 further comprises a polypeptide having an amino acid sequence comprising any of SEQ ID NOS: 1-13, 265, 266 and 267.

In certain embodiments, the vaccine formulation comprises at least three different polypeptides having an amino acid sequence comprising any of SEQ ID NOS: 14-21, 268, 269 and 270, or an immunogenic fragment thereof. In certain such embodiments, the vaccine formulation comprises three of (i)-(v): (i) one of SEQ ID NOS: 14-17 or an immunogenic fragment thereof, (ii) one of SEQ ID NOS: 18-19 or an immunogenic fragment thereof; and (iii) one of SEQ ID NOS: 20-21 or an immunogenic fragment thereof, (iv) one of SEQ ID NO: 268 or an immunogenic fragment thereof, and (v) one of SEQ ID NOS: 269-270 or an immunogenic fragment thereof. Examples of such combinations are listed below. The combinations below specify consensus sequences. However, additional combinations may be made by replacing one of the consensus sequences with the corresponding non-consensus sequence, e.g., one of SEQ ID NOS: 1-13 or 266-267. In some embodiments, one of the polypeptides is SEQ ID NO: 268 or an immunogenic fragment thereof. In some embodiments, the vaccine formulation further comprises a pneumolysoid. In some embodiments, the vaccine formulation further comprises CbpA or a derivative thereof. In some embodiments, the vaccine formulation further comprises PspA or a derivative thereof comprising all or a fragment of the proline-rich region of PspA.

SEQ ID NO: 14, SEQ ID NO: 18, and SEQ ID NO: 20
SEQ ID NO: 14, SEQ ID NO: 18, and SEQ ID NO: 21
SEQ ID NO: 14, SEQ ID NO: 18, and SEQ ID NO: 268
SEQ ID NO: 14, SEQ ID NO: 18, and SEQ ID NO: 269
SEQ ID NO: 14, SEQ ID NO: 18, and SEQ ID NO: 270
SEQ ID NO: 14, SEQ ID NO: 19, and SEQ ID NO: 20
SEQ ID NO: 14, SEQ ID NO: 19, and SEQ ID NO: 21
SEQ ID NO: 14, SEQ ID NO: 19, and SEQ ID NO: 268
SEQ ID NO: 14, SEQ ID NO: 19, and SEQ ID NO: 269

SEQ ID NO: 14, SEQ ID NO: 19, and SEQ ID NO: 270
SEQ ID NO: 14, SEQ ID NO: 268, and SEQ ID NO: 269
SEQ ID NO: 14, SEQ ID NO: 268, and SEQ ID NO: 270
SEQ ID NO: 15, SEQ ID NO: 18, and SEQ ID NO: 20
SEQ ID NO: 15, SEQ ID NO: 18, and SEQ ID NO: 21
SEQ ID NO: 15, SEQ ID NO: 18, and SEQ ID NO: 268
SEQ ID NO: 15, SEQ ID NO: 18, and SEQ ID NO: 269
SEQ ID NO: 15, SEQ ID NO: 18, and SEQ ID NO: 270
SEQ ID NO: 15, SEQ ID NO: 19, and SEQ ID NO: 20
SEQ ID NO: 15, SEQ ID NO: 19, and SEQ ID NO: 21
SEQ ID NO: 15, SEQ ID NO: 19, and SEQ ID NO: 268
SEQ ID NO: 15, SEQ ID NO: 19, and SEQ ID NO: 269
SEQ ID NO: 15, SEQ ID NO: 19, and SEQ ID NO: 270
SEQ ID NO: 15, SEQ ID NO: 268, and SEQ ID NO: 269
SEQ ID NO: 15, SEQ ID NO: 268, and SEQ ID NO: 270
SEQ ID NO: 16, SEQ ID NO: 18, and SEQ ID NO: 20
SEQ ID NO: 16, SEQ ID NO: 18, and SEQ ID NO: 21
SEQ ID NO: 16, SEQ ID NO: 18, and SEQ ID NO: 268
SEQ ID NO: 16, SEQ ID NO: 18, and SEQ ID NO: 269
SEQ ID NO: 16, SEQ ID NO: 18, and SEQ ID NO: 270
SEQ ID NO: 16, SEQ ID NO: 19, and SEQ ID NO: 20
SEQ ID NO: 16, SEQ ID NO: 19, and SEQ ID NO: 21
SEQ ID NO: 16, SEQ ID NO: 19, and SEQ ID NO: 268
SEQ ID NO: 16, SEQ ID NO: 19, and SEQ ID NO: 269
SEQ ID NO: 16, SEQ ID NO: 19, and SEQ ID NO: 270
SEQ ID NO: 16, SEQ ID NO: 268, and SEQ ID NO: 269
SEQ ID NO: 16, SEQ ID NO: 268, and SEQ ID NO: 270
SEQ ID NO: 17, SEQ ID NO: 18, and SEQ ID NO: 20
SEQ ID NO: 17, SEQ ID NO: 18, and SEQ ID NO: 21
SEQ ID NO: 17, SEQ ID NO: 18, and SEQ ID NO: 268
SEQ ID NO: 17, SEQ ID NO: 18, and SEQ ID NO: 269
SEQ ID NO: 17, SEQ ID NO: 18, and SEQ ID NO: 270
SEQ ID NO: 17, SEQ ID NO: 19, and SEQ ID NO: 20
SEQ ID NO: 17, SEQ ID NO: 19, and SEQ ID NO: 21
SEQ ID NO: 17, SEQ ID NO: 19, and SEQ ID NO: 268
SEQ ID NO: 17, SEQ ID NO: 19, and SEQ ID NO: 269
SEQ ID NO: 17, SEQ ID NO: 19, and SEQ ID NO: 270
SEQ ID NO: 17, SEQ ID NO: 268, and SEQ ID NO: 269
SEQ ID NO: 17, SEQ ID NO: 268, and SEQ ID NO: 270
SEQ ID NO: 18, SEQ ID NO: 20, and SEQ ID NO: 268
SEQ ID NO: 18, SEQ ID NO: 20, and SEQ ID NO: 269
SEQ ID NO: 18, SEQ ID NO: 20, and SEQ ID NO: 270
SEQ ID NO: 18, SEQ ID NO: 21, and SEQ ID NO: 268
SEQ ID NO: 18, SEQ ID NO: 21, and SEQ ID NO: 269
SEQ ID NO: 18, SEQ ID NO: 21, and SEQ ID NO: 270
SEQ ID NO: 19, SEQ ID NO: 20, and SEQ ID NO: 268
SEQ ID NO: 19, SEQ ID NO: 20, and SEQ ID NO: 269
SEQ ID NO: 19, SEQ ID NO: 20, and SEQ ID NO: 270
SEQ ID NO: 19, SEQ ID NO: 21, and SEQ ID NO: 268
SEQ ID NO: 19, SEQ ID NO: 21, and SEQ ID NO: 269
SEQ ID NO: 19, SEQ ID NO: 21, and SEQ ID NO: 270
SEQ ID NO: 20, SEQ ID NO: 268, and SEQ ID NO: 269
SEQ ID NO: 20, SEQ ID NO: 268, and SEQ ID NO: 270
SEQ ID NO: 21, SEQ ID NO: 268, and SEQ ID NO: 269
SEQ ID NO: 21, SEQ ID NO: 268, and SEQ ID NO: 270

A polypeptide may comprise one or more immunogenic portions and one or more non-immunogenic portions. The immunogenic portions may be identified by various methods, including protein microarrays, ELISPOT/ELISA techniques, and/or specific assays on different deletion mutants (e.g., fragments) of the polypeptide in question. Immunogenic portions may also be identified by computer algorithms. Some such algorithms, like EpiMatrix (produced by EpiVax), use a computational matrix approach. Other computational tools for identifying antigenic epitopes include PEPVAC (Promiscuous EPitope-based VACcine, hosted by Dana Farber Cancer Institute on the world wide web at immunax.dfci.harvard.edu/PEPVAC), MHCPred (which uses a partial least squares approach and is hosted by The Jenner Institute on the world wide web at www.jenner.ac.uk/MHCPred), and Immune Epitope Database algorithms on the world wide web at tools.immuneepitope.org. An immunogenic fragment of a polypeptide described herein comprises at least one immunogenic portion, as measured experimentally or identified by algorithm. Peptides identified by the tools described above include the following:

| SP2108 Fragments (SEQ ID NOS 34-57, respectively, in order of appearance) | SP0148 Fragments (SEQ ID NOS 58-82, respectively, in order of appearance) | SP1634 Fragments (SEQ ID NOS 83-109, respectively, in order of appearance) | SP0882 Fragments (SEQ ID NOS 110-130, respectively, in order of appearance) | SP0314 Fragments (SEQ ID NOS 131-169, respectively, in order of appearance) |
|---|---|---|---|---|
| AIIDGPWKA | ALGLVAAGV | RLLDLAPQV | HLDNLVLKV | MLKDKIAFL |
| VMMAPYDRV | ELTGYEIEV | MLEIPAHQI | DLIAGRVHL | SLADYTYKV |
| SIAGINYAK | AVNNLSYTK | KNFFAHHPK | ILLPKDYEK | FLLLGAFYL |
| VWDPAKNML | TYLPAEADI | KVILAGHSK | EYQDQIGCL | VLIDGLSQL |
| QPLPNISQM | RYNMAVNNL | SFDNLVSTL | YFHDGQNVF | ILASLGFLL |
| APYDRVGSL | DFQQIMVRL | YYDLPLNEL | NPDISRMIV | GLSQLLPVI |
| APAVIESLV | EHTDNPTIL | YFDLFFGTI | IPWSENLPD | FLLNHYMTV |
| FYYTYGLLA | APIAQNPNV | ALEYIHHLF | QFGGKGVEY | MLIPNVDRA |
| SKYAFAGE | LPSDQQPYV | LPLNELDIL | IGLEYDQI | KLEEMAKQV |
| TEGAGNLI | YVYPLLAQG | IPQGSIIGM | VYFHDGQN | VLKRGVYTI |
| LADWTNFYY | QGLDNLKVI | DPELQKQFA | MEVVKPFI | KVIAGLLRK |
| SLVMYYNKD | KYLYAAPI | AVYTFDAPG | YLKMKEHKL | TLNYEHMNK |
| KEAGVKVTL | GELTGYEI | QSLTPEERE | KLSPDQRIF | NIGYFFFKK |

-continued

| SP2108 Fragments (SEQ ID NOS 34-57, respectively, in order of appearance) | SP0148 Fragments (SEQ ID NOS 58-82, respectively, in order of appearance) | SP1634 Fragments (SEQ ID NOS 83-109, respectively, in order of appearance) | SP0882 Fragments (SEQ ID NOS 110-130, respectively, in order of appearance) | SP0314 Fragments (SEQ ID NOS 131-169, respectively, in order of appearance) |
|---|---|---|---|---|
| KSTAVLGTV | NPNVLVVKK | AIYAASQI | RIFIYVGTE | KYTDVIEKF |
| GAKTDDTTK | KLSKQFFGD | LEIPAHQI | FIDETYRTK | KYDDSVSTI |
| SQKFVDFLV | GSPRPFIYE | LLDLAPQVP | DTDRSYPVV | TFNQMIKEL |
| QAFKDAKVN | AVNNLSYTK | WQIEDKHFV | YIDSSLCYY | DYPETQSVF |
| AVIESLVMY | KIFDKIGVE | TLGRLTQLL | TQFIGLEYQ | TPRAINNTL |
| DAKTAANDA | MVRLSDGQF | LYFDLFFGT | KDTDRSYPV | APLLVNGEL |
| YGVATIPTL | YVYPLLAQG | SINDLASLK | LCYYHDLIA | YIDHTNVAY |
| KTAAIIDGP | VVQATTSAK | SINDLASLK | NVFNSKESF | KQNGDSYGY |
| KAYEKEAGV | TLEKLSKQF | YDLPLNEL | | FLLNHYMTV |
| AGNGAYVFG | VAAGVLAAC | QKVILAGHS | | FYLYNGDLS |
| AWVIPQAVK | LDNLKVIEL | GTDDSIIGW | | KSFAPLLV |
| | NMAVNNLSY | TYLSFDNLV | | DETVVRTV |
| | | FGTILDAGI | | YIDHTNVAY |
| | | NQITAVYTF | | MLKDKIAFL |
| | | | | KLRFKIKTD |
| | | | | KLELFYETG |
| | | | | KIAFLGSNI |
| | | | | SVPRTSYLS |
| | | | | FGFGLSLFS |
| | | | | STIRSIEQV |
| | | | | FRKTTDNPF |
| | | | | TVVRTVRDS |
| | | | | STIRSIEQV |
| | | | | DGLSQLLPV |
| | | | | FGFGLSLFS |
| | | | | KLVDQGEGF |

| SP0024 Fragments (SEQ ID NOS 170-193, respectively, in order of appearance) | SP1072 Fragments (SEQ ID NOS 194-227, respectively, in order of appearance) | SP0641 Fragments (SEQ ID NOS 228-264, respectively, in order of appearance) | SP1912 Fragments (SEQ ID NOS 277-300, respectively, in order of appearance) |
|---|---|---|---|
| AIVTCMDSR | GIEVEKPLY | AAYAPNEVV | KMWMAGLALLGIGSL |
| AQTFENEPF | AEAHLLYRM | AGDLRGKII | LLGIGSLALATKKVA |
| AYVALHGQL | ALLNQDNMR | DEIANEVWY | MAGLALLGIGSLALA |
| DDVIISGAI | APPERNYLY | DNYLIYGDL | WMAGLALLGIGSLAL |
| FENEPFQEY | AQNSYIHIL | DQKEHPEKF | GLALLGIGSLALATK |

-continued

| SP0024 Fragments (SEQ ID NOS 170-193, respectively, in order of appearance) | SP1072 Fragments (SEQ ID NOS 194-227, respectively, in order of appearance) | SP0641 Fragments (SEQ ID NOS 228-264, respectively, in order of appearance) | SP1912 Fragments (SEQ ID NOS 277-300, respectively, in order of appearance) |
|---|---|---|---|
| FMQANQAYV | AVASMGTAL | DSLTDRLKL | LALLGIGSLALATKK |
| ISQQQMGTR | AYLLTKTRI | EAKNKNKFV | FSDMGEIATLYVQVY |
| KPKTRVAIV | DAAKFYHAI | EGQGRNRKL | KAKKMWMAGLALLGI |
| LHGQLNLPL | DTALEELER | EIKGAGDLR | ALLGIGSLALATKKVAK |
| LHVAQALGL | EEYQGVPFI | EPIAEGQYF | KMWMAGLALLGIG |
| LPLKPKTRV | EFLEKIAPL | EVSELKPHR | SDMGEIATLYVQVYE |
| MGTREIVVL | EFQVLYDLL | GAFFDKSKI | DMGEIATLYVQVYES |
| MQLLIESPL | EHVEHLKRL | GDLKWDGLI | AGLALLGIGSLALAT |
| QANQAYVAL | ELSEVEMTR | GEVEKNLEV | MGEIATLYVQVYESS |
| QFMQANQAY | ESPLVLNDY | IHFESVEEM | KKMWMAGLALLGIGS |
| QLNLPLKPK | GEKTPSFNV | IMFIVGIFL | GMKAKKMWMAGLALL |
| QQMGTREIV | GLCPFHGEK | IPGTLNKGI | MKAKKMWMAGLALLG |
| REIVVLHHT | IGDMPVQIV | IRYQVFTFK | HFSDMGEIATLYVQV |
| SPLIPDDVI | ITMPVTKQL | ISDKGGFNW | MNGMKAKKMWMAGLA |
| SRLHVAQAL | KALLNQDNM | IVSEEDFIL | MWMAGLALLGIGSLA |
| TEDMIRSLV | KRLTKKLVL | KEIGVEEAI | DHFSDMGEIATLYVQ |
| VDVSDQDFL | LTKTRISPI | KIVVKDFAR | RDHFSDMGEIATLYV |
| VSDQDFLPF | LVLVYDGDK | KKINFQPSL | NGMKAKKMWMAGLAL |
| VTEDMIRSL | MRAEAHLLY | KLKFVYIGK | |
| | NGPEDLAYL | KVYYGNNYK | |
| | QTEEVERAW | KYWQAIRAL | |
| | SEIYLMEGF | LHIDNTRDF | |
| | SPHQALYDM | MRFKKEDLK | |
| | VDKQVIEEI | NESVVDNYL | |
| | VEMTRNKAL | NEVWYAGAA | |
| | VLYDLLGQY | NINDIVDGL | |
| | VPFIEAVQI | QYLLKDNII | |
| | WYQVLAQDL | SPRQQGAGL | |
| | YLMEGFMDV | SRSKTLGGY | |
| | | SSLKNTKVL | |
| | | TAAVILAAY | |
| | | WTELPAMGY | |

Thus, in some aspects, this application provides an immunogenic fragment of an antigen described herein. The fragments, in some instances, are close in size to the full-length polypeptide or the polypeptide of Table 1 or 2. For example, they may lack at most one, two, three, four, five, ten, twenty, or thirty amino acids from one or both termini. In certain embodiments, the polypeptide is 100-500 amino acids in length, or 150-450, or 200-400, or 250-250 amino acids in length. In some embodiments, the polypeptide is 100-200, 150-250, 200-300, 250-350, 300-400, 350-450, or 400-500 amino acids in length. In certain embodiments, the fragments result from processing, or partial processing, of signal sequences by an expression host, e.g. *E. coli*, an insect cell line (e.g., the baculovirus expression system), or a mammalian (e.g., human or Chinese Hamster Ovary) cell line. The fragments described above or sub-fragments thereof (e.g., fragments of 8-50, 8-30, or 8-20 amino acid residues) preferably have one of the biological activities described below, such as increasing the amount of IL-17 released by at least 1.5 fold or 2 fold or more (e.g., either as an absolute measure or relative to an immunologically inactive protein). A fragment may be used as the polypeptide in the vaccines described herein or may be fused to another protein, protein fragment or a polypeptide.

In some embodiments, the fragment is a truncated fragment of any of SEQ ID NOS: 1-21 or 265-270, having from 1-5, 1-10, or 1-20 amino acid residues removed from the N-terminus, C-terminus, or both. In some such embodiments, the same number of residues is removed from the N-terminus and the C-terminus, while in other embodiments, a different number of residues is removed from the N-terminus compared to the C-terminus.

In certain aspects, this application provides immunogenic polypeptides with at least 90%, 95%, 97%, 98%, 99%, or 99.5% identity to a polypeptide of Table 1 or 2. In certain embodiments, the vaccine formulation comprises at least two different polypeptides having an amino acid sequence comprising a sequence at least 90%, 95%, 98%, or 99% identical to any of SEQ ID NOS: 1-21 or 265-270, or an immunogenic fragment thereof.

In some embodiments, one or more, e.g., two, three, four, or more polypeptides from Table 1 or 2 or immunogenic fragments or variants thereof are provided in a mixture. In some embodiments, the mixture contains both full-length polypeptides and fragments resulting from processing, or partial processing, of signal sequences by an expression host, e.g. *E. coli*, an insect cell line (e.g., the baculovirus expression system), or a mammalian (e.g., human or Chinese Hamster Ovary) cell line.

In some embodiments, rather than being in a simple physical mixture, two, three, four, or more polypeptides from Table 1 or 2 or immunogenic fragments or variants thereof are covalently bound to each other, e.g. as a fusion protein. In some embodiments, the vaccine formulation contains substantially no other *S. pneumoniae* polypeptides other than polypeptides having an amino acid sequence comprising any of SEQ ID NOS: 1-23 or 265-270. In some embodiments, the vaccine formulation contains substantially no other *S. pneumoniae* polypeptides other than polypeptides of Table 1. In some embodiments, the vaccine formulation contains substantially no other *S. pneumoniae* polypeptides other than polypeptides of Tables 1 and/or 2.

In certain embodiments, vaccine formulations or immunogenic compositions contain substantially no other *S. pneumoniae* polypeptides other than polypeptides having an amino acid sequence comprising any of SEQ ID NO: 1-23 or 265-270. In certain such embodiments, vaccine formulations or immunogenic compositions contain substantially no other *S. pneumoniae* polypeptides other than polypeptides having an amino acid sequence consisting of any of SEQ ID NO: 1-23 or 265-270. In some embodiments, vaccine formulations or immunogenic compositions contain substantially no other *S. pneumoniae* polypeptides other than polypeptides having an amino acid sequence comprising (or consisting of) any of the amino acid sequences of the polypeptides of Tables 1 and/or 2. Substantially, in this context, refers to less than 50%, less than 40%, less than 30%, less than 20%, less than 10%, less than 5%, less than 3%, less than 2, or even less than 1% of the other *S. pneumoniae* polypeptides.

In certain embodiments, the vaccine composition induces a $T_H17$ cell response at least 1.5-fold greater than that induced by a control unrelated antigen (such as the HSV-2 protein ICP47 with the gene name US12) after contacting $T_H17$ cells. In some embodiments, the vaccine formulation inhibits infection by *S. pneumoniae* in an uninfected subject. In certain embodiments, the vaccine formulation reduces occurrence or duration of *S. pneumoniae* nasopharyngeal colonization in an individual infected by *S. pneumoniae*. In some embodiments, the vaccine formulation inhibits development of sepsis in an individual infected by *S. pneumoniae*. In some embodiments, the vaccine formulation inhibits development of pneumonia, meningitis, otitis media, sinusitis or infection of other sites or organs with *S. pneumoniae*.

In certain embodiments, this application provides nucleic acids encoding one or more of the polypeptides described above, such as DNA, RNA, or an analog thereof. The underlying DNA sequences for the polypeptides described above may be modified in ways that do not affect the sequence of the protein product, and such sequences are included in the invention. For instance, the DNA sequence may be codon-optimized to improve expression in a host such as *E. coli*, an insect cell line (e.g., using the baculovirus expression system), or a mammalian (e.g., human or Chinese Hamster Ovary) cell line.

In certain embodiments, this application provides nucleic acids (such as DNA, RNA, or an analog thereof) that are at least 70%, 80%, 90%, 95%, 97%, 98%, 99%, or 100% identical to a gene in Table 1 or 2, or a variant or portion of said gene. In certain embodiments, the nucleic acid is 600-2000, 800-1800, 1000-1600, 1200-1400 nucleotides in length. In some embodiments, the nucleic acid is 600-1600, 800-1800, or 1000-2000 nucleotides in length. The nucleic acids may be used, for example, for recombinant production of the polypeptides of Tables 1 and 2, or immunogenic fragments thereof.

In some embodiments, the vaccine or immunogenic composition may comprise fusion proteins and/or fusion DNA constructs. The polypeptides described herein may be used without modification. In certain embodiments, when smaller related polypeptides are used, such as fragments or the like, and their molecular weight is less than about 5000 daltons, e.g., 1500 to 5000 daltons, modification may be useful in eliciting the desired immune response. For example, the smaller polypeptides can be conjugated to an appropriate immunogenic carrier such as tetanus toxoid, pneumolysin, keyhole limpet hemocyanin or the like.

In certain embodiments, the vaccine formulation comprises at least one lipidated polypeptide. Conjugation to the lipid moiety may be direct or indirect (e.g., via a linker). The lipid moiety may be synthetic or naturally produced. In certain embodiments, a polypeptide from Table 1 or 2 may be chemically conjugated to a lipid moiety. In certain embodiments, a construct may comprise a gene or polypeptide from Table 1 or 2, or an immunogenic fragment or variant thereof, and a lipidation sequence including a lipobox motif. A canonical lipobox motif is shown as SEQ ID NO: 274. A lipidation sequence may be N-terminal or C-terminal to the protein, and may be embedded in a signal or other sequence, or in a fusion protein. Exemplary lipidation sequences include the signal sequence of SP2108 (SEQ ID NO: 275) and the signal sequence of the *E. coli* gene RlpB (SEQ ID NO: 276). A signal sequence may be, for example, an *E. coli* or *S. pneumoniae* signal sequence. Exemplary *E. coli* signal sequences include the mlpA signal sequence (Lin, J. J. et al., "An *Escherichia coli* mutant with an amino acid alteration within the signal sequence of outer membrane prolipoprotein" Proc Natl Acad Sci USA. 1978 October; 75 (10):4891-5), the lamB signal sequence (Emr, S. D. et al. "Mutations altering the cellular localization of the phage lambda receptor, an *Escherichia coli* outer membrane protein", Proc Natl Acad Sci USA. 1978 December; 75 (12):5802-6), the MBP signal sequence (Bassford, P. J., "Use of gene fusion to study secretion of maltose-binding protein into *Escherichia coli* periplasm" J. Bacteriol. 1979 July; 139 (1):19-31). Lpp is an exemplary *E. coli* signal sequence that directs lipidation (Cullen, P. A. et al. "Construction and evaluation of a plasmid vector for the expression of recombinant lipoproteins in *Escherichia coli*" Plasmid. 2003 January; 49 (1):18-29.) *E. coli* signal sequences that direct lipidation are also described in Legrain, M. et al. ("Production of lipidated meningococcal transferrin binding protein 2 in *Escherichia coli*" Protein Expr Purif. 1995 October; 6 (5):570-8), e.g. the signal sequence of the gene RlpB (SEQ ID NO: 276) Numerous *S. pneumoniae* signal sequences are known in the art. One such signal sequence is SEQ ID NO: 275.

In other embodiments, a construct may comprise a gene or protein from Table 1 or 2, or an immunogenic fragment or variant thereof, and a tag. A tag may be N-terminal or C-terminal. For instance, tags may be added to the nucleic acid or polypeptide to facilitate purification, detection, solubility, or confer other desirable characteristics on the protein or nucleic acid. For instance, a purification tag may be a peptide, oligopeptide, or polypeptide that may be used in affinity purification. Examples include His, GST, TAP, FLAG, myc, HA, MBP, VSV-G, thioredoxin, V5, avidin, streptavidin, BCCP, Calmodulin, Nus, S tags, lipoprotein D, and β galactosidase. Particular exemplary His tags include HHHHHH (SEQ ID NO: 32) and MSYYHHHHHH (SEQ ID NO: 33). In other embodiments, the polypeptide is free of tags such as protein purification tags, and is purified by a method not relying on affinity for a purification tag. In some embodiments, the fused portion is short. This, in some instances, the fusion protein comprises no more than 1, 2, 3, 4, 5, 10, or 20 additional amino acids on one or both termini of the polypeptide of Table 1 or 2.

B. Immunogenic Compositions

The present disclosure also provides pharmaceutical compositions containing immunogenic polypeptides or polynucleotides encoding these immunogenic polypeptides together with a pharmaceutical carrier. Antigens from *S. pneumoniae* were identified by screening immune cells from mice infected with *S. pneumoniae*, or from healthy human donors. The human donors had presumably been exposed to *S. pneumoniae* at some point during their lifetimes, because *S. pneumoniae* is a very common disease and colonizing pathogen. Briefly, a library of *S. pneumoniae* antigens was expressed in bacteria and mixed with antigen presenting cells (APCs). The APCs, in turn, presented *S. pneumoniae*-derived polypeptides to lymphocytes that had been isolated from mice or from human donors. Lymphocyte responses were assayed for reactivity to *S. pneumoniae*. Human donors, as well as mice immunized with *S. pneumoniae*, produced lymphocytes specific to *S. pneumoniae* antigens. Thus, the present disclosure contemplates compositions of the *S. pneumoniae* antigens that elicit a strong immune response in immunized or infected mice or humans for counteracting infection by *S. pneumoniae*.

Tables 1 and 2 list the protein sequence and corresponding nucleotide sequence for *S. pneumoniae* antigens identified according to the screening methods described herein. The antigens were identified in screens of mouse and human T cells. In the screens of mouse T cells, the identified antigens were subjected to at least two rounds of screening: a genome-wide round to identify pools of 4 antigens that elicited an immune response, followed by a deconvolution round to individually test and identify single antigens that elicited an immune response from a pool identified in the genome-wide round. In contrast, in the screens of human T cells, two different sets of antigen pools were created, such that a polypeptide was combined with different polypeptides between the first and second pools. Consequently, it is possible to determine which polypeptides are antigens by identifying which polypeptides are in positive pools in both the first and second sets. Table 1 lists antigens (and variants thereof) that were identified by one of the above screening methods, and were subsequently subjected to further testing in the mouse models described in Examples 5-12. Thus, compositions according to this disclosure may include one or two or more of the genes listed in Table 1 or 2, or the corresponding gene products.

An immunogenic composition may also comprise portions of said *Streptococcus* polypeptides, for example deletion mutants, truncation mutants, oligonucleotides, and peptide fragments. In some embodiments, the portions of said polypeptides are immunogenic. The immunogenicity of a portion of a protein is readily determined using the same assays that are used to determine the immunogenicity of the full-length protein. In some embodiments, the portion of the polypeptide has substantially the same immunogenicity as the full-length proteins. In some embodiments, the immunogenicity is no more than 10%, 20%, 30%, 40%, or 50% less than that of the full-length protein (e.g., polypeptides of Tables 1 and 2). The peptide fragments may be, for example, linear, circular, or branched.

Some embodiments of the vaccine formulations and immunogenic compositions described herein include an immunogenic polypeptide (e.g., a polypeptide of Table 1 or 2) that contains a membrane translocating sequence (MTS), to facilitate introduction of the polypeptide into the mammalian cell and subsequent stimulation of the cell-mediated immune response. Exemplary membrane translocating sequences include hydrophobic region in the signal sequence of Kaposi fibroblast growth factor, the MTS of α-synuclein, β-synuclein, or γ-synuclein, the third helix of the Antennapedia homeodomain, SN50, integrin β3 h-region, HIV Tat, pAntp, PR-39, abaecin, apidaecin, Bac5, Bac7, *P. berghei* CS protein, and those MTSs described in U.S. Pat. Nos. 6,248,558, 6,432,680 and 6,248,558.

In certain embodiments, an antigen (e.g., a polypeptide of Table 1 or 2) is covalently bound to another molecule. This may, for example, increase the half-life, solubility, bioavailability, or immunogenicity of the antigen. Molecules that may be covalently bound to the antigen include a carbohydrate, biotin, poly(ethylene glycol) (PEG), polysialic acid, N-propionylated polysialic acid, nucleic acids, polysaccharides, and PLGA. There are many different types of PEG, ranging from molecular weights of below 300 g/mol to over 10,000,000 g/mol. PEG chains can be linear, branched, or with comb or star geometries. In some embodiments, the naturally produced form of a protein is covalently bound to a moiety that stimulates the immune system. An example of such a moiety is a lipid moiety. In some instances, lipid moieties are recognized by a Toll-like receptor (TLR) such as TLR-2 or TLR-4, and activate the innate immune system.

C. Antibodies Specific to the Proteins of Tables 1 and 2

Another aspect disclosed herein is an antibody preparation generated against an antigenic composition (e.g., one of the proteins listed in Table 1 or 2 or an immunogenic fragment thereof). For instance, this disclosure provides combinations of two, three, four, or five antibodies each recognizing a different protein of Table 1 or 2. Any of a variety of antibodies are included. Such antibodies include, e.g., polyclonal, monoclonal, recombinant, humanized or partially humanized, single chain, Fab, and fragments thereof, etc. The antibodies can be of any isotype, e.g., IgG, various IgG isotypes such as IgG1, IgG2, IgG2a, IgG2b, IgG3, IgG4, etc.; and they can be from any animal species that produces antibodies, including goat, rabbit, mouse, chicken or the like. In some embodiments, Fab molecules are expressed and assembled in a genetically transformed host like E. coli. A lambda vector system is available thus to express a population of Fab's with a potential diversity equal to or exceeding that of subject generating the predecessor antibody. See Huse et al. (1989), Science 246, 1275-81.

D. Components of a Vaccine or Immunogenic Composition Comprising S. pneumoniae Antigens or Antibodies Recognizing the Same In certain embodiments, the vaccine or immunogenic composition comprises an antigen and one or more of the following: an adjuvant, stabilizer, buffer, surfactant, controlled release component, salt, preservative, and/or an antibody specific to said antigen.

1. Adjuvants

The vaccine formulations and immunogenic compositions described herein may include an adjuvant. Adjuvants can be broadly separated into two classes, based on their principal mechanisms of action: vaccine delivery systems and immunostimulatory adjuvants (see, e.g., Singh et al., Curr. HIV Res. 1:309-20, 2003). In many vaccine formulations, the adjuvant provides a signal to the immune system so that it generates a response to the antigen, and the antigen is required for driving the specificity of the response to the pathogen. Vaccine delivery systems are often particulate formulations, e.g., emulsions, microparticles, immune-stimulating complexes (ISCOMs), nanoparticles, which may be, for example, particles and/or matrices, and liposomes. In contrast, immunostimulatory adjuvants are sometimes derived from pathogens and can represent pathogen associated molecular patterns (PAMP), e.g., lipopolysaccharides (LPS), monophosphoryl lipid (MPL), or CpG-containing DNA, which activate cells of the innate immune system.

Alternatively, adjuvants may be classified as organic and inorganic. Inorganic adjuvants include alum salts such as aluminum phosphate, amorphous aluminum hydroxyphosphate sulfate, and aluminum hydroxide, which are commonly used in human vaccines. Organic adjuvants comprise organic molecules including macromolecules. An example of an organic adjuvant is cholera toxin.

Adjuvants may also be classified by the response they induce. In some embodiments, the adjuvant induces the activation of $T_H1$ cells or $T_H2$ cells. In other embodiments, the adjuvant induces the activation of B cells. In yet other embodiments, the adjuvant induces the activation of antigen-presenting cells. These categories are not mutually exclusive; in some cases, an adjuvant activates more than one type of cell.

In certain embodiments, the adjuvant induces the activation of $T_H17$ cells. It may promote the CD4$^+$ or CD8$^+$ T cells to secrete IL-17. In some embodiments, an adjuvant that induces the activation of $T_H17$ cells is one that produces at least a 2-fold, and in some cases a 10-fold, experimental sample to control ratio in the following assay. In the assay, an experimenter compares the IL-17 levels secreted by two populations of cells: (1) cells from animals immunized with the adjuvant and a polypeptide known to induce $T_H17$ activation, and (2) cells from animals treated with the adjuvant and an irrelevant (control) polypeptide. An adjuvant that induces the activation of $T_H17$ cells may cause the cells of population (1) to produce more than 2-fold, or more than 10-fold more IL-17 than the cells of population (2). IL-17 may be measured, for example, by ELISA or ELISPOT. Certain toxins, such as cholera toxin and labile toxin (produced by enterotoxigenic E. coli, or ETEC), activate a $T_H17$ response. Thus, in some embodiments, the adjuvant is a toxin. Cholera toxin was successfully used in the mouse model to induce protective immunity in conjunction with certain polypeptides from Table 1 (see Examples 5-8). One form of labile toxin is produced by Intercell. Mutant derivates of labile toxin that are active as adjuvants but significantly less toxic can be used as well. Exemplary detoxified mutant derivatives of labile toxin include mutants lacking ADP-ribosyltransferase activity. Particular detoxified mutant derivatives of labile toxin include LTK7 (Douce et al., "Mutants of Escherichia coli heat-labile toxin lacking ADP-ribosyltransferase activity act as nontoxic, mucosal adjuvants" PNAS Vol. 92, pp. 1644-1648, February 1995) and LTK63 (Williams et al., "Innate Imprinting by the Modified Heat-Labile Toxin of Escherichia coli (LTK63) Provides Generic Protection against Lung Infectious Disease" The Journal of Immunology, 2004, 173: 7435-7443), LT-G192 (Douce et al. "Genetically detoxified mutants of heat-labile toxin from Escherichia coli are able to act as oral adjuvants" Infect Immun. 1999 September; 67 (9):4400-6), and LTR72 ("Mucosal adjuvanticity and immunogenicity of LTR72, a novel mutant of Escherichia coli heat-labile enterotoxin with partial knockout of ADP-ribosyltransferase activity." J Exp Med. 1998 Apr. 6; 187 (7):1123-32).

In some embodiments, the adjuvant comprises a VLP (virus-like particle). One such adjuvant platform, Alphavirus replicons, induces the activation of $T_H17$ cells using alphavirus and is produced by Alphavax. In certain embodiments of the Alphavirus replicon system, alphavirus may be engineered to express an antigen of interest, a cytokine of interest (for example, IL-17 or a cytokine that stimulates IL-17 production), or both, and may be produced in a helper cell line. More detailed information may be found in U.S. Pat. Nos. 5,643,576 and 6,783,939. In some embodiments, a vaccine formulation is administered to a patient in combination with a nucleic acid encoding a cytokine.

Certain classes of adjuvants activate toll-like receptors (TLRs) in order to activate a $T_H17$ response. TLRs are well known proteins that may be found on leukocyte membranes, and recognize foreign antigens (including microbial antigens). Administering a known TLR ligand together with an antigen of interest (for instance, as a fusion protein) can promote the development of an immune response specific to the antigen of interest. One exemplary adjuvant that activates TLRs comprises Monophosphoryl Lipid A (MPL). Traditionally, MPL has been produced as a detoxified lipopolysaccharide (LPS) endotoxin obtained from gram negative bacteria, such as S. minnesota. In particular, sequential acid and base hydrolysis of LPS produces an immunoactive lipid A fraction (which is MPL), and lacks the saccharide groups and all but one of the phosphates present in LPS. A number of synthetic TLR agonists (in particular, TLR-4 agonists) are disclosed in Evans J T et al. "Enhancement of antigen-specific immunity via the TLR-4 ligands MPL adjuvant and Ribi.529." Expert Rev Vaccines 2003 April; 2 (2):219-29. Like MPL adjuvants, these synthetic compounds activate the innate immune system via TLR. Another type of TLR agonist is a synthetic phospholipid dimer, for example E6020 (Ishizaka S T et al. "E6020: a synthetic Toll-like receptor 4 agonist as a vaccine adjuvant." Expert Rev. Vaccines. 2007 October; 6 (5):773-84). Various TLR agonists (including TLR-4 agonists) have been produced and/or sold by, for example, the Infectious Disease Research Institute (IRDI), Corixa, Esai, Avanti Polar Lipids, Inc., and Sigma Aldrich. Another exemplary adjuvant that activates TLRs comprises a mixture of MPL, Trehalose Dicoynomycolate (TDM), and dioctadecyldimethylammonium bromide (DDA). Another TLR-activating adjuvant is R848 (resiquimod).

In some embodiments, the adjuvant is or comprises a saponin. Typically, the saponin is a triterpene glycoside, such as those isolated from the bark of the *Quillaja saponaria* tree. A saponin extract from a biological source can be further fractionated (e.g., by chromatography) to isolate the portions of the extract with the best adjuvant activity and with acceptable toxicity. Typical fractions of extract from *Quillaja saponaria* tree used as adjuvants are known as fractions A and C.

A particular form of saponins that may be used in vaccine formulations described herein is immunostimulating complexes (ISCOMs). ISCOMs are an art-recognized class of adjuvants, that generally comprise *Quillaja* saponin fractions and lipids (e.g., cholesterol and phospholipids such as phosphatidyl choline). In certain embodiments, an ISCOM is assembled together with a polypeptide or nucleic acid of interest. However, different saponin fractions may be used in different ratios. In addition, the different saponin fractions may either exist together in the same particles or have substantially only one fraction per particle (such that the indicated ratio of fractions A and C are generated by mixing together particles with the different fractions). In this context, "substantially" refers to less than 20%, 15%, 10%, 5%, 4%, 3%, 2% or even 1%. Such adjuvants may comprise fraction A and fraction C mixed into a ratio of 70-95 A:30-5 C, such as 70 A:30 C to 75 A:5 C, 75 A:5 C to 80 A:20 C, 80 A:20 C to 85 A:15 C, 85 A:15 C to 90 A:10 C, 90 A:10 C to 95 A:5 C, or 95 A:5 C to 99 A:1 C.

In certain embodiments, combinations of adjuvants are used. Three exemplary combinations of adjuvants are MPL and alum, E6020 and alum, and MPL and an ISCOM.

Adjuvants may be covalently bound to antigens. In some embodiments, the adjuvant may comprise a protein which induces inflammatory responses through activation of antigen-presenting cells (APCs). In some embodiments, one or more of these proteins can be recombinantly fused with an antigen of choice, such that the resultant fusion molecule promotes dendritic cell maturation, activates dendritic cells to produce cytokines and chemokines, and ultimately, enhances presentation of the antigen to T cells and initiation of T cell responses (see Wu et al., Cancer Res 2005; 65 (11), pp 4947-4954). In certain embodiments, a polypeptide described herein is presented in the context of the trivalent conjugate system, comprising a fusion protein of *S. pneumoniae* Pneumococcal surface adhesin A (PsaA) with the pneumolysoid PdT and a cell wall polysaccharide (PsaA:PdT-CPs), described in Lu et al. ("Protection against Pneumococcal colonization and fatal pneumonia by a trivalent conjugate of a fusion protein with the cell wall polysaccharide." Infect Immun. 2009 May; 77 (5):2076-83). PdT carries three amino acid substitutions (W433F, D385N, and C428G) which render the molecule nontoxic but do not interfere with its TLR-4-mediated inflammatory properties. Conjugation of a polysaccharide to the fusion of a polypeptide to the TLR-4-agonist PdT results in greatly enhances immunological response to the polypeptide. In some embodiments, one or more polypeptides described herein are used in place of PsaA in the trivalent conjugate. The trivalent conjugate system typically includes alum and is usually administered parenterally. Other exemplary adjuvants that may be covalently bound to antigens comprise polysaccharides, pneumolysin, synthetic peptides, lipopeptides, and nucleic acids.

Typically, the same adjuvant or mixture of adjuvants is present in each dose of a vaccine. Optionally, however, an adjuvant may be administered with the first dose of vaccine and not with subsequent doses (i.e., booster shots). Alternatively, a strong adjuvant may be administered with the first dose of vaccine and a weaker adjuvant or lower dose of the strong adjuvant may be administered with subsequent doses. The adjuvant can be administered before the administration of the antigen, concurrent with the administration of the antigen or after the administration of the antigen to a subject (sometimes within 1, 2, 6, or 12 hours, and sometimes within 1, 2, or 5 days). Certain adjuvants are appropriate for human patients, non-human animals, or both.

2. Additional Components of a Vaccine or Immunogenic Composition

In addition to the antigens and the adjuvants described above, a vaccine formulation or immunogenic composition may include one or more additional components.

In certain embodiments, the vaccine formulation or immunogenic composition may include one or more stabilizers such as sugars (such as sucrose, glucose, or fructose), phosphate (such as sodium phosphate dibasic, potassium phosphate monobasic, dibasic potassium phosphate, or monosodium phosphate), glutamate (such as monosodium L-glutamate), gelatin (such as processed gelatin, hydrolyzed gelatin, or porcine gelatin), amino acids (such as arginine, asparagine, histidine, L-histidine, alanine, valine, leucine, isoleucine, serine, threonine, lysine, phenylalanine, tyrosine, and the alkyl esters thereof), inosine, or sodium borate.

In certain embodiments, the vaccine formulation or immunogenic composition includes one or more buffers such as a mixture of sodium bicarbonate and ascorbic acid. In some embodiments, the vaccine formulation may be administered in saline, such as phosphate buffered saline (PBS), or distilled water.

In certain embodiments, the vaccine formulation or immunogenic composition includes one or more surfactants such as polysorbate 80 (Tween 80), Triton X-100, Polyethylene glycol tert-octylphenyl ether t-Octylphenoxypolyethoxyethanol 4-(1,1,3,3-Tetramethylbutyl)phenyl-polyethylene glycol (TRITON X-100); Polyoxyethylenesorbitan monolaurate Polyethylene glycol sorbitan monolaurate (TWEEN 20); and 4-(1,1,3,3-Tetramethylbutyl)phenol polymer with formaldehyde and oxirane (TYLOXAPOL). A surfactant can be ionic or nonionic.

In certain embodiments, the vaccine formulation or immunogenic composition includes one or more salts such as sodium chloride, ammonium chloride, calcium chloride, or potassium chloride.

In certain embodiments, a preservative is included in the vaccine or immunogenic composition. In other embodiments, no preservative is used. A preservative is most often used in multi-dose vaccine vials, and is less often needed in single-dose vaccine vials. In certain embodiments, the preservative is 2-phenoxyethanol, methyl and propyl parabens, benzyl alcohol, and/or sorbic acid.

In certain embodiments, the vaccine formulation or immunogenic composition is a controlled release formulation.

E. DNA Vaccines

In certain aspects, the vaccine comprises one or more of the nucleic acids disclosed herein or corresponding to the polypeptides described herein. When a nucleic acid vaccine is administered to a patient, the corresponding gene product (such as a desired antigen) is produced in the patient's body. In some embodiments, nucleic acid vaccine vectors that include optimized recombinant polynucleotides can be delivered to a mammal (including humans) to induce a therapeutic or prophylactic immune response. The nucleic acid may be, for example, DNA, RNA, or a synthetic nucleic acid. The nucleic acid may be single stranded or double stranded.

Nucleic acid vaccine vectors (e.g., adenoviruses, liposomes, papillomaviruses, retroviruses, etc.) can be administered directly to the mammal for transduction of cells in vivo. The nucleic acid vaccines can be formulated as pharmaceutical compositions for administration in any suitable manner, including parenteral administration. Plasmid vectors are typically more efficient for gene transfer to muscle tissue. The potential to deliver DNA vectors to mucosal surfaces by oral administration has also been reported (PLGA encapsulated Rotavirus and Hepatitis B) and DNA plasmids have been utilized for direct introduction of genes into other tissues. DNA vaccines have been introduced into animals primarily by intramuscular injection, by gene gun delivery, or by electroporation. After being introduced, the plasmids are generally maintained episomally without replication. Expression of the encoded proteins has been shown to persist for extended time periods, providing stimulation of B and T cells.

In determining the effective amount of the vector to be administered in the treatment or prophylaxis of an infection or other condition, the physician evaluates vector toxicities, progression of the disease, and the production of anti-vector antibodies, if any. Often, the dose equivalent of a naked nucleic acid from a vector is from about 1 µg to 1 mg for a typical 70 kilogram patient, and doses of vectors used to deliver the nucleic acid are calculated to yield an equivalent amount of therapeutic nucleic acid. Administration can be accomplished via single or divided doses. The toxicity and therapeutic efficacy of the nucleic acid vaccine vectors can be determined using standard pharmaceutical procedures in cell cultures or experimental animals.

A nucleic acid vaccine can contain DNA, RNA, a modified nucleic acid, or a combination thereof. In some embodiments, the vaccine comprises one or more cloning or expression vectors; for instance, the vaccine may comprise a plurality of expression vectors each capable of autonomous expression of a nucleotide coding region in a mammalian cell to produce at least one immunogenic polypeptide. An expression vector often includes a eukaryotic promoter sequence, such as the nucleotide sequence of a strong eukaryotic promoter, operably linked to one or more coding regions. The compositions and methods herein may involve the use of any particular eukaryotic promoter, and a wide variety are known; such as a CMV or RSV promoter. The promoter can be heterologous with respect to the host cell. The promoter used may be a constitutive promoter.

A vector useful in the present compositions and methods can be circular or linear, single-stranded or double stranded and can be a plasmid, cosmid, or episome. In a suitable embodiment, each nucleotide coding region is on a separate vector; however, it is to be understood that one or more coding regions can be present on a single vector, and these coding regions can be under the control of a single or multiple promoters.

Numerous plasmids may be used for the production of nucleic acid vaccines. Suitable embodiments of the nucleic acid vaccine employ constructs using the plasmids VR1012 (Vical Inc., San Diego Calif.), pCMVI.UBF3/2 (S. Johnston, University of Texas) or pcDNA3.1 (InVitrogen Corporation, Carlsbad, Calif.) as the vector. In addition, the vector construct can contain immunostimulatory sequences (ISS), such as unmethylated dCpG motifs, that stimulate the animal's immune system. The nucleic acid vaccine can also encode a fusion product containing the immunogenic polypeptide. Plasmid DNA can also be delivered using attenuated bacteria as delivery system, a method that is suitable for DNA vaccines that are administered orally. Bacteria are transformed with an independently replicating plasmid, which becomes released into the host cell cytoplasm following the death of the attenuated bacterium in the host cell.

DNA vaccines, including the DNA encoding the desired antigen, can be introduced into a host cell in any suitable form including, the fragment alone, a linearized plasmid, a circular plasmid, a plasmid capable of replication, an episome, RNA, etc. Preferably, the gene is contained in a plasmid. In certain embodiments, the plasmid is an expression vector. Individual expression vectors capable of expressing the genetic material can be produced using standard recombinant techniques. See e.g., Maniatis et al., 1985 Molecular Cloning: A Laboratory Manual or DNA Cloning, Vol. I and II (D. N. Glover, ed., 1985) for general cloning methods.

Routes of administration include, but are not limited to, intramuscular, intranasal, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Typical routes of administration include intramuscular, intraperitoneal, intradermal and subcutaneous injection. Genetic constructs may be administered by means including, but not limited to, traditional syringes, needleless injection devices, "microprojectile bombardment gene guns", or other physical methods such as electroporation ("EP"), "hydrodynamic method", or ultrasound. DNA vaccines can be delivered by any method that can be used to deliver DNA as long as the DNA is expressed and the desired antigen is made in the cell.

In some embodiments, a DNA vaccine is delivered via known transfection reagents such as cationic liposomes, fluorocarbon emulsion, cochleate, tubules, gold particles, biodegradable microspheres, or cationic polymers. Cochleate delivery vehicles are stable phospholipid calcium precipitants consisting of phosphatidyl serine, cholesterol, and calcium; this nontoxic and noninflammatory transfection reagent can be present in a digestive system. Biodegradable microspheres comprise polymers such as poly(lactide-co-glycolide), a polyester that can be used in producing microcapsules of DNA for transfection. Lipid-based microtubes often consist of a lipid of spirally wound two layers packed with their edges joined to each other. When a tubule is used, the nucleic acid can be arranged in the central hollow part thereof for delivery and controlled release into the body of an animal.

In some embodiments, DNA vaccine is delivered to mucosal surfaces via microspheres. Bioadhesive microspheres can be prepared using different techniques and can be tailored to adhere to any mucosal tissue including those found in eye, nasal cavity, urinary tract, colon and gastrointestinal tract, offering the possibilities of localized as well as systemic controlled release of vaccines. Application of bioadhesive microspheres to specific mucosal tissues can also be used for localized vaccine action. In some embodiments, an alternative approach for mucosal vaccine delivery is the direct administration to mucosal surfaces of a plasmid DNA expression vector which encodes the gene for a specific protein antigen.

The DNA plasmid vaccines according to the present invention are formulated according to the mode of administration to be used. In some embodiments where DNA plasmid vaccines are injectable compositions, they are sterile, and/or pyrogen free and/or particulate free. In some embodiments, an isotonic formulation is preferably used. Generally, additives for isotonicity can include sodium chloride, dextrose, mannitol, sorbitol and lactose. In some embodiments, isotonic solutions such as phosphate buffered saline are preferred. In some embodiments, stabilizers include gelatin and albumin. In some embodiments, a vasoconstriction agent is added to the formulation. In some embodiments, a stabilizing agent that allows the formulation to be stable at room or ambient temperature for extended periods of time, such as LGS or other polycations or polyanions is added to the formulation.

In some embodiments, the DNA vaccine may further comprises a pharmacologically acceptable carrier or diluent. Suitable carriers for the vaccine are well known to those skilled in the art and include but are not limited to proteins, sugars, etc. Such carriers may be aqueous or non-aqueous solutions, suspensions, and emulsions. Examples of non-aqueous carriers are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's or fixed oils. Intravenous vehicles include fluid and nutrient replenishers, electrolyte replenishers such as those based on Ringer's dextrose, and the like. Preservatives and antimicrobials include antioxidants, chelating agents, inert gases and the like. Preferred preservatives include formalin, thimerosal, neomycin, polymyxin B and amphotericin B.

An alternative approach to delivering the nucleic acid to an animal involves the use of a viral or bacterial vector. Examples of suitable viral vectors include adenovirus, polio virus, pox viruses such as vaccinia, canary pox, and fowl pox, herpes viruses, including catfish herpes virus, adenovirus-associated vector, and retroviruses. Exemplary bacterial vectors include attenuated forms of *Salmonella, Shigella, Edwardsiella ictaluri, Yersinia ruckerii,* and *Listeria monocytogenes*. In some embodiments, the nucleic acid is a vector, such as a plasmid, that is capable of autologous expression of the nucleotide sequence encoding the immunogenic polypeptide.

F. Use of Vaccines

The *S. pneumoniae* vaccines described herein may be used for prophylactic and/or therapeutic treatment of *S. pneumoniae*. Accordingly, this application provides a method for treating a subject suffering from or susceptible to *S. pneumoniae* infection, comprising administering an effective amount of any of the vaccine formulations described herein. In some aspects, the method inhibits *S. pneumoniae* colonization in an individual. In some aspects, the method inhibits *S. pneumoniae* symptoms or sequelae, such as sepsis. The subject receiving the vaccination may be a male or a female, and may be a child or adult. In some embodiments, the subject being treated is a human. In other embodiments, the subject is a non-human animal.

1. Prophylactic Use

In prophylactic embodiments, the vaccine is administered to a subject to induce an immune response that can help protect against the establishment of *S. pneumoniae*, for example by protecting against colonization, the first and necessary step in disease. Thus, in some aspects, the method inhibits infection by *S. pneumoniae* in a non-colonized or uninfected subject. In another aspect, the method may reduce the duration of colonization in an individual who is already colonized.

In some embodiments, the vaccine compositions of the invention confer protective immunity, allowing a vaccinated individual to exhibit delayed onset of symptoms or sequelae, or reduced severity of symptoms or sequelae, as the result of his or her exposure to the vaccine. In certain embodiments, the reduction in severity of symptoms or sequelae is at least 25%, 40%, 50%, 60%, 70%, 80% or even 90%. In particular embodiments, vaccinated individuals may display no symptoms or sequelae upon contact with *S. pneumoniae*, do not become colonized by *S. pneumoniae*, or both. Protective immunity is typically achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes, that result in sIGA production by B lymphocytes on mucosa-lined tissues of the body. Humoral immunity is typically the result of IgG antibodies and IgM antibodies in serum. Cellular immunity can be achieved through cytotoxic T lymphocytes or through delayed-type hypersensitivity that involves macrophages and T lymphocytes, as well as other mechanisms involving T cells without a requirement for antibodies. In particular, cellular immunity may be mediated by $T_H1$ or $T_H17$ cells.

Essentially any individual has a certain risk of becoming infected with *S. pneumoniae*. However, certain sub-populations have an increased risk of infection. In some embodiments, a vaccine formulation as described herein (e.g., a composition comprising one or more polypeptides from Table 1 or 2, or nucleic acids encoding the polypeptides, or antibodies reactive with the polypeptides) is administered to patients that are immunocompromised.

An immunocompromising condition arising from a medical treatment is likely to expose the individual in question to a higher risk of infection with *S. pneumoniae*. It is possible to treat an infection prophylactically in an individual having the immunocompromised condition before or during treatments known to compromise immune function. By prophylactically treating with an antigenic composition (e.g., two or more antigens from Table 1 or 2, or nucleic acids encoding the antigens), or with antibodies reactive to two or more antigens from Table 1 or 2, before or during a treatment known to compromise immune function, it is possible to prevent a subsequent *S. pneumoniae* infection or to reduce the risk of the individual contracting an infection due to the immunocompromised condition. Should the individual contract an *S. pneumoniae* infection e.g., following a treatment leading to an immunocompromised condition it is also possible to treat the infection by administering to the individual an antigen composition.

The following groups are at increased risk of pneumococcal disease or its complications, and therefore it is advantageous for subjects falling into one or more of these groups to receive a vaccine formulation described herein: children, especially those from 1 month to 5 years old or 2 months to 2 years old; children who are at least 2 years of age with asplenia, splenic dysfunction or sickle-cell disease; children who are at least 2 years of age with nephrotic syndrome, chronic cerebrospinal fluid leak, HIV infection or other conditions associated with immunosuppression.

In another embodiment, at least one dose of the pneumococcal antigen composition is given to adults in the following groups at increased risk of pneumococcal disease or its complications: all persons 65 years of age; adults with asplenia, splenic dysfunction or sickle-cell disease; adults with the following conditions: chronic cardiorespiratory disease, cirrhosis, alcoholism, chronic renal disease, nephrotic syndrome, diabetes mellitus, chronic cerebrospinal fluid leak, HIV infection, AIDS and other conditions associated with immunosuppression (Hodgkin's disease, lymphoma, multiple myeloma, immunosuppression for organ transplantation), individuals with cochlear implants; individuals with long-term health problems such as heart disease and lung disease, as well as individuals who are taking any drug or treatment that lowers the body's resistance to infection, such as long-term steroids, certain cancer drugs, radiation therapy; Alaskan natives and certain Native American populations.

2. Therapeutic Use

In therapeutic applications, the vaccine may be administered to a patient suffering from S. pneumoniae infection, in an amount sufficient to treat the patient. Treating the patient, in this case, refers to reducing S. pneumoniae symptoms and/or bacterial load and/or sequelae bin an infected individual. In some embodiments, treating the patient refers to reducing the duration of symptoms or sequelae, or reducing the intensity of symptoms or sequelae. In some embodiments, the vaccine reduces transmissibility of S. pneumoniae from the vaccinated patient. In certain embodiments, the reductions described above are at least 25%, 30%, 40%, 50%, 60%, 70%, 80% or even 90%.

In therapeutic embodiments, the vaccine is administered to an individual post-infection. The vaccine may be administered shortly after infection, e.g. before symptoms or sequelae manifest, or may be administered during or after manifestation of symptoms or sequelae.

A therapeutic S. pneumoniae vaccine can reduce the intensity and/or duration of the various symptoms or sequelae of S. pneumoniae infection. Symptoms or sequelae of S. pneumoniae infection can take many forms. In some cases, an infected patient develops pneumonia, acute sinusitis, otitis media (ear infection), meningitis, bacteremia, sepsis, osteomyelitis, septic arthritis, endocarditis, peritonitis, pericarditis, cellulitis, or brain abscess.

Sepsis is a rare but life-threatening complication of S. pneumoniae infection, where the bacterium invades the bloodstream and systemic inflammation results. Typically, fever is observed and white blood cell count increases. A further description of sepsis is found in Goldstein, B. et al. "International pediatric sepsis consensus conference: definitions for sepsis and organ dysfunction in pediatrics." Pediatr Crit. Care Med. January 2005; 6 (1):2-8.

3. Assaying Vaccination Efficacy

The efficacy of vaccination with the vaccines disclosed herein may be determined in a number of ways, in addition to the clinical outcomes described above. First, one may assay IL-17 levels (particularly IL-17A) by stimulating T cells derived from the subject after vaccination. The IL-17 levels may be compared to IL-17 levels in the same subject before vaccination. Increased IL-17 (e.g., IL-17A) levels, such as a 1.5 fold, 2-fold, 5-fold, 10-fold, 20-fold, 50-fold or 100-fold or more increase, would indicate an increased response to the vaccine. Alternatively (or in combination), one may assay neutrophils in the presence of T cells or antibodies from the patient for pneumococcal killing. Increased pneumococcal killing, such as a 1.5 fold, 2-fold, 5-fold, 10-fold, 20-fold, 50-fold or 100-fold or more increase, would indicate an increased response to the vaccine. In addition, one may measure $T_H17$ cell activation, where increased $T_H17$ cell activation, such as a 1.5 fold, 2-fold, 5-fold, 10-fold, 20-fold, 50-fold or 100-fold or more increase, correlates with an increased response to the vaccine. One may also measure levels of an antibody specific to the vaccine, where increased levels of the specific antibody, such as a 1.5 fold, 2-fold, 5-fold, 10-fold, 20-fold, 50-fold or 100-fold or more increase, are correlated with increased vaccine efficacy. In certain embodiments, two or more of these assays are used. For example, one may measure IL-17 levels and the levels of vaccine-specific antibody. Alternatively, one may follow epidemiological markers such as incidence of, severity of, or duration of pneumococcal infection in vaccinated individuals compared to unvaccinated individuals.

Vaccine efficacy may also be assayed in various model systems such as the mouse model. For instance, BALB/c or C57BL/6 strains of mice may be used. After administering the test vaccine to a subject (as a single dose or multiple doses), the experimenter administers a challenge dose of S. pneumoniae. In some cases, a challenge dose administered intranasally is sufficient to cause S. pneumoniae colonization (especially nasal colonization) in an unvaccinated animal, and in some cases a challenge dose administered via aspiration is sufficient to cause sepsis and a high rate of lethality in unvaccinated animals. One can then measure the reduction in colonization or the reduction in lethality in vaccinated animals. Examples 5-8 and 10 show the efficacy of polypeptides of Table 1 in inhibiting S. pneumoniae nasal colonization following intranasal challenge in the mouse model. Examples 11 and 12 show the efficacy of polypeptides of Table 1 in protecting against sepsis and death following infection with S. pneumoniae via aspiration in the mouse model.

G. Use of Immunogenic Compositions

1. Defense Against S. pneumoniae Infection

The immunogenic compositions of the present disclosure are designed to elicit an immune response against S. pneumoniae. Compositions described herein (e.g., ones comprising one or more polypeptides of Table 1 or 2, or nucleic acids encoding the polypeptides) may stimulate an antibody response or a cell-mediated immune response, or both, in the mammal to which it is administered. In some embodiments, the composition stimulates a $T_H1$-biased CD4$^+$ T cell response, a $T_H17$-biased CD4$^+$ T cell response and/or a CD8$^+$ T cell response. In some embodiments, the composition stimulates an antibody response. In some embodiments, the composition stimulates a $T_H1$-biased CD4$^+$ T cell response, $T_H17$-biased CD4$^+$ T cell response and/or a CD8$^+$ T cell response, and an antibody response.

In certain embodiments, the composition (e.g., one comprising one or more polypeptides of Table 1 or 2, or nucleic acids encoding the polypeptides, or antibodies reactive with the peptides) includes a cytokine or nucleotide coding region encoding a cytokine such as IL-17, to provide additional stimulation to the immune system of the mammal. In certain embodiments, the composition comprises a cytokine such as IL-17.

While not wishing to be bound by theory, in some embodiments a $T_H17$ cell response is desirable in mounting an immune response to the compositions disclosed herein, e.g., ones comprising one or more polypeptides of Table 1 or 2. In certain embodiments, an active $T_H17$ response is beneficial in clearing a pneumococcal infection. For instance, mice lacking the IL-17A receptor show decreased whole cell vaccine-based protection from a pneumococcal challenge (Lu et al., "Interleukin-17A mediates acquired immunity to pneumococcal colonization." PLoS Pathog. 2008 Sep. 19; 4 (9)).

Thus, herein is provided a method of increasing IL-17 production by administering the compositions described herein (e.g., ones comprising one or more polypeptides of Table 1 or 2) to a subject. Furthermore, this application provides a method of activating $T_H17$ cells by administering said compositions to a subject. In certain embodiments, increased IL-17A levels result in increased pneumococcal killing by neutrophils or neutrophil-like cells, for instance by inducing recruitment and activation of neutrophils of neutrophil-like cells. In certain embodiments, this pneumococcal killing is independent of antibodies and complement. However, specific antibody production and complement activation may be useful additional mechanisms that contribute to clearing of a pneumococcal infection.

Immunogenic compositions containing immunogenic polypeptides or polynucleotides encoding immunogenic polypeptides together with a pharmaceutical carrier are also provided.

In some instances, the immunogenic composition comprises one or more nucleic acids encoding one or more polypeptides of SEQ ID NOS: 1-13, 265, 266 and 267, such as one or more nucleic acids selected from SEQ ID Nos. 24-31, 271, 272 and 273. In some embodiments these nucleic acids are expressed in the immunized individual, producing the encoded S. pneumoniae antigens, and the S. pneumoniae antigens so produced can produce an immunostimulatory effect in the immunized individual.

Such a nucleic acid-containing immunostimulatory composition may comprise, for example, an origin of replication, and a promoter that drives expression of one or more nucleic acids encoding one or more polypeptides of SEQ ID NOS: 1-13, 265, 266 and 267. Such a composition may also comprise a bacterial plasmid vector into which is inserted a promoter (sometimes a strong viral promoter), one or more nucleic acids encoding one or more polypeptides of SEQ ID NOS: 1-13, 265, 266 and 267, and a polyadenylation/transcriptional termination sequence. In some instances, the nucleic acid is DNA.

H. Diagnostic Uses

This application provides, inter alia, a rapid, inexpensive, sensitive, and specific method for detection of S. pneumoniae in patients. In this respect it should be useful to all hospitals and physicians examining and treating patients with or at risk for S. pneumoniae infection. Detection kits can be simple enough to be set up in any local hospital laboratory, and the antibodies and antigen-binding portions thereof can readily be made available to all hospitals treating patients with or at risk for S. pneumoniae infection. As used herein, "patient" refers to an individual (such as a human) that either has an S. pneumoniae infection or has the potential to contract an S. pneumoniae infection. A patient may be an individual (such as a human) that has an S. pneumoniae infection, has the potential to contract an S. pneumoniae infection, who has recovered from S. pneumoniae infection, and/or an individual whose infection status is unknown.

In some embodiments, one may perform a diagnostic assay using two or more antibodies, each of which binds one of the antigens of Table 1 or 2 to detect S. pneumoniae in an individual. In some embodiment, one of the antigens is SEQ ID NO: 265, 266, or 268. The instant disclosure also provides a method of phenotyping biological samples from patients suspected of having a S. pneumoniae infection: (a) obtaining a biological sample from a patient; (b) contacting the sample with two or more S. pneumoniae-specific antibodies or antigen-binding portions thereof under conditions that allow for binding of the antibody or antigen-binding portion to an epitope of S. pneumoniae; where binding indicates the presence of S. pneumoniae in the sample. In some embodiments, the binding to the biological sample is compared to binding of the same antibody to a negative control tissue, wherein if the biological sample shows the presence of S. pneumoniae as compared to the negative control tissue, the patient is identified as likely having a S. pneumoniae infection. In some cases, binding of one antibody indicates the presence of S. pneumoniae; in other cases, the binding of two or more antibodies indicates the presence of S. pneumoniae. The aforementioned test may be appropriately adjusted to detect other bacterial infections, for instance by using an antibody immunoreactive a homolog (from another bacterial species) of one of the proteins described in Table 1. In some embodiments, the antibodies raised against a S. pneumoniae protein in Table 1 or 2 will also bind the homolog in another Streptococcus species, especially if the homologs have a high percentage sequence identity.

Alternatively, one may use an antigen of Table 1 or 2 (such as SEQ ID NO: 265, 266, or 268) to detect anti-S. pneumoniae antibodies in an individual. The instant disclosure also provides a method of phenotyping biological samples from patients suspected of having a S. pneumoniae infection: (a) obtaining a biological sample from a patient; (b) contacting the sample with two or more S. pneumoniae-specific antigens selected from Table 1 or 2 or portions thereof under conditions that allow for binding of the antigen (or portion thereof) to any host antibodies present in the sample; where binding indicates the presence of anti-S. pneumoniae antibodies in the sample. In some embodiments, the binding to the biological sample is compared to binding of the same antigen to a negative control tissue, wherein if the biological sample shows the presence of anti-S. pneumoniae antibodies as compared to the negative control tissue, the patient is identified as likely either (1) having a S. pneumoniae infection, or (2) having had a S. pneumoniae infection in the past. In some cases, detecting one antibody indicates a current or past infection with S. pneumoniae; in other cases, detecting two or more antibodies indicates a current or past infection with S. pneumoniae. The aforementioned test may be appropriately adjusted to detect other bacterial infections, for instance by using a homolog (from another bacterial species (e.g., a Streptococcal species) of the proteins described in Table 1.

In some embodiments, the immune cell response of a mammalian cell may be quantified ex vivo. A method for such quantification comprises administering the compositions herein disclosed to a mammalian T cell ex vivo, and quantifying the change in cytokine production of the mammalian T cell in response to the composition. In these methods, the cytokine may be, for example, IL-17.

The binding of an S. pneumoniae antibody to an antigen (e.g., a polypeptide of Table 1 or 2, such as SEQ ID NO: 265, 266, or 268) may be measured using any appropriate method. Such methods include ELISA (enzyme-linked immunosorbent assay), Western blotting, competition assay, and spot-blot. The detection step may be, for instance, chemiluminescent, fluorescent, or colorimetric. One suitable method for measuring antibody-protein binding is the Luminex xMAP system, where peptides are bound to a dye-containing microsphere. Certain systems, including the xMAP system, are amenable to measuring several different markers in multiplex, and could be used to measure levels of antibodies at once. In some embodiments, other systems are used to assay a plurality of markers in multiplex. For example, profiling may be performed using any of the following systems: antigen microarrays, bead microarrays, nanobarcodes particle technology, arrayed proteins from cDNA expression libraries, protein in situ array, protein arrays of living transformants, universal protein array, lab-on-a-chip microfluidics, and peptides on pins. Another type of clinical assay is a chemiluminescent assay to detect antibody binding. In some such assays, including the VITROS Eci anti-HCV assay, antibodies are bound to a solid-phase support made up of microparticles in liquid suspension, and a surface fluorometer is used to quantify the enzymatic generation of a fluorescent product.

In some embodiments, if the biological sample shows the presence of S. pneumoniae (e.g., by detecting one or more polypeptide of Table 1 or 2, such as SEQ ID NO: 265, 266, or 268, or an antibody that binds one of said polypeptides), one may administer a therapeutically effective amount of the compositions and therapies described herein to the patient. The biological sample may comprise, for example, blood, semen, urine, vaginal fluid, mucus, saliva, feces, urine, cerebrospinal fluid, or a tissue sample. In some embodiments, the biological sample is an organ intended for transplantation. In certain embodiments, before the detection step, the biological sample is subject to culture conditions that promote the growth of S. pneumoniae.

The diagnostic tests herein (e.g., those that detect a polypeptide of Table 1 or 2, such as SEQ ID NO: 265, 266, or 268, or an antibody that binds one of said polypeptides) may be used to detect S. pneumoniae in a variety of samples, including samples taken from patients and samples obtained from other sources. For example, the diagnostic tests may be used to detect S. pneumoniae in food, drink, or ingredients for food and drink; on objects such as medical instruments, medical devices such as cochlear implants and pacemakers, shoes, clothing, furniture including hospital furniture, and drapes including hospital drapes; or in samples taken from the environment such as plant samples. In some embodiments, the tests herein may be performed on samples taken from animals such as agricultural animals (cows, pigs, chickens, goats, horses and the like), companion animals (dogs, cats, birds, and the like), or wild animals. In certain embodiments, the tests herein may be performed on samples taken from cell cultures such as cultures of human cells that produce a therapeutic protein, cultures of bacteria intended to produce a useful biological molecule, or cultures of cells grown for research purposes.

This disclosure also provides a method of determining the location of a S. pneumoniae infection in a patient comprising: (a) administering a pharmaceutical composition comprising a labeled S. pneumoniae antibody or antigen-binding portion thereof to the patient, and (b) detecting the label, wherein binding indicates a S. pneumoniae infection in a particular location in the patient. Such a diagnostic may also comprise comparing the levels of binding in the patient to a control. In certain embodiments, the method further comprises, if the patient has a S. pneumoniae infection, treating the infection by administering a therapeutically effective amount of a S. pneumoniae-binding antibody or antigen-binding portion thereof to the patient. In certain embodiments, the method further comprises, if the patient has a S. pneumoniae infection, treating the infection by administering a therapeutically effective amount of a S. pneumoniae protein of Table 1 or 2, or immunogenic portion thereof, to the patient. The method may further comprise determining the location and/or volume of the S. pneumoniae in the patient. This method may be used to evaluate the spread of S. pneumoniae in the patient and determine whether a localized therapy is appropriate.

In some embodiments, the anti-S. pneumoniae antibodies or T cells described herein may be used to make a prognosis of the course of infection. In some embodiments, the anti-S. pneumoniae antibodies or T cells herein may be detected in a sample taken from a patient. If antibodies or T cells are present at normal levels, it would indicate that the patient has raised an immune response against anti-S. pneumoniae. If antibodies or T cells are absent, or present at reduced levels, it would indicate that the patient is failing to raise a sufficient response against anti-S. pneumoniae, and a more aggressive treatment would be recommended. In some embodiments, antibodies or T cells present at reduced levels refers to antibodies that are present at less than 50%, 20%, 10%, 5%, 2%, or 1% the level of antibodies or T cells typical in a patient with a normal immune system. Antibodies may be detected by affinity for any of the antigens described herein (e.g., those in Table 1 and/or 2), for example using ELISA. T cells may be detected by ex vivo responses for any of the antigens described herein (e.g., those in Table 1 and/or 2), for example using ELISA or ELISPOT assays.

In some embodiments, detection of specific S. pneumoniae antigens (e.g., those in Table 1 and/or 2, such as SEQ ID NO: 265, 266, or 268) may be used to predict the progress and symptoms of S. pneumoniae infection in a patient. It will be understood by one of skill in the art that the methods herein are not limited to detection of S. pneumoniae. Other embodiments include the detection of related bacteria including bacteria with proteins homologous to the proteins described in Table 1 or 2. Such related bacteria include, for example, other strains of Streptococcus.

I. Doses and Routes of Administration

1. Dosage Forms, Amounts, and Timing

The amount of antigen in each vaccine or immunogenic composition dose is selected as an effective amount, which induces a prophylactic or therapeutic response, as described above, in either a single dose or over multiple doses. Preferably, the dose is without significant adverse side effects in typical vaccinees. Such amount will vary depending upon which specific antigen is employed. Generally, it is expected that a dose will comprise 1-1000 µg of each protein, in some instances 2-100 µg, for instance 4-40 µg. In some aspects, the vaccine formulation comprises 1-1000 µg of the polypeptide and 1-250 µg of the adjuvant. In some embodiments, the appropriate amount of antigen to be delivered will depend on the age, weight, and health (e.g. immunocompromised status) of a subject. When present, typically an adjuvant will be present in amounts from 1 µg-250 µg per dose, for example 50-150 µg, 75-125 µg or 100 µg.

In some embodiments, only one dose of the vaccine is administered to achieve the results described above. In other embodiments, following an initial vaccination, subjects receive one or more boost vaccinations, for a total of two, three, four or five vaccinations. Advantageously, the number is three or fewer. A boost vaccination may be administered, for example, about 1 month, 2 months, 4 months, 6 months, or 12 months after the initial vaccination, such that one vaccination regimen involves administration at 0, 0.5-2 and 4-8 months. It may be advantageous to administer split doses of vaccines which may be administered by the same or different routes.

The vaccines and immunogenic compositions described herein may take on a variety of dosage forms. In certain embodiments, the composition is provided in solid or powdered (e.g., lyophilized) form; it also may be provided in solution form. In certain embodiments, a dosage form is provided as a dose of lyophilized composition and at least one separate sterile container of diluent.

In some embodiments, the composition will be administered in a dose escalation manner, such that successive administrations of the composition contain a higher concentration of composition than previous administrations. In some embodiments, the composition will be administered in a manner such that successive administrations of the composition contain a lower concentration of composition than previous administrations.

In therapeutic applications, compositions are administered to a patient suffering from a disease in an amount sufficient to treat the patient. Therapeutic applications of a composition described herein include reducing transmissibility, slowing disease progression, reducing bacterial viability or replication, or inhibiting the expression of proteins required for toxicity, such as by 90%, 80%, 70%, 60%, 50%, 40%, 30%, 20% or 10% of the levels at which they would occur in individuals who are not treated with the composition.

In prophylactic embodiments, compositions are administered to a human or other mammal to induce an immune response that can inhibit the establishment of an infectious disease or other condition. In some embodiments, a composition may partially block the bacterium from establishing an infection.

In some embodiments, the compositions are administered in combination with antibiotics. This co-administration is particularly appropriate when the pharmaceutical composition is administered to a patient who has recently been exposed (or is suspected of having been recently exposed) to *S. pneumoniae*. Many antibiotics are used to treat pneumococcal infections, including penicillin, amoxicillin, amoxicillin/clavulanate, cefuroxime, cefotaxime, ceftriaxone, and vancomycin. The appropriate antibiotic may be selected based on the type and severity of the infection, as well as any known antibiotic resistance of the infection (Jacobs M R "Drug-resistant *Streptococcus pneumoniae*: rational antibiotic choices" Am J. Med. 1999 May 3; 106 (5A):19S-25S).

2. Routes of Administration

The vaccine formulations and pharmaceutical compositions herein can be delivered by administration to an individual, typically by systemic administration (e.g., intravenous, intraperitoneal, intramuscular, intradermal, subcutaneous, subdermal, transdermal, intracranial, intranasal, mucosal, anal, vaginal, oral, buccal route or they can be inhaled) or they can be administered by topical application. In some embodiments, the route of administration is intramuscular. In other embodiments, the route of administration is subcutaneous. In yet other embodiments, the route of administration is mucosal. In certain embodiments, the route of administration is transdermal or intradermal Certain routes of administration are particularly appropriate for vaccine formulations and immunogenic compositions comprising specified adjuvants. In particular, transdermal administration is one suitable route of administration for *S. pneumoniae* vaccines comprising toxins (e.g. cholera toxin or labile toxin); in other embodiments, the administration is intranasal. Vaccines formulated with Alphavirus replicons may be administered, for example, by the intramuscular or the subcutaneous route. Vaccines comprising Monophosphory Lipid A (MPL), Trehalose Dicoynomycolate (TDM), and dioctadecyldimethylammonium bromide (DDA) are suitable (inter alia) for intramuscular and subcutaneous administration. A vaccine comprising resiquimod may be administered topically or subcutaneously, for example.

3. Formulations

The vaccine formulation or immunogenic composition may be suitable for administration to a human patient, and vaccine or immunogenic composition preparation may conform to USFDA guidelines. In some embodiments, the vaccine formulation or immunogenic composition is suitable for administration to a non-human animal. In some embodiments, the vaccine or immunogenic composition is substantially free of either endotoxins or exotoxins. Endotoxins may include pyrogens, such as lipopolysaccharide (LPS) molecules. The vaccine or immunogenic composition may also be substantially free of inactive protein fragments which may cause a fever or other side effects. In some embodiments, the composition contains less than 1%, less than 0.1%, less than 0.01%, less than 0.001%, or less than 0.0001% of endotoxins, exotoxins, and/or inactive protein fragments. In some embodiments, the vaccine or immunogenic composition has lower levels of pyrogens than industrial water, tap water, or distilled water. Other vaccine or immunogenic composition components may be purified using methods known in the art, such as ion-exchange chromatography, ultrafiltration, or distillation. In other embodiments, the pyrogens may be inactivated or destroyed prior to administration to a patient. Raw materials for vaccines, such as water, buffers, salts and other chemicals may also be screened and depyrogenated. All materials in the vaccine may be sterile, and each lot of the vaccine may be tested for sterility. Thus, in certain embodiments the endotoxin levels in the vaccine fall below the levels set by the USFDA, for example 0.2 endotoxin (EU)/kg of product for an intrathecal injectable composition; 5 EU/kg of product for a non-intrathecal injectable composition, and 0.25-0.5 EU/mL for sterile water.

In certain embodiments, the preparation comprises less than 50%, 20%, 10%, or 5% (by dry weight) contaminating protein. In certain embodiments, the desired molecule is present in the substantial absence of other biological macromolecules, such as other proteins (particularly other proteins which may substantially mask, diminish, confuse or alter the characteristics of the component proteins either as purified preparations or in their function in the subject reconstituted mixture). In certain embodiments, at least 80%, 90%, 95%, 99%, or 99.8% (by dry weight) of biological macromolecules of the same type present (but water, buffers, and other small molecules, especially molecules having a molecular weight of less than 5000, can be present). In some embodiments, the vaccine or immunogenic composition comprising purified subunit proteins contains less than 5%, 2%, 1%, 0.5%, 0.2%, 0.1% of protein from host cells in which the subunit proteins were expressed, relative to the amount of purified subunit. In some embodiments, the desired polypeptides are substantially free of nucleic acids and/or carbohydrates. For instance, in some embodiments, the vaccine or immunogenic composition contains less than 5%, less than 2%, less than 1%, less than 0.5%, less than 0.2%, or less than 0.1% host cell DNA and/or RNA. In certain embodiments, at least 80%, 90%, 95%, 99%, or 99.8% (by dry weight) of biological macromolecules of the same type are present in the preparation (but water, buffers, and other small molecules, especially molecules having a molecular weight of less than 5000, can be present).

It is preferred that the vaccine or immunogenic composition has low or no toxicity, within a reasonable risk-benefit ratio. In certain embodiments, the vaccine or immunogenic composition comprises ingredients at concentrations that are less than $LD_{50}$ measurements for the animal being vaccinated. $LD_{50}$ measurements may be obtained in mice or other experimental model systems, and extrapolated to humans and other animals. Methods for estimating the $LD_{50}$ of compounds in humans and other animals are well-known in the art. A vaccine formulation or immunogenic composition, and any component within it, might have an $LD_{50}$ value in rats of greater than 100 g/kg, greater than 50 g/kg, greater than 20 g/kg, greater than 10 g/kg, greater than 5 g/kg, greater than 2 g/kg, greater than 1 g/kg, greater than 500 mg/kg, greater than 200 mg/kg, greater than 100 mg/kg, greater than 50 mg/kg, greater than 20 mg/kg, or greater than 10 mg/kg. A vaccine formulation or immunogenic composition that comprises a toxin such as botulinum toxin (which can be used as an adjuvant) should contain significantly less than the $LD_{50}$ of botulinum toxin.

The formulations suitable for introduction of the vaccine formulations or pharmaceutical composition vary according to route of administration. Formulations suitable for parenteral administration, such as, for example, by intraarticular (in the joints), intravenous, intramuscular, intradermal, intraperitoneal, intranasal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials.

Injection solutions and suspensions can be prepared from sterile powders, granules, and tablets of the kind previously described. In the case of adoptive transfer of therapeutic T cells, the cells can be administered intravenously or parenterally.

Formulations suitable for oral administration can consist of (a) liquid solutions, such as an effective amount of the polypeptides or packaged nucleic acids suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. The pharmaceutical compositions can be encapsulated, e.g., in liposomes, or in a formulation that provides for slow release of the active ingredient.

The antigens, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like. Aerosol formulations can be delivered orally or nasally.

Suitable formulations for vaginal or rectal administration include, for example, suppositories, which consist of the polypeptides or packaged nucleic acids with a suppository base. Suitable suppository bases include natural or synthetic triglycerides or paraffin hydrocarbons. In addition, it is also possible to use gelatin rectal capsules which consist of a combination of the polypeptides or packaged nucleic acids with a base, including, for example, liquid triglycerides, polyethylene glycols, and paraffin hydrocarbons.

J. Preparation and Storage of Vaccine Formulations and Immunogenic Compositions

The *S. pneumoniae* vaccines and immunogenic compositions described herein may be produced using a variety of techniques. For example, a polypeptide may be produced using recombinant DNA technology in a suitable host cell. A suitable host cell may be bacterial, yeast, mammalian, or other type of cell. The host cell may be modified to express an exogenous copy of one of the relevant polypeptide genes. Typically, the gene is operably linked to appropriate regulatory sequences such as a strong promoter and a polyadenylation sequence. In some embodiments, the promoter is inducible or repressible. Other regulatory sequences may provide for secretion or excretion of the polypeptide of interest or retention of the polypeptide of interest in the cytoplasm or in the membrane, depending on how one wishes to purify the polypeptide. The gene may be present on an extrachromosomal plasmid, or may be integrated into the host genome. One of skill in the art will recognize that it is not necessary to use a nucleic acid 100% identical to the naturally-occurring sequence. Rather, some alterations to these sequences are tolerated and may be desirable. For instance, the nucleic acid may be altered to take advantage of the degeneracy of the genetic code such that the encoded polypeptide remains the same. In some embodiments, the gene is codon-optimized to improve expression in a particular host. The nucleic acid may be produced, for example, by PCR or by chemical synthesis.

Once a recombinant cell line has been produced, a polypeptide may be isolated from it. The isolation may be accomplished, for example, by affinity purification techniques or by physical separation techniques (e.g., a size column).

In a further aspect of the present disclosure, there is provided a method of manufacture comprising mixing one or more polypeptides or an immunogenic fragment or variant thereof with a carrier and/or an adjuvant.

In some embodiments, antigens for inclusion the vaccine formulations and immunogenic compositions may be produced in cell culture. One method comprises providing one or more expression vectors and cloning nucleotides encoding one or more polypeptides selected from polypeptides having an amino acid sequence of Table 1 or 2, such as SEQ ID NO: 265, 266, or 268, then expressing and isolating the polypeptides.

The immunogenic polypeptides described herein, and nucleic acid compositions that express the polypeptides, can be packaged in packs, dispenser devices, and kits for administering nucleic acid compositions to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition, such as those disclosed herein.

V. EXAMPLES

Example 1

Antigen Identification and Pooled Murine Screens

Each open reading frame predicted in the *S. pneumoniae* TIGR4 genome was cloned into an expression vector comprising a tag that is able to be presented by the major histocompatibility complex (MHC). Each construct was then expressed in *E. coli*, and full-length expression validated by a surrogate assay that identifies the tag in the context of MHC. The screen is described in more detail in International Application WO 2010/002993. In order to facilitate screening the large library, the library was pooled such that four induced library clones were present in each well. In order to screen T cells from mice immunized against *S. pneumoniae*, an aliquot of the pooled library was added to peritoneal-derived macrophages. The macrophages were allowed to bind the tagged *S. pneumoniae* antigens via the MHC. After 2 hr at 37° C., the macrophages were washed with PBS. The macrophages were then fixed with 1% paraformaldehyde for 15 min and washed extensively with PBS. $10^5$ T cells were added to each well in 200 μL of RP-10 media. The T cells had previously been isolated from mice that had been immunized 2 times with killed *S. pneumoniae* bacteria with cholera toxin adjuvant. The assay plates were incubated for 72 hrs at 37° C. The amount of IL-17 in the supernatant of each well was determined through the use of an IL-17 ELISA assay. The threshold for a positive result was set at two standard deviations above the mean of all samples.

Example 2

Deconvolution of the Positive Murine Pools

A secondary screen was used to determine which antigen(s) out of the four clones in each well induced the positive response observed in the pooled screen described in Example 1. All the clones in each positive pool were pulsed individually onto peritoneal macrophages in duplicate wells. T cells isolated from immunized mice from the same genetic background as the initial screen were used to screen the pulsed macrophages using the IL-17 assay described in Example 1. Individual antigens that induced an average response in the duplicate wells greater than two standard deviations above the mean of negative control samples were considered positive responses. The library plasmids present in these positive clones were sequenced to confirm the identity of the antigen. The antigens SP1574, SP1655, SP2106, SP0148, SP1473, SP0605, SP1177, SP0335, SP0906, SP1828, SP2157, SP1229, SP1128, SP1836, SP1865, SP0904, SP0882, SP0765, SP1634, SP0418, SP1923, SP1313, SP0775, SP0314, SP0912, SP0159, SP0910, SP2148, SP1412, SP0372, SP1304, SP2002, SP0612, SP1988, SP0484, SP0847, SP1527, SP0542, SP0441, SP0350, SP0014, SP1965, SP0117, and SP2108 were confirmed using this method.

Example 3

Antigen Identification and Pooled Human Screens

CD4+ T cells and CD14+ monocytes were isolated from peripheral blood acquired from human donors. The monocytes were differentiated into dendritic cells by culturing them in GM-CSF and IL-4 containing media, essentially as described in Tedder T F and Jansen P J (1997 "Isolation and generation of human dendritic cells." *Current Protocols in Immunology* Supp 23: 7.32.1-7.32.16). After five days in culture, the dendritic cells were seeded into 384 well plates. The CD4+ T cells were non-specifically expanded in culture to ensure sufficient quantities.

Each open reading frame predicted in the *S. pneumoniae* TIGR4 genome was cloned into an expression vector comprising a tag that is able to be presented by the major histocompatibility complex (MHC). Each construct was then expressed in *E. coli*, and full-length expression validated by a surrogate assay that identifies the tag in the context of MHC. In order to facilitate screening the large library, the library was pooled such that four induced library clones were present in each well. In order to screen the human T cells, an aliquot of the pooled library was added to the seeded dendritic cells in 384-well plates. After 2 hr at 37° C., the dendritic cells were fixed with 1% paraformaldehyde for 15 min and washed extensively with phosphate buffer and lysine buffer. 40,000 of the CD4+ T cells in 70 μL of RP-10 media were added to each well of a 384-well plate. The assay plates were incubated for 3 days at 37° C. The amount of IL-17 in the supernatant of each well was determined through the use of an IL-17 ELISA assay. In different iterations of the screen, the threshold for a positive result was set at two standard deviations above the mean of all samples, two standard deviations above the mean of negative controls, or 1.78 times the median absolution deviation of the data set. Positive pools were then deconvoluted as described in Example 4.

Example 4

Deconvolution of the Positive Human Pools

For all antigens, deconvolution was performed by comparing the results of two pool screens. In this method, two different sets of pools were prepared, so that a polypeptide was with three different polypeptides between the first and second pools. Consequently, it is possible to determine which polypeptides are antigens by identifying which polypeptides are in positive pools in both the first and second sets. In this deconvolution method, a pool was identified as positive if it was at least 1.78 times the median absolution deviation of the data set.

An antigen was identified as a positive hit if it was positive in at least two repeated secondary screens. The antigens SP2108, SP0641, SP1393, SP0024, SP0641.1, SP1072, SP1384 and SP2032 were identified using the above approach.

Example 5

SP2108, SP0148 and SP1634 Polypeptides

Figure 1:
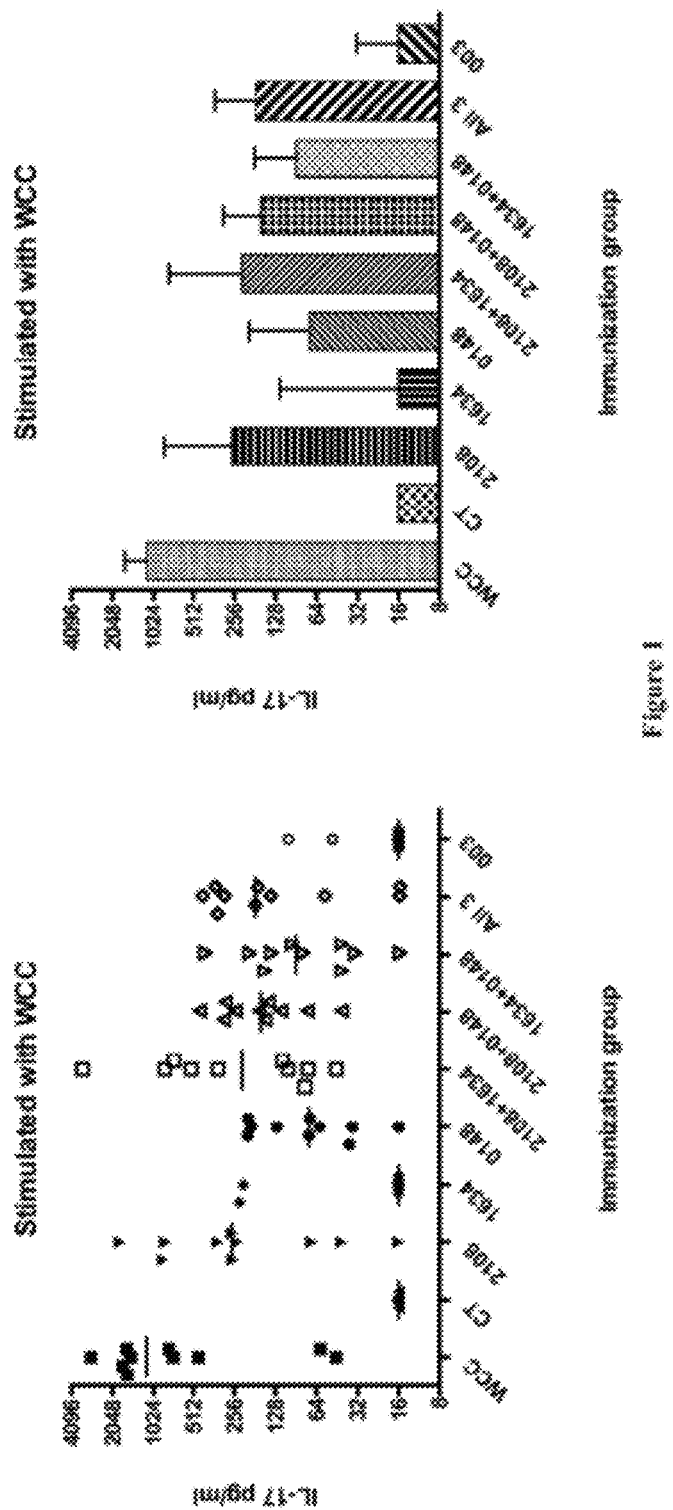
Figure 2:
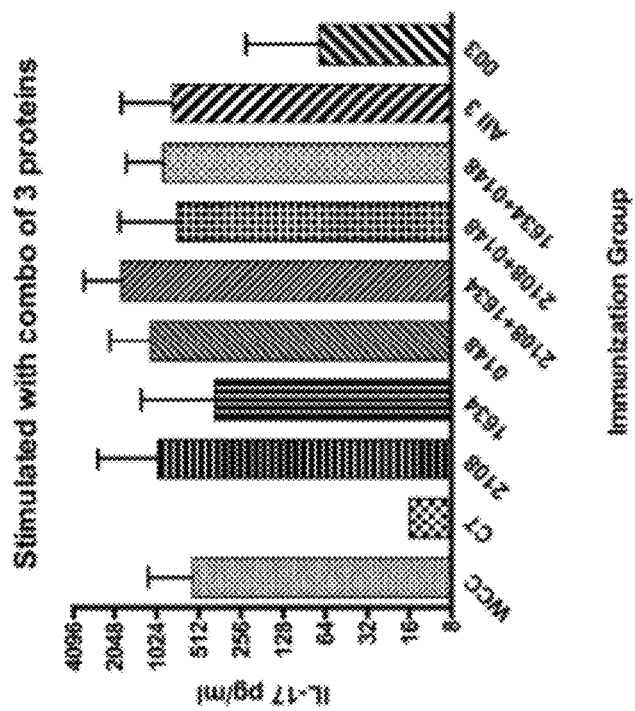
FIG. 2 shows the concentration of IL-17 generated by blood samples from mice that were immunized with the indicated protein(s) and cholera toxin adjuvant, then stimulated with a combination of three proteins (SP2108, SP0148, and SP1634), as described in Example 5.
Figure 2:
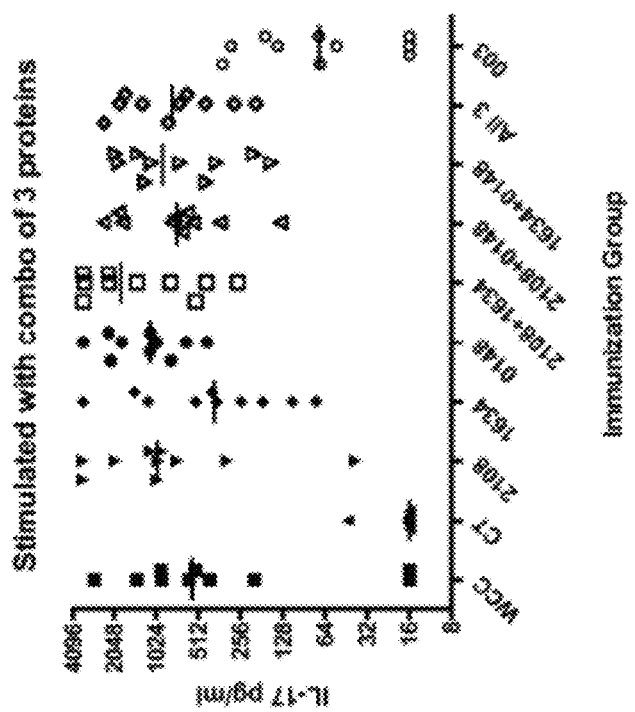
Figure 3:
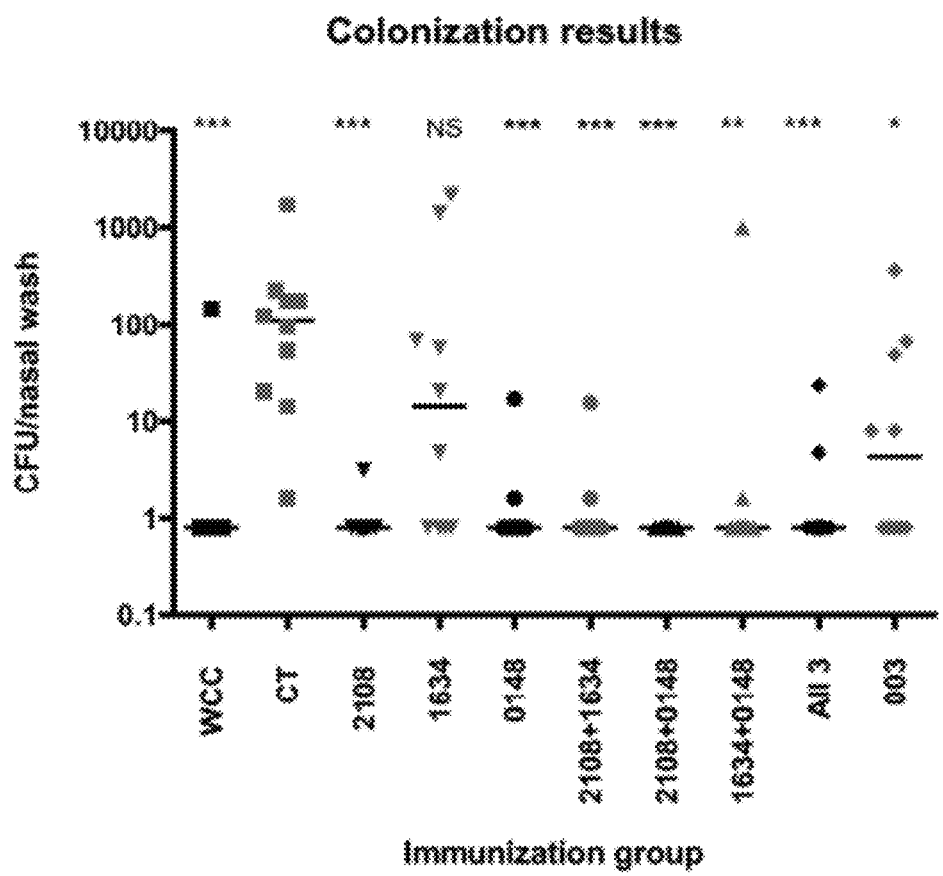
FIG. 3 shows the number of *S. pneumoniae* colonies obtained from a nasal wash in mice that were immunized with the indicated protein(s) and cholera toxin adjuvant, then challenged with intranasal administration of *S. pneumoniae*, as described in Example 5. 003 represents a control unrelated antigen.

The SP2108 polypeptide (SEQ ID NO: 9), SP0148 polypeptide (SEQ ID NO: 7) and SP1634 polypeptide (see Table 2) were formulated as vaccine compositions using 4 μg of the polypeptide in combination with 1 μg cholera toxin adjuvant (CT). For combinations, 4 μg of each polypeptide was used. The compositions were administered intranasally to C57BL/6 mice three times, one week apart. The subjects were then allowed to rest for 3 weeks, and bled at that time for immunogenicity. For this assay, heparinized whole blood was collected from the retrograde orbital sinus. The total PBMC were stimulated with either killed, unencapsulated whole cell *S. pneumoniae* (WCC) or a combination of the three polypeptides in round bottomed tubes for three days. The supernatants were then harvested and evaluated by ELISA for IL-17 levels. Cholera toxin alone (CT) or an unrelated antigen from HSV (003) were used as negative controls. Results of the IL-17 immunogenicity assay are shown in FIGS. 1 and 2, where the left panels show data in scatter format, and the right panels show data as averages with standard deviations. The subjects were allowed to rest an additional 2 weeks, at which time they were challenged with intranasal administration of live, encapsulated *S. pneumoniae*. The subjects were sacrificed a week later, and the number of colony-forming units (CFU) was counted from nasal washes. Results of the colonization assay are shown in FIG. 3.

Example 6

SP0882 and SP0314 Polypeptides

Figure 4:
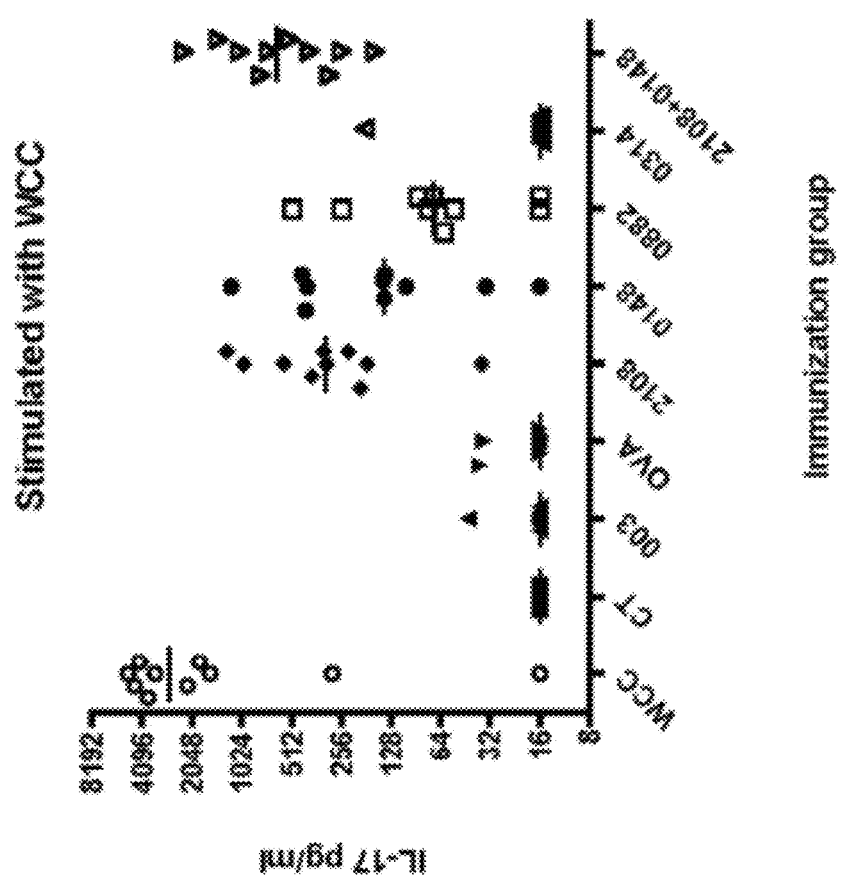
FIG. 4 shows the concentration of IL-17 generated by blood samples from mice that were immunized with the indicated protein(s) and cholera toxin adjuvant, then stimulated with killed, unencapsulated whole cell *S. pneumoniae*, as described in Example 6.
Figure 5:
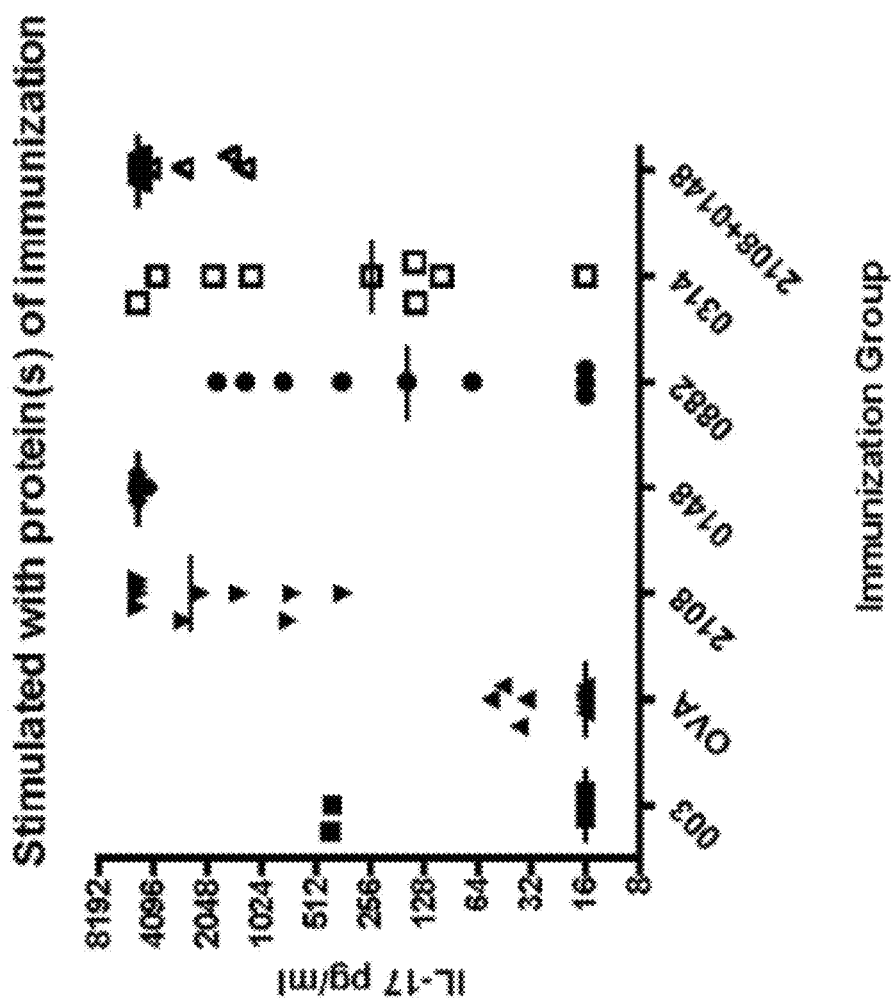
FIG. 5 shows the concentration of IL-17 generated by blood samples from mice that were immunized with the indicated protein(s) and cholera toxin adjuvant, then stimulated by the indicated protein(s), as described in Example 6.

This example used the same protocols as Example 5, except that only two doses of the vaccine composition were administered. In these experiments, the SP0882 polypeptide (SEQ ID NO: 2) and SP0314 polypeptides (see Table 2) were tested in parallel with two of the three polypeptides tested in Example 5. Results of the IL-17 immunogenicity assay are shown in FIGS. 4 and 5. Results of the colonization assay are shown in FIG. 6.

Example 7

SP1072, SP0641N, and SP0024 Polypeptides

This example used a protocol similar to that of Example 5, except that two doses of the vaccine compositions were administered, one week apart. Vaccine compositions comprised the polypeptides SP1072 (SEQ ID NO: 8), SP0641N (SEQ ID NO: 13) or SP0024 (SEQ ID NO: 1), and cholera toxin adjuvant (CT). Four weeks after the last immunization, the mice were challenged intranasally with live type 6B *S. pneumoniae*. One week later the bacterial burden was assessed in each mouse by plating a nasal lavage on selective media and counting resultant CFU. The number of CFU isolated from each mouse is plotted for each immunized cohort. The results of this colonization assay are shown in FIG. 7. Statistically significant results are indicated in the figure (*=p-value<0.05).

Example 8

SP0148, SP0314, SP0882, and SP2108 Polypeptides Tested in the BALB/c Mouse

To determine whether similar immune responses were seen across different mouse genotypes, vaccine compositions were administered to BALB/c mice. Vaccine compositions comprised the polypeptides SP0148 (SEQ ID NO: 2), SP0314 (see Table 2), SP0882 (SEQ ID NO: 2) or SP2108 (SEQ ID NO: 9), and cholera toxin adjuvant (CT). Using a protocol similar to that of Example 5, the mice were immunized, challenged intranasally with *S. pneumoniae*, and the number of CFU was recorded. The results of this colonization experiment are shown in FIG. 8.

Example 9

SP1912, SP2108 and SP0148 Polypeptides

IL-17A Immunogenicity Assay

The polypeptides SP1912 (SEQ ID NO: 265), SP2108 (SEQ ID NO: 9) or SP0148 (SEQ ID NO: 7) were formulated as vaccine compositions with cholera toxin adjuvant (CT). The vaccine compositions were administered to mice two times, one week apart. The positive control was killed, unencapsulated whole cell *S. pneumoniae*+CT (WCB), and the negative controls were CT alone or recombinant proteins without CT (with the exception of SP1912). Three weeks after the last immunization, peripheral blood was collected from the retroorbital sinus and evaluated in a whole blood assay. Briefly, the heparizined whole blood was diluted in media and then cultured in duplicate with A) the protein of immunization, or B) the whole cell vaccine for six days. The supernatants were harvested and IL-17A levels measured by ELISA. Results of the IL-17A immunogenicity assay are shown in FIG. 9. Each symbol in the graph represents responses from individual mice, and the line indicates the median response of the group.

Example 10

SP1912, SP2108 and SP0148 Polypeptides

Colonization Assay

Animals were immunized with vaccine formulations comprising the polypeptides SP1912 (SEQ ID NO: 265), SP2108 (SEQ ID NO: 9) or SP0148 (SEQ ID NO: 7) and cholera toxin adjuvant (CT) as described in Example 9, and then challenged intranasally with $10^7$ live type 6B *S. pneumoniae* four weeks after the last immunization (and one week after retroorbital blood collection). Seven days after challenge, animals were euthanized and the nasopharyngeal cavities lavaged and cultured on permissive media to evaluate the *S. pneumoniae* titers. Results are shown in FIG. 10 as the colony forming units of bacteria (CFU) per lavage. Each symbol represents a titer from an individual mouse response, and the horizontal line represents the median of the group. (***=p-value<0.05).

Example 11

SP1912 Polypeptide

Aspiration Challenge (Sepsis Assay)

Polypeptide SP1912 was evaluated for its ability to protect mice from sepsis. Groups of ten mice were subcutaneously immunized three times, two weeks apart with vaccine compositions comprising either the SP1912 polypeptide (SEQ ID NO: 265) or pneumolysoid (PdT) adsorbed to alum. The positive control was killed, unencapsulated whole cell *S. pneumoniae*+alum (WCB), and the negative control was alum alone. Three weeks after the final immunization, blood was collected for evaluation of IL-17A response and antibody levels, and then one week later, the mice underwent aspiration challenge with $10^7$ live strain 0603 (type 6B) *S. pneumoniae*. Animals were monitored for survival for eight days. Results of the aspiration challenge are shown in FIG. 11 as survival curves for each immunized group.

Example 12

Pneumolysoid PdT, SP0148 and SP0641N Polypeptides

Aspiration Challenge (Sepsis Assay)

Polypeptide SP0148 was evaluated for its ability to protect mice from sepsis when immunized singly or in combination with SP0641N and/or pneumolysoid (PdT). Groups of ten mice were subcutaneously immunized three times, two weeks apart with vaccine compositions comprising polypeptide SP0148 (SEQ ID NO: 7), singly or in combination with polypeptide SP0641N (SEQ ID NO: 13) and/or PdT, adsorbed to alum. The positive control was killed, unencapsulated whole cell *S. pneumoniae*+alum (WCB), and the negative control was alum alone. Three weeks after the final immunization, blood was collected for evaluation of IL-17 and antibody, and then one week later, the mice underwent aspiration challenge with $10^7$ live strain 0603 (type 6B) *S. pneumoniae*. Animals were monitored for survival for eight days. The data are shown in FIG. 12 as survival curves for each immunized group.

Example 13

SP1912, SP2108 and SP0148 Polypeptides

Colonization Assay

Additional studies were performed essentially as described in Example 10, for a total of four separate studies. Briefly, animals were immunized with vaccine formulations comprising the polypeptides SP1912 (SEQ ID NO: 265), SP2108

(SEQ ID NO: 9), SP0148 (SEQ ID NO: 7), or additionally SP2108 plus SP0148, and cholera toxin adjuvant (CT) as described in Example 9. Control animals were immunized with killed, unencapsulated whole cell *S. pneumoniae* plus CT (WCB), or CT alone. Immunized animals were challenged intranasally with $10^7$ live type 6B *S. pneumoniae* four weeks after the last immunization. Seven days after challenge, animals were euthanized and the nasopharyngeal cavities lavaged and cultured on permissive media to evaluate the *S. pneumoniae* titers. Pooled results of four studies are shown in FIG. 13 as the colony forming units of bacteria (CFU) per lavage. Each symbol represents a titer from an individual mouse response, and the horizontal line represents the median of the group. (***=p-value<0.05). N indicates the total number of animals evaluated. Percentages refer to the number of animals protected from colonization.

Example 14

SP1912 and SP0148 Polypeptides

IL-17A Immunogenicity Assay

Groups of ten mice were subcutaneously immunized twice, two weeks apart with vaccine compositions comprising either SP1912 polypeptide (SEQ ID NO: 265), SP0148 polypeptide (SEQ ID NO: 7), or both adsorbed to alum. Control animals were immunized with alum alone. Three weeks after the last immunization, heparinized blood was collected by cardiac puncture and evaluated for IL-17A levels in a whole blood assay. Briefly, the heparizined whole blood was diluted in media and then cultured for six days with the protein(s) of immunization. The supernatants were harvested and IL-17A levels measured by ELISA. Results of the IL-17A immunogenicity assay are shown in FIG. 14. Each symbol in the graph represents responses from individual mice, and the line indicates the median response of the group.

Example 15

SP1912 and SP0148 Polypeptides

Colonization Assay

Animals were subcutaneously immunized three times, two weeks apart with vaccine formulations comprising the polypeptides SP0148 (SEQ ID NO: 7) at different doses plus and minus SP1912 (SEQ ID NO: 265), adsorbed to alum. Control animals were immunized with killed, unencapsulated whole cell *S. pneumoniae* plus alum (WCV), or alum alone. Immunized animals were challenged intranasally with $10^7$ live type 6B *S. pneumoniae* four weeks after the last immunization. Seven days after challenge, animals were euthanized and the nasopharyngeal cavities lavaged and cultured on permissive media to evaluate the *S. pneumoniae* titers. Results are shown in FIG. 15 as the colony forming units of bacteria (CFU) per lavage. Each symbol represents a titer from an individual mouse response, and the horizontal line represents the median of the group. The number of animals protected from colonization out of the number of animals in the group is indicated at the top of the figure.

Example 16

SP1912, SP0148, and SP2108 Polypeptides

Colonization Assay

In two separate studies, animals were subcutaneously immunized three times, two weeks apart with vaccine formulations comprising the polypeptides SP0148 (SEQ ID NO: 7) and SP0148 plus SP1912 (SEQ ID NO: 265), or additionally with SP2108 (SEQ ID NO: 9), SP2108 plus SP0148, and SP2108 plus SP1912, adsorbed to alum. Control animals were immunized with killed, unencapsulated whole cell *S. pneumoniae* plus alum (WCV), or alum alone. Immunized animals were challenged intranasally with $10^7$ live type 6B *S. pneumoniae* four weeks after the last immunization. Seven days after challenge, animals were euthanized and the nasopharyngeal cavities lavaged and cultured on permissive media to evaluate the *S. pneumoniae* titers. Pooled results of the two studies are shown in FIG. 16 as the colony forming units of bacteria (CFU) per lavage. Each symbol represents a titer from an individual mouse response, and the horizontal line represents the median of the group. The number of animals protected from colonization out of the number of animals in the group and corresponding percentage of animals protected from colonization are indicated at the top of the figure. (*p<0.05, p<0.01, *p<0.001 Dunn's Multiple Comparison Test compared to Alum control)

Example 17

Pneumolysoid L460D, PspA derivative PR+NPB, SP1912, SP0148, and SP2108 Polypeptides Colonization Assay Animals were subcutaneously immunized three times, two weeks apart with vaccine formulations comprising the polypeptides SP0148 (SEQ ID NO: 7), SP2108 (SEQ ID NO: 9), SP0148 plus SP2108, and SP0148 plus SP2108 in combination with SP1912 (SEQ ID NO: 265) or known *S. pneumoniae* antigens L460D plus PR+NPD, adsorbed to alum. Two separate studies were conducted. Control animals were immunized with alum alone. Immunized animals were challenged intranasally with $10^7$ live type 6B *S. pneumoniae* four weeks after the last immunization. Seven days after challenge, animals were euthanized and the nasopharyngeal cavities lavaged and cultured on permissive media to evaluate the *S. pneumoniae* titers. Results of the second study are shown in FIG. 17 as the colony forming units of bacteria (CFU) per lavage. Each symbol represents a titer from an individual mouse response, and the horizontal line represents the median of the group. The number of animals protected from colonization out of the number of animals in the group is indicated at the top of the figure.

The chart below shows the absolute number and corresponding percentage of animals protected from colonization in the four studies described in Examples 16 and 17.

|  | 1 | 2 | 3 | 4 | # not colonized/ total | % not colonized |
|---|---|---|---|---|---|---|
| Alum | 0/9 | 1/10 | 2/10 | 4/10 | 7/39 | 18% |
| WCB | 9/9 | 9/10 | 9/10 | 9/10 | 36/39 | 92% |
| 0148 | 8/18 | 4/10 | 5/9 | 1/10 | 18/47 | 38% |
| 2108 |  | 8/10 | 6/10 | 4/10 | 18/30 | 60% |
| 1912 |  | 4/10 |  |  | 4/10 | 40% |
| 0148 + 2108 |  | 6/10 | 3/10 | 6/10 | 15/30 | 50% |
| 0148 + 1912 | 13/18 | 3/10 |  |  | 16/28 | 57% |
| 2108 + 1912 |  | 3/10 |  |  | 3/10 | 30% |
| 0148 + 2108 + 1912 |  | 8/9 | 8/10 | 6/10 | 22/29 | 76% |
| 0148 + 2108 + L460D + PR + NPB |  |  | 2/10 | 6/10 | 8/20 | 40% |

Example 18

PspA, SP0148 and SP2108 Passive Antibody Transfer and Aspiration Challenge

Sepsis Assay

Groups of ten mice were injected with monoclonal antibodies specific for PspA, heat-inactivated rabbit sera specific for SP0148, SP2108, or combinations of these. Antibody and antisera concentrations and total injection volumes were adjusted with normal rabbit serum (NRS) and PBS. Control animals were injected with NRS, or serum against killed, unencapsulated whole cell *S. pneumoniae* (WCB). One day after injection, the mice underwent aspiration challenge with $10^6$ live *S. pneumoniae* type WU-2 (ST-3). Animals were monitored for survival for eight days. The data are shown in FIG. 18 as survival curves for each immunized group. FIG. 19 shows the percent of animals protected from sepsis in the studies described in Examples 12 and 18, as well as two additional studies.

SEQUENCE LISTING

In accordance with 37 C.F.R. §1.52(e)(5), a Sequence Listing in the form of a text file (entitled "Sequence_Listing", created on Apr. 9, 2012, and 188 kilobytes) is incorporated herein by reference in its entirety.

```
                                              SEQ ID NO: 1
SP0024
>gi|14971488|gb|AAK74215.1|conserved hypothetical protein Streptococcus
pneumoniae TIGR4
MSYFEQFMQANQAYVALHGQLNLPLKPKTRVAIVTCMDSRLHVAQALGLALGDAHILRNAGGRVTEDMIRSLVISQQ

QMGTREIVVLHHTDCGAQTFENEPFQEYLKEELGVDVSDQDFLPFQDIEESVREDMQLLIESPLIPDDVIISGAIYN

VDTGSMTVVEL

SEQ ID NO: 2
SP0882
>gi|14972356|gb|AAK75009.1|conserved hypothetical protein (Streptococcus
pneumoniae TIGR4)
MNQSYFYLKMKEHKLKVPYTGKERRVRILLPKDYEKDTDRSYPVVYFHDGQNVFNSKESFIGHSWKIIPAIKRNPDI

SRMIVVAIDNDGMGRMNEYAAWKFQESPIPGQQFGGKGVEYAEFVMEVVKPFIDETYRTKADCQHTAMIGSSLGGNI

TQFIGLEYQDQIGCLGVFSSANWLHQEAFNRYFECQKLSPDQRIFIYVGTEEADDTDKTLMDGNIKQAYIDSSLCYY

HDLIAGGVHLDNLVLKVQSGAIHSEIPWSENLPDCLRFFAEKW

SEQ ID NO: 3
SP0882N
MNQSYFYLKMKEHKLKVPYTGKERRVRILLPKDYEKDTDRSYPVVYFHDGQNVFNSKESFIGHSWKIIPAIKRNPDI

SRMIVVAIDNDGMGRMNEYAAWKFQESPIPGQQFGGKGVEYAEFVMEVVKPFI

SEQ ID NO: 4
SP0882 with exogenous signal sequence
MSSKFMKSAAVLGTATLASLLLVACMNQSYFYLKMKEHKLKVPYTGKERRVRILLPKDYEKDTDRSYPVVYFHDGQN

VFNSKESFIGHSWKIIPAIKRNPDISRMIVVAIDNDGMGRMNEYAAWKFQESPIPGQQFGGKGVEYAEFVMEVVKPF

IDETYRTKADCQHTAMIGSSLGGNITQFIGLEYQDQIGCLGVFSSANWLHQEAFNRYFECQKLSPDQRIFIYVGTEE

ADDTDKTLMDGNIKQAYIDSSLCYYHDLIAGGVHLDNLVLKVQSGAIHSEIPWSENLPDCLRFFAEKW

SEQ ID NO: 5
SP0882N with exogenous signal sequence
MSSKFMKSAAVLGTATLASLLLVACMNQSYFYLKMKEHKLKVPYTGKERRVRILLPKDYEKDTDRSYPVVYFHDGQN

VFNSKESFIGHSWKIIPAIKRNPDISRMIVVAIDNDGMGRMNEYAAWKFQESPIPGQQFGGKGVEYAEFVMEVVKPF

I

SEQ ID NO: 6
SP0148 lacking signal sequence
MCSGGAKKEGEAASKKEIIVATNGSPKPFIYEENGELTGYEIEVVRAIFKDSDKYDVKFEKTEWSGVFAGLDADRYN

MAVNNLSYTKERAEKYLYAAPIAQNPNVLVVKKDDSSIKSLDDIGGKSTEVVQATTSAKQLEAYNAEHTDNPTILNY

TKADFQQIMVRLSDGQFDYKIFDKIGVETVIKNQGLDNLKVIELPSDQQPYVYPLLAQGQDELKSFVDKRIKELYKD

GTLEKLSKQFFGDTYLPAEADIKE

SEQ ID NO: 7
SP0148 including signal sequence (277 amino acids with N-terminal E)
MKKIVKYSSLAALALVAAGVLAACSGGAKKEGEAASKKEIIVATNGSPKPFIYEENGELTGYEIEVVRAIFKDSDKY DVKFEKTEWSGVFAGLDADRYNMAVNNLSYTKERAEKYLYAAPIAQNPNVLVVKKDDSSIKSLDDIGGKSTEVVQAT
```

```
TSAKQLEAYNAEHTDNPTILNYTKADFQQIMVRLSDGQFDYKIFDKIGVETVIKNQGLDNLKVIELPSDQQPYVYPL

LAQGQDELKSFVDKRIKELYKDGTLEKLSKQFFGDTYLPAEADIKE
```

SEQ ID NO: 8
SP1072
>gi|14972547|gb|AAK75185.1|DNA primase Streptococcus pneumoniae TIGR4
```
MVDKQVIEEIKNNANIVEVIGDVISLQKAGRNYLGLCPFHGEKTPSFNVVEDKQFYHCFGCGRSGDVFKFIEEYQGV

PFIEAVQILGQRVGIEVEKPLYSEQKSASPHQALYDMHEDAAKFYHAILMTTTMGEEARNYLYQRGLTDEVLKHFWI

GLAPPERNYLYQRLSDQYREEDLLDSGLFYLSDANQFVDTFHNRIMFPLTNDQGKVIAFSGRIWQKTDSQTSKYKNS

RSTAIFNKSYELYHMDRAKRSSGKASEIYLMEGFMDVIAAYRAGIENAVASMGTALSREHVEHLKRLTKKLVLVYDG

DKAGQAATLKALDEIGDMPVQIVSMPDNLDPDEYLQKNGPEDLAYLLTKTRISPIEFYIHQYKPENSENLQAQIEFL

EKIAPLIVQEKSIAAQNSYIHILADSLASFDYTQIEQIVNESRQVQRQNRMEGISRPTPITMPVTKQLSAIMRAEAH

LLYRMMESPLVLNDYRLREDFAFATPEFQVLYDLLGQYGNLPPEVLAEQTEEVERAWYQVLAQDLPAEISPQELSEV

EMTRNKALLNQDNMRIKKKVQEASHVGDTDTALEELERLISQKRRME
```

SEQ ID NO: 9
SP2108 including signal sequence
>gi|14973620|gb|AAK76167.1|maltose/maltodextrin ABC transporter,
maltose/maltodextrin-binding protein (Streptococcus pneumoniae TIGR4)
```
MSSKFMKSAAVLGTATLASLLLVACGSKTADKPADSGSSEVKELTVYVDEGYKSYIEEVAKAYEKEAGVKVTLKTGD

ALGGLDKLSLDNQSGNVPDVMMAPYDRVGSLGSDGQLSEVKLSDGAKTDDTTKSLVTAANGKVYGAPAVIESLVMYY

NKDLVKDAPKTFADLENLAKDSKYAFAGEDGKTTAFLADWTNFYYTYGLLAGNGAYVFGQNGKDAKDIGLANDGSIV

GINYAKSWYEKWPKGMQDTEGAGNLIQTQFQEGKTAAIIDGPWKAQAFKDAKVNYGVATIPTLPNGKEYAAFGGGKA

WVIPQAVKNLEASQKFVDFLVATEQQKVLYDKTNEIPANTEARSYAEGKNDELTTAVIKQFKNTQPLPNISQMSAVW

DPAKNMLFDAVSGQKDAKTAANDAVTLIKETIKQKFGE
```

SEQ ID NO: 10
SP2108 lacking signal sequence
```
MCGSKTADKPADSGSSEVKELTVYVDEGYKSYIEEVAKAYEKEAGVKVTLKTGDALGGLDKLSLDNQSGNVPDVMMA

PYDRVGSLGSDGQLSEVKLSDGAKTDDTTKSLVTAANGKVYGAPAVIESLVMYYNKDLVKDAPKTFADLENLAKDSK

YAFAGEDGKTTAFLADWTNFYYTYGLLAGNGAYVFGQNGKDAKDIGLANDGSIVGINYAKSWYEKWPKGMQDTEGAG

NLIQTQFQEGKTAAIIDGPWKAQAFKDAKVNYGVATIPTLPNGKEYAAFGGGKAWVIPQAVKNLEASQKFVDFLVAT

EQQKVLYDKTNEIPANTEARSYAEGKNDELTTAVIKQFKNTQPLPNISQMSAVWDPAKNMLFDAVSGQKDAKTAAND

AVTLIKETIKQKFGE
```

SEQ ID NO: 11
SP0641M
```
MSGTSMATPIVAASTVLIRPKLKEMLERPVLKNLKGDDKIDLTSLTKIALQNTARPMMDATSWKEKSQYFASPRQQG

AGLINVANALRNEVVATFKNTDSKGLVNSYGSISLKEIKGDKKYFTIKLHNTSNRPLTFKVSASAITTDSLTDRLKL

DETYKDEKSPDGKQIVPEIHPEKVKGANITFEHDTFTIGANSSFDLNAVINVGEAKNKNKFVESFIHFESVEEMEAL

NSNGKKINFQPSLSMPLMGFAGNWNHEPILDKWAWEEGSRSKTLGGYDDDGKPKIPGTLNKGIGGEHGIDKFNPAGV

IQNRKDKNTTSLDQNPELFAFNNEGINAPSSSGSKIANIYPLDSNGNPQDAQLERGLTPSPLVLRSAEEGLISIVNT

NKEGENQRDLKVISREHFIRGILNSKSNDAKGIKSSKLKVWGDLKWDGLIYNPRGREENAPESKDNQDPATKIRGQF

EPIAEGQYFYKFKYRLTKDYPWQVSYIPVKIDNTAPKIVSVDFSNPEKIKLITKDTYHKVKDQYKNETLFARDQKEH

PEKFDEIANEVWYAGAALVNEDGEVEKNLEVTYAGEGQGRNRKLDKDGNTIYEIKGAGDLRGKIIEVIALDGSSNFT

KIHRIKFANQADEKGMISYYLVDPDQDSSKYQ
```

SEQ ID NO: 12
SP0641
>gi|14972117|gb|AAK74791.1|serine protease, subtilase family [Streptococcus
pneumoniae TIGR4]
```
MKKSTVLSLTTAAVILAAYAPNEVVLADTSSSEDALNISDKEKVAENEKHENIHSAMETSQDFKEKKTAVIKEKEV VSKNPVIDNNTSNEEAKIKEENSNKSQGDYTDSFVNKNTENPKKEDKVVYIAEFKDKESGEKAIKELSSLKNTKVLY
```

-continued

```
TYDRIFNGSAIETTPDNLDKIKQIEGISSVERAQKVQPMMNHARKEIGVEEAIDYLKSINAPFGKNFDGRGMVISNI

DTGTDYRHKAMRIDDDAKASMRFKKEDLKGTDKNYWLSDKIPHAFNYYNGGKITVEKYDDGRDYFDPHGMHIAGILA

GNDTEQDIKNFNGIDGIAPNAQIFSYKMYSDAGSGFAGDETMFHAIEDSIKHNVDVVSVSSGFTGTGLVGEKYWQAI

RALRKAGIPMVVATGNYATSASSSSWDLVANNHLKMTDTGNVTRTAAHEDAIAVASAKNQTVEFDKVNIGGESFKYR

NIGAFFDKSKITTNEDGTKAPSKLKFVYIGKGQDQDLIGLDLRGKIAVMDRIYTKDLKNAFKKAMDKGARAIMVVNT

VNYYNRDNWTELPAMGYEADEGTKSQVFSISGDDGVKLWNMINPDKKTEVKRNNKEDFKDKLEQYYPIDMESFNSNK

PNVGDEKEIDFKFAPDTDKELYKEDIIVPAGSTSWGPRIDLLLKPDVSAPGKNIKSTLNVINGKSTYGYMSGTSMAT

PIVAASTVLIRPKLKEMLERPVLKNLKGDDKIDLTSLTKIALQNTARPMMDATSWKEKSQYFASPRQQGAGLINVAN

ALRNEVVATFKNTDSKGLVNSYGSISLKEIKGDKKYFTIKLHNTSNRPLTFKVSASAITTDSLTDRLKLDETYKDEK

SPDGKQIVPEIHPEKVKGANITFEHDTFTIGANSSFDLNAVINVGEAKNKNKFVESFIHFESVEEMEALNSNGKKIN

FQPSLSMPLMGFAGNWNHEPILDKWAWEEGSRSKTLGGYDDDGKPKIPGTLNKGIGGEHGIDKFNPAGVIQNRKDKN

TTSLDQNPELFAFNNEGINAPSSSGSKIANIYPLDSNGNPQDAQLERGLTPSPLVLRSAEEGLISIVNTNKEGENQR

DLKVISREHFIRGILNSKSNDAKGIKSSKLKVWGDLKWDGLIYNPRGREENAPESKDNQDPATKIRGQFEPIAEGQY

FYKFKYRLTKDYPWQVSYIPVKIDNTAPKIVSVDFSNPEKIKLITKDTYHKVKDQYKNETLFARDQKEHPEKFDEIA

NEVWYAGAALVNEDGEVEKNLEVTYAGEGQGRNRKLDKDGNTIYEIKGAGDLRGKIIEVIALDGSSNFTKIHRIKFA

NQADEKGMISYYLVDPDQDSSKYQKLGEIAESKFKNLGNGKEGSLKKDTTGVEHHHQENEESIKEKSSFTIDRNIST

IRDFENKDLKKLIKKKFREVDDFTSETGKRMEEYDYKYDDKGNIIAYDDGTDLEYETEKLDEIKSKIYGVLSPSKDG

HFEILGKISNVSKNAKVYYGNNYKSIEIKATKYDFHSKTMTFDLYANINDIVDGLAFAGDMRLFVKDNDQKKAEIKI

RMPEKIKETKSEYPYVSSYGNVIELGEGDLSKNKPDNLTKMESGKIYSDSEKQQYLLKDNIILRKGYALKVTTYNPG

KTDMLEGNGVYSKEDIAKIQKANPNLRALSETTIYADSRNVEDGRSTQSVLMSALDGFNIIRYQVFTFKMNDKGEAI

DKDGNLVTDSSKLVLFGKDDKEYTGEDKFNVEAIKEDGSMLFIDTKPVNLSMDKNYFNPSKSNKIYVRNPEFYLRGK

ISDKGGFNWELRVNESVVDNYLIYGDLHIDNTRDFNIKLNVKDGDIMDWGMKDYKANGFPDKVTDMDGNVYLQTGYS

DLNAKAVGVHYQFLYDNVKPEVNIDPKGNTSIEYADGKSVVFNINDKRNNGFDGEIQEQHIYINGKEYTSFNDIKQI

IDKTLNIKIVVKDFARNTTVKEFILNKDTGEVSELKPHRVTVTIQNGKEMSSTIVSEEDFILPVYKGELEKGYQFDG

WEISGFEGKKDAGYVINLSKDTFIKPVFKKIEEKKEEENKPTFDVSKKKDNPQVNHSQLNESHRKEDLQREEHSQKS

DSTKDVTATVLDKNNISSKSTTNNPNKLPKTGTASGAQTLLAAGIMFIVGIFLGLKKKNQD
```

SEQ ID NO: 13
SP0641N
```
MVVLADTSSSEDALNISDKEKVAENKEKHENIHSAMETSQDFKEKKTAVIKEKEVVSKNPVIDNNTSNEEAKIKEEN

SNKSQGDYTDSFVNKNTENPKKEDKVVYIAEFKDKESGEKAIKELSSLKNTKVLYTYDRIFNGSAIETTPDNLDKIK

QIEGISSVERAQKVQPMMNHARKEIGVEEAIDYLKSINAPFGKNFDGRGMVISNIDTGTDYRHKAMRIDDDAKASMR

FKKEDLKGTDKNYWLSDKIPHAFNYYNGGKITVEKYDDGRDYFDPHGMHIAGILAGNDTEQDIKNFNGIDGIAPNAQ

IFSYKMYSDAGSGFAGDETMFHAIEDSIKHNVDVVSVSSGFTGTGLVGEKYWQAIRALRKAGIPMVVATGNYATSAS

SSSWDLVANNHLKMTDTGNVTRTAAHEDAIAVASAKNQTVEFDKVNIGGESFKYRNIGAFFDKSKITTNEDGTKAPS

KLKFVYIGKGQDQDLIGLDLRGKIAVMDRIYTKDLKNAFKKAMDKGARAIMVVNTVNYYNRDNWTELPAMGYEADEG

TKSQVFSISGDDGVKLWNMINPDKKTEVKRNNKEDFKDKLEQYYPIDMESFNSNKPNVGDEKEIDFKFAPDTDKELY

KEDIIVPAGSTSWGPRIDLLLKPDVSAPGKNIKSTLNVINGKSTYG
```

SEQ ID NO: 14
SP0882 consensus
```
MNQSYFYLKMKEHKLKVPYTGKERRVRILLPKDYEKDTDRSYPVVYFHDGQNVFNSKESF
I                                                          Y IGHSWKIIPAIKRNPDISRMIVVAIDNDGMGRMNEYAAWKFQESPIPGQQFGGKGVEYAE
    Y       H           E       E
```

```
                                    -continued
FVMEVVKPFIDETYRTKADCQHTAMIGSSLGGNITQFIGLEYQDQIGCLGVFSSANWLHQ
                              EK EAFNRYFECQKLSPDQRIFIYVGTEEADDTDKTLMDGNIKQAYIDSSLCYYHDLIAGGVH
      I       H                                            R

LDNLVLKVQSGAIHSEIPWSENLPDCLRFFAEKW

SEQ ID NO: 15
SP0882N consensus
MNQSYFYLKMKEHKLKVPYTGKERRVRILLPKDYEKDTDRSYPVVYFHDGQNVFNSKESF
 I                                                         Y IGHSWKIIPAIKRNPDISRMIVVAIDNDGMGRMNEYAAWKFQESPIPGQQFGGKGVEYAE
    Y           H                 E        E

FVMEVVKPFI

SEQ ID NO: 16
SP0882 consensus with exogenous signal sequence
MSSKFMKSAAVLGTATLASLLLVACMNQSYFYLKMKEHKLKVPYTGKERRVRILLPKDYE
     T  T        V          I KDTDRSYPVVYFHDGQNVFNSKESFIGHSWKIIPAIKRNPDISRMIVVAIDNDGMGRMNE
             Y          Y           H

YAAWKFQESPIPGQQFGGKGVEYAEFVMEVVKPFIDETYRTKADCQHTAMIGSSLGGNIT
    E        E

QFIGLEYQDQIGCLGVFSSANWLHQEAFNRYFECQKLSPDQRIFIYVGTEEADDTDKTLM
         EK                   I       H

DGNIKQAYIDSSLCYYHDLIAGGVHLDNLVLKVQSGAIHSEIPWSENLPDCLRFFAEKW
                        R

SEQ ID NO: 17
SP0882N consensus with exogenous signal sequence
MSSKFMKSAAVLGTATLASLLLVACMNQSYFYLKMKEHKLKVPYTGKERRVRILLPKDYE
     T  T        V          I KDTDRSYPVVYFHDGQNVFNSKESFIGHSWKIIPAIKRNPDISRMIVVAIDNDGMGRMNE
             Y          Y           H

YAAWKFQESPIPGQQFGGKGVEYAEFVMEVVKPFI
    E        E

SEQ ID NO: 18
SP0148 consensus lacking signal sequence
MCSGGAKKEGEAASKKEIIVATNGSPKPFIYEENGELTGYEIEVVRAIFKDSDKYDVKFE
         Q          S  R  N                               N X KTEWSGVFAGLDADRYNMAVNNLSYTKERAEKYLYAAPIAQNPNVLVVKKDDSSIKSLDD
                 I                                 E IGGKSTEVVQATTSAKQLEAYNAEHTDNPTILNYTKADLQQIMVRLSDGQFDYKIFDKIG
                                     F VETVIKNQGLDNLKVIELPSDQQPYVYPLLAQGQDELKSFVDKRIKELYKDGTLEKLSKQ
         Y              S

FFGDTYLPAEADIK(E)

SEQ ID NO: 19
SP0148 consensus including signal sequence
MKKIVKYSSLAALALVAAGVLAACSGGAKKEGEAASKKEIIVATNGSPKPFIYEENGELT
         G  L           Q          S  R  N GYEIEVVRAIFKDSDKYDVKFEKTEWSGVFAGLDADRYNMAVNNLSYTKERAEKYLYAAP
             N X                      I

IAQNPNVLVVKKDDSSIKSLDDIGGKSTEVVQATTSAKQLEAYNAEHTDNPTILNYTKAD
            E

LQQIMVRLSDGQFDYKIFDKIGVETVIKNQGLDNLKVIELPSDQQPYVYPLLAQGQDELK
 F                              Y              S

SFVDKRIKELYKDGTLEKLSKQFFGDTYLPAEADIK(E)
```

SEQ ID NO: 20
SP2108 consensus lacking signal sequence
MCGSKTADKPADSGSSEVKELTVYVDEGYKSYIEEVAKAYEKEAGVKVTLKTGDALGGLD
                A                             I KLSLDNQSGNVPDVMMAPYDRVGSLGSDGQLSEVKLSDGAKTDDTTKSLVTAANGKVYGA
          I                X           T PAVIESLVMYYNKDLVKDAPKTFADLENLAKDSKYAFAGEDGKTTAFLADWTNFYYTYGL
                                              A LAGNGAYVFGQNGKDAKDIGLANDSIVGINYAKSWYEKWPKGMQDTEGAGNLIQTQFQE
       G         P      A       X                      H GKTAAIIDGPWKAQAFKDAKVNYGVATIPTLPNGKEYAAFGGGKAWVIPQAVKNLEASQK
                                                           A FVDFLVATEQQKVLYDKTNEIPANTEARSYAEGKNDELTTAVIKQFKNTQPLPNISQMSA
     S       A                                    S

VWDPAKNMLFDAVSGQKDAKTAANDAVTLIKETIKQKFGE

SEQ ID NO: 21
SP2108 consensus including signal sequence
MSSKFMKSAAVLGTATLASLLLVACGSKTADKPADSGSSEVKELTVYVDEGYKSYIEEVA
    T    T        V                      A KAYEKEAGVKVTLKTGDALGGLDKLSLDNQSGNVPDVMMAPYDRVGSLGSDGQLSEVKLS
       I                          I           X

DGAKTDDTTKSLVTAANGKVYGAPAVIESLVMYYNKDLVKDAPKTFADLENLAKDSKYAF
  T

AGEDGKTTAFLADWTNFYYTYGLLAGNGAYVFGQNGKDAKDIGLANDSIVGINYAKSWY
             A          G         P      A       X

EKWPKGMQDTEGAGNLIQTQFQEGKTAAIIDGPWKAQAFKDAKVNYGVATIPTLPNGKEY
              H

AAFGGGKAWVIPQAVKNLEASQKFVDFLVATEQQKVLYDKTNEIPANTEARSYAEGKNDE
              A             S       A

LTTAVIKQFKNTQPLPNISQMSAVWDPAKNMLFDAVSGQKDAKTAANDAVTLIKETIKQK
                    S

FGE

SEQ ID NO: 22
SP1634
>gi|14973124|gb|AAK75714.1|hypothetical protein SP_1634 Streptococcus
pneumoniae TIGR4
MANIFDYLKDVAYDSYYDLPLNELDILTLIEITYLSFDNLVSTLPQRLLDLAPQVPRDPTMLTSKNRLQLLDELAQH

KRFKNCKLSHFINDIDPELQKQFAAMTYRVSLDTYLIVFRGTDDSIIGWKEDFHLTYMKEIPAQKHALRYLKNFFAH

HPKQKVILAGHSKGGNLAIYAASQIEQSLQNQITAVYTFDAPGLHQELTQTAGYQRIMDRSKIFIPQGSIIGMMLEI

PAHQIIVQSTALGGIAQHDTFSWQIEDKHFVQLDKTNSDSQQVDTTFKEWVATVPDEELQLYFDLFFGTILDAGISS

INDLASLKALEYIHHLFVQAQSLTPEERETLGRLTQLLIDTRYQAWKNR

SEQ ID NO: 23
SP0314
>gi|14971788|gb|AAK74491.1|hyaluronidase Streptococcus pneumoniae
TIGR4MQTKTKKLIVSLSSLVLSGFLLNHYMTIGAEETTTNTIQQSQKEVQYQQRDTKNLVENGDFGQTEDGSSPWT

GSKAQGWSAWVDQKNSADASTRVIEAKDGAITISSHEKLRAALHRMVPIEAKKKYKLRFKIKTDNKIGIAKVRIIEE

SGKDKRLWNSATTSGTKDWQTIEADYSPTLDVDKIKLELFYETGTGTVSFKDIELVEVADQLSEDSQTDKQLEEKID

LPIGKKHVFSLADYTYKVENPDVASVKNGILEPLKEGTTNVIVSKDGKEVKKIPLKILASVKDAYTDRLDDWNGIIA

GNQYYDSKNEQMAKLNQELEGKVADSLSSISSQADRTYLWEKFSNYKTSANLTATYRKLEEMAKQVTNPSSRYYQDE

TVVRTVRDSMEWMHKHVYNSEKSIVGNWWDYEIGTPRAINNTLSLMKEYFSDEEIKKYTDVIEKFVPDPEHFRKTTD

NPFKALGGNLVDMGRVKVIAGLLRKDDQEISSTIRSIEQVFKLVDQGEGFYQDGSYIDHTNVAYTGAYGNVLIDGLS

QLLPVIQKTKNPIDKDKMQTMYHWIDKSFAPLLVNGELMDMSRGRSISRANSEGHVAAVEVLRGIHRIADMSEGETK

QCLQSLVKTIVQSDSYYDVFKNLKTYKDISLMQSLLSDAGVASVPRPSYLSAFNKMDKTAMYNAEKGFGFGLSLFSS

-continued

RTLNYEHMNKENKRGWYTSDGMFYLYNGDLSHYSDGYWPTVNPYKMPGTTETDAKRADSDTGKVLPSAFVGTSKLDD

ANATATMDFTNWNQTLTAHKSWFMLKDKIAFLGSNIQNTSTDTAATTIDQRKLESGNPYKVYVNDKEASLTEQEKDY

PETQSVFLESFDSKKNIGYFFFKKSSISMSKALQKGAWKDINEGQSDKEVENEFLTISQAHKQNRDSYGYMLIPNVD

RATFNQMIKELESSLIENNETLQSVYDAKQGVWGIVKYDDSVSTISNQFQVLKRGVYTIRKEGDEYKIAYYNPETQE

SAPDQEVFKKLEQAAQPQVQNSKEKEKSEEEKNHSDQKNLPQTGEGQSILASLGFLLLGAFYLFRRGKNN

SEQ ID NO: 24
SP0882N DNA
ATGAATCAATCCTACTTTTATCTAAAAATGAAAGAACACAAACTCAAGGTTCCTTATACAGGTAAGGAGCGCCGTGT

ACGTATTCTTCTTCCTAAAGATTATGAGAAAGATACAGACCGTTCCTATCCTGTTGTATACTTTCATGACGGGCAAA

ATGTTTTTAATAGCAAAGAGTCTTTCATTGGACATTCATGGAAGATTATCCCAGCTATCAAACGAAATCCGGATATC

AGTCGCATGATTGTCGTTGCTATTGACAATGATGGTATGGGGCGGATGAATGAGTATGCGGCTTGGAAGTTCCAAGA

ATCTCCTATCCCAGGGCAGCAGTTTGGTGGTAAGGGTGTGGAGTATGCTGAGTTTGTCATGGAGGTGGTCAAGCCTT

TTATC

SEQ ID NO: 25
SP0882 with exogenous signal sequence (nucleotides)
ATGTCATCTAAATTTATGAAGAGCGCTGCGGTGCTTGGAACTGCTACACTTGCTAGCTTGCTTTTGGTAGCTTGCAT

GAATCAATCCTACTTTTATCTAAAAATGAAAGAACACAAACTCAAGGTTCCTTATACAGGTAAGGAGCGCCGTGTAC

GTATTCTTCTTCCTAAAGATTATGAGAAAGATACAGACCGTTCCTATCCTGTTGTATACTTTCATGACGGGCAAAAT

GTTTTTAATAGCAAAGAGTCTTTCATTGGACATTCATGGAAGATTATCCCAGCTATCAAACGAAATCCGGATATCAG

TCGCATGATTGTCGTTGCTATTGACAATGATGGTATGGGGCGGATGAATGAGTATGCGGCTTGGAAGTTCCAAGAAT

CTCCTATCCCAGGGCAGCAGTTTGGTGGTAAGGGTGTGGAGTATGCTGAGTTTGTCATGGAGGTGGTCAAGCCTTTT

ATCGATGAGACCTATCGTACAAAAGCAGACTGCCAGCATACGGCTATGATTGGTTCCTCACTAGGAGGCAATATTAC

CCAGTTTATCGGTTTGGAATACCAAGACCAAATTGGTTGCTTGGGCGTTTTTTCATCTGCAAACTGGCTCCACCAAG

AAGCCTTTAACCGCTATTTCGAGTGCCAGAAACTATCGCCTGACCAGCGCATCTTCATCTATGTAGGAACAGAAGAA

GCAGATGATACAGACAAGACCTTGATGGATGGCAATATCAAACAAGCCTATATCGACTCGTCGCTTTGCTATTACCA

TGATTTGATAGCAGGGGGAGTACATCTGGATAATCTTGTGCTAAAAGTTCAGTCTGGTGCCATCCATAGTGAAATCC

CTTGGTCAGAAAATCTACCAGATTGTCTGAGATTTTTTGCAGAAAAATGGTAA

SEQ ID NO: 26
SP0882N with exogenous signal sequence (nucleotides)
ATGTCATCTAAATTTATGAAGAGCGCTGCGGTGCTTGGAACTGCTACACTTGCTAGCTTGCTTTTGGTAGCTTGCAT

GAATCAATCCTACTTTTATCTAAAAATGAAAGAACACAAACTCAAGGTTCCTTATACAGGTAAGGAGCGCCGTGTAC

GTATTCTTCTTCCTAAAGATTATGAGAAAGATACAGACCGTTCCTATCCTGTTGTATACTTTCATGACGGGCAAAAT

GTTTTTAATAGCAAAGAGTCTTTCATTGGACATTCATGGAAGATTATCCCAGCTATCAAACGAAATCCGGATATCAG

TCGCATGATTGTCGTTGCTATTGACAATGATGGTATGGGGCGGATGAATGAGTATGCGGCTTGGAAGTTCCAAGAAT

CTCCTATCCCAGGGCAGCAGTTTGGTGGTAAGGGTGTGGAGTATGCTGAGTTTGTCATGGAGGTGGTCAAGCCTTTT

ATC

SEQ ID NO: 27
SP0148 lacking signal sequence (nucleotides)
ATGTGCTCAGGGGGTGCTAAGAAAGAAGGAGAAGCAGCTAGCAAGAAAGAAATCATCGTTGCAACCAATGGATCACC

AAAGCCATTTATCTATGAAGAAAATGGCGAATTGACTGGTTACGAGATTGAAGTCGTTCGCGCTATCTTTAAAGATT

CTGACAAATATGATGTCAAGTTTGAAAAGACAGAATGGTCAGGTGTCTTTGCTGGTCTTGACGCTGATCGTTACAAT

ATGGCTGTCAACAATCTTAGCTACACTAAAGAACGTGCGGAGAAATACCTCTATGCCGCACCAATTGCCCAAAATCC

TAATGTCCTTGTCGTGAAGAAAGATGACTCTAGTATCAAGTCTCTCGATGATATCGGTGGAAAATCGACGGAAGTCG

TTCAAGCCACTACATCAGCTAAGCAGTTAGAAGCATACAATGCTGAACACACGGACAACCCAACTATCCTTAACTAT

-continued

ACTAAGGCAGACTTCCAACAAATCATGGTACGTTTGAGCGATGGACAATTTGACTATAAGATTTTTGATAAAATCGG

TGTTGAAACAGTGATCAAGAACCAAGGTTTGGACAACTTGAAAGTTATCGAACTTCCAAGCGACCAACAACCGTACG

TTTACCCACTTCTTGCTCAGGGTCAAGATGAGTTGAAATCGTTTGTAGACAAACGCATCAAAGAACTTTATAAAGAT

GGAACTCTTGAAAAATTGTCTAAACAATTCTTCGGAGACACTTATCTACCGGCAGAAGCTGATATTAAAGAGTAA

SEQ ID NO: 28
SP0148 including signal sequence (nucleotides)
ATGAAAAAAATCGTTAAATACTCATCTCTTGCAGCCCTTGCTCTTGTTGCTGCAGGTGTGCTTGCGGCTTGCTCAGG

GGGTGCTAAGAAAGAAGGAGAAGCAGCTAGCAAGAAAGAAATCATCGTTGCAACCAATGGATCACCAAAGCCATTTA

TCTATGAAGAAAATGGCGAATTGACTGGTTACGAGATTGAAGTCGTTCGCGCTATCTTTAAAGATTCTGACAAATAT

GATGTCAAGTTTGAAAAGACAGAATGGTCAGGTGTCTTTGCTGGTCTTGACGCTGATCGTTACAATATGGCTGTCAA

CAATCTTAGCTACACTAAAGAACGTGCGGAGAAATACCTCTATGCCGCACCAATTGCCCAAAATCCTAATGTCCTTG

TCGTGAAGAAAGATGACTCTAGTATCAAGTCTCTCGATGATATCGGTGGAAAATCGACGGAAGTCGTTCAAGCCACT

ACATCAGCTAAGCAGTTAGAAGCATACAATGCTGAACACACGGACAACCCAACTATCCTTAACTATACTAAGGCAGA

CTTCCAACAAATCATGGTACGTTTGAGCGATGGACAATTTGACTATAAGATTTTTGATAAAATCGGTGTTGAAACAG

TGATCAAGAACCAAGGTTTGGACAACTTGAAAGTTATCGAACTTCCAAGCGACCAACAACCGTACGTTTACCCACTT

CTTGCTCAGGGTCAAGATGAGTTGAAATCGTTTGTAGACAAACGCATCAAAGAACTTTATAAAGATGGAACTCTTGA

AAAATTGTCTAAACAATTCTTCGGAGACACTTATCTACCGGCAGAAGCTGATATTAAAGAGTAA

SEQ ID NO: 29
SP2108 lacking signal sequence (nucleotides)
ATGTGCGGAAGCAAAACTGCTGATAAGCCTGCTGATTCTGGTTCATCTGAAGTCAAAGAACTCACTGTATATGTAGA

CGAGGGATATAAGAGCTATATTGAAGAGGTTGCTAAAGCTTATGAAAAAGAAGCTGGAGTAAAAGTCACTCTTAAAA

CTGGTGATGCTCTAGGAGGTCTTGATAAACTTTCTCTTGACAACCAATCTGGTAATGTCCCTGATGTTATGATGGCT

CCATACGACCGTGTAGGTAGCCTTGGTTCTGACGGACAACTTTCAGAAGTGAAATTGAGCGATGGTGCTAAAACAGA

CGACACAACTAAATCTCTTGTAACAGCTGCTAATGGTAAAGTTTACGGTGCTCCTGCCGTTATCGAGTCACTTGTTA

TGTACTACAACAAAGACTTGGTGAAAGATGCTCCAAAAACATTTGCTGACTTGGAAAACCTTGCTAAAGATAGCAAA

TACGCATTCGCTGGTGAAGATGGTAAAACTACTGCCTTCCTAGCTGACTGGACAAACTTCTACTATACATATGGACT

TCTTGCCGGTAACGGTGCTTACGTCTTTGGCCAAAACGGTAAAGACGCTAAAGACATCGGTCTTGCAAACGACGGTT

CTATCGTAGGTATCAACTACGCTAAATCTTGGTACGAAAAATGGCCTAAAGGTATGCAAGATACAGAAGGTGCTGGA

AACTTAATCCAAACTCAATTCCAAGAAGGTAAAACAGCTGCTATCATCGACGGACCTTGAAAGCTCAAGCCTTTAA

AGATGCTAAAGTAAACTACGGAGTTGCAACTATCCCAACTCTTCCAAATGGAAAAGAATATGCTGCATTCGGTGGTG

GTAAAGCTTGGGTCATTCCTCAAGCCGTTAAGAACCTTGAAGCTTCTCAAAAATTTGTAGACTTCCTTGTTGCAACT

GAACAACAAAAAGTATTATATGATAAGACTAACGAAATCCCAGCTAATACTGAGGCTCGTTCATACGCTGAAGGTAA

AAACGATGAGTTGACAACAGCTGTTATCAAACAGTTCAAGAACACTCAACCACTGCCAAACATCTCTCAAATGTCTG

CAGTTTGGGATCCAGCGAAAAATATGCTCTTTGATGCTGTAAGTGGTCAAAAAGATGCTAAAACAGCTGCTAACGAT

GCTGTAACATTGATCAAAGAAACAATCAAACAAAATTTGGTGAATAA

SEQ ID NO: 30
SP0641M (nucleotides)
ATGTCAGGAACTAGTATGGCGACTCCAATCGTGGCAGCTTCTACTGTTTTGATTAGACCGAAATTAAAGGAAATGCT

TGAAAGACCTGTATTGAAAAATCTTAAGGGAGATGACAAAATAGATCTTACAAGTCTTACAAAAATTGCCCTACAAA

ATACTGCGCGACCTATGATGGATGCAACTTCTTGGAAAGAAAAAAGTCAATACTTTGCATCACCTAGACAACAGGGA

GCAGGCCTAATTAATGTGGCCAATGCTTTGAGAAATGAAGTTGTAGCAACTTTCAAAAACACTGATTCTAAAGGTTT

GGTAAACTCATATGGTTCCATTTCTCTTAAAGAAATAAAAGGTGATAAAAAATACTTTACAATCAAGCTTCACAATA

CATCAAACAGACCTTTGACTTTTAAAGTTTCAGCATCAGCGATAACTACAGATTCTCTAACTGACAGATTAAAACTT

GATGAAACATATAAAGATGAAAAATCTCCAGATGGTAAGCAAATTGTTCCAGAAATTCACCCAGAAAAAGTCAAAGG

-continued

```
AGCAAATATCACATTTGAGCATGATACTTTCACTATAGGCGCAAATTCTAGCTTTGATTTGAATGCGGTTATAAATG

TTGGAGAGGCCAAAAACAAAAATAAATTTGTAGAATCATTTATTCATTTTGAGTCAGTGGAAGAAATGGAAGCTCTA

AACTCCAACGGGAAGAAAATAAACTTCCAACCTTCTTTGTCGATGCCTCTAATGGGATTTGCTGGGAATTGGAACCA

CGAACCAATCCTTGATAAATGGGCTTGGGAAGAAGGGTCAAGATCAAAAACACTGGGAGGTTATGATGATGATGGTA

AACCGAAAATTCCAGGAACCTTAAATAAGGGAATTGGTGGAGAACATGGTATAGATAAATTTAATCCAGCAGGAGTT

ATACAAAATAGAAAAGATAAAAATACAACATCCCTGGATCAAAATCCAGAATTATTTGCTTTCAATAACGAAGGGAT

CAACGCTCCATCATCAAGTGGTTCTAAGATTGCTAACATTTATCCTTTAGATTCAAATGGAAATCCTCAAGATGCTC

AACTTGAAAGAGGATTAACACCTTCTCCACTTGTATTAAGAAGTGCAGAAGAAGGATTGATTTCAATAGTAAATACA

AATAAAGAGGGAGAAAATCAAAGAGACTTAAAAGTCATTTCGAGAGAACACTTTATTAGAGGAATTTTAAATTCTAA

AAGCAATGATGCAAAGGGAATCAAATCATCTAAACTAAAAGTTTGGGGTGACTTGAAGTGGGATGGACTCATCTATA

ATCCTAGAGGTAGAGAAGAAAATGCACCAGAAAGTAAGGATAATCAAGATCCTGCTACTAAGATAAGAGGTCAATTT

GAACCGATTGCGGAAGGTCAATATTTCTATAAATTTAAATATAGATTAACTAAAGATTACCCATGGCAGGTTTCCTA

TATTCCTGTAAAAATTGATAACACCGCCCCTAAGATTGTTTCGGTTGATTTTTCAAATCCTGAAAAAATTAAGTTGA

TTACAAAGGATACTTATCATAAGGTAAAAGATCAGTATAAGAATGAAACGCTATTTGCGAGAGATCAAAAAGAACAT

CCTGAAAAATTTGACGAGATTGCGAACGAAGTTTGGTATGCTGGCGCCGCTCTTGTTAATGAAGATGGAGAGGTTGA

AAAAAATCTTGAAGTAACTTACGCAGGTGAGGGTCAAGGAAGAAATAGAAAACTTGATAAAGACGGAAATACCATTT

ATGAAATTAAAGGTGCGGGAGATTTAAGGGGAAAAATCATTGAAGTCATTGCATTAGATGGTTCTAGCAATTTCACA

AAGATTCATAGAATTAAATTTGCTAATCAGGCTGATGAAAAGGGGATGATTTCCTATTATCTAGTAGATCCTGATCA

AGATTCATCTAAATATCAA
```

SEQ ID NO: 31
SP0641N (nucleotides)
```
ATGGTAGTCTTAGCAGACACATCTAGCTCTGAAGATGCTTTAAACATCTCTGATAAAGAAAAAGTAGCAGAAAATAA

AGAGAAACATGAAAATATCCATAGTGCTATGGAAACTTCACAGGATTTTAAAGAGAAGAAAACAGCAGTCATTAAGG

AAAAAGAAGTTGTTAGTAAAAATCCTGTGATAGACAATAACACTAGCAATGAAGAAGCAAAAATCAAAGAAGAAAAT

TCCAATAAATCCCAAGGAGATTATACGGACTCATTTGTGAATAAAAACACAGAAAATCCCAAAAAAGAAGATAAAGT

TGTCTATATTGCTGAATTTAAAGATAAAGAATCTGGAGAAAAAGCAATCAAGGAACTATCCAGTCTTAAGAATACAA

AAGTTTTATATACTTATGATAGAATTTTTAACGGTAGTGCCATAGAAACAACTCCAGATAACTTGGACAAAATTAAA

CAAATAGAAGGTATTTCATCGGTTGAAAGGGCACAAAAAGTCCAACCCATGATGAATCATGCCAGAAAGGAAATTGG

AGTTGAGGAAGCTATTGATTACCTAAAGTCTATCAATGCTCCGTTTGGGAAAAATTTTGATGGTAGAGGTATGGTCA

TTTCAAATATCGATACTGGAACAGATTATAGACATAAGGCTATGAGAATCGATGATGATGCCAAAGCCTCAATGAGA

TTTAAAAAAGAAGACTTAAAAGGCACTGATAAAAATTATTGGTTGAGTGATAAAATCCCTCATGCGTTCAATTATTA

TAATGGTGGCAAATCACTGTAGAAAAATATGATGATGGAAGGGATTATTTTGACCCACATGGGATGCATATTGCAG

GGATTCTTGCTGGAAATGATACTGAACAAGACATCAAAAACTTTAACGGCATAGATGGAATTGCACCTAATGCACAA

ATTTTCTCTTACAAAATGTATTCTGACGCAGGATCTGGGTTTGCGGGTGATGAAACAATGTTTCATGCTATTGAAGA

TTCTATCAAACACAACGTTGATGTTGTTTCGGTATCATCTGGTTTTACAGGAACAGGTCTTGTAGGTGAGAAATATT

GGCAAGCTATTCGGGCATTAAGAAAAGCAGGCATTCCAATGGTTGTCGCTACGGGTAACTATGCGACTTCTGCTTCA

AGTTCTTCATGGGATTTAGTAGCAAATAATCATCTGAAAATGACCGACACTGGAAATGTAACACGAACTGCAGCACA

TGAAGATGCGATAGCGGTCGCTTCTGCTAAAAATCAAACAGTTGAGTTTGATAAAGTTAACATAGGTGGAGAAAGTT

TTAAATACAGAAATATAGGGGCCTTTTTCGATAAGAGTAAAATCACAACAAATGAAGATGGAACAAAAGCTCCTAGT

AAATTAAAATTTGTATATATAGGCAAGGGGCAAGACCAAGATTTGATAGGTTTGGATCTTAGGGGCAAAATTGCAGT

AATGGATAGAATTTATACAAAGGATTTAAAAAATGCTTTTAAAAAAGCTATGGATAAGGGTGCACGCGCCATTATGG
```

```
TTGTAAATACTGTAAATTACTACAATAGAGATAATTGGACAGAGCTTCCAGCTATGGGATATGAAGCGGATGAAGGT

ACTAAAAGTCAAGTGTTTTCAATTTCAGGAGATGATGGTGTAAAGCTATGGAACATGATTAATCCTGATAAAAAAAC

TGAAGTCAAAAGAAATAATAAAGAAGATTTTAAAGATAAATTGGAGCAATACTATCCAATTGATATGGAAAGTTTTA

ATTCCAACAAACCGAATGTAGGTGACGAAAAAGAGATTGACTTTAAGTTTGCACCTGACACAGACAAAGAACTCTAT

AAAGAAGATATCATCGTTCCAGCAGGATCTACATCTTGGGGGCCAAGAATAGATTTACTTTTAAAACCCGATGTTTC

AGCACCTGGTAAAAATATTAAATCCACGCTTAATGTTATTAATGGCAAATCAACTTATGGC
```

SEQ ID NO: 32

HHHHHH

SEQ ID NO: 33

MSYYHHHHHH

SEQ ID NO: 265

SP1912
MNGMKAKKMWMAGLALLGIGSLALATKKVADDRKLMKTQEELTEIVRDHFSDMGEIATLYVQVYESSLESLVGGVIF

EDGRHYTFVYENEDLVYEEEVL

SEQ ID NO: 266

SP1912L
MRYLATLLLSLAVLITAGCKKVADDRKLMKTQEELTEIVRDHFSDMGEIATLYVQVYESSLESLVGGVIFEDGRHYT

FVYENEDLVYEEEVL

SEQ ID NO: 267

SP0641.1
DTSSSEDALNISDKEKVAENKEKHENIHSAMETSQDFKEKKTAVIKEKEVVSKNPVIDNNTSNEEAKIKEENSNKSQ

GDYTDSFVNKNTENPKKEDKVVYIAEFKDKESGEKAIKELSSLKNTKVLYTYDRIFNGSAIETTPDNLDKIKQIEGI

SSVERAQKVQPMMNHARKEIGVEEAIDYLKSINAPFGKNFDGRGMVISNIDTGTDYRHKAMRIDDDAKASMRFKKED

LKGTDKNYWLSDKIPHAFNYYNGGKITVEKYDDGRDYFDPHGMHIAGILAGNDTEQDIKNFNGIDGIAPNAQIFSYK

MYSDAGSGFAGDETMFHAIEDSIKHNVDVVSVSSGFTGTGLVGEKYWQAIRALRKAGIPMVVATGNYATSASSSSWD

LVANNHLKMTDTGNVTRTAAHEDAIAVASAKNQTVEFDKVNIGGESFKYRNIGAFFDKSKITTNEDGTKAPSKLKFV

YIGKGQDQDLIGLDLRGKIAVMDRIYTKDLKNAFKKAMDKGARAIMVVNTVNYYNRDNWTELPAMGYEADEGTKSQV

FSISGDDGVKLWNMINPDKKTEVKRNNKEDFKDKLEQYYPIDMESFNSNKPNVGDEKEIDFKFAPDTDKELYKEDII

VPAGSTSWGPRIDLLLKPDVSAPGKNIKSTLNVINGKSTYGYMSGTSMATPIVAASTVLIRPKLKEMLERPVLKNLK

GDDKIDLTSLTKIALQNTARPMMDATSWKEKSQYFASPRQQGAGLINVANALRNEVVATFKNTDSKGLVNSYGSISL

KEIKGDKKYFTIKLHNTSNRPLTFKVSASAITTDSLTDRLKLDETYKDEKSPDGKQIVPEIHPEKVKGANITFEHDT

FTIGANSSFDLNAVINVGEAKNKNKFVESFIHFESVEEMEALNSNGKKINFQPSLSMPLMGFAGNWNHEPILDKWAW

EEGSRSKTLGGYDDDGKPKIPGTLNKGIGGEHGIDKFNPAGVIQNRKDKNTTSL

SEQ ID NO: 268

SP1912 consensus
MNGMKAKKMWMAGLALLGIGSLALATKKVADDRKLMKTQEELTEIVRDHFSDMGEIATLYVQVYESSLESLVGGVIF
                H    A    L       I                                    L S

EDGRHYTFVYENEDLVYEEEVL
      I

SEQ ID NO: 269

SP641N consensus
MVVLADTSSSEDALNISDKEKVA-----ENKEKHENIHSAMETSQDFKEKKTAVIKEKEVVSKNPVIDNNTSNEEAK
-      N   S         VVDKET     KD N I   K TE   TI EG A       T TK        R
              L IKEENSNKSQGDYTDSFVNKNTENPKKEDKVVYIAEFKDKESGEKAIKELSSLKNTKVLYTYDRIFNGSAIETTPDN
    D-    H              Q                S    Q N                  G       Q
          NAH SA  G         RL                  G LDKIKQIEGISSVERAQKVQPMMNHARKEIGVEEAIDYLKSINAPFGKNFDGRGMVISNIDTGTDYRHKAMRIDDDA
       T I

```
KASMRFKKEDLKGTDKNYWLSDKIPHAFNYYNGGKITVEKYDDGRDYFDPHGMHIAGILAGNDTEQDIKNFNGIDGI

APNAQIFSYKMYSDAGSGFAGDETMFHAIEDSIKHNVDVVSVSSGFTGTGLVGEKYWQAIRALRKAGIPMVVATGNY

ATSASSSSWDLVANNHLKMTDTGNVTRTAAHEDAIAVASAKNQTVEFDKVNIGGESFKYRNIGAFFDKSKITTNEDG
                                        Q                        N

TKAPSKLKFVYIGKGQDQDLIGLDLRGKIAVMDRIYTKDLKNAFKKAMDKGARAIMVVNTVNYYNRDNWTELPAMGY

EADEGTKSQVFSISGDDGVKLWNMINPDKKTEVKRNNKEDFKDKLEQYYPIDMESFNSNKPNVGDEKEIDFKFAPDT
                                N

DKELYKEDIIVPAGSTSWGPRIDLLLKPDVSAPGKNIKSTLNVINGKSTYG

SEQ ID NO: 270
SP641M consensus
MSGTSMATPIVAASTVLIRPKLKEMLERPVLKNLKGDDKIDLTSLTKIALQNTARPMMDATSWKEKSQYFASPRQQG
                K    T AGLINVANALRNEVVATFKNTDSKGLVNSYGSISLKEIKGDKKYFTIKLHNTSNRPLTFKVSASAITTDSLTDRLKL
                                                                 V DETYKDEKSPDGKQIVPEIHPEKVKGANITFEHDTFTIGANSSFDLNAVINVGEAKNKNKFVESFIHFESVEEMEAL
         Y                                       R                   A NSNGKKINFQPSLSMPLMGFAGNWNHEPILDKWAWEEGSRSKTLGGYDDDGKPKIPGTLNKGIGGEHGIDKFNPAGV
S       TD                            K    ME IQNRKDKNTTSLDQNPELFAFNNEGINAPSSSGSKIANIYPLDSNGNPQDAQLERGLTPSPLVLRSAEEGLISIVNT
         R     D D     Q VH E T NKEGENQRDLKVISREHFIRGILNSKSNDAKGIKSSKLKVWGDLKWDGLIYNPRGREENAPESKDNQDPATKIRGQF
        K V           G

EPIAEGQYFYKFKYRLTKDYPWQVSYIPVKIDNTAPKIVSVDFSNPEKIKLITKDTYHKVKDQYKNETLFARDQKEH

PEKFDEIANEVWYAGAALVNEDGEVEKNLEVTYAGEGQGRNRKLDKDGNTIYEIKGAGDLRGKIIEVIALDGSSNFT
                                                                 S       A

KIHRIKFANQADEKGMISYYLVDPDQDSSKYQ
        DH           K A   E

SEQ ID NO: 271
SP1912 (nucleotides)
ATGAATGGTATGAAAGCTAAAAAAATGTGGATGGCAGGCTTGGCTCTGCTAGGTATCGGAAGCCTTGCTCTTGCTAC

GAAAAAGTTGCAGATGACCGTAAGCTCATGAAGACTCAGGAAGAGTTGACAGAGATTGTGCGAGACCATTTTTCCG

ACATGGGGGAAATTGCGACCCTTTATGTTCAAGTTTACGAAAGCAGTCTGGAGAGCTTGGTTGGTGGCGTCATTTTT

GAGGATGGCCGTCATTATACCTTTGTCTATGAAAATGAAGACCTAGTCTATGAGGAGGAAGTCTTATGA

SEQ ID NO: 272
SP1912L (nucleotides)
ATGAGATACCTGGCAACATTGTTGTTATCTCTGGCGGTGTTAATCACCGCCGGGTGCAAAAAGTTGCAGATGACCG

TAAGCTCATGAAGACTCAGGAAGAGTTGACAGAGATTGTGCGAGACCATTTTTCCGACATGGGGGAAATTGCGACCC

TTTATGTTCAAGTTTACGAAAGCAGTCTGGAGAGCTTGGTTGGTGGCGTCATTTTTGAGGATGGCCGTCATTATACC

TTTGTCTATGAAAATGAAGACCTAGTCTATGAGGAGGAAGTCTTATGA

SEQ ID NO: 273
SP0641.1(nucleotides)
GACACATCTAGCTCTGAAGATGCTTTAAACATCTCTGATAAAGAAAAAGTAGCAGAAATAAAGAGAAACATGAAAA

TATCCATAGTGCTATGGAAACTTCACAGGATTTTAAAGAGAAGAAAACAGCAGTCATTAAGGAAAAGAAGTTGTTA

GTAAAAATCCTGTGATAGACAATAACACTAGCAATGAAGAAGCAAAAATCAAAGAAGAAAATTCCAATAAATCCCAA

GGAGATTATACGGACTCATTTGTGAATAAAAACACAGAAAATCCCAAAAAAGAAGATAAAGTTGTCTATATTGCTGA

ATTTAAAGATAAAGAATCTGGAGAAAAAGCAATCAAGGAACTATCCAGTCTTAAGAATACAAAAGTTTTATATACTT

ATGATAGAATTTTTAACGGTAGTGCCATAGAAACAACTCCAGATAACTTGGACAAAATTAAACAAATAGAAGGTATT

TCATCGGTTGAAAGGGCACAAAAAGTCCAACCCATGATGAATCATGCCAGAAAGGAAATTGGAGTTGAGGAAGCTAT

TGATTACCTAAAGTCTATCAATGCTCCGTTTGGGAAAAATTTTGATGGTAGAGGTATGGTCATTTCAAATATCGATA

CTGGAACAGATTATAGACATAAGGCTATGAGAATCGATGATGATGCCAAAGCCTCAATGAGATTTAAAAAAGAAGAC
```

-continued

```
TTAAAAGGCACTGATAAAAATTATTGGTTGAGTGATAAAATCCCTCATGCGTTCAATTATTATAATGGTGGCAAAAT
CACTGTAGAAAAATATGATGATGGAAGGGATTATTTTGACCCACATGGGATGCATATTGCAGGGATTCTTGCTGGAA
ATGATACTGAACAAGACATCAAAAACTTTAACGGCATAGATGGAATTGCACCTAATGCACAAATTTTCTCTTACAAA
ATGTATTCTGACGCAGGATCTGGGTTTGCGGGTGATGAAACAATGTTTCATGCTATTGAAGATTCTATCAAACACAA
CGTTGATGTTGTTTCGGTATCATCTGGTTTTACAGGAACAGGTCTTGTAGGTGAGAAATATTGGCAAGCTATTCGGG
CATTAAGAAAAGCAGGCATTCCAATGGTTGTCGCTACGGGTAACTATGCGACTTCTGCTTCAAGTTCTTCATGGGAT
TTAGTAGCAAATAATCATCTGAAAATGACCGACACTGGAAATGTAACACGAACTGCAGCACATGAAGATGCGATAGC
GGTCGCTTCTGCTAAAAATCAAACAGTTGAGTTTGATAAAGTTAACATAGGTGGAGAAAGTTTTAAATACAGAAATA
TAGGGGCCTTTTTCGATAAGAGTAAAATCACAACAAATGAAGATGGAACAAAAGCTCCTAGTAAATTAAAATTTGTA
TATATAGGCAAGGGGCAAGACCAAGATTTGATAGGTTTGGATCTTAGGGGCAAAATTGCAGTAATGGATAGAATTTA
TACAAAGGATTTAAAAAATGCTTTTAAAAAAGCTATGGATAAGGGTGCACGCGCCATTATGGTTGTAAATACTGTAA
ATTACTACAATAGAGATAATTGGACAGAGCTTCCAGCTATGGGATATGAAGCGGATGAAGGTACTAAAAGTCAAGTG
TTTTCAATTTCAGGAGATGATGGTGTAAAGCTATGGAACATGATTAATCCTGATAAAAAAACTGAAGTCAAAAGAAA
TAATAAAGAAGATTTTAAAGATAAATTGGAGCAATACTATCCAATTGATATGGAAAGTTTTAATTCCAACAAACCGA
ATGTAGGTGACGAAAAAGAGATTGACTTTAAGTTTGCACCTGACACAGACAAAGAACTCTATAAAGAAGATATCATC
GTTCCAGCAGGATCTACATCTTGGGGGCCAAGAATAGATTTACTTTTAAAACCCGATGTTTCAGCACCTGGTAAAAA
TATTAAATCCACGCTTAATGTTATTAATGGCAAATCAACTTATGGCTATATGTCAGGAACTAGTATGGCGACTCCAA
TCGTGGCAGCTTCTACTGTTTTGATTAGACCGAAATTAAAGGAAATGCTTGAAAGACCTGTATTGAAAAATCTTAAG
GGAGATGACAAAATAGATCTTACAAGTCTTACAAAAATTGCCCTACAAAATACTGCGCGACCTATGATGGATGCAAC
TTCTTGGAAAGAAAAAAGTCAATACTTTGCATCACCTAGACAACAGGGAGCAGGCCTAATTAATGTGGCCAATGCTT
TGAGAAATGAAGTTGTAGCAACTTTCAAAAACACTGATTCTAAAGGTTTGGTAAACTCATATGGTTCCATTTCTCTT
AAAGAAATAAAAGGTGATAAAAAATACTTTACAATCAAGCTTCACAATACATCAAACAGACCTTTGACTTTTAAAGT
TTCAGCATCAGCGATAACTACAGATTCTCTAACTGACAGATTAAAACTTGATGAAACATATAAAGATGAAAAATCTC
CAGATGGTAAGCAAATTGTTCCAGAAATTCACCCAGAAAAAGTCAAAGGAGCAAATATCACATTTGAGCATGATACT
TTCACTATAGGCGCAAATTCTAGCTTTGATTTGAATGCGGTTATAAATGTTGGAGAGGCCAAAAACAAAATAAATT
TGTAGAATCATTTATTCATTTTGAGTCAGTGAAGAAATGGAAGCTCTAAACTCCAACGGGAAGAAAATAAACTTCC
AACCTTCTTTGTCGATGCCTCTAATGGGATTTGCTGGGAATTGGAACCACGAACCAATCCTTGATAAATGGGCTTGG
GAAGAAGGGTCAAGATCAAAAACACTGGGAGGTTATGATGATGATGGTAAACCGAAAATTCCAGGAACCTTAAATAA
GGGAATTGGTGGAGAACATGGTATAGATAAATTTAATCCAGCAGGAGTTATACAAATAGAAAAGATAAAAATACAA
CATCCCTG
```

```
                                                          SEQ ID NO: 274
Canonical lipobox motif
[LIVMFESTAGPC]-[LVIAMFTG]-[IVMSTAGCP]-[AGS]-C SEQ ID NO: 275
SP2108 signal sequence
MSSKFMKSAAVLGTATLASLLLVAC SEQ ID NO: 276
E. coli RlpB signal sequence
MRYLATLLLSLAVLITAG[C]

SEQ ID NO: 301
Immunogenic PspA/PspC polypeptides including the coiled-coil structure (PR +
NPB)
MSDKIIHLTDDSFDTDVLKADGAILVDFWAEWCGPCKMIAPILDEIADEYQGKLTVA

KLNIDQNPGTAPKYGIRGIPTLLLFKNGEVAATKVGALSKGQLKEFLDANLAGSGSG

HMHHHHHHSSGLVPRGSGMKETAAAKFERQHMDSPDLGTDDDDKAMADLKKAVNE
```

```
                                                            -continued
PEKPAEEPENPAPAPKPAPAPQPEKPAPAPAPKPEKSADQQAEEDYARRSEEEYNRLTQQ

QPPKAEKPAPAPVPKPEQPAPAPKTGWGQENGMWCRQACGRTRAPPPPPLRSGC

SEQ ID NO: 302
Immunogenic PspA/PspC polypeptides including the coiled-coil structure (PR
only)
MSDKIIHLTDDSFDTDVLKADGAILVDFWAEWCGPCKMIAPILDEIADEYQGKLTVA

KLNIDQNPGTAPKYGIRGIPTLLLFKNGEVAATKVGALSKGQLKEFLDANLAGSGSG

HMHHHHHHSSGLVPRGSGMKETAAAKFERQHMDSPDLGTDDDDKAMADLKKAVNE

PETPAPAPAPAPAPAPTPEAPAPAPAPAPKPAPAPKPAPAPKPAPAPKPAPAPKPAPAPKP

APAPAPAPKPEKPAEKPAPAPKPETPKTGWKQENGMWCRQACGRTRAPPPPPLRSG

SEQ ID NO: 303
Immunogenic PspA/PspC polypeptides lacking the coiled-coil structure (PR +
NPB)
DLKKAVNEPEKPAEEPENPAPAPKPAPAPQPEKPAPAPAPKPEKSADQQAEEDYARR

SEEEYNRLTQQQPPKAEKPAPAPVPKPEQPAPAPKTGWGQENGMW

SEQ ID NO: 304
Immunogenic PspA/PspC polypeptides lacking the coiled-coil structure (PR
only)
DLKKAVNEPETPAPAPAPAPAPAPTPEAPAPAPAPAPAPKPAPAPKPAPAPKPAPAPKPA

PAPKPAPAPKPAPAPAPAPKPEKPAEKPAPAPKPETPKTGWKQENGMW

SEQ ID NO: 305
Immunogenic PspA/PspC polypeptides lacking the coiled-coil structure (PR +
NPB)
MAKKAELEKTPEKPAEEPENPAPAPQPEKSADQQAEEDYARRSEEEYNRLTQQQPPKA SEQ ID NO: 306
Non-proline Block (NPB)
EKSADQQAEEDYARRSEEEYNRLTQQQ SEQ ID NO: 307
Non-proline Block (NPB)
DQQAEEDYARRSEEEYNRLTQQQ SEQ ID NO: 308
Non-proline Block (NPB)
MEKSADQQAEEDYARRSEEEYNRLTQQQ SEQ ID NO: 309
Amino-terminal boundary to the PR-region
DLKKAVNE SEQ ID NO: 310
Carboxy-terminal boundary to the PR-region
(K/G)TGW(K/G)QENGMW
```

---

We claim:

1. A vaccine formulation comprising:
   a pharmaceutically acceptable carrier;
   an effective amount of an adjuvant;
   a first isolated polypeptide comprising the amino acid sequence of SEQ ID NO: 265, 266, or 268, or comprising the amino acid sequence of SEQ ID NO:265, 266, or 268 lacking 1-3 amino acids from the N-terminus, C-terminus, or both; and
   a second isolated polypeptide comprising the amino acid sequence of SEQ ID NO:9 or 10, or comprising the amino acid sequence of SEQ ID NO:9 or 10 lacking 1-3 amino acids from the N-terminus, C-terminus, or both.

2. The vaccine formulation of claim 1, further comprising a third isolated polypeptide comprising the amino acid sequence of SEQ ID NO:6 or 7, or comprising the amino acid sequence of SEQ ID NO:6 or 7 lacking 1-3 amino acids from the N-terminus, C-terminus, or both.

3. The vaccine formulation of claim 2, wherein the third polypeptide consists of the amino acid sequence of SEQ ID NO:6.

4. The vaccine formulation of claim 2, wherein the third polypeptide consists of the amino acid sequence of SEQ ID NO:7.

5. A vaccine formulation comprising:
a pharmaceutically acceptable carrier;
an effective amount of an adjuvant;
a first isolated polypeptide comprising the amino acid sequence of SEQ ID NO:265, 266, or 268, or comprising the amino acid sequence of SEQ ID NO:265, 266, or 268 lacking 1-3 amino acids from the N-terminus, C-terminus, or both; and
a second isolated polypeptide comprising the amino acid sequence of SEQ ID NO:6 or 7, or comprising the amino acid sequence of SEQ ID NO:6 or 7 lacking 1-3 amino acids from the N-terminus, C-terminus, or both.

6. The vaccine formulation of claim 1 or 5, wherein the first polypeptide consists of the amino acid sequence of SEQ ID NO:265.

7. The vaccine formulation of claim 1 or 5, wherein the first polypeptide consists of the amino acid sequence of SEQ ID NO:266.

8. The vaccine formulation of claim 1 or 5, wherein the first polypeptide consists of the amino acid sequence of SEQ ID NO:268.

9. The vaccine formulation of claim 1, wherein the second polypeptide consists of the amino acid sequence of SEQ ID NO:9.

10. The vaccine formulation of claim 1 or 5, wherein one or more polypeptides are conjugated to an immunogenic carrier.

11. The vaccine formulation of claim 1 or 5, which comprises at least one lipidated polypeptide.

12. The vaccine formulation of claim 5, wherein the second polypeptide consists of the amino acid sequence of SEQ ID NO:6.

13. The vaccine formulation of claim 5, wherein the second polypeptide consists of the amino acid sequence of SEQ ID NO:7.

14. A vaccine formulation comprising:
a pharmaceutically acceptable carrier;
an effective amount of an adjuvant;
a first isolated polypeptide comprising the amino acid sequence of SEQ ID NO: 265, 266, or 268 or comprising the amino acid sequence of SEQ ID NO:265, 266, or 268 lacking 1-3 amino acids from the N-terminus, C-terminus, or both;
a second isolated polypeptide comprising the amino acid sequence of SEQ ID NO: 6 or comprising the amino acid sequence of SEQ ID NO:6 lacking 1-3 amino acids from the N-terminus, C-terminus, or both; and
a third isolated polypeptide comprising the amino acid sequence of SEQ ID NO:7 or comprising the amino acid sequence of SEQ ID NO:7 lacking 1-3 amino acids from the N-terminus, C-terminus, or both.

15. The vaccine formulation of claim 14, wherein the second polypeptide is lipidated.

16. The vaccine formulation of claim 14 or 15, further comprising one or both of:
a fourth isolated polypeptide comprising the amino acid sequence of SEQ ID NO: 9 or comprising the amino acid sequence of SEQ ID NO: 9 lacking 1-3 amino acids from the N-terminus, C-terminus, or both; and
a fifth isolated polypeptide comprising the amino acid sequence of SEQ ID NO: 10 or comprising the amino acid sequence of SEQ ID NO: 10 lacking 1-3 amino acids from the N-terminus, C-terminus, or both.

17. The vaccine formulation of claim 16, wherein the fifth polypeptide is lipidated.

18. A vaccine formulation comprising:
a pharmaceutically acceptable carrier;
an effective amount of an adjuvant;
a first isolated polypeptide comprising the amino acid sequence of SEQ ID NO: 265, 266, or 268 or comprising the amino acid sequence of SEQ ID NO: 265, 266, or 268 lacking 1-3 amino acids from the N-terminus, C-terminus, or both;
a second isolated polypeptide comprising the amino acid sequence of SEQ ID NO: 9 or comprising the amino acid sequence of SEQ ID NO: 9 lacking 1-3 amino acids from the N-terminus, C-terminus, or both; and
a third isolated polypeptide comprising the amino acid sequence of SEQ ID NO: 10 or comprising the amino acid sequence of SEQ ID NO: 10 lacking 1-3 amino acids from the N-terminus, C-terminus, or both.

19. The vaccine formulation of claim 18, wherein the third polypeptide is lipidated.

20. A vaccine formulation comprising:
a pharmaceutically acceptable carrier;
an effective amount of an adjuvant;
a first isolated polypeptide comprising the amino acid sequence of SEQ ID NO: 265 or comprising the amino acid sequence of SEQ ID NO:265 lacking 1-3 amino acids from the N-terminus, C-terminus, or both;
a second isolated polypeptide comprising the amino acid sequence of SEQ ID NO: 6 or comprising the amino acid sequence of SEQ ID NO:6 lacking 1-3 amino acids from the N-terminus, C-terminus, or both;
a third isolated polypeptide comprising the amino acid sequence of SEQ ID NO:7 or comprising the amino acid sequence of SEQ ID NO:7 lacking 1-3 amino acids from the N-terminus, C-terminus, or both;
a fourth isolated polypeptide comprising the amino acid sequence of SEQ ID NO: 9 or comprising the amino acid sequence of SEQ ID NO: 9 lacking 1-3 amino acids from the N-terminus, C-terminus, or both; and
a fifth isolated polypeptide comprising the amino acid sequence of SEQ ID NO: 10 or comprising the amino acid sequence of SEQ ID NO: 10 lacking 1-3 amino acids from the N-terminus, C-terminus, or both.

21. The vaccine formulation of claim 20, wherein the adjuvant is alum.

22. The vaccine formulation of claim 20, wherein the vaccine formulation comprises 1-1000 μg of each polypeptide.

23. The vaccine formulation of any one of claim 1, 5, 14, 18, or 20, wherein upon administration to a subject, the vaccine formulation induces an immune response against *S. pneumoniae*.

24. A pharmaceutical composition comprising:
a pharmaceutically acceptable carrier;
an effective amount of an adjuvant;
a first isolated polypeptide comprising an amino acid sequence at least 98% identical to the amino acid sequence of SEQ ID NO:265, 266, or 268, or comprising an amino acid sequence at least 98% identical to the amino acid sequence of SEQ ID NO:265, 266, or 268 lacking 1-3 amino acids from the N-terminus, C-terminus, or both; and
a second isolated polypeptide comprising an amino acid sequence at least 98% identical to the amino acid sequence of SEQ ID NO:9 or 10, or comprising an amino acid sequence at least 98% identical to the amino acid sequence of SEQ ID NO:9 or 10 lacking 1-3 amino acids from the N-terminus, C-terminus, or both.

25. The pharmaceutical composition of claim 24, further comprising a third isolated polypeptide comprising an amino acid sequence at least 98% identical to the amino acid sequence of SEQ ID NO:6 or 7, or comprising an amino acid sequence at least 98% identical to the amino acid sequence of SEQ ID NO:6 or 7 lacking 1-3 amino acids from the N-terminus, C-terminus, or both.

26. A pharmaceutical composition comprising:
a pharmaceutically acceptable carrier;
an effective amount of an adjuvant;
a first isolated polypeptide comprising an amino acid sequence at least 98% identical to the amino acid sequence of SEQ ID NO:265, 266, or 268, or comprising an amino acid sequence at least 98% identical to the amino acid sequence of SEQ ID NO:265, 266, or 268 lacking 1-3 amino acids from the N-terminus, C-terminus, or both; and
a second isolated polypeptide comprising an amino acid sequence at least 98% identical to the amino acid sequence of SEQ ID NO:6 or 7, or comprising an amino acid sequence at least 98% identical to the amino acid sequence of SEQ ID NO:6 or 7 lacking 1-3 amino acids from the N-terminus, C-terminus, or both.

27. The pharmaceutical composition of 90 or 92, wherein upon administration to a subject, the pharmaceutical composition induces an immune response against *S. pneumoniae*.

28. A pharmaceutical composition comprising:
a pharmaceutically acceptable carrier;
an effective amount of an adjuvant;
a first polypeptide comprising an amino acid sequence from a strain of *S. pneumoniae* that corresponds to the amino acid sequence of SEQ ID NO: 265, 266, or 268, or to the amino acid sequence of SEQ ID NO:265, 266, or 268 lacking 1-3 amino acids from the N-terminus, C-terminus, or both; and
a second polypeptide comprising an amino acid sequence from a strain of *S. pneumoniae* that corresponds to the amino acid sequence of SEQ ID NO:9 or 10, or to the amino acid sequence of SEQ ID NO:9 or 10 lacking 1-3 amino acids from the N-terminus, C-terminus, or both.

29. The pharmaceutical composition of claim 28, further comprising a third polypeptide comprising an amino acid sequence from a strain of *S. pneumoniae* that corresponds to the amino acid sequence of SEQ ID NO:6 or 7, or to the amino acid sequence of SEQ ID NO:6 or 7 lacking 1-3 amino acids from the N-terminus, C-terminus, or both.

* * * * *